(12) United States Patent
Blumenfeld et al.

(10) Patent No.: US 6,479,238 B1
(45) Date of Patent: Nov. 12, 2002

(54) POLYMORPHIC MARKERS OF THE LSR GENE

(76) Inventors: Marta Blumenfeld, Paris (FR); Lydie Bougueleret, Vanves (FR); Bernard Bihain, Encinitas, CA (US)

( * ) Notice: Subject to any disclaimer, the term of this patent is extended or adjusted under 35 U.S.C. 154(b) by 0 days.

(21) Appl. No.: 09/499,522

(22) Filed: Feb. 10, 2000

Related U.S. Application Data

(60) Provisional application No. 60/119,592, filed on Feb. 10, 1999, and provisional application No. 60/144,784, filed on Jul. 20, 1999.

(51) Int. Cl.$^7$ ................................................. C12Q 1/68
(52) U.S. Cl. ........................................ 435/6; 435/91.2
(58) Field of Search ..................................... 435/6, 91.2

(56) References Cited

U.S. PATENT DOCUMENTS 5,270,170 A   12/1993   Schatz et al.

FOREIGN PATENT DOCUMENTS

| | | |
|---|---|---|
| FR | 2 767 136 | 2/1999 |
| WO | WO 96/30400 | 10/1996 |
| WO | WO 96/34981 | 11/1996 |
| WO | WO 96/39429 | 12/1996 |
| WO | WO 97/27286 | 7/1997 |
| WO | WO 98/01257 | 1/1998 |
| WO | WO 98/20165 | 5/1998 |
| WO | WO 98/54311 | 12/1998 |
| WO | WO 99/07736 | 2/1999 |
| WO | WO 99/10492 | 3/1999 |
| WO | WO 99/21577 | 6/1999 |

OTHER PUBLICATIONS

Bihain, B., et al.; "The lipolysis stimulated receptor: a gene at last"; Current Opinion in Lipidology, GB, London, vol. 9, No. 3, Jun. 1, 1998, pp. 221–224; ISSN: 0957–9672 1998 Lippincott–Raven Publishers [XP–002096548].

Bihain, B., et al.; "Lipolysis—stimulated receptor: A newcomer on the lipoprotein research scene"; Diabete & Metabolisme, (1995) vol. 21, No. 2, pp. 121–126 [XP–000925423].

Ducobu, J.; "Lipoprotein receptors. Old acquaintances and newcomers!; Les recepteurs des lipoproteines. Vieilles connaissances et nouveaux venus", Revue Medicale de Burxelles (Feb. 1997) 18 (1) 10–5 [XP–000925412].

Zhao, L. P., et al.; "Mapping of complex traits by single-nucleotide polymorphisms", American Journal of Human Gneetics, U.S., University of Chicago Press, Chicago, vol. 63, No. 1, 1998, pp. 225–240 [XP–000920771] ISSN: 0002–9297.

Alexeev and Yoon, "Stable and inheritable changes in genotype and penotype of albino melanocytes induced by an RNA–DNA oligonucleotide," Nature Biotech., 16:1343–1346, 1998.

Arita, et al., "Paradoxical Decrease of an Adipose–Specific Protein, Adiponectin, in Obesity," Biochem. and Biophys. Research Comm. 257:79–83, 1999.

Austin, et al., "Hypertriglyceridemia as a Cardiovascular Risk Factor," Am. J. Cardiol., 81:7B–12B, 1998.

Baldo, et al., "The Adipsin–Acylation Stimulating Protein System and Regulation of Intracellular Triglyceride Synthesis," J. Clin. Invest., 92:1543–1547 (1993).

Bartles, J.R., et al., "Biogenesis of the Rate Hepatocyte Plasma Membrane," Methods Enzymol., 191: 825–841, 1990.

Bihain, B.E., et al., "Characterization and purification of the lipolysis–stimulated receptor," Elsevier Science B.V., pp. 465–470, 1995.

Bihain, B.E., et al., "Free Fatty Acitds Activate a High–Affinity Saturable Pathway for Degradation of Low–Density Lipoproteins in Fibroblasts from a Subject Homozygous for Familial Hypercholesterolemia" Biochemistry, 31:4628–4636, 1992.

Brendel, V., et al., "Methods and algorithms for statistical analysis of protein sequences," Proc. Natl. Acad. Sci. USA, 89:2002–2006, 1992.

Chen, .W.J., et al., "NPXY, a Sequence Often Found in Cytoplasmic Tails, Is Required for Coated Pit–mediated Internalization of the Low Density Lipoprotein Receptor*", J. Biol. Chem., 265:3116–3123, 1990.

Cole–Strauss et al., "Correction of the Mutation Responsible for Sickle Cell Anemia by an RNA–DNA Oligonucleotide," Science, 273:1386–1389, 1996.

Costet, P., et al., "Peroxisome Proliferator–activated Receptor α–Isoform Deficiency Leads to Progressive Dyslipidemia with Sexually Dimorphic Obesity and Steatosis*", J. Biol. Chem., 273, 29577–29585, 1998.

Davis, C.G., et al., "The J.D. Mutation in Familial Hypercholesterolemia: Amino Acid Sustitution in Cytoplasmic Domain Impedes Internalization of LDL Receptors," Cell, 45:15–24, 1986.

Dietrich, J., et al., "CD3γContains a Phosphoserine–Dependent Di–Leucine Motif Involved in Down–Regulation of the T Cell Receptor", EMBO Journal 13:2156–2166 1994.

Everhart, J.E., "Weight Change and Obesity After Liver Transplantation: Incidence and Risk Factors," Liver Transpl. Surg., 4:285–296, 1998.

(List continued on next page.)

Primary Examiner—James Ketter

(57) ABSTRACT

The invention provides novel LSR genomic sequences, polypeptides, antibodies, and polynucleotides including biallelic markers derived from the LSR locus. Primers hybridizing to regions flanking these biallelic markers are also provided. This invention also provides polynucleotides and methods suitable for genotyping a nucleic acid containing sample for one or more biallelic markers of the invention. Further, the invention provides methods to detect a statistical correlation between a biallelic marker allele and a phenotype and/or between a biallelic marker haplotype and a phenotype.

21 Claims, 7 Drawing Sheets

OTHER PUBLICATIONS

Feeman, Jr., W.E., "Hypertriglyceridemia and Atherosclerosis," *Annals of Internal Medicine*, vol. 128, No. 1, pp. 73–74, 1998.

Ghebrehiwet, et al., "Isolation, cDNA Cloning, and Overexpression of a 33–kD Cell Surface Glycoprotein that Binds to the Globular "Heads" of C1q," *J. Exp. Med.*, 179:1809–1821 (1994).

Goldstein, J.L., et al., "Familial Hypercholesterolemia," *The Metabolic and Molecular Bases of Inherited Disease*, vol. II, 7th Edition (Sciver, C.R., et al., ed). McGraw–Hill, New York, pp. 1981–2030, 1995.

Goldstein, et al., "Hyperlipidemia in Coronary Heart Disease," *J. Clin, Invest.*, 52:1533–1543, 1973.

Gura, et al., "Obesity Sheds Its Secrets", *Science*, 275:781–753, Feb. 7, 1997.

Hayward, et al., "The cDNA Sequence of Human Endothelial Cell Multimerin," *J. Biol Chem.*, 270:18246–18251, 1995.

Henrion, et al., "Structure, Sequence, and Chromosomal Location of the Gene for USF2 Transcription Factors in Mouse," Genomics, 25:36–43 (1995).

Herz, J., et al., "Structure location and high affinity for calcium of a 500–kd liver membrane protein closely related to the LDL–receptor suggest a physiological role as lipoprotein receptor," European Molecular Biology Laboratory, 7:4119–4127 (1988).

Honoré, B. et al., "Cloning and expression of a cDNA covering the complete coding region of the P32 subunit of human pre–mRNA splicing factor SF2," *Gene*, 134:283–287 (1993).

Hu, et al., "AdipoQ is a Novel Adipose–specifc Gene Dysregulated in Obesity," *J. Biol. Chem.*, 271:10697–10703 (1996).

Huettinger, M., et al., "Characteristics of Chylomicron Remnant Uptake into Rat Liver," *Clin. Biochem.*, 21:87–92 (1988).

Huto, et al., "AdipoQ Is a Novel Adipose–specific Gene Dysregulated in Obesity," *Jr. of Biol. Chem.*, 271, 18:10697–10703 (1996).

Imagawa, et al., "Structure–Function Studies of Human Leptin," *J. Biol. Chem.*, 273:35245–35249, 1998.

Karpe, F., et al., "Clearance of lipoprotein remnant particles in adipose tissue and musle in humans," *J. Lipid Res.* 38:2335–2343 (1997).

Karpe, F., et al., "Magnitude of alimentary lipemia is related to intima–media thickness of the common carotid artery in middle–aged men" *Elsevier Science Ireland*, 141:307–314, 1998.

Kersten, S., et al., "Peroxisome proliferator–activited receptor α mediates the adaptive response to fasting," *J. Clin. Invest.*, 103:1489–1498, Jun. 1999.

Khallou, et al., "Correction of Delayed Postprandial Plasma Lipid Response in Genetically Obese Mice by Injection of Recombinant Leptin," Abstract from the 69th Scientific Sessions, New Orleans, LA; Supplemental to Circulation, American Heart Assoc., vol. 94:8 (1996).

Krainer, A.R., et al., "Functional Expression of Cloned Human Splicing Factor SF2: Homolgy to RNA–Binding Proteins, U1 70K, and Drosophila Splicing Regulators," *Cell*, 66:383–394, 1991.

Lee, M.G–S., et al., "Charaterization of a cDNA Encoding a Csyteine–Rich Cell Surface Protein Located in Flagellar Pocket of the Protozoan *Trypanosoma brucei*," *Molec. Cell. Biol.*, 10:4506–4517 (1990).

Letoureur, F., et al., "A Novel Di–Leucine Motif and a Tyrosine–Based Motif Independently Mediate Lysosomal Targeting and Endocytosis of CD3 Chains," *Cell*, 69:1143–1157 (1992).

Lewis, G.F., et al., "Postprandial Lipoprotein Metabolism in Normal and Obese Subjects: Comparison after the Vitamin A Fat–Loading Test," *Jr. of Clinic. Endo.*, 71:1041–1050, (1990).

Lin, et al., "Archaic Structure of the Gene Ecoding Transciption Factor USF*," *Jr. of Bio. Chem.*, 269:23894–23903, (1994).

Liu, Q., et al., "Design of Polydactyl zinc–finger proteins for unique addressing within complex genomes," *Proc. Natl. Acad. Sci. USA*, 94:5525–5530, 1997.

Maeda, et al., "cDNA Cloning and Expression of a Novel Adipose Specific Collagen–like Factor, apM1 (Adipose Most Abundant Gene Transcript 1)," *Biochem. and Biophys. Research Comm.*, 221:286–289, 1996.

Mahley, R.W., et al., "Type III Hyperlipoproteinemia (Dysbetalipoproteinemia): The Role of Apolipoprotein E in Normal and Abnormal Lipoprotein Metabolism," *The Molecular Basis of Inherited Disease*, eds. Scriver, et al., McGraw Hill Inc., New York, pp. 1953–1980, 1995.

Mann, C.J., et al., "Mechanism of Activation and Functional Significance of the Lipolysis–Stimulated Receptor. Evidence for a Role as Chylomicron Remnant Receptor," *Biochemistry*, 34:10421–10431 (1995).

Mann, et al., "ApoCIII Inhibits the Binding of Trglyceride–Rich Lipoproteins to the Lipolysis Stimulated Receptor," Abstract, (1996).

Massie, et al., "Inducible Overexpression of a Toxic Protein by an Adenovirus Vector with a Tetracycline–Regulatable Expression Cassette," *Journal of Virology*, 72:2289–2296, 1998.

Montague, et al., "Congenital leptin deficiency is associated with severe early–onset obesity in humans," *Nature*, 387:903–908, 1997.

Parra–Lopez, C.A., et al., "Presentation on Class II MHC Molecules of Endogenous Lysozyme Targeted to Endocytic Pathway[1]" *J. Immunol.*, 158:2670–2679, 1997.

Pengue, G., et al., "Repression of transcriptional activity at a distance by the evolutionarily conserved KRAB domain present in a subfamily of zinc finger proteins," *Nucleic Acids Research*, vol. 22, No. 15, 2908–2914 (1994).

Perusse, L., et al., "The Human Obesity Gene Map: The 1998 Update," *Obes. Res.* 7:111–129, Jan. 1999.

Rajput–Williams, J., et al., "Variation of Apolipoprotein–B gene is associated with obesity, high blood cholesterol levels, and increased risk of coronary heart disease," The Lancet, pp. 1442–1446, 1988.

Rutherford, S., et al., "Association of a low density lipoprotein receptor micro–satellite variant with obesity," *Intl. Jr. of Obesity*, 21:1032–1037, 1997.

Saito, et al., "Organization of the gene for gelatin–binding protein (GBP28)," *GENE*, 229:67–73, Jan. 12, 1999.

Schäffler, et al., "Identification and characterization of the human adipocyte apM–1 promoter," *Biochem. and Biophys. Res. Comm.* 1399:187–197, 1998.

Schäffler, et al., "The Human apM–1, an Adipocyte–Specific Gene Linked to the Family of TNF's and to Genes Expressed in Activated T Cells, is Mapped to Chromosome 1q21.3–q23, a Susceptibility Locus Identified for Familial Combined Hyperlipidaemia (FCH)," *Biochem. and Biophys. Res. Comm.* 260:416–425, May 7, 1999.

Scherer, et al., "A Novel Serum Protein Similar to C1q, Produced Exclusively in Adipocytes*," *J. Biol. Chem.,* 270:26746–26749, 1995.

Sellar, et al., "Characterization and organization of the genes encoding the A–, B–and C–chains of human complement subcomponent C1q," Biochemical Journal, 274:481–490, (1991).

Shimabukuro, M., et al., "Direct antidiabetic effect of leptin through triglyceride depletion of tissues," *Proc. Natl. Acad. Sci. USA,* 94:4637–4641, 1997.

Shimano, H., et al., "Overproduction of Cholesterol and Fatty Acids Causes Massive–Liver Enlargement in Transgenic Mice Expressing Truncated SREBP–1a," *J. Clin. Invest.,* 98:1575–1584, 1996.

Shimomura, et al., "Leptin reverses insulin resistance and diabetes mellitus in mice with congenital lipodystrophy," *Nature,* 401:73–76, Sep. 2, 1999.

Shin, J. et al., "Phosphorylation–dependent Down–modulation of CD4 Requires a Specific Structure within the Cytoplasmic Domain of CD4," *Jr. of Biol. Chem.,* vol. 266:10658–10665, 1991.

Simos, G. et al., "The lamin B receptor–associated protein p34 shares sequence homology and antigenic determinants with the splicing factor 2–associated protein p32," FEBS Letters 346:225–228, 1994.

Steingrimsson, E., et al., "Murine Chromosomal Location of Five bHLH–Zip Transcription Factor Genes," *Genomics,* 28:179–183, 1995.

Troussard, A.A., et al., "Inhibitory Effect on the Lipolysis––stimulated Receptor of the 39–kDa Receptor–associated Protein*," *Jr. of Biol. Chem.,* 270:17068–71, 1995.

Urade, Y., et al., "Precerebellin is a cerebellum–specific protein with similarity to the globular domain of complement C1q B chain," *Proc. Natl. Sci. USA,* 88:1069–1073, 1991.

Uotani, S., "Functional Properties of Leptin Receptor Isoforms Internalization and Degradation of Leptin and Ligand–Induced Receptor Downregulation Diabetes," 48:279–286, Feb. 1999.

Van den Berg, R. H., et al., "Intracellular Localization of the Human Receptor for the Globular Domains of C1q$^1$," American Association of Immunologists, 158:3909–3916, 1997.

Vansant, G., et al., "Determinants of postprandial lipemia in obese women," Intl. Jr. of Obesity, 23:Supp. 1, 14–21, 1999.

Verhey, K.J., et al., "A Leu–Leu Sequence is Essential for COOH–terminal Targeting Signal of GLUT4 Glucose Transporter in Fibroblasts," *J. Biol. Chem.,* 269:2353–2356, 1994.

Wang, et al., "Upstream Stimulatory Factor Binding to the E–box at—65 is required for Insulin Regulation of the Fatty Acid Synthase Promoter," *J. Biol. Chem.,* 272:26367–26374, 1997.

Yen, et al., "Molecular Cloning of a Lipolysis–stimulated Remnant Receptor Expressed in the Liver," *J. Biol. Chem.,* 274:13390–13398, 1999.

Yen, F.T., et al., "Identification of a Lipolysis–stimulated Receptor That is Distinct from the LDL Receptor and the LDL Receptor–Related Protein," *Biochemistry,* 33:1172–1180, 1994.

Zhang, M., et al., "Tumor Necrosis Factor," *The Cytokine Handbook,* Third Ed., pp. 517–548, 1998.

Zhong, G., et al., "Related Leucine–based Cytoplasmic Targeting Signals in Invariant Chain and Major Histocompatibility Complex Class II Molecules Control Endocytic Presentation of Distinct Determinants in a Single Protein," *J. Exp. Med.,* 185:429–438, 1997.

POLYMORPHIC MARKERS OF THE LSR GENE

This application claims priority to U.S. provisional application No. 60/119,592 by Blumenfeld, et al. entitled "Polymorphic Markers of the LSR Gene" filed Feb. 10, 1999 and U.S. provisional application No. 60/144,784 by Blumenfeld, et al. entitled "Polymorphic Markers of the LSR Gene" filed Jul. 20, 1999, both of which are hereby incorporated herein in their entirety including any figures, drawings, or tables

FIELD OF THE INVENTION

The invention concerns biallelic markers of the LSR gene, as well as methods and kits for detecting these polynucleotides. The present invention encompasses methods of establishing associations between these markers and obesity or disorders related to obesity. The invention also concerns the genomic sequence and the cDNAs encoding a subunit of LSR and comprising a biallelic marker of the present invention as well as vectors, host cells and transgenic animals comprising said polynucleotides. The invention further concerns modified LSR proteins comprising at least one amino acid change resulting from the biallelic markers of the present invention as well as antibodies which are specific to these modified LSR proteins.

BACKGROUND

Obesity is a public health problem that is both serious and widespread. One-third of the population in industrialized countries has an excess weight of at least 20% relative to the ideal weight. The phenomenon continues to worsen particularly in regions of the globe where economies are modernizing. In the United States, the number of obese people has escalated from 25% at the end of the 70s to 33% at the beginning of the 90s.

Obesity considerably increases the risk of developing cardiovascular or metabolic diseases. It is estimated that if the entire population had an ideal weight, the risk of coronary insufficiency would decrease by 25% and that of cardiac insufficiency and of cerebral vascular accidents by 35%. Coronary insufficiency, atheromatous disease and cardiac insufficiency are at the forefront of the cardiovascular complications induced by obesity. For an excess weight greater than 30% the incidence of coronary diseases is doubled in subjects under 50 years. Studies carried out for other diseases are equally eloquent. For an excess weight of 20%, the risk of high blood pressure is doubled. For an excess weight of 30%, the risk of developing a non-insulin-dependent diabetes is tripled, and that of hyperlipidemias is multiplied six-fold.

The list of diseases having onsets promoted by obesity includes: hyperuricemia (11.4% in obese subjects, against 3.4% in the general population), digestive pathologies, abnormalities in hepatic functions, and even certain cancers.

Whether the physiological changes in obesity are characterized by an increase in the number of adipose cells, or by an increase in the quantity of triglycerides stored in each adipose cell, or by both, this excess weight results mainly from an imbalance between the quantities of calories consumed and the quantity of calories used by the body. Studies on the causes of this imbalance have been in several directions. Some have focused on studying the mechanism of absorption of foods and therefore the molecules that control food intake and the feeling of satiety. Other studies have characterized the pathways through which the body uses its calories.

The proposed treatments for obesity are of five types. (1) Food restriction is the most frequently used. The obese individuals are advised to change their dietary habits so as to consume fewer calories. Although this type of treatment is effective in the short-term, the recidivation rate is very high. (2) Increased calorie use through physical exercise is also proposed. This treatment is ineffective when applied alone, but it improves weight-loss in subjects on a low-calorie diet. (3) Gastrointestinal surgery, which reduces the absorption of the calories ingested, is effective, but has been virtually abandoned because of the side effects it causes. (4) The medicinal approach uses either the anorexigenic action of molecules involved at the level of the central nervous system, or the effect of molecules that increase energy use by increasing the production of heat. The prototypes of this type of molecule are the thyroid hormones that uncouple oxidative phosphorylations of the mitochondrial respiratory chain. The side effects and the toxicity of this type of treatment make their use dangerous. (5) An approach that aims to reduce the absorption of dietary lipids by sequestering them in the lumen of the digestive tube is also in place. However, it induces physiological imbalances which are difficult to tolerate: deficiency in the absorption of fat-soluble vitamins, flatulence and steatorrhoea. Whatever the envisaged therapeutic approach, the treatments of obesity are all characterized by an extremely high recidivation rate.

The molecular mechanisms responsible for obesity in man are complex and involve genetic and environmental factors. Because of the low efficiency of the current treatments, it is urgent to define the genetic mechanisms which determine obesity, so as to be able to develop better targeted medicaments.

More than 20 genes have been studied as possible candidates, either because they have been implicated in diseases of which obesity is one of the clinical manifestations, or because they are homologues of genes involved in obesity in animal models. Situated in the 7q31 chromosomal region, the OB gene is one of the most widely studied. Its product, leptin, is involved in the mechanisms of satiety. Leptin is a plasma protein of 16 kDa produced by adipocytes under the action of various stimuli. Obese mice of the ob/ob type exhibit a deficiency in the leptin gene; this protein is undetectable in the plasma of these animals. The administration of leptin obtained by genetic engineering to ob/ob mice corrects their relative hyperphagia and allows normalization of their weight. This anorexigenic effect of leptin calls into play a receptor the central nervous system: the ob receptor that belongs to the family of class 1 cytokine receptors. The ob receptor is deficient in obese mice of the db/db strain. The administration of leptin to these mice has no effect on their food intake and does not allow substantial reduction in their weight. The mechanisms by which the ob receptors transmit the signal for satiety are not precisely known. It is possible that neuropeptide Y is involved in this signalling pathway. It is important to specify at this stage that the ob receptors are not the only regulators of appetite. The Melanocortin 4 receptor is also involved since mice made deficient in this receptor are obese (Gura, (1997)).

The discovery of leptin, and the characterization of the leptin receptor at the level of the central nervous system, opened a new route for the search for medicaments against obesity. This model, however, rapidly proved disappointing. With only one exception (Montague et al., (1997)), the genes encoding leptin or its ob receptor, have proved to be normal in obese human subjects. Furthermore and paradoxically, the plasma concentrations of leptin, the satiety hormone, are abnormally high in most obese human subjects.

Clearly there remains a need for novel medicaments that are useful for reducing body weight in humans. Such pharmaceutical compositions advantageously would help to control obesity and thereby alleviate many of the cardiovascular consequences associated with this condition.

The discovery of new genes which are associated to obesity would also allow the design of novel diagnostic and therapeutic tools acting on the lipid metabolism, useful for diagnosing and treating obesity disorders.

SUMMARY OF THE INVENTION

The invention is directed, inter alia, to biallelic markers that are located within the LSR genomic sequence. These biallelic markers represent useful tools to identify statistically significant associations between specific alleles of the LSR gene, and obesity, or a disorder related to obesity. Association studies have already shown that a coding mutation in LSR exon 6 influences both fasting and postprandial plasma triglyceride levels in obese adolescent girls. An intronic SNP, located near the splice site determining the LSR subunit, has been associated with insulin and glucose levels. Hence, the biallelic markers of the LSR gene can lead to the identification of new targets for medicaments acting against obesity or obesity-related disorders. Furthermore, they can be used to diagnose a susceptibility to obesity or to identify the cause of obesity for an individual.

The invention also concerns the genomic sequence and the cDNA sequence encoding subunits of LSR, and comprising a biallelic marker of the present invention, as well as vectors, host cells and transgenic animals comprising said polynucleotides. The invention further concerns modified LSR proteins comprising at least one amino acid change resulting from the biallelic markers of the present invention as well as antibodies which are specific to these modified LSR proteins.

In a first aspect, the invention features, an isolated, purified, or recombinant polynucleotide comprising a contiguous span of at least 12 nucleotides of any one of SEQ ID Nos: 1 to 13, 15, 17, or the complements thereof, wherein said contiguous span comprises an LSR-related biallelic marker. In a preferred embodiment, said LSR-related biallelic marker is selected from the group consisting of A'1 to A'20, and A1 to A32. In a preferred embodiment, said LSR-related biallelic marker is selected from the group consisting of A2, A15, A16, A17, A21, A23, A24, A26, and A31. Preferably, said LSR-related biallelic marker is selected from the group consisting of A15, A17, and A21.

Alternatively, the invention features an isolated, purified, or recombinant polynucleotide comprising a contiguous span of 8 to 50 nucleotides of any one of SEQ ID Nos: 1 to 13, 15, 17, or the complements thereof, wherein said contiguous span comprises an LSR-related biallelic marker. In a preferred embodiment said LSR-related biallelic marker is selected from the group consisting of A'1 to A'20, and A1 to A32. In a preferred embodiment said LSR-related biallelic marker is selected from the group consisting of A2, A15, A16, A17, A21, A23, A24, A26, and A31. Preferably, said LSR-related biallelic marker is selected from the group consisting of A15, A17, and A21.

Alternatively, the invention features any of the above polynucleotides, wherein said contiguous span is 18 to 35 nucleotides in length and said biallelic marker is within 4 nucleotides of the center of said polynucleotide. In a preferred embodiment, said polynucleotide consists of said contiguous span and said contiguous span is 25 nucleotides in length and said biallelic marker is at the center of said polynucleotide.

Alternatively, the invention features any of the above polynucleotides, wherein the 3' end of said contiguous span is present at the 3' end of said polynucleotide. In a preferred embodiment, the 3' end of said contiguous span is located at the 3' end of said polynucleotide and said biallelic marker is present at the 3' end of said polynucleotide.

Alternatively, the invention features an isolated, purified or recombinant polynucleotide consisting essentially of a contiguous span of 8 to 50 nucleotides of any one of SEQ ID Nos: 1 to 13, 15, 17, or the complements thereof, wherein the 3' end of said contiguous span is located at the 3' end of said polynucleotide, and wherein the 3' end of said polynucleotide is located within 20 nucleotides upstream of an LSR-related biallelic marker in said sequence. In a preferred embodiment, the 3' end of said polynucleotide is located 1 nucleotide upstream of said LSR-related biallelic marker in said sequence. Preferably, said polynucleotide consists essentially of a sequence selected from the following sequences: D1 to D32 and E1 to E31.

Alternatively, the invention features an isolated, purified, or recombinant polynucleotide consisting essentially of a sequence selected from the following sequences: B1 to B53, and C1 to C52.

Alternatively, the invention features an isolated, purified, or recombinant polynucleotide which encodes a polypeptide comprising a contiguous span of at least 6 amino acids of any one of SEQ ID Nos: 14, 16, and 18, wherein said contiguous span includes any one of the following: a serine residue at position 363 of SEQ ID NO: 14; an asparagine residue at position 363 of SEQ ID NO: 14; a proline residue at position 420 of SEQ ID NO: 14; an arginine residue at position 420 of SEQ ID NO: 14; an arginine residue at position 519 of SEQ ID NO: 14; a one amino acid deletion at position 519 of SEQ ID NO: 14; a serine residue at position 344 of SEQ ID NO: 16; an asparagine residue at position 344 of SEQ ID NO: 16; a proline residue at position 401 of SEQ ID NO: 16; an arginine residue at position 401 of SEQ ID NO: 16; an arginine residue at position 500 of SEQ ID NO: 16; a one amino acid deletion at position 500 of SEQ ID NO: 16; a serine residue at position 295 of SEQ ID NO: 18; an asparagine residue at position 295 of SEQ ID NO: 18; a proline residue at position 352 of SEQ ID NO: 18; an arginine residue at position 352 of SEQ ID NO: 15 an arginine residue at position 451 of SEQ ID NO: 18; and a one amino acid deletion at position 451 of SEQ ID NO: 18.

Alternatively, the invention features a polynucleotide for use in a hybridization assay for determining the identity of the nucleotide at an LSR-related biallelic marker in any one of SEQ ID Nos: 1 to 13, 15, 17 or the complements thereof.

Alternatively, the invention features a polynucleotide for use in a sequencing assay for determining the identity of the nucleotide at an LSR-related biallelic marker in any one of SEQ ID Nos: 1 to 13, 15, 17 or the complements thereof.

Alternatively, the invention features a polynucleotide for use in a allele-specific amplification assay for determining the identity of the nucleotide at an LSR-related biallelic marker in any one of SEQ ID Nos: 1 to 13, 15, 17 or the complements thereof.

Alternatively, the invention features a polynucleotide for use in amplifying a segment of nucleotides comprising an LSR-related biallelic marker in any one of SEQ ID Nos: 1 to 13, 15, 17 or the complements thereof.

Alternatively, the invention features any of the above-described polynucleotides attached to a solid support.

Alternatively, the invention features an array of polynucleotides comprising at least one polynucleotide attached to a solid support. In preferred embodiments the array is addressable.

Alternatively, the invention features any of the above-described polynucleotides further comprising a label.

In a second embodiment, the invention features a recombinant vector comprising any of, or any combination of, the above-described polynucleotides.

In a third embodiment, the invention features a host cell comprising a recombinant vector described above.

In a fourth embodiment, the invention features a non-human host animal or mammal comprising a recombinant vector described above.

In a fifth embodiment, the invention features a method of genotyping comprising determining the identity of a nucleotide at an LSR-related biallelic marker of any one of SEQ ID Nos: 1 to 13, 15, 17 or the complements thereof in a biological sample. In a preferred embodiment, said biological sample is derived from a single subject. In a preferred embodiment, the identity of the nucleotides at said biallelic marker is determined for both copies of said biallelic marker present in said single subject's genome. In a preferred embodiment, said biological sample is derived from multiple subjects. In a preferred embodiment, the method further comprises amplifying a portion of said sequence comprising the biallelic marker prior to said determining. In a preferred embodiment, said amplifying is performed by PCR. In a preferred embodiment, said determining is performed by a hybridization assay. In a preferred embodiment, said determining is performed by a sequencing assay. In a preferred embodiment, said determining is performed by a microsequencing assay. In a preferred embodiment, said determining is performed by an allele-specific amplification assay.

In a sixth aspect, the invention features a method of estimating the frequency of an allele in a population comprising determining the proportional representation of a nucleotide at an LSR-related biallelic marker in any one of SEQ ID Nos: 1 to 13, 15, 17 or the complements thereof in a pooled biological sample derived from said population.

In a seventh aspect, the invention features a method of detecting an association between a genotype and a phenotype, comprising: a) genotyping at least one LSR-related biallelic marker in a trait positive population according to the method described above; b) genotyping said LSR-related biallelic marker in a control population according to the method described above; and c) determining whether a statistically significant association exists between said genotype and said phenotype.

In an eighth aspect, the invention features a method of estimating the frequency of a haplotype for a set of biallelic markers in a population, comprising: a) genotyping at least one LSR-related biallelic marker according to a method described above for each individual in said population; b) genotyping a second biallelic marker by determining the identity of the nucleotides at said second biallelic marker for both copies of said second biallelic marker present in the genome of each individual in said population; and c) applying a haplotype determination method to the identities of the nucleotides determined in steps a) and b) to obtain an estimate of said frequency. In preferred embodiments, said haplotype determination method is selected from the group consisting of asymmetric PCR amplification, double PCR amplification of specific alleles, the Clark algorithm, or an expectation-maximization algorithm. In a preferred embodiment, wherein said second biallelic marker is an LSR-related biallelic marker in any one of SEQ ID Nos: 1 to 13, 15, 17 or the complements thereof.

In a ninth aspect, the invention features a method of detecting an association between a haplotype and a phenotype, comprising: a) estimating the frequency of at least one haplotype in a trait-positive population according to the method described above: b) estimating the frequency of said haplotype in a control population according to the method described above; and c) determining whether a statistically significant association exists between said haplotype and said phenotype. In a preferred embodiment said control population is a trait negative-population. In a preferred embodiment, said case control population is a random population. In a preferred embodiment, each of said genotyping of a) and b) is performed on a single pooled biological sample derived from each of said populations. In a preferred embodiment said genotyping of a) and b) is performed separately on biological samples derived from each individual in said populations. In a preferred embodiment said phenotype is a disease involving obesity or disorder related to obesity. Preferably said disorder related to obesity is selected from the group consisting of atherosclerosis, insulin resistance, hypertension, hyperlipidemia, hypertriglyceridemia, cardiovascular disease, microangiopathic in obese individuals with Type II diabetes, ocular lesions associated with microangiopathy in obese individuals with Type II diabetes, renal lesions associated with microangiopathy in obese individuals with Type II diabetes, and Syndrome X. In a preferred embodiment of any of the above methods said LSR-related biallelic marker is selected from the group consisting of A'1 to A'20, and A1 to A32. Preferably said LSR-related biallelic marker is selected from the group consisting of A2, A15, A16, A17, A21, A23, A24, A26, and A31. More preferably said LSR-related biallelic marker is selected from the group consisting of A15, A17, and A21.

In a tenth aspect, the invention features an isolated, purified, or recombinant polypeptide comprising a contiguous span of at least 6 amino acids of any one of SEQ ID Nos: 14, 16, and 18, wherein said contiguous span includes any one of the following: a serine residue at position 363 of SEQ ID NO: 14; an asparagine residue at position 363 of SEQ ID NO: 14; a proline residue at position 420 of SEQ ID NO: 14; an arginine residue at position 420 of SEQ ID NO: 14; an arginine residue at position 519 of SEQ ID NO: 14; a one amino acid deletion at position 519 of SEQ ID NO: 14; a serine residue at position 344 of SEQ ID NO: 16; an asparagine residue at position 344 of SEQ ID NO: 16; a proline residue at position 401 of SEQ ID NO: 16; an arginine residue at position 401 of SEQ ID NO: 16; an arginine residue at position 500 of SEQ ID NO: 16; a one amino acid deletion at position 500 of SEQ ID NO: 16; a serine residue at position 295 of 2' SEQ ID NO: 18; and asparagine residue at position 295 of SEQ ID NO: 18; a proline residue at position 352 of SEQ ID NO: 18; an arginine residue at position 352 of SEQ ID NO: 18; an arginine residue at position 451 of SEQ ID NO: 18; and a one amino acid deletion at position 451 of SEQ ID NO: 18.

In an eleventh aspect the invention features an isolated or purified antibody composition that selectively binds to an epitope-containing fragment of the above-described polypeptide, wherein said epitope comprises one of the following: a serine residue at position 363 of SEQ ID NO: 14; an asparagine residue at position 363 of SEQ ID NO: 14; a proline residue at position 420 of SEQ ID NO: 14; an arginine residue at position 420 of SEQ ID NO: 14; an arginine residue at position 519 of SEQ ID NO: 14; a one amino acid deletion at position 519 of SEQ ID NO: 14; a serine residue at position 344 of SEQ ID NO: 16; an asparagine residue at position 344 of SEQ ID NO: 16; a proline residue at position 401 of SEQ ID NO: 16; an arginine residue at position 401 of SEQ ID NO: 16; an arginine residue at position 500 of SEQ ID NO: 16; a one amino acid deletion at position 500 of SEQ ID NO: 16; a serine residue at position 295 of SEQ ID NO: 18; an asparagine residue at position 295 of SEQ ID NO: 18; a proline residue at position 352 of SEQ ID NO: 18; an arginine residue at position 352 of SEQ ID NO: 18; an arginine residue at position 451 of SEQ ID NO: 18; and a one amino acid deletion at position 451 of SEQ ID NO: 18.

In an eleventh aspect, the invention features a use of the previously described genotyping methods to determine whether an individual is at risk of developing a detectable trait or whether a detectable trait that an individual suffers from is statistically associated with one or more LSR biallelic markers.

In a twelfth aspect, the invention features a method for determining whether an individual is at risk of developing a detectable trait or whether a detectable trait that an individual suffers from is statistically associated with one or more LSR biallelic markers, comprising obtaining a nucleic acid sample from said individual and determining the identity of the polymorphic base of said one or more LSR biallelic markers in said nucleic acid sample.

In a thirteenth aspect, the invention features a method of using a drug, comprising obtaining a nucleic acid sample from an individual determining the identity of the polymorphic base of one or more LSR biallelic markers in said nucleic acid sample and administering said drug to said individual if said polymorphic base of said one or more LSR biallelic markers is associated with a positive response to treatment with said drug or is not associated with a negative response to treatment with said drug.

In a fourteenth aspect, the invention features a method of screening an individual for inclusion in a clinical trial of a drug comprising: obtaining a nucleic acid sample from said individual; determining the identity of the polymorphic base of one or more LSR balletic markers in said nucleic acid sample; and including said individual in said clinical trial if said polymorphic base of said one or more LSR biallelic markers is associated with a positive response to treatment with said drug or is not associated with a negative response, treatment with said drug.

In a fifteenth aspect, the invention features a method of identifying one or more LSR biallelic markers associated with a detectable trait comprising: determining the frequencies of each allele of said one or more LSR biallelic markers in individuals with said detectable trait and in individuals without said detectable trait; and identifying one or more alleles of said one or more LSR biallelic markers that are statistically associated with said detectable trait.

BRIEF DESCRIPTION OF THE FIGURES

FIG. 2A is a schematic diagram of chromosome 19 and of the genomic organization of LSR. The exon and intron lengths in bp are indicated as normal and italicized numbers, respectively. The location of USF2 further downstream is also shown. FIG. 2B shows SNPs on 19q13.1 and identifies those used for the association studies (highlighted in boxes).

FIG. 4D is a plot of postprandial lipemic response taking into account the genotype of both LSR SNPs #1 and #3. Statistical comparison of the differences between means was first performed by analysis of variance. Significant results were then tested by unpaired t-test. The significance of the t-test is indicated on the graph. The data are presented using the pooled samples of hetero- and homozygous subjects in order to obtain a sufficient number of subjects in each group.

BRIEF DESCRIPTION OF THE SEQUENCES PROVIDED IN THE SEQUENCE LISTING

Figure 1:
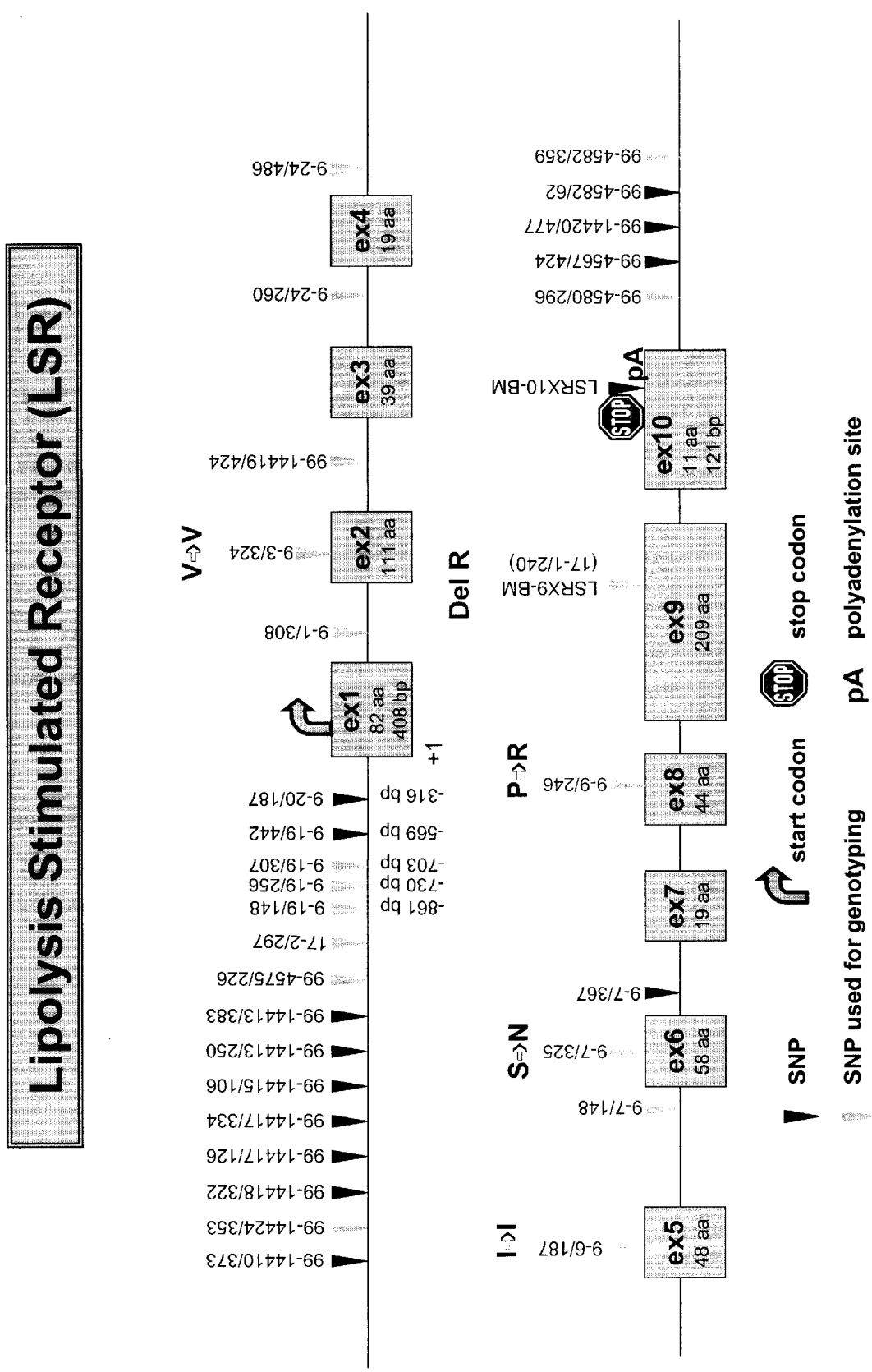
FIG. 1 is a map of the genomic sequence of the human LSR with validated biallelic markers of the present invention indicated.

SEQ ID NO: 1 contains a genomic sequence of human LSR comprising the 5' regulatory region (upstream untranscribed region), the exons and introns, and the 3' regulatory region (downstream untranscribed region).

SEQ ID NO: 2 contains a partial DNA sequence of human LSR.

SEQ ID NO: 3 contains a partial DNA sequence of human LSR.

SEQ ID NO: 4 contains a partial DNA sequence of human LSR.

SEQ ID NO: 5 contains a partial DNA sequence of human LSR.

SEQ ID NO: 6 contains a partial DNA sequence of human LSR.

SEQ ID NO: 7 contains a partial DNA sequence of human LSR.

SEQ ID NO: 8 contains a partial DNA sequence of human LSR.

SEQ ID NO: 9 contains a partial DNA sequence of human LSR.

SEQ ID NO: 10 contains a partial DNA sequence of human LSR.

SEQ ID NO: 11 contains a partial DNA sequence of human LSR.

SEQ ID NO: 12 contains a partial DNA sequence of human LSR.

SEQ ID NO: 13 contains a cDNA sequence of human LSR with amino acid translation.

SEQ ID NO: 14 contains a protein sequence of human LSR.

SEQ ID NO: 15 contains a variant cDNA sequence of human LSR with amino acid translation.

SEQ ID NO: 16 contains a variant protein sequence of human LSR.

SEQ ID NO: 17 contains a variant cDNA sequence of human LSR with amino acid translation.

SEQ ID NO: 18 contains a variant protein sequence of human LSR.

SEQ ID NO: 19 contains a DNA sequencing oligonucleotide for PrimerPU.

SEQ ID NO: 20 contains a DNA sequencing oligonucleotide for PrimerRP.

In accordance with the regulations relating to Sequence Listings, the following codes have been used in the Sequence Listing to indicate the locations of biallelic markers within the sequences and to identify each of the alleles present at the polymorphic base. The code "r" in the sequences indicates that one allele of the polymorphic base is a guanine, while the other allele is an adenine. The code "y" in the sequences indicates that one allele of the polymorphic base is a thymine, while the other allele is a cytosine. The code "m" in the sequences indicates that one allele of the polymorphic base is an adenine, while the other allele is an cytosine. The code "k" in the sequences indicates that one allele of the polymorphic base is a guanine, while the other allele is a thymine. The code "s" in the sequences indicates that one allele of the polymorphic base is a guanine, while the other allele is a cytosine. The code "w" in the sequences indicates that one allele of the polymorphic base is an adenine, while the other allele is a thymine. The nucleotide code of the original allele for each biallelic marker is the following:

| Biallelic Marker | Original allele |
| --- | --- |
| 99-14410/373 | C |
| 99-14424/353 | A |

-continued

| Biallelic Marker | Original allele |
| --- | --- |
| 99-14418/322 | A |
| 99-14417/126 | C |
| 99-14417/334 | C |
| 99-14415/106 | C |
| 99-14413/250 | A |
| 99-14413/383 | G |
| 99-4575/226 | T |
| 9-19/148 | C |
| 9-19/307 | A |
| 9-19/442 | C |
| 9-20/187 | A |
| 9-1/308 | C |
| 9-3/324 | C |
| 99-14419/424 | C |
| 9-24/260 | A |
| 9-24/486 | G |
| 9-6/187 | C |
| 9-7/148 | G |
| 9-7/325 | G |
| 9-7/367 | A |
| 9-9/246 | C |
| LSRX9-BM (17-1/240) | AGG |
| LSRX10-BM | T |
| 99-4580/296 | A |
| 99-4567/424 | C |
| 99-14420/477 | G |
| 99-4582/62 | A |
| 99-4582/359 | G |
| 17-2/297 | C |
| 9-19/256 | A |

In some instances, the polymorphic bases of the biallelic markers alter the identity of amino acids in the encoded polypeptide. This is indicated in the accompanying Sequence Listing by use of the feature VARIANT, placement of a Xaa at the position of the polymorphic amino acid, and definition of Xaa as the two alternative amino acids. For example, if one allele of a biallelic marker is the codon CAC, which encodes histidine, while the other allele of the biallelic marker is CAA which encodes glutamine, the Sequence Listing for the encoded polypeptide will contain an Xaa at the location of the polymorphic amino acid. In this instance, Xaa would be defined as being histidine or glutamine.

In other instances, Xaa may indicate an amino acid whose identity is unknown because of nucleotide sequence ambiguity. In this instance, the feature UNSURE is used, Xaa is placed at the position of the unknown amino acid, and Xaa is defined as being any of the 20 amino acids or a limited number of amino acids suggested by the genetic code.

DETAILED DESCRIPTION OF THE INVENTION

The LSR (Lipolysis Stimulated Receptor), which is described in PCT publication No WO IB98/01257 (hereby incorporated herein in its entirety including any figures, tables, or drawings), its expressed on the surface of hepatic cells and binds lipoproteins in the presence of free fatty acids. The LSR gene encodes by alternative splicing three types of subunits, namely LSR α, LSR α' and LSR β. LSR can also bind a cytokine, preferably leptin. As LSR is involved in the partitioning of dietary lipids between the liver and peripheral tissues, including adipose tissue, this gene is a good candidate for an association with obesity and disorders related to obesity. Consequently, polymorphic markers of the LSR gene can be useful to establish the involvement of LSR in obesity, and to design diagnostics and treatments of obesity. In fact, association studies have already linked a LSR biallelic marker with both fasting and postprandial plasma triglyceride levels in obese adolescent girls, and a different LSR biallelic marker with insulin and glucose levels in obese adolescent girls. A combination of LSR biallelic markers have been shown to be associated with obesity in adolescent girls.

I. Biallelic Markers and Polynucleotides
Comprising Biallelic Markers

Advantages of the Biallelic Markers of the Present Invention

The LSR biallelic markers of the present invention offer a number of important advantages over other genetic markers such as RFLP (Restriction fragment length polymorphism) and VNTR (Variable Number of Tandem Repeats) markers.

The first generation of markers was RFLPs, which are variations that modify the length of a restriction fragment. But methods used to identify and to type RFLPs are relatively wasteful of materials, effort, and time. The second Generation of genetic markers was VNTRs, which can be categorized as either minisatellites or microsatellites. Minisatellites are tandemly repeated DNA sequences present in units of 5–50 repeats which are distributed along regions of the human chromosomes ranging from 0.1 to 20 kilobases in length. Since they present many possible alleles, their informative content is very high. Minisatellites are scored by performing Southern blots to identify the number of tandem repeats present in a nucleic acid sample from the individual being tested. However, there are only $10^4$ potential VNTRs that can be typed by Southern blotting. Moreover, both RFLP and VNTR markers are costly and time-consuming to develop and assay in large numbers.

Single nucleotide polymorphism (SNP) or biallelic markers can be used in the same manner as RFLPs and VNTRs but offer several advantages. SNP are densely spaced in the human genome and represent the most frequent type of variation. An estimated number of more than $10^7$ sites are scattered along the $3 \times 10^9$ base pairs of the human genome. Therefore, SNP occur at a greater frequency and with greater uniformity than RFLP or VNTR markers which means that there is a greater probability that such a marker will be found in close proximity to a genetic locus of interest. SNP are less variable than VNTR markers but are mutationally more stable.

Also, the different forms of a characterized SNP, such as the biallelic markers of the present invention, are often easier to distinguish and can therefore be typed easily on a routine basis. Biallelic markers have single nucleotide based alleles and they have only two common alleles, which allows highly parallel detection and automated scoring. The biallelic markers of the present invention offer the possibility of rapid, high throughput genotyping of a large number of individuals.

Biallelic markers are densely spaced in the genome, sufficiently informative and can be assayed in large numbers. The combined effects of these advantages make biallelic markers extremely valuable in genetic studies. Biallelic markers can be used in linkage studies in families, in allele sharing methods, in linkage disequilibrium studies in populations, in association studies of case-control populations. An important aspect of the present invention is that biallelic markers allow association studies to be performed to identify genes involved in complex traits. Association studies examine the frequency of marker alleles in unrelated case- and control-populations and are generally employed in the detection of polygenic or sporadic traits. Association studies may be conducted within the general population and are not limited to studies performed on related individuals in affected families (linkage studies). Biallelic markers in different genes can be screened in parallel for direct association with disease or response to a treatment. This multiple gene approach is a powerful tool for a variety of human genetic studies as it provides the necessary statistical power to examine the synergistic effect of multiple genetic factors on a particular phenotype, drug response, sporadic trait, or disease state with a complex genetic etiology.

Candidate Gene of the Present Invention

Different approaches can be employed to perform association studies: genome-wide association studies, candidate region association studies and candidate gene association studies. Genome-wide association studies rely on the screening of genetic markers evenly spaced and covering the entire genome. Candidate region association studies rely on the screening of genetic markers evenly spaced covering a region identified as linked to the trait of interest. The candidate gene approach is based on the study of genetic markers specifically derived from genes potentially involved in a biological pathway related to the trait of interest In the present invention, LSR is involved in the partitioning of dietary lipids between the liver and peripheral tissues, including adipose tissue. Consequently, a polymorphism of the LSR gene can be associated to obesity or to a disorder related to obesity. That LSR is a good candidate gene for obesity has been confirmed by association studies showing a link between a LSR biallelic marker and both fasting and postprandial plasma triglyceride levels, and an association between another marker and insulin and glucose levels, in obese adolescent girls. LSR markers have also been shown to be directly associated with obesity.

The candidate gene analysis clearly provides a short-cut approach to the identification of genes and gene polymorphisms related to a particular trait when some information concerning the biology of the trait is available. However, it should be noted that all of the biallelic markers disclosed in the instant application can be employed as part of genome-wide association studies or as part of candidate region association studies and such uses are specifically contemplated in the present invention and claims.

Definitions

Before describing the invention in greater detail, the following definitions are set forth to illustrate and define the meaning and scope of the terms used to describe the invention herein.

As used interchangeably herein, the term "oligonucleotides", and "polynucleotides" include RNA, DNA, or RNA/DNA hybrid sequences of more than one nucleotide in either single chain or duplex form. The term "nucleotide" is used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" that comprise at least one modification: (a) an alternative linking group, (b) an analogous form of purine, (c) an analogous form of pyrimidine, or (d) an analogous sugar. For examples of analogous linking groups, purines, pyrimidines, and sugars, see for example PCT publication No. WO 95/04064. The polynucleotide sequences of the invention may be prepared by any known method, including synthetic, recombinant, ex vivo generation, or a combination thereof, as well as utilizing any purification methods known in the art.

The term "purified" is used herein to describe a polynucleotide or polynucleotide vector of the invention that has been separated from other compounds including, but not limited to, other nucleic acids, carbohydrates lipids and proteins (such as the enzymes used in the synthesis of the polynucleotide), or the separation of covalently closed polynucleotides from linear polynucleotides. A polynucleotide is substantially pure when at least about 50, preferably 60 to 75% of a sample exhibits a single polynucleotide sequence and conformation (linear versus covalently closed). A substantially pure polynucleotide typically comprises about 50, preferably 60 to 90% weight/weight of a nucleic acid sample, more usually about 95%, and preferably is over about 99% pure. Polynucleotide purity or homogeneity may be indicated by a number of means well known in the art such as agarose or polyacrylamide gel electrophoresis of a sample, followed by visualizing a single polynucleotide band upon staining the gel. For certain purposes, higher resolution can be provided by using HPLC or other means well known in the art.

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

Throughout the present specification, the expression "nucleotide sequence" may be employed to designate indifferently a polynucleotide or a nucleic acid. More precisely, the expression "nucleotide sequence" encompasses the nucleic material itself and is thus not restricted to the sequence information (i.e. the succession of letters chosen among the four bases) that biochemically characterizes a specific DNA or RNA molecule.

The term "primer" denotes a specific oligonucleotide sequence that is complementary to a target nucleotide sequence and used to hybridize to the target nucleotide sequence. A primer serves as an initiation point for nucleotide polymerization catalyzed by DNA polymerase, RNA polymerase, or reverse transcriptase.

The term "probe" denotes a defined nucleic acid segment (or nucleotide analog segment, e.g., PNA as defined hereinbelow) that can be used to identify a specific polynucleotide sequence present in samples, said nucleic acid segment comprising a nucleotide sequence complementary of the specific polynucleotide sequence to be identified.

The terms "polynucleotide construct" and "recombinant polynucleotide" are used interchangeably herein to refer to linear or circular polynucleotides that have been artificially designed and which comprise at least two nucleotide sequences that are not found as contiguous nucleotide sequences in their initial natural environment.

The term "polypeptide" refers to a polymer of amino acids without regard to the length of the polymer. Thus, peptides, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide. Also included within the definition are polypeptides that contain one or more analogs of an amino acid (including, for example, non-naturally occurring amino acids, amino acids that only occur naturally in an unrelated biological system, modified amino acids from mammalian systems etc.), polypeptides with substituted linkages, as well as other modifications known in the art, both naturally occurring and non-naturally- occurring.

The term "purified" is also used herein to describe a polypeptide of the invention that has been separated from other compounds including, but not limited to, nucleic acids, lipids, carbohydrates and other proteins. A polypeptide is substantially pure when at least about 50%, preferably 60 to 75% of a sample exhibits a single polypeptide sequence. A substantially pure 30, polypeptide typically comprises about 50%, preferably 60 to 90% weight/weight of a protein sample, more usually about 95%, and preferably is over about 99% pure. Polypeptide purity or homogeneity is indicated by a number of means well known in the art, such as agarose or polyacrylamide gel electrophoresis of a sample, followed by visualizing a single polypeptide band upon staining the gel. For certain purposes, higher resolution can be provided by HPLC or other means well known in the art.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide (supra).

As used herein, the term "non-human animal" refers to any non-human vertebrate, birds and more usually mammals, preferably primates, farm animals such as swine goats, sheep, donkeys, and horses, rabbits or rodents, more preferably rats or mice. As used herein, the term "animal" is used to refer to any vertebrate, preferable a mammal. Both the terms "animal" and "mammal" expressly embrace human subjects unless preceded with the term "non-human".

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, and that allows an immunological reaction with the antigen. Antibodies include recombinant proteins comprising the binding domains, as wells as fragments, including Fab, Fab', F(ab)$_2$, and F(ab')$_2$ fragments.

As used herein, an "antigenic determinant" is the portion of an antigen molecule, in this case an LSR polypeptide, which determines the specificity of the antigen-antibody reaction. An "epitope" refers to an antigenic determinant of a polypeptide. An epitope can comprise as few as 3 amino acids in a spatial conformation that is unique to the epitope. Generally, an epitope consists of at least 6 such amino acids, and more usually at least 8–10 such amino acids. Methods for determining the amino acids which make up an epitope include x-ray crystallography, 2-dimensional nuclear magnetic resonance, and epitope mapping, e.g. the Pepscan method described by H. Mario Geysen et al. 1984, Proc. Natl. Acad. Sci. U.S.A. 81:3998–4002; PCT Publication No. WO 84/03564; and PCT Publication No. WO 84/03506, the disclosures of which are incorporated by reference herein in their entirety.

The term "disease involving the partitioning of dietary lipids between the liver and peripheral tissues" particularly refers to obesity and obesity-related disorders, such as obesity-related atherosclerosis, obesity-related insulin resistance, obesity-related hypertension, obesity-related hyperlipidemia, obesity-related hypertriglyceridemia, obesity-related myocardial infarction/cardiovascular disease (primarily for women), microangiopathic lesions resulting from obesity-related Type II diabetes, ocular lesions caused by microangiopathy in obese individuals with Type II diabetes, renal lesions caused by microangiopathy in obese individuals with Type II diabetes, and Syndrome X.

The term "agent acting on the partitioning of dietary lipids between the liver and peripheral tissues" refers to a drug or a compound modulating the activity of the LSR or the partitioning of dietary lipids to the liver, reducing food intake in obese individuals, reducing the levels of free fatty acids in obese individuals, decreasing the body weight of obese individuals, or treating an obesity related condition selected from the group consisting of obesity-related atherosclerosis, obesity-related insulin resistance, obesity-related hypertension, obesity-related hyperlipidemia, obesity-related hypertriglyceridemia, obesity-related myocardial infarction/cardiovascular disease (primarily for women), microangiopathic lesions resulting from obesity-related Type II diabetes, ocular lesions caused by microangiopathy in obese individuals with Type II diabetes, renal lesions caused by microangiopathy in obese individuals with Type II diabetes and Syndrome X.

The term "response to an agent acting on the partitioning of dietary lipids between the liver and peripheral tissues" refers to drug efficacy, including but not limited to, the ability to metabolize a compound, the ability to convert a pro-drug to an active drug, and the pharmacokinetics (absorption, distribution, elimination) and the pharmacodynamics (receptor-related) of a drug in an individual.

The term "side effects to an agent acting on the partitioning of dietary lipids between the liver and peripheral tissues" refers to adverse effects of therapy resulting from extensions of the principal pharmacological action of the drug or to idiosyncratic adverse reactions resulting from an interaction of the drug with unique host factors. "Side effects to an agent acting on the partitioning of dietary lipids between the liver and peripheral tissues" include, but are not limited to, adverse reactions such as dermatologic, hematologic or hepatologic toxicities, and further include gastric and intestinal ulceration, disturbance in platelet function, renal injury, nephritis, vasomotor rhinitis with profuse watery secretions, angioneurotic edema, generalized urticaria, and bronchial asthma leading to laryngeal edema and bronchoconstriction, hypotension, and shock.

The terms "trait" and "phenotype" are used interchangeably herein and refer to any visible, detectable or otherwise measurable property of an organism such as symptoms of, or susceptibility to a disease for example. Typically the terms "trait" or "phenotype" are used herein to refer to symptoms of, or susceptibility to, a disease involving the partitioning of dietary lipids between the liver and peripheral tissues, more particularly obesity and disorders related to obesity; or to refer to an individual's response to an agent acting on the partitioning of dietary lipids between the liver and peripheral tissues; or to refer to symptoms of, or susceptibility to, side effects of an agent acting on the partitioning of dietary, lipids between the liver and peripheral tissues.

The term "allele" is used herein to refer to variants of a nucleotide sequence. A biallelic polymorphism has two forms. Typically the first identified allele is designated as the original allele whereas other alleles are designated as alternative alleles. Diploid organisms may be homozygous or heterozygous for an allelic form.

The term "heterozygosity rate" is used herein to refer to the incidence of individuals in a population, which are heterozygous at a particular allele. In a biallelic system the heterozygosity rate is on average equal to $2P_a(1-P_a)$, where $P_a$ is the frequency, of the least common allele. In order to be useful in genetic studies a genetic marker should have an adequate level of heterozygosity to allow a reasonable probability that a randomly selected person will be heterozygous.

The term "genotype" as used herein refers to the identity of the alleles present in an individual or a sample. In the context of the present invention, a genotype preferably refers to the description of the biallelic marker alleles present in an individual or a sample. The term "genotyping" a sample or an individual for a biallelic marker consists of determining the specific allele or the specific nucleotide carried by an individual at a biallelic marker.

The term "mutation" as used herein refers to a difference in DNA sequence between or among different genomes or individuals which has a frequency below 1%.

The term "haplotype" refers to a combination of alleles present in an individual or a sample. In the context of the present invention, a haplotype preferably refers to a combination of biallelic marker alleles found in a given individual and which may be associated with a phenotype.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is a single base pair change. Typically a single nucleotide polymorphism is the replacement of one nucleotide by another nucleotide at the polymorphic site. Deletion of a single nucleotide or insertion of a single nucleotide, also lives rise to single nucleotide polymorphisms. In the context of the present invention "single nucleotide polymorphism" preferably refers to a single nucleotide substitution. Typically, between different genomes or between different individuals, the polymorphic site may be occupied by two different nucleotides. However, the nucleotide modification can also involve an insertion or a deletion of at least one nucleotide, preferably between 1 and 8 nucleotides. This type of polymorphism is also contemplated in the present invention.

The terms "biallelic polymorphism" and "biallelic marker" are used interchangeably herein to refer to a polymorphism having two alleles at a fairly high frequency in the population. A "biallelic marker allele" refers to the nucleotide variants present at a biallelic marker site. Typically the frequency of the less common allele of the biallelic markers of the present invention has been validated to be greater than 1%, preferably the frequency is greater than 10%, more preferably the frequency is at least 20% (i.e. heterozygosity rate of at least 0.32), even more preferably the frequency is at least 30% (i.e. heterozygosity rate of at least 0.42). A biallelic marker, wherein the frequency of the less common allele is 30% or more, is termed a "high quality biallelic marker."

The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center" and so on. For polymorphisms which involve the substitution, insertion or deletion of 1 or more nucleotides, the polymorphism, allele or biallelic marker is "at the center" of a polynucleotide if the difference between the distance from the substituted, inserted, or deleted polynucleotides of the polymorphism and the 3' end of the polynucleotide, and the distance from the substituted, inserted, or deleted polynucleotides of the polymorphism and the 5' end of the polynucleotide is zero or one nucleotide. If this difference is 0 to 3, then the polymorphism is considered to be "within 1 nucleotide of the center." If the difference is 0 to 5, the polymorphism is considered to be "within 2 nucleotides of the center." If the difference is 0 to 7, the polymorphism is considered to be "within 3 nucleotides of the center," and so on.

The term "upstream" is used herein to refer to a location that is toward the 5' end of the polynucleotide from a specific reference point.

As used herein the term "LSR-related biallelic marker" relates to a set of biallelic markers in linkage disequilibrium with the LSR gene. The term LSR-related biallelic marker includes both genic and non-genic markers. Unless otherwise specified, the term "LSR-related biallelic marker" embraces both validated and non-validated biallelic markers. Any of the genotyping, association, and determination of frequency of allele or haplotype methods of the invention can be specified as being performed using only validated markers (e.g. A1 to A32) or as using both validated and non-validated markers (e.g. A1 to A32 and A'1 to A'20). More preferably, the biallelic marker is selected from the group consisting of A2, A15, A16, A17, A21, A24, A26, and A31, and the complements thereof. Alternatively, the biallelic marker is selected from the group consisting of A21, A23, and A24 and the complements thereof. In an especially preferred embodiment, the biallelic marker is A26. An alternative embodiment is any combination of A15, A17, and A21. Again, any of the genotyping, association, and determination of frequency of allele or haplotype methods of the invention can be specified as being performed using only preferred, more preferred, or the especially preferred marker, or any combination of markers.

The terms "base paired" and "Watson & Crick base paired" are used interchangeably herein to refer to nucleotides which can be hydrogen bonded to one another by virtue of their sequences in a manner like that found in double-helical DNA with thymine or uracil residues linked to adenine residues by two hydrogen bonds and cytosine and guanine residues linked by three hydrogen bonds (See Stryer, L., *Biochemistry*, 4$^{th}$ edition, 1995).

The terms "complementary" or "complement thereof" are used herein to refer to the polynucleotide sequence that is capable of forming Watson & Crick base pairing with another specified polynucleotide sequence throughout the entirety of the indicated region. For the purpose of the present invention, a first polynucleotide is deemed to be complementary to a second polynucleotide when each base in the first polynucleotide is paired with its complementary base in the second polynucleotide. Complementary bases are, generally. A and T (or A and U), or C and G. "Complement" is used herein as a synonym for "complementary poly nucleotide", "complementary nucleic acid" and "complementary nucleotide sequence". These terms are applied to pairs of polynucleotides based solely upon their sequences and not any particular set of conditions under which the two polynucleotides would actually bind.

The term "non-genic" is used herein to describe LSR-related biallelic markers, as well as polynucleotides and primers that occur outside the nucleotide positions shown in the human LSR genomic sequences of SEQ ID Nos: 1 to 13, 15, 17, or the complements thereof. The term "genic is used herein to describe LSR-related biallelic markers as well as polynucleotides and primers which do occur in the nucleotide positions shown in the human LSR genomic sequences of SEQ ID Nos: 1 to 13, 15, 17, or the complements thereof.

Stringent Hybridization Conditions

By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll. 0.02% BSA, and 500 μg/ml denatured salmon sperm DNA. Filters are hybridized for 48 h at 65° C. the preferred hybridization temperature, in prehybridization mixture containing 100 μg/ml denatured salmon sperm DNA and 5–20× $10^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989; and Ausubel et al., 1989, are incorporated herein in their entirety.

These hybridization conditions are suitable for a nucleic acid molecule of about 20 nucleotides in length. There is no need to say that the hybridization conditions described above are to be adapted according to the length of the desired nucleic acid, following techniques well known to the one skilled in the art. The suitable hybridization conditions may for example be adapted according to the teachings disclosed in the book of Hames and Higgins (1985) or in Sambrook et al. (1989).

Variants and Fragments

Polynucleotides

The invention also relates to variants and fragments of the polynucleotides described herein. particularly of a LSR gene containing one or more biallelic markers according to the invention.

Variants of polynucleotides, as the term is used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Variants of polynucleotides according to the invention include, without being limited to, nucleotide sequences which are at least 95% identical to a polynucleotide selected from the group consisting of the nucleotide sequences of SEQ ID Nos: 1, 13, 15, and 17 or to any polynucleotide fragment of at least 8 consecutive nucleotides of a polynucleotide selected from the group consuming of the nucleotide sequences of SEQ ID Nos 1, 13, 15, and 17, and preferably at least 99% identical, more particularly at least 99.5% identical, and most preferably at least 99.8% identical to a polynucleotide selected from the group consisting of the nucleotide sequences of SEQ ID Nos 1, 13, 15, and 17 or to any polynucleotide fragment of at least 8 consecutive nucleotides of a polynucleotide selected from the group consisting of the nucleotide sequences of SEQ ID Nos 1, 13, 15, and 17.

Nucleotide changes present in a variant polynucleotide may be silent, which means that they do not alter the amino acids encoded by the polynucleotide.

However, nucleotide changes may also result in amino acid substitutions, additions, deletions, fusions and truncations in the polypeptide encoded by the reference sequence. The substitutions, deletions or additions may involve one or more nucleotides. The variants may be altered in coding or non-coding regions or both. Alterations in the coding regions may produce conservative or non-conservative amino acid substitutions, deletions or additions.

In the context of the present invention, particularly preferred embodiments are those in which the polynucleotides encode polypeptides which retain substantially the same biological function or activity as a mature LSR protein.

A polynucleotide fragment is a polynucleotide having a sequence that entirely is the same as part but not all of a given nucleotide sequence, preferably the nucleotide sequence of a LSR gene, and variants thereof. The fragment can be a portion of an exon or of an intron of a LSR gene. It can also be a portion of the regulatory sequences, preferably of the promoter sequence, of the LSR gene. Preferably, such fragments comprise at least one of the biallelic markers A1 to A32, and A'1 to A'20 and the complements thereof or a biallelic marker in linkage disequilibrium with one or more of the biallelic markers A1 to A32, and A'1 to A'20.

Such fragments may be "free-standing", i.e. not part of or fused to other polynucleotides, or they may be comprised within a single larger polynucleotide of which they form a part or region. However, several fragments may be comprised within a single larger polynucleotide.

Optionally, such fragments may consist of, or consist essentially of a contiguous span which ranges in length from 8, 10, 12, 15, 18 or 20 to 25, 35, 40, 50, 70, 80, 100, 250, 500 or 1000 nucleotides, or be specified as being 12, 15, 18, 20, 25, 35, 40, 50, 100, 250, 500 or 1000 nucleotides in length. Preferred are those fragments containing at least one of the biallelic markers A1 to A32, and A'1 to A'20 of the LSR gene and the complements thereof which are described herein.

A preferred embodiment of the invention includes isolated, purified, or recombinant polynucleotides consisting of, consisting essentially of, or comprising a contiguous span of at least 12, 15, 18, 20, 25, 30, 35, 40, 50, 60, 70, 80, 90, 100, 150, 200, 500, or 1000 nucleotides of any one of SEQ ID Nos: 1 to 13, 15, 17, or the complements thereof, wherein said contiguous span comprises an LSR-related biallelic marker; optionally, wherein said LSR-related biallelic marker is selected from the group consisting of A'1 to A'20, and A1 to A32; optionally, wherein said LSR-related biallelic marker is selected from the group consisting of A2, A15, A16, A17, A21, A24, A26, and A31; optionally, wherein the 3' end of said contiguous span is present at the 3' end of said polynucleotide; optionally, wherein said polynucleotide is attached to a solid support; and optionally wherein said polynucleotide further comprises a label.

An additional preferred embodiment of the invention includes isolated, purified, or recombinant polynucleotides consisting of, consisting essentially of, or comprising, a contiguous span of 8 to 50 nucleotides of any one of SEQ ID Nos: 1 to 13, 15, 17, or the complements thereof, wherein said continuous span comprises an LSR-related biallelic marker; optionally, wherein said LSR-related biallelic marker is selected from the croup consisting of A'1 to A'20, and A1 to A32; optionally, wherein said LSR-related biallelic marker is selected from the group consisting of A2, A15, A16, A17, A21, A24, A26, and A31; optionally, wherein said contiguous span is 18 to 35 nucleotides in length and said biallelic marker is within 4 nucleotides of the center of said polynucleotide; optionally, wherein said polynucleotide consists of said contiguous span and said contiguous span is 25 nucleotides in length and said biallelic marker is at the center of said polynucleotide; optionally, wherein the 3' end of said contiguous span is present at the 3' end of said polynucleotide; optionally, wherein the 3' end of said contiguous span is located at the 3' end of said polynucleotide and said biallelic marker is present at the 3' end of said polynucleotide; optionally, wherein said polynucleotide is attached to a solid support; and optionally wherein said polynucleotide further comprises a label.

A further preferred embodiment of the invention includes isolated, purified, or recombinant polynucleotides consisting of, consisting essentially of, or comprising a contiguous span of 8 to 50 nucleotides of any one of SEQ ID Nos: 1 to 13, 15, 17, or the complements thereof, wherein the 3' end of said contiguous span is located at the 3' end of said polynucleotide, and wherein the 3' end of said polynucleotide is located within 20 nucleotides upstream of an LSR-related biallelic marker in said sequence; optionally, wherein the 3' end of said polynucleotide is located 1 nucleotide upstream of said LSR-related biallelic marker in said sequence; optionally, wherein said polynucleotide consists essentially of a sequence selected from the following sequences: D1 to D32 and E1 to E31; optionally, wherein said polynucleotide is attached to a solid support; and optionally wherein said polynucleotide further comprises a label.

Another preferred embodiment of the invention includes isolated, purified or recombinant polynucleotides consisting of, or consisting essentially of a sequence selected from the following sequences: B1 to B53, and C1 to C52; optionally, wherein said polynucleotide is attached to a solid support; and optionally, wherein said polynucleotide further comprises a label.

An additional set of preferred nucleic acids of the invention includes isolated, purified, or recombinant polynucleotides which encodes a polypeptide comprising a contiguous span of at least 6 amino acids, preferably at least 8 or 10 amino acids, more preferably at least 12, 15, 20, 25, 30, 40, 50, or 100 amino acids of any one of SEQ ID Nos: 14, 16, and 18, wherein said contiguous span includes any one of the following: a serine residue at position 363 of SEQ ID NO: 14; an asparagine residue at position 363 of SEQ ID NO: 14; a proline residue at position 420 of SEQ ID NO: 14; an arginine residue at position 420 of SEQ ID NO: 14; an arginine residue at position 519 of SEQ ID NO: 14; a one amino acid deletion at position 519 of SEQ ID NO: 14; a serine residue at position 344 of SEQ ID NO: 16; an asparagine residue at position 344 of SEQ ID NO: 16; a proline residue at position 401 of SEQ ID NO: 16; an arginine residue at position 401 of SEQ ID NO: 16; an arginine residue at position 500 of SEQ ID NO: 16; a one amino acid deletion at position 500 of SEQ ID NO: 16; a serine residue at position 295 of SEQ ID NO: 18; an asparagine residue at position 295 of SEQ ID NO: 18; a proline residue at position 352 of SEQ ID NO: 18; an arginine residue at position 352 of SEQ ID NO: 18; an arginine residue at position 451 of SEQ ID NO: 18; and a one amino acid deletion at position 451 of SEQ ID NO: 18; optionally, wherein said polynucleotide is attached to a solid support; and optionally wherein said polynucleotide further comprises a label.

A further set of preferred nucleic acids of the invention includes polynucleotide for use in a hybridization assay, a sequencing assay, an allele-specific amplification assay, for determining the identity of the nucleotide at an LSR-related biallelic marker in any one of SEQ ID Nos: 1 to 13, 15, 17 or the complements thereof, or for use in amplifying a segment of nucleotides comprising an LSR-related biallelic marker in any one of SEQ ID Nos: 1 to 13, 15, 17 or the complements thereof; optionally, wherein said polynucleotide is attached to a solid support; and optionally wherein said polynucleotide further comprises a label.

Polypeptides

The invention also relates to variants, fragments, analogs and derivatives of the polypeptides described herein, including modified LSR proteins.

The variant may be 1) one in which one or more of the amino acid residues are substituted with a conserved or non-concerned amino acid residue and such substituted amino acid residue may or may not be one encoded by the genetic code, or 2) one in which one or more of the amino acid residues includes a substituent group, or 3) one in which a modified LSR is fused with another compound, such as a compound to increase the half-life of the polypeptide (for example, polyethylene glycol), or 4) one in which the additional amino acids are fused to a modified LSR, such as a leader or secretory sequence or a sequence which is employed for purification of the modified LSR or a preprotein sequence. Such variants are deemed to be within the scope of those skilled in the art.

A polypeptide fragment is a polypeptide having a sequence that entirely is the same as part but not all of a given polypeptide sequence, preferably a polypeptide encoded by a LSR gene and variants thereof.

Such fragments may be "free-standing", i.e. not part of or fused to other polypeptides, or they may be comprised within a single larger polypeptide of which they form a part or region. However, several fragments may be comprised within a single larger polypeptide.

As representative examples of polypeptide fragments of the invention, there may be mentioned those which have from about 5, 6, 7, 8, 9 or 10 to 15, 10 to 20, 15 to 40, or 30 to 55 amino acids long. Preferred are those fragments containing at least one amino acid substitution or deletion in a LSR protein.

The present invention is particularly focused on a set of variant LSR polypeptides and the fragments thereof. These variants include a serine residue at position 363 of SEQ ID NO: 14; an asparagine residue at position 363 of SEQ ID NO: 14; a proline residue at position 420 of SEQ ID NO: 14; an arginine residue at position 420 of SEQ ID NO: 14; an arginine residue at position 519 of SEQ ID NO: 14; a one amino acid deletion at position 519 of SEQ ID NO: 14; a serine residue at position 344 of SEQ ID NO: 16; an asparagine residue at position 344 of SEQ ID NO: 16; a proline residue at position 401 of SEQ ID NO: 16; an arginine residue at position 401 of SEQ ID NO: 16; an arginine residue at position 500 of SEQ ID NO: 16; a one amino acid deletion at position 500 of SEQ ID NO: 16; a serine residue at position 295 of SEQ ID NO: 18; an asparagine residue at position 295 of SEQ ID NO: 18; a proline residue at position 352 of SEQ ID NO: 18; an arginine residue at position 352 of SEQ ID NO: 18; an arginine residue at position 451 of SEQ ID NO: 18; and a one amino acid deletion at position 451 of SEQ ID NO: 18. These variant proteins and the fragments thereof which contain the specified alleles at amino acid positions 363, 420, and 519 of SEQ ID NO: 14 are collectively referred to herein as the 363-Ser, 363-Asp, 420-Pro, 420-Arg, 519-Arg, and 519-Del variants of SEQ ID NO: 14; respectively. These variant proteins and the fragments thereof which contain the specified alleles at amino acid positions 344, 401, and 500 of SEQ ID NO: 16 are collectively referred to herein as the 344-Ser, 344-Asp, 401-Pro, 401-Arg, 500-Arg, and 500-Del variants of SEQ ID NO: 16; respectively. These variant proteins and the fragments thereof which contain the specified alleles at amino acid positions 295, 352, and 451 of SEQ ID NO: 18 are collectively referred to herein as the 295-Ser, 295-Asp, 352-Pro, 352-Arg, 451-Arg, and 451-Del variants of SEQ ID NO: 18; respectively.

A preferred set of polypeptides of the invention include isolated, purified, or recombinant polypeptides comprising a contiguous span of at least 6 amino acids of any one of SEQ ID Nos: 14, 16, and 18, wherein said contiguous span includes any one of the following: a serine residue at position 363 of SEQ ID NO: 14; an asparagine residue at position 363 of SEQ ID NO: 14; a proline residue at position 420 of SEQ ID NO: 14; an arginine residue at position 420 of SEQ ID NO: 14; an arginine residue at position 519 of SEQ ID NO: 14; a one amino acid deletion at position 519 of SEQ ID NO: 14; a serine residue at position 344 of SEQ ID NO: 16; an asparagine residue at position 344 of SEQ ID NO: 16; a proline residue at position 401 of SEQ ID NO: 16; an arginine residue at position 401 of SEQ ID NO: 16; an arginine residue at position 500 of SEQ ID NO: 16; a one amino acid deletion at position 500 of SEQ ID NO: 16; a serine residue at position 295 of SEQ ID NO: 18; an asparagine residue at position 295 of SEQ ID NO: 18; a proline residue at position 352 of SEQ ID NO: 18; an arginine residue at position 352 of SEQ ID NO: 18; an arginine residue at position 451 of SEQ ID NO: 18; and a one amino acid deletion at position 451 of SEQ ID NO: 18.

Polynucleotides and Polypeptides of the Present Invention

The invention concerns biallelic markers, wherein said biallelic markers are from the sequence of the LSR gene. In one embodiment, the invention concerns a biallelic marker selected from the group of biallelic markers A1 to A32, and the complements thereof. A preferred biallelic marker of the invention consists of a biallelic marker selected from the group consisting of A2, A16, A17, A24, A26 and A31, and the complements thereof. A highly preferred biallelic marker consists of the biallelic marker A26 and the complement thereof. In another especially preferred embodiment, the biallelic marker is selected from the group consisting of A15, A17, and A21 or any combination thereof, and the complements thereof. In a further embodiment, the invention concerns a biallelic marker selected from the group of biallelic markers A'1 to A'20, and the complements thereof.

The group of biallelic markers A'1 to A'20 refers to the biallelic markers A'1, A'2, A'3, A'4, A'5, A'6, A'7, A'8, A'9, A'10, A'11, A'12, A'13, A'14, A'15, A'16, A'17, A'18, A'19, and A'20, The group of biallelic markers A1 to A32 refers to the biallelic markers A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, and A32.

The biallelic markers of the present invention are disclosed in Tables A and B. Their location on the LSR gene is indicated in Tables A and B and also as a polymorphism in the features of SEQ ID Nos 1–13, 15, and 17. The pairs of primers allowing the amplification of a nucleic acid containing the polymorphic base of one LSR biallelic marker are listed in Table 1 of Example 2.

TABLE A

| Biallelic Marker | Marker Name | Localization In LSR Gene | Polymorphism | Frequency Of Allele 2 | AA Change | Marker Position |
|---|---|---|---|---|---|---|
| 99-14410/373 | A1 | 5' regulatory region | Allele 1: C<br>Allele 2: T | | | 373 of SEQ ID No 2 |
| 99-144241353 | A2 | 5' regulatory region | Allele 1: A<br>Allele 2: G | | | 353 of SEQ ID No 3 |
| 99-14418/322 | A3 | 5' regulatory region | Allele 1: A<br>Allele 2: G | | | 322 of SEQ ID No 4 |
| 99-14417/126 | A4 | 5' regulatory region | Allele 1: C<br>Allele 2: T | | | 126 of SEQ ID No 5 |
| 99-14417/334 | A5 | 5' regulatory region | Allele 1: C<br>Allele 2: T | | | 334 of SEQ ID No 5 |
| 99-14415/106 | A6 | 5' regulatory region | Allele 1: C<br>Allele 2: T | | | 106 of SEQ ID No 6 |
| 99-14413/250 | A7 | 5' regulatory region | Allele 1: A<br>Allele 2: C | | | 250 of SEQ ID No 7 |
| 99-14413/383 | A8 | 5' regulatory region | Allele 1: G<br>Allele 2: T | | | 383 of SEQ ID No 7 |
| 99-4575/226 | A9 | 5' regulatory region | Allele 1: T<br>Allele 2: C | 25% | | 226 of SEQ ID No 8 |
| 9-19/148 | A10 | 5' regulatory region | Allele 1: C<br>Allele 2: T | 15% | | 1243 of SEQ ID No 1 |
| 9-19/307 | A11 | 5' regulatory region | Allele 1: A<br>Allele 2: T | 12% | | 1401 of SEQ ID No 1 |
| 9-19/442 | A12 | 5' regulatory region | Allele 1: C<br>Allele 2: Del C | | | 1535 of SEQ ID No 1 |
| 9-20/187 | A13 | 5' regulatory region | Allele 1: A<br>Allele 2: C | | | 1788 of SEQ ID No 1 |
| 9-1/308 | A14 | Intron 1 | Allele 1: C<br>Allele 2: G | 24% | | 2391 of SEQ ID No 1 |
| 9-3/324 | A15 | Exon 2 | Allele 1: C<br>Allele 2: T | 29% | | 3778 of SEQ ID No 1; 595 of SEQ ID Nos 13, 15, and 17 |
| 99-14419/424 | A16 | Intron2 | Allele 1: C<br>Allele 2: A | 22% | | 4498 of SEQ ID No 1 |
| 9-24/260 | A17 | Intron 3 | Allele 1: A<br>Allele 2: G | 35% | | 15007 of SEQ ID No 1 |
| 9-24/486 | A18 | Intron 4 | Allele 1: G<br>Allele 2: A | 15% | | 15233 of SEQ ID No 1 |
| 9-6/187 | A19 | Exon5 | Allele 1: C<br>Allele 2: T | 1% | | 15826 of SEQ ID No 1; 940 of SEQ ID No 13; 883 of SEQ ID No 15 |
| 9-7/148 | A20 | Intron 5 | Allele 1: G<br>Allele 2: A | 35% | | 19567 of SEQ ID No 1 |
| 9-7/325 | A21 | Exon 6 | Allele 1: G<br>Allele 2: A | 14% | S→N | 19744 of SEQ ID No 1; 1191 of SEQ ID No 13; 1134 of SEQ ID No 15; 987 of SEQ ID No 17 |
| 9-7/367 | A22 | Intron 6 | Allele 1: A<br>Allele 2: C | | | 19786 of SEQ ID No 1 |
| 9-9/246 | A23 | Exon 8 | Allele 1: C<br>Allele 2: G | 0.5% | P→R | 20158 of SEQ ID No 1; 1362 of SEQ ID No 13; |

TABLE A-continued

| Biallelic Marker | Marker Name | Localization In LSR Gene | Polymorphism | Frequency Of Allele 2 | AA Change | Marker Position |
|---|---|---|---|---|---|---|
| LSRX9-BM (17-1/240) | A24 | Exon 9 | Allele 1: AGG Allele 2: Del AGG | Del 26% | Del R | 1305 of SEQ ID No 15; 1158 of SEQ ID No 17 20595 of SEQ ID No 1; 1658 of SEQ ID No 13; 1601 of SEQ ID No 15; 1454 of SEQ ID No 17 |
| LSRX10-BM | A25 | Exon 10 | Allele 1: T Allele 2: G | | | 21108 of SEQ ID No 1; 2079 of SEQ ID No. 13; 2022 of SEQ ID No 15; 1875 of SEQ ID No 17 |
| 99-4580/296 | A26 | 3' regulatory region | Allele 1: A Allele 2: G | 24% | | 296 of SEQ ID No 9 |
| 99-4567/424 | A27 | 3' regulatory region | Allele 1: C Allele 2: T | | | 424 of SEQ ID No 10 |
| 99-14420/477 | A28 | 3' regulatory region | Allele 1: G Allele 2: T | | | 477 of SEQ ID No 11 |
| 99-4582/62 | A29 | 3' regulatory region | Allele 1: A Allele 2: G | | | 62 of SEQ ID No 12 |
| 99-4582/359 | A30 | 3' regulatory region | Allele 1: G Allele 2: T | 24% | | 359 of SEQ ID No 12 |
| 17-2/297 | A31 | 5' regulatory region | Allele 1: C Allele 2: G | 48% | | 818 of SEQ ID No 1 |
| 9-19/256 | A32 | 5' regulatory regio | Allele 1: A Allele 2: G | | | 1374 of SEQ ID No 1 |

The term "Del" refers to a deletion of at least one nucleotide. The term "Ins" refers to a insertion at least one nucleotide.

The 5' regulatory region of the LSR gene refers to a nucleotide region that is located upstream of the transcribed region of LSR. The 3' regulatory region of the LSR gene refers to a nucleotide region that is located downstream of the transcribed region of LSR. The intron 1 refers to nucleotide region located between exon 1 and exon 2 of LSR. The intron 2 refers to nucleotide region located between exon 2 and exon 3 of LSR, and so on.

Five biallelic markers have been identified in the exons of the LSR gene, namely A15, A19, A21, A23, A24, and A25. Three of them change an amino acid of a LSR protein sequence. The amino acid changes consist of asparagine instead of serine (position 295 in SEQ ID No 18; position 344 in SEQ ID No 16; position 363 in SEQ ID No 14), arginine instead of proline (position 352 in SEQ ID No 18; position 401 in SEQ ID No 16; position 420 in SEQ ID No 14), and a deletion of arginine (position 451 in SEQ ID No 18; position 500 in SEQ ID No 16; position 519 in SEQ ID No 14). The biallelic markers responsible for these mutations are respectively A21, A23 and A24. The amino acid sequences of the LSR proteins in SEQ ID Nos 18, 16 and 14 are annotated to provide the exact location of these mutations.

Without wishing to be bound by any particular theory, the inventors believe that the arginine deletion may modulate the activity of the LSR receptor. Indeed, the LSR subunits α and β present a motif RSRS that is likely to be involved in the interaction with the gC1qR protein. The arginine deletion could change the interaction between the LSR receptor and the gC1qR protein. As gC1qR protein seems to be able to modulate the activity of the LSR receptor, the deletion could have consequences on LSR activity. Further, the change associated with A21 has been shown to be linked to increased triglyceride levels.

Therefore, the invention relates to purified or isolated modified LSR proteins and to fragments and variants thereof. The term "modified LSR protein" is intended to designate a LSR protein which, when compared to the native LSR proteins of SEQ ID Nos 18, 16, and 14, bears at least one amino acid substitution, deletion or addition. More particularly, preferred modified LSR proteins include those bearing at least one of the amino acid substitutions or deletion set forth:

in SEQ ID No 18 and selected from the group consisting of a substitution from S to N at position 295, a substitution from P to R at position 352, and a deletion of R at position 451;

in SEQ ID No 16 and selected in the group consisting of a substitution from S to N at position 344, a substitution from P to R at position 401, and a deletion of R at position 500; or in SEQ ID No 14 and selected in the group consisting of a substitution from S to N at position 361, a substitution from P to R at position 420, and a deletion of R at position 519.

Modified proteins bearing two or more of such substitutions and deletion also fall within the scope of the present invention. Other preferred embodiments include fragments of the modified LSR proteins of the invention, and particularly those fragments bearing at least one of the substitutions and deletion described above. Particularly preferred fragments are those possessing antigenic properties and comprising at least one of the substitutions and deletion described above.

The invention further encompasses a purified or isolated nucleic acid encoding a LSR protein or a fragment thereof, preferably a modified LSR protein bearing at least one substitution or deletion set forth in SEQ ID Nos 14, 16 and 18 or variants or fragments thereof.

Furthermore, the invention relates to a purified or isolated cDNA sequence encoding a modified LSR protein, a variant or a fragment thereof, said cDNA sequence comprising at least one biallelic marker of the present invention. More preferably, the biallelic markers are selected from the group consisting of A21, A23, and A24 and the cDNA sequence encoding a LSR protein is selected from the group consisting of SEQ ID Nos 13, 15, and 17, a fragment or a variant thereof or a complementary sequence thereto. More particularly, the invention concerns a purified or isolated nucleic acid having a nucleotide sequence selected from the group consisting of SEQ ID Nos 13, 15, and 17, a fragment or a variant thereof or a complementary sequence thereto and comprising at least one of the biallelic markers set forth:

in SEQ ID No 13, namely A21 corresponding to a substitution from G to A in position 1191, A23 corresponding to a substitution from C to G in position 1362, and A24 corresponding to a deletion of AGG in position 1658; or in SEQ ID No 15, namely A21 corresponding to a substitution from G to A in position 1134, A23 corresponding to a substitution from C to G in position 1305, and A24 corresponding to a deletion of AGG in position 1601; or in SEQ ID No 13, namely A21 corresponding to a substitution from G to A in position 987, A23 corresponding to a substitution from C to G in position 1158, and A24 corresponding to a deletion of AGG in position 1454.

The table B comprises potential biallelic markers that can be validated as described in "Validation of the biallelic markers of the present invention".

TABLE B

| Marker Name | Localization in LSR gene | Polymorphism | Marker position in SEQ ID No 1 |
|---|---|---|---|
| A'1 | 5' regulatory region | Allele 1: C<br>Allele 2: T | 606 |
| A'2 | Intron 2 | Allele 1:<br>Allele 2: Ins G | 5141 |
| A'3 | Intron 2 | Allele 1:<br>Allele 2: Ins C | 7428 |
| A'4 | Intron 2 | Allele 1: C<br>Allele 2: G | 8394 |
| A'5 | Intron 2 | Allele 1: T<br>Allele 2: C | 8704 |
| A'6 | Intron 2 | Allele 1: G<br>Allele 2: A | 9028 |
| A'7 | Intron 2 | Allele 1: GAATGAAA<br>Allele 2: Del GAATGAAA | 9950 |
| A'8 | Intron 2 | Allele 1: T<br>Allele 2: C | 9977 |
| A'9 | Intron 2 | Allele 1: A<br>Allele 2: G | 10021 |
| A'10 | Intron 2 | Allele 1: C<br>Allele 2: T | 11878 |
| A'11 | Intron 5 | Allele 1: G<br>Allele 2: Del G | 19040 |
| A'12 | 3' regulatory region | Allele 1: A<br>Allele 2: G | 21363 |

TABLE B-continued

| Marker Name | Localization in LSR gene | Polymorphism | Marker position in SEQ ID No 1 |
|---|---|---|---|
| A'13 | 3' regulatory region | Allele 1: C<br>Allele 2: T | 21449 |
| A'14 | 3' regulatory region | Allele 1: G<br>Allele 2: C | 21451 |
| A'15 | 3' regulatory region | Allele 1: A<br>Allele 2: G | 21454 |
| A'16 | 3' regulatory region | Allele 1: G<br>Allele 2: A | 21455 |
| A'17 | 3' regulatory region | Allele 1: T<br>Allele 2: A | 21569 |
| A'18 | 3' regulatory region | Allele 1: C<br>Allele 2: Del C | 21683 |
| A'19 | 3' regulatory region | Allele 1:<br>Allele 2: Ins T | 21694 |
| A'20 | 3' regulatory region | Allele 1: G<br>Allele 2: Del G | 21728 |

The invention concerns a purified or isolated nucleic acid encoding a LSR protein, a variant or a fragment thereof, wherein said nucleic acid comprises an allele of at least one biallelic marker selected from the group consisting of A1 to A32 or A'1 to A'20 and the complements thereof. In a preferred embodiment, said nucleic acid encoding a LSR protein, a variant or a fragment thereof is selected from the group consisting of the nucleotide sequences of SEQ ID Nos 1, 13, 15, and 17, a complementary sequence thereto or a variant or a fragment thereof. In a further preferred embodiment, the biallelic marker is selected from the group consisting of A14 to A25 and the complements thereof, the more preferred biallelic markers being A15, A19, A21, A23, and A24, and the complements thereof.

The invention further concerns a purified or isolated regulatory nucleic acid of the LSR gene comprising an allele of at least one biallelic marker selected from the group consisting of A1 to A32 or A'1 to A'20 and the complements thereof, preferably from the group consisting of A1 to A13 and A26 to A32, and the complements thereof.

The invention also concerns the sequences comprising an allele of one of the biallelic markers listed in Table A and being selected from the group consisting of the nucleotide sequences that have a contiguous span of, that consist of, that are comprised in, or that comprise a polynucleotide selected from the group consisting of the nucleic acids of the sequences set forth as SEQ ID Nos 2–12, and 9-19, 9-20, 9-1, 9-3, 99-14419, 9-24, 9-6, 9-7, 9-9, LSRX9, LSRX9-I10, (listed in Table 1) or a complementary sequence thereto. Alternatively, the sequences can comprise an allele of one of the biallelic markers listed in Table A, and can be selected from the group consisting of the nucleotide sequences that have a contiguous span of, that consist of, that are comprised in, or that comprise, a polynucleotide selected from the group consisting of 99-14424, 99-14419, 9-24, 17-1, 99-4580, and 17-2, (listed in Table 1).

The invention also relates to a purified and/or isolated nucleotide sequence comprising a polymorphic base of a biallelic marker located in the sequence of the LSR gene. Preferably, the biallelic marker is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof. The sequence has between 8 and 1000 nucleotides in length, and ranges preferably between 8, 10, 12, 15, 18 or 20 to 25, 35, 40, 50, 60, 70, 80, 100, 250, 500 or 1000 contiguous nucleotides of a nucleotide sequence selected from the group consisting of SEQ ID Nos 1–12, 13, 15, and 17 or a variant thereof or a complementary sequence thereto, or is specified to be 12, 15, 18, 20, 25, 35, 40, 50, 60, 70, 80, 100, 250, 500 or 1000 contiguous nucleotides of a nucleotide sequence selected from the group consisting of SEQ ID Nos 1–12, 13, 15, and 17 or a variant thereof or a complementary sequence thereto. These nucleotide sequences comprise the polymorphic base of either allele 1 or allele 2 of the considered biallelic marker. Optionally, said biallelic marker may be within 6, 5, 4, 3, 2, or 1 nucleotides of the center of said polynucleotide or at the center of said polynucleotide. Optionally, the 3' end of said contiguous span may be present at the 3' end of said polynucleotide. Optionally, the biallelic marker may be present at the 3' end of said polynucleotide. Optionally, the 3' end of said polynucleotide may be located within, or at least 2, 4, 6, 8, 10, 12, 15, 18, 20, 25, 50, 100, 250, 500, or 1000 nucleotides upstream of a biallelic marker of the LSR gene in said sequence. Optionally, the 3' end of said polynucleotide may be located 1 nucleotide upstream of a biallelic marker of the LSR gene in said sequence. Optionally, said polynucleotide may further comprise a label. Optionally, said polynucleotide can be attached to solid support. In a further embodiment, the polynucleotides defined above can be used alone or in any combination.

The present invention encompasses polynucleotides for use as primers and probes in the methods of the invention. These polynucleotides may consist of, consist essentially of, or comprise a contiguous span of nucleotides of a nucleotide sequence selected from the group consisting of SEQ ID Nos 1–12, 13, 15 and 17 or a variant thereof or a complementary sequence thereto. The "contiguous span" may be at least 6, 8, 10, 12, 15, 20, 25, or 30 nucleotides in length. It should be noted that the polynucleotides of the present invention are not limited to having the exact flanking sequences surrounding the polymorphic bases which are enumerated in SEQ ID Nos 1–12, 13, 15, and 17. Rather, it will be appreciated that the flanking sequences surrounding the biallelic markers, or any of the primers or probes of the invention which are more distant from the markers, may be lengthened or shortened to any extent compatible with their intended use and the present invention specifically contemplates such sequences. It will be appreciated that the polynucleotides may be of any length compatible with their intended use. Also, the flanking regions outside of the contiguous span need not be homologous to native flanking sequences that actually occur in human subjects. The addition of any nucleotide sequence that is compatible with the nucleotides intended use is specifically contemplated. The contiguous span may optionally include a LSR biallelic marker in said sequence. Preferably, the biallelic marker is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof. Optionally either the allele 1 or the allele 2 of the biallelic markers disclosed in Tables A and B may be specified as being present at the LSR-related biallelic marker. The invention also relates to polynucleotides that hybridize, under conditions of high stringency, to a polynucleotide of a sequence selected from the group consisting of SEQ ID Nos 1–12, 13, 15, and 17 or a complementary sequence thereto. Preferably such polynucleotides may be at least 6, 8, 10, 12, 15, 20, 25, 30, 35, 40, 50, 60, 70, or 80 nucleotides in length. Preferred polynucleotides comprise a LSR-related biallelic marker. Preferably, the biallelic marker is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof. Optionally either allele 1 or allele 2 of the biallelic markers disclosed in tables A and B may be specified as being present at the LSR-related biallelic marker. Conditions of high and intermediate stringency are described in "Definitions".

The primers of the present invention may be designed from the disclosed sequences for any method known in the art. A preferred set of primers is fashioned such that the 3' end of the contiguous span of identity with a sequence selected from the group consisting of SEQ ID Nos 1–12, 13, 15 and 17 or a variant thereof or a complementary sequence thereto is present at the 3' end of the primer. Such a configuration allows the 3' end of the primer to hybridize to a selected nucleic acid sequence and dramatically increases the efficiency of the primer for amplification or sequencing reactions. Allele specific primers may be designed such that a biallelic marker is at the 3' end of the contiguous span and the contiguous span is present at the 3' end of the primer. Such allele specific primers tend to selectively prime an amplification or sequencing reaction so long as they are used with a nucleic acid sample that contains one of the two alleles present at a biallelic marker. The 3' end of a primer of the invention may be located within, or at least 2, 4, 6, 8, 10, 12, 15, 18, 20, 25, 50, 100, 250, 500, or 1000 nucleotides upstream, of a LSR-related biallelic marker in said sequence or at any other location which is appropriate for their intended use in sequencing, amplification or the location of novel sequences or markers. Preferably the biallelic marker is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof. Preferred amplification primers are disclosed in Table 1 and are selected from the group consisting of B1 to B52 and C1 to C51. Primers with their 3' ends located 1 nucleotide upstream of a LSR-related biallelic marker have a special utility in microsequencing assays. Preferably, the biallelic marker is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof. Preferred microsequencing primers are described in Table 3 and are selected from the group consisting of D1 to D32 and E1 to E31, and more preferably from the group consisting of D2, D9, D10, D11, D15, D17, D19, D23, D29, D32, E1, E6, E8, E13, E17, E19, E20, E23, E25, E26, E29, and E31. Other preferred microsequencing primers are selected from the group consisting of D2, D16, D17, D24, D26, D31, E2, E15, E16, E23, E25 and E30.

The probes of the present invention may be designed from the disclosed sequences for any method known in the art, particularly methods which allow for testing if a particular sequence or marker disclosed herein is present. A preferred set of probes may be designed for use in the hybridization assays of the invention in any manner known in the art such that they selectively bind to one allele of a biallelic marker, but not the other under any particular set of assay conditions. Preferred hybridization probes may consist of, consist essentially of, or comprise a contiguous span of a nucleotide sequence selected from the group consisting of SEQ ID Nos 1–12, 13, 15 and 17 or variants thereof, or complementary sequences thereto, that range in length from 8, 10, 12, 15, 18 or 20 to 25, 35, 40, 50, 60, 70, to 80 nucleotides, or are specified as being 12, 15, 18, 20, 25, 35, 40, or 50 nucleotides in length and include a LSR-related biallelic marker of said sequence. Preferably, the biallelic marker is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof. Optionally either the allele 1 or allele 2 disclosed in Tables A and B may be specified as being present at the biallelic marker site. Optionally, said biallelic marker may be within 6, 5, 4, 3, 2, or 1 nucleotides of the center of the hybridization probe or at the center of said probe. Preferred probes comprise a nucleotide sequence selected from the group consisting of SEQ ID Nos 2–12, and 9-19, 9-20, 9-1, 9-3, 99-14419, 9-24, 9-6, 9-7, 9-9, LSRX9, LSRX9-I10, and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. Alternatively, preferred probes comprise a nucleotide sequence selected from the group consisting of 99-14424, 99-14419, 9-24, 17-1, 99-4580, and 17-2, (listed in Table 1), and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base.

Any of the polynucleotides of the present invention can be labeled, if desired, by incorporating a label detectable by spectroscopic, photochemical, biochemical, immunochemical, or chemical means. For example, useful labels include radioactive substances, fluorescent dyes or biotin. Preferably, polynucleotides are labeled at their 3' or 5' ends. A label can also be used to capture the primer, so as to facilitate the immobilization of either the primer or a primer extension product, such as amplified DNA, on a solid support. A capture label is attached to the primers or probes and can be a specific binding member which forms a binding pair with the solid phase reagent's specific binding member (e.g. biotin and streptavidin). Therefore, depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA Labeling techniques are well known to the skilled technician.

Any of the polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes® and others. The solid support is not critical and can be selected by one skilled in the art. Thus, latex particles, microparticles, magnetic or non-magnetic beads, membranes, plastic tubes, walls of microtiter wells, glass or silicon chips, red blood cells of sheep (or other suitable animals), and duracytes are all suitable examples. Suitable methods for immobilizing nucleic acids on solid phases include ionic, hydrophobic, covalent interactions and the like. A solid support, as used herein, refers to any material that is insoluble, or can be made insoluble by a subsequent reaction. The solid support can be chosen for its intrinsic ability to attract and immobilize the capture reagent. Alternatively, the solid phase can retain an additional receptor that has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, red blood cells of sheep (or other suitable animals), duracytes® and other configurations known to those of ordinary skill in the art. The polynucleotides of the invention can be attached to or immobilized on a solid support individually or in groups of at least 2, 5, 8, 10, 12, 15, 20, or 25 distinct polynucleotides of the inventions to a single solid support. In addition, polynucleotides other than those of the invention may be attached to the same solid support as one or more polynucleotides of the invention.

Any polynucleotide provided herein may be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotide's location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092, the disclosures of which are incorporated by reference herein in their entirety. These arrays may generally be produced using mechanical synthesis methods or light directed synthesis methods, which incorporate a combination of photolithographic methods and solid phase oligonucleotide synthesis (Fodor et al., 1991). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ technologies are provided in U.S. Pat. Nos. 5,143,854 and 5,412,087 and in PCT Publications WO 90/15070, WO 92/10092 and WO 95/11995, the disclosures of which are incorporated by reference herein in their entirety, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256, the disclosures of which are incorporated by reference herein in their entirety.

The invention also encompasses the use of any polynucleotide for, or any polynucleotide for use in, determining the identity of one or more nucleotides at a LSR-related biallelic marker. In addition, the polynucleotides of the invention for use in determining the identity of one or more nucleotides at a LSR-related biallelic marker encompass polynucleotides with any further limitation described in this disclosure, or those following, specified alone or in any combination. Preferably, the biallelic marker is selected from the group consisting of A1 to A32 and the complements thereof. More preferably, the biallelic marker is selected from the group consisting of A2, A16, A17, A24, A26, and A31, and the complements thereof. Attentively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof. Optionally, said polynucleotide may comprise a sequence disclosed in the present specification. Optionally, said polynucleotide may consist of, or consist essentially of any polynucleotide described in the present specification. Optionally, said determining may be performed in a hybridization assay, sequencing assay, microsequencing assay, or allele-specific amplification assay. Optionally, said polynucleotide may be attached to a solid support, array, or addressable array. Optionally, said polynucleotide may be labeled.

Additionally, the invention encompasses the use of any polynucleotide for, or any polynucleotide for use in, amplifying a segment of nucleotides comprising a LSR-related biallelic marker. In addition, the polynucleotides of the invention for use in amplifying a segment of nucleotides comprising a LSR-related biallelic marker encompass polynucleotides with any further limitation described in this disclosure, or those following, specified alone or in any combination. Preferably, the biallelic marker is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof. Optionally, said polynucleotide may comprise a sequence disclosed in the present specification. Optionally, said polynucleotide may consist of, or consist essentially of, any polynucleotide described in the present specification. Optionally, said amplifying may be performed by a PCR or LCR. Optionally, said polynucleotide may be attached to a solid support, array, or addressable array. Optionally, said polynucleotide may be labeled.

Thus, the invention also encompasses methods of genotyping a biological sample comprising determining the identity of a nucleotide at a LSR-related biallelic marker. In addition, the genotyping methods of the invention encompass methods with any further limitation described in this disclosure, or those following, specified alone or in any combination. Preferably, the LSR-related biallelic marker is present in one or more of SEQ ID Nos: 1 to 13, 15, and 17, and more preferably is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof. Optionally, said biological sample is derived from a single individual or subject. Optionally, said method is performed in vitro. Optionally, said biallelic marker is determined for both copies of said biallelic marker present in said individual's genome. Optionally, said biological sample is derived from multiple subjects or individuals. Optionally, said method further comprises amplifying a portion of said sequence comprising the biallelic marker prior to said determining step. Optionally, said amplifying is performed by PCR, LCR, or replication of a recombinant vector comprising an origin of replication and said portion in a host cell. Optionally, said determining is performed by a hybridization assay, sequencing assay, microsequencing assay, or allele-specific amplification assay. Optionally, said control population is a trait negative population or a random population. Optionally, said phenotype is a disease involving obesity or disorders related to obesity. Optionally, said disorder related to obesity is selected from the group consisting of atherosclerosis, insulin resistance, hypertension, hyperlipidemia, hypertriglyceridemia, myocardial infarction/cardiovascular disease (primarily for women) microangiopathic in obese individuals with Type II diabetes, ocular lesions associated with microangiopathy in obese individuals with Type II diabetes, renal lesions associated with microangiopathy in obese individuals with Type II diabetes and Syndrome X.

The present invention also encompasses diagnostic kits comprising one or more polynucleotides of the invention with a portion or all of the necessary reagents and instructions for genotyping a test subject by determining the identity of a nucleotide at a biallelic marker of LSR. Preferably, the biallelic marker is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof. The polynucleotides of a kit may optionally be attached to a solid support, or be part of an array or addressable array of polynucleotides. The kit may provide for the determination of the identity of the nucleotide at a marker position by any method known in the art including, but not limited to, a sequencing assay method, a microsequencing assay method, a hybridization assay method, or an allele specific amplification method. Optionally such a kit may include instructions for scoring the results of the determination with respect to the test subjects' risk of contracting a disease involving the partitioning of dietary lipids between the liver and peripheral tissues, more particularly obesity and disorders related to obesity, or likely response to an agent acting, on the partitioning of dietary lipids between the liver and peripheral tissues, or chances of suffering from side effects to an agent acting on the partitioning of dietary lipids between the liver and peripheral tissues.

II. Methods for De Novo Identification of Biallelic Markers

Any of a variety of methods can be used to screen a genomic fragment for SNPs such as differential hybridization with oligonucleotide probes, detection of changes in the mobility measured by gel electrophoresis or direct sequencing of the amplified nucleic acid. A preferred method for identifying biallelic markers involves comparative sequencing of genomic DNA fragments from an appropriate number of unrelated individuals.

In a first embodiment, DNA samples from unrelated individuals are pooled together, following which the genomic DNA of interest is amplified and sequenced. The nucleotide sequences thus obtained are then analyzed to identify significant polymorphisms. One of the major advantages of this method resides in the fact that the poolin of the DNA samples substantially reduces the number of DNA amplification reactions and sequencing reactions, which must be carried out. Moreover, this method is sufficiently sensitive so that a biallelic marker obtained thereby usually demonstrates a sufficient frequency of its less common allele to be useful in conducting association studies.

In a second embodiment, the DNA samples are not pooled and are therefore amplified and sequenced individually. This method is usually preferred when biallelic markers need to be identified in order to perform association studies within candidate genes. Preferable, highly relevant gene regions such as promoter regions or exon regions may be screened for biallelic markers. A biallelic marker obtained using this method may show a lower degree of informativeness for conducting association studies, e.g. if the frequency of its less frequent allele may be less than about 10%. Such a biallelic marker will however be sufficiently informative to conduct association studies and it will further be appreciated that including less informative biallelic markers in the genetic analysis studies of the present invention, may allots in some cases the direct identification of causal mutations, which may, depending on their penetrance, be rare mutations.

The following is a description of the various parameters of a preferred method used by the inventors for the identification of the biallelic markers of the present invention.

Genomic DNA Samples

The genomic DNA samples from which the biallelic markers of the present invention are generated are preferably obtained from unrelated individuals corresponding to a heterogeneous population of known ethnic background. The number of individuals from whom DNA samples are obtained can vary substantially, preferably from about 10 to about 1000, preferably from about 50 to about 200 individuals. It is usually preferred to collect DNA samples from at least about 100 individuals in order to have sufficient polymorphic diversity in a given population to identify as many markers as possible and to generate statistically significant results.

As for the source of the genomic DNA to be subjected to analysis, any test sample can be foreseen without any particular limitation. These test samples include biological samples, which can be tested by the methods of the present invention described herein, and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens including tumor and non-tumor tissue and lymph node tissues; bone marrow aspirates and fixed cell specimens. The preferred source of genomic DNA used in the present invention is from peripheral venous blood of each donor. Techniques to prepare genomic DNA from biological samples are well known to the skilled technician.

Details of a preferred embodiment are provided in Example 1. The person skilled in the art can choose to amplify pooled or unpooled DNA samples.

DNA Amplification

The identification of biallelic markers in a sample of genomic DNA may be facilitated through the use of DNA amplification methods. DNA samples can be pooled or unpooled for the amplification step. DNA amplification techniques are well know to those skilled in the art. Various methods to amplify DNA fragments carrying biallelic markers are further described hereinbefore in "Amplification of DNA fragments comprising biallelic markers". The PCR technology is the preferred amplification technique used to identify new biallelic markers. A typical example of a PCR reaction suitable for the purposes of the present invention is provided in Example 2.

In a first embodiment of the present invention, biallelic markers are identified using genomic sequence information generated by the inventors. Sequenced genomic DNA fragments are used to design primers for the amplification of 500 bp fragments. These 500 bp fragments are amplified from genomic DNA and are scanned for biallelic markers. Primers may be designed using the OSP software (Hillier and Green, 1991). All primers may contain, upstream of the specific target bases, a common oligonucleotide tail that serves as a sequencing primer. Those skilled in the art are familiar with primer extensions, which can be used for these purposes.

Preferred primers, useful for the amplification of genomic sequence encoding the candidate gene, focus on promoter, exons and splice sites of the gene. A biallelic marker presents a higher probability to be an eventual causal mutation if it is located in these functional regions of the gene.

Preferred primers of the invention include the nucleotide sequences disclosed in Table 1.

Sequencing of Amplified Genomic DNA and Identification of Single Nucleotide Polymorphisms The amplification products generated as described above, are then sequenced using any method known and available to the skilled technician. Methods for sequencing DNA using either the dideoxy-mediated method (Sanser method) or the Maxam-Gilbert method are widely known to those of ordinary skill in the art. Such methods are for example disclosed in Sambrook et al., 1989. Alternative approaches include hybridization to high-density DNA probe arrays as described in Chee et al. (1996).

Preferably, the amplified DNA is subjected to automated dideoxy terminator sequencing reactions using a dye-primer cycle sequencing protocol. The products of the sequencing reactions are run on sequencing gels and the sequences are determined using gel image analysis. The polymorphism search is based on the presence of superimposed peaks in the electrophoresis pattern resulting from different bases occurring at the same position. Because each dideoxy terminator is labeled with a different fluorescent molecule, the two peaks corresponding to a biallelic site present distinct colors corresponding to two different nucleotides at the same position on the sequence. However, the presence of two peaks can be an artifact due to background noise. To exclude such an artifact, the two DNA strands are sequenced and a comparison between the peaks is carried out. In order to be registered as a polymorphic sequence, the polymorphism has to be detected on both strands.

The above procedure permits those amplification products, which contain biallelic markers to be identified. The detection limit for the frequency of biallelic polymorphisms detected by sequencing pools of 100 individuals is approximately 0.1 for the minor allele, as verified by sequencing pools of known allelic frequencies. However, more than 90% of the biallelic polymorphisms detected by the pooling method have a frequency for the minor allele higher than 0.25. Therefore, the biallelic markers selected by this method have a frequency of at least 0.1 for the minor allele and less than 0.9 for the major allele. Preferably at least 0.2 for the minor allele and less than 0.8 for the major allele, more preferably at least 0.3 for the minor allele and less than 0.7 for the major allele, thus a heterozygosity rate higher than 0.18, preferably higher than 0.32, more preferably higher than 0.42.

In another embodiment, biallelic markers are detected by sequencing individual DNA samples, the frequency of the minor allele of such a biallelic marker may be less than 0.1.

Validation of the Biallelic Markers of the Present Invention

The polymorphisms are evaluated for their usefulness as genetic markers by validating that both alleles are present in a population. Validation of the biallelic markers is accomplished by genotyping a group of individuals by a method of the invention and demonstrating that both alleles are present. Microsequencing is a preferred method of genotyping alleles. The validation by genotyping step may be performed on individual samples derived from each individual in the group or by genotyping a pooled sample derived from more than one individual. The group can be as small as one individual if that individual is heterozygous for the allele in question. Preferably the group contains at least three individuals, more preferably the group contains five or six individuals, so that a single validation test will be more likely to result in the validation of more of the biallelic markers that are being tested. It should be noted, however, that when the validation test is performed on a small group it may result in a false negative result if as a result of sampling error none of the individuals tested carries one of the two alleles. Thus, the validation process is less useful in demonstrating that a particular initial result is an artifact, than it is at demonstrating that there is a bonafide biallelic marker at a particular position in a sequence. All of the genotyping, haplotyping, association, and interaction study methods of the invention may optionally be performed solely with validated biallelic markers.

Evaluation of the Frequency of the Biallelic Markers of the Present Invention

The validated biallelic markers are further evaluated for their usefulness as genetic markers by determining the frequency of the least common allele at the biallelic marker site. The higher the frequency of the less common allele the greater the usefulness of the biallelic marker is association and interaction studies. The determination of the least common allele is accomplished by genotyping a group of individuals by a method of the invention and demonstrating that both alleles are present. This determination of frequency by genotyping step may be performed on individual samples derived from each individual in the group or by genotyping a pooled sample derived from more than one individual. The group must be large enough to be representative of the population as a whole. Preferably the group contains at least 20 individuals, more preferably the group contains at least 50 individuals, most preferably the group contains at least 100 individuals. Of course the larger the group the greater the accuracy of the frequency determination because of reduced sampling error. For an indication of the frequency for the less common allele of a particular biallelic marker of the invention see Tables A and B. A biallelic marker wherein the frequency of the less common allele is 30% or more is termed a "high quality biallelic marker." All of the genotyping, haplotyping, association, and interaction study methods of the invention may optionally be performed solely with high quality biallelic markers.

The invention also relates to methods of estimating the frequency of an allele in a population comprising determining the proportional representation of a nucleotide at a LSR-related biallelic marker in said population. In addition, the methods of estimating the frequency of an allele in a population of the invention encompass methods with any further limitation described in this disclosure, or those following, specified alone or in any combination. Preferably, the LSR-related biallelic marker is present in one or more of SEQ ID Nos: 1 to 13, 15, and 17, and more preferably is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof. Optionally, determining the proportional representation of a nucleotide at a LSR-related biallelic marker may be accomplished by determining the identity of the nucleotides for both copies of said biallelic marker present in the genome of each individual in said population and calculating the proportional representation of said nucleotide at said LSR-related biallelic marker for the population. Optionally, said method is performed in vitro. Optionally, determining the proportional representation may be accomplished by performing a genotyping method of the invention on a pooled biological sample derived from a representative number of individuals, or each individual, in said population, and calculating the proportional amount of said nucleotide compared with the total.

III. Methods for Genotyping an Individual for Biallelic Markers

Methods are provided to genotype a biological sample for one or more biallelic markers of the present invention, all of which may be performed in vitro. Such methods of genotyping comprise determining the identity of a nucleotide at a LSR biallelic marker site by any method known in the art. These methods find use in genotyping case-control populations in association studies as well as individuals in the context of detection of alleles of biallelic markers which are known to be associated with a given trait, in which case both copies of the biallelic marker present in individual's genome are determined so that an individual may be classified as homozygous or heterozygous for a particular allele.

These genotyping methods can be performed nucleic acid samples derived from a single individual or pooled DNA samples.

Genotyping can be performed using similar methods as those described above for the identification of the biallelic markers, or using other genotyping methods such as those further described below. In preferred embodiments, the comparison of sequences of amplified genomic fragments from different individuals is used to identify new biallelic markers whereas microsequencing is used for genotyping known biallelic markers in diagnostic and association study applications.

Source of DNA for Genotyping

Any source of nucleic acids, in purified or non-purified form, can be utilized as the starting nucleic acid, provided it contains or is suspected of containing the specific nucleic acid sequence desired. DNA or RNA may be extracted from cells, tissues, body fluids and the like as described above in "Genomic DNA samples". While nucleic acids for use in the genotyping methods of the invention can be derived from any mammalian source, the test subjects and individuals from which nucleic acid samples are taken are generally understood to be human.

Amplification of DNA Fragments Comprising Biallelic Markers

Methods and polynucleotides are provided to amplify a segment of nucleotides comprising one or more biallelic markers of the present invention. It will be appreciated that amplification of DNA fragments comprising biallelic markers may be used in various methods and for various purposes and is not restricted to genotyping. Nevertheless, many genotyping methods, although not all, require the previous amplification of the DNA region carrying the biallelic marker of interest. Such methods specifically increase the concentration or total number of sequences that span the biallelic marker or include that site and sequences located either distal or proximal to it. Diagnostic assays may also rely on amplification of DNA segments carrying a biallelic marker of the present invention.

Amplification of DNA may be achieved by any method known in the art. The established PCR (polymerase chain reaction) method or by developments thereof or alternatives. Amplification methods which can be utilized herein include but are not limited to Ligase Chain Reaction (LCR) as described in EP A 320 308 and EP A 439 182. Gap LCR (Wolcott, M. J., 1992), the so-called "NASBA" or "3SR" technique described in Guatelli J. C. et al. (1990) and in Compton J. (1991), Q-beta amplification as described in European Patent Application no 4544610, strand displacement amplification as described in Walker et al. (1996) and EP A 684 315 and, target mediated amplification as described in PCT Publication WO 9322461.

LCR and Gap LCR are exponential amplification techniques, both depend on DNA ligase to join adjacent primers annealed to a DNA molecule. In Ligase Chain Reaction (LCR), probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5' phosphate-3' hydroxyl relationship, and so that a lizase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. A method for multiplex LCR has also been described (WO 9320227) the disclosure of which is incorporated by reference herein in its entirety. Gap LCR (GLCR)

is a version of LCR where the probes are not adjacent but are separated by 2 to 3 bases.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770, the disclosure of which is incorporated by reference herein in its entirety, or, to use Asymmetric Gap LCR (RT-AGLCR) as described by Marshall R. L. et al. (1994). AGLCR is a modification of GLCR that allows the amplification of RNA.

Some of these amplification methods are particularly suited for the detection of SNPs and allow the simultaneous amplification of a target sequence and the identification of the polymorphic nucleotide as it is further described below.

The PCR technology is the preferred amplification technique used in the present invention. A variety of PCR techniques are familiar to those skilled in the art. For a review of PCR technology, see White, B. A. (1997) and the publication entitled "PCR Methods and Applications" (1991, Cold Spring Harbor Laboratory Press). In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683, 195, 4,693,202 and 4,965,188, the disclosures of which are incorporated be reference herein in their entirety.

The identification of biallelic markers as described above allows the design of appropriate oligonucleotides, which can be used as primers to amplify DNA fragments comprising the biallelic markers of the present invention. Amplification can be performed using the primers initially used to discover new biallelic markers which are described herein or any set of primers allowing the amplification of a DNA fragment comprising a biallelic marker of the present invention. Primers can be prepared by an suitable method. As for example, direct chemical synthesis by a method such as the phosphodiester method of Narang S. A. et al. (1979), the phosphodiester method of Brown E. L. et al. 1979), the diethylphosphoramridite method of Beaucage et al. (1981) and the solid support method described in EP 0 707 592, the disclosure of which is incorporated by reference herein in its entirety.

In some embodiments the present invention provides primers for amplifying a DNA fragment containing one or more biallelic markers of the present invention. Preferred amplification primers are listed in Table 1. It will be appreciated that the primers listed are merely exemplary and that any other set of primers which produce amplification products containing one or more biallelic markers of the present invention.

The primers are selected to be substantially complementary to the different strands of each specific sequence to be amplified. The length of the primers of the present invention can range from 8 to 100 nucleotides, preferably from 8 to 50, 8 to 30 or more preferably 8 to 25 nucleotides. Shorter primers tend to lack specificity for a target nucleic acid sequence and generally require cooler temperatures to form sufficiently stable hybrid complexes with the template. Longer primers are expensive to produce and can sometimes self-hybridize to form hairpin structures. The formation of stable hybrids depends on the melting temperature (Tm) of the DNA. The Tm depends on the length of the primer the ionic strength of the solution and the G+C content. The higher the G+C content of the primer, the higher is the melting temperature because G:C pairs are held by three H bonds whereas A:T pairs have only two. The G+C content of the amplification primers of the present invention preferably ranges between 10 and 75%, more preferably between 35 and 60%, and most preferably between 40 and 55%. The appropriate length for primers under a particular set of assay conditions may be empirically determined by one of skill in the art.

The spacing of the primers determines the length of the segment to be amplified. In the context of the present invention amplified segments carying biallelic markers can range in size from at least about 25 bp to 35 kbp. Amplification fragments from 25–3000 bp are typical, fragments from 50–1000 bp are preferred and fragments from 100–600 bp are highly preferred. It will be appreciated that amplification primers for the biallelic markers may be any sequence which allow the specific amplification of any DNA fragment carrying the markers. Amplification primers may be labeled or immobilized on a solid support as described in "Polynucleotides and polypeptides of the present invention".

Methods of Genotyping DNA Samples for Biallelic Markers

Any method known in the art can be used to identify the nucleotide present at a biallelic marker site. Since the biallelic marker allele to be detected has been identified and specified in the present invention, detection will prove simple for one of ordinary skill in the art by employing any of a number of techniques. Many genotyping methods require the previous amplification of the DNA region carrying the biallelic marker of interest. While the amplification of target or signal is often preferred at present, ultrasensitive detection methods which do not require amplification are also encompassed by the present genotyping methods. Methods well-known to those skilled in the art that can be used to detect biallelic polymorphisms include methods such as, conventional dot blot analyzes, single strand conformational polymorphism analysis (SSCP) described by Orita et al. (1989), denaturing gradient gel electrophoresis (DGGE), heteroduplex analysis, mismatch cleavage detection, and other conventional techniques as described in Sheffield et al. (1991), White et al. (1992), Grompe et al. (1989 and 1993). Another method for determining the identity of the nucleotide present at a particular polymorphic site employs a specialized exonuclease-resistant nucleotide derivative as described in U.S. Pat. No. 4,656,127, the disclosure of which is incorporated by reference herein in its entirety.

Preferred methods involve directly determining the identify of the nucleotide present at a biallelic marker site by sequencing assay, allele-specific amplification assay, or hybridization assay. The following is a description of some preferred methods. A highly preferred method is the microsequencing technique. The term "sequencing" is used herein to refer to polymerase extension of duplex primer/template complexes and includes both traditional sequencing and microsequencing.

1) Sequencing Assays

The nucleotide present at a polymorphic site can be determined by sequencing methods. In a preferred embodiment, DNA samples are subjected to PCR amplification before sequencing as described above. DNA sequencing methods are described in "Sequencing of amplified genomic DNA and identification of single nucleotide polymorphisms".

Preferably, the amplified DNA is subjected to automated dideoxy terminator sequencing reactions using a dye-primer cycle sequencing protocol. Sequence analysis allows the identification of the base present at the biallelic marker site.

2) Microsequencing Assays

In microsequencing methods, the nucleotide at a polymorphic site in a target DNA is detected by a single nucleotide primer extension reaction. This method involves appropriate microsequencing primers which hybridize just upstream of the polymorphic base of interest in the target nucleic acid. A polymerase is used to specifically extend the 3' end of the primer with one single ddNTP (chain terminator) complementary to the nucleotide at the polymorphic site. Next the identity of the incorporated nucleotide is determined in any sortable way.

Typically, microsequencing reactions are carried out using fluorescent ddNTPs and the extended microsequencing primers are analyzed by electrophoresis on ABI 377 sequencing machines to determine the identity of the incorporated nucleotide as described in EP 412 883. Alternatively capillary electrophoresis can be used in order to process a higher number of assays simultaneously. An example of a typical microsequencing procedure that can be used in the context of the present invention is provided in Example 4.

Different approaches can be used for the labeling and detection of ddNTPs. A homogeneous phase detection method based on fluorescence resonance energy transfer has been described by Chen and Kwok (1997) and Chen et al. (1997). In this method, amplified genomic DNA fragments containing polymorphic sites are incubated with 5'-fluorescein-labeled primer in the presence of allelic dye-labeled dideoxyribonucleoside triphosphuates and a modified Taq polymerase. The dye-labeled primer is extended one base by the dye-terminator specific for the allele present on the template. At the end of the genotyping reaction, the fluorescence intensities of the two dyes in the reaction mixture are analyzed directly without separation or purification. All these steps can be performed in the same tube and the fluoreszence changes can be monitored in real time. Alternatively, the extended primer may be analyzed by MALDI-TOF Mass Spectrometry. The base at the polymorphic site is identified by the mass added onto the microsequencing primer (see Haff and Smirnov, 1997).

Microsequencing may be achieved by the established microsequencing method or by developments or derivatives thereof. Alternative methods include several solid-phase microsequencing techniques. The basic microsequencing protocol is the same as described previously, except that the method is conducted as a heterogeneous phase assay, in which the primer or the target molecule is immobilized or captured onto a solid support. To simplify the primer separation and the terminal nucleotide addition analysis, oligonucleotides are attached to solid supports or are modified in such ways that permit affinity separation as well as polymerase extension. The 5' ends and internal nucleotides of synthetic oligonucleotides can be modified in a number of different ways to permit different affinity separation approaches, e.g., biotinylation. If a single affinity group is used on the oligonucleotides, the oligonucleotides can be separated from the incorporated terminator reagent. This eliminates the need of physical or size separation. More than one oligonucleotide can be separated from the terminator reagent and analyzed simultaneously if more than one affinity group is used. This permits the analysis of several nucleic acid species or more nucleic acid sequence information per extension reaction. The affinity group need not be on the priming oligonucleotide but could alternatively be present on the template. For example, immobilization can be carried out via an interaction between biotinylated DNA and streptavidin-coated microtitration wells or avidin-coated polystrene particles. In the same manner oligonucleotides or templates may be attached to a solid support in a high-density format. In such solid phase microsequencing reactions, incorporated ddNTPs can be radiolabeled (Syvänen, 1994) or linked to fluorescein (Livak and Hainer, 1994). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate). Other possible reporter-detection pairs include: ddNTP linked to dinitrophenyl (DNP) and anti-DNP alkaline phosplutase conjugate (Harju et al., 1993) or biotinylated ddNTP and horseradish peroxidase-conjugated streptavidin with o-phenylenediamine as a substrate (WO 92/15712), the disclosure of which is incorporated by reference herein in its entirety. As yet another alternative solid-phase microsequencing procedure, Nyren et al. (1993) described a method relying on the detection of DNA poymerase activity by an enzymatic luminometric inorganic pyrophosphate detection assays (ELIDA).

Pastinen et al. (1997) describe a method for multiplex detection of single nucleotide polymorphism in which the solid phase minisequencing principle is applied to an oligonucleotide array format. High-density arrays of DNA probes attached to a solid support (DNA chips) are further described below.

In one aspect the present invention provides polynucleotides and methods to genotype one or more biallelic markers of the present invention by performing a microsequencing assay. Preferred microsequencing primers include the nucleotide sequences Nos D1 to D32 and E1 to E31. More preferred microsequencing primers are selected from the group consisting of the nucleotide sequences Nos D2, D9, D10, D11, D15, D17, D19, D23, D29, D32, E1, E6, E8, E13, E17, E19, E20, E23, E25, E26, E29, and E31. Other preferred microsequencing primers are selected from the group consisting of D2, D16, D17, D24, D26, D31, E2, E15, E16, E23, E25 and E30.

It will be appreciated that the microsequencing primers listed in Example 4 are merely exemplary and that, any primer having a 3' end immediately adjacent to the polymorphic nucleotide may be used. Similarly, it will be appreciated that microsequencing analysis may be performed for any biallelic marker or any combination of biallelic markers of the present invention. One aspect of the present invention is a solid support which includes one or more microsequencing primers listed in Example 4, or fragments comprising at least 8, at least 12, at least 15, or at least 20 consecutive nucleotides thereof and having a 3' terminus immediately upstream of the corresponding biallelic marker, for determining the identity of a nucleotide at a biallelic marker site. Preferably, the biallelic marker is selected from the group consisting of A1 to A32 and the complements thereof. More preferably, the biallelic marker is selected from the group consisting of A2, A16, A17, A24, A26, and A31, and the complements thereof.

Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof.

3) Mismatch Detection Assays Based on Polymerases and Ligases

In one aspect the present invention provides polynucleotides and methods to determine the allele of one or more biallelic markers of the present invention in a biological sample, by mismatch detection assays based on polymerases and/or ligases. These assays are based on the specificity of polymerases and ligases. Polymerization reactions places particularly stringent requirements on correct base pairing of the 3' end of the amplification primer and the joining of two oligonucleotides hybridized to a target DNA sequence is quite sensitive to mismatches close to the ligation site, especially at the 3' end. Methods, primers and various parameters to amplify DNA fragments comprising biallelic markers of the present invention are further described above in "Amplification of DNA fragments comprising biallelic markers".

Allele Specific Amplification

Discrimination between the two alleles of a biallelic marker can also be achieved by allele specific amplification, a selective strategy, whereby one of the alleles is amplified without amplification of the other allele. This is accomplished by placing the polymorphic base at the 3' end of one of the amplification primers. Because the extension forms from the 3' end of the primer, a mismatch at or near this position has an inhibitory effect on amplification. Therefore, under appropriate amplification conditions, these primers only direct amplification on their complementary allele. Designing the appropriate allele-specific primer and the corresponding assay conditions are well with the ordinary skill in the art.

Ligation/amplification Based Methods

The "Oligonucleotide Ligation Assay" (OLA) uses two oligonucleotides which are designed to be capable of hybridizing to abutting sequences of a single strand of a target molecule. One of the oligonucleotides is biotinylated, and the other is detectably labeled. If the precise complementary sequence is found in a target molecule, the oligonucleotides will hybridize such that their termini abut and create a ligation substrate that can be captured and detected. OLA is capable of detecting SNPs and may be advantageously combined with PCR as described by Nickerson D. A. et al. (1990). In this method, PCR is used to achieve the exponential amplification of target DNA, which is then detected using OLA.

Other methods which are particularly suited for the detection of single nucleotide polymorphism include LCR (ligase chain reaction), Gap LCR (GLCR) which are described above in "Amplification of DNA fragments comprising biallelic markers". As mentioned above LCR uses two pairs of probes to exponentially amplify a specific target. The sequences of each pair of oligonucleotides are selected to permit the pair to hybridize to abutting sequences of the same strand of the target. Such hybridization forms a substrate for a template-dependant ligase. In accordance with the present invention. LCR can be performed with oligonucleotides having the proximal and distal sequences of the same strand of a biallelic marker site. In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide. In an alternative embodiment, the oligonucleotides will not include the biallelic marker, such that ashen they hybridize to the target molecule, a "gap" is created as described in WO 90/01069, the disclosure of which is incorporated by reference herein in its entirety. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained.

Ligase/Polymerase-mediated Genetic Bit Analysis™ is another method for determining the identity of a nucleotide at a preselected site in a nucleic acid molecule (WO 95/21271), the disclosure of which is incorporated by reference herein in its entirety. This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

4) Hybridization Assay Methods

A preferred method of determining the identity of the nucleotide present at a biallelic marker site involves nucleic acid hybridization. The hybridization probes, which can be conveniently used in such reactions, preferably include the probes defined herein. Any hybridization assay may be used including Southern hybridization, Northern hybridization, dot blot hybridization and solid-phase hybridization (see Sambrook et al., 1989).

Hybridization refers to the formation of a duplex structure by two single stranded nucleic acids due to complementary base pairing. Hybridization can occur between exactly complementary nucleic acid strands or between nucleic acid strands that contain minor regions of mismatch. Specific probes can be designed that hybridize to one form of a biallelic marker and not to the other and therefore are able to discriminate between different allelic forms. Allele-specific probes are often used in pairs, one member of a pair showing perfect match to a target sequence containing the original allele and the other showing a perfect match to the target sequence containing the alternative allele. Hybridization conditions should be sufficiently stringent that there is a significant difference in hybridization intensity between alleles, and preferably an essentially binary response, whereby a probe hybridizes to only one of the alleles. Stringent, sequence specific hybridization conditions, under which a probe will hybridize only to the exactly complementary target sequence are well known in the art (Sambrook et al., 1989). Stringent conditions are sequence dependent and will be different in different circumstances. Generally, stringent conditions are selected to be about 5° C. lower than the thermal melting point (Tm) for the specific sequence at a defined ionic strength and pH. Although such hybridizations can be performed in solution, it is preferred to employ a solid-phase hybridization assay. The target DNA comprising a biallelic marker of the present invention may be amplified prior to the hybridization reaction. The presence of a specific allele in the sample is determined by detecting the presence or the absence of stable hybrid duplexes formed between the probe and the target DNA. The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acids and the labels bound to the duplexes are then detected. Those skilled in the art will recognize that wash steps may be employed to wash away excess target DNA or probe. Standard heterogeneous assay formats are suitable for detecting the hybrids using the labels present on the primers and probes.

Two recently developed assays allow hybridization-based allele discrimination with no need for separations or washes (see Landegren U. et al., 1998). The TaqMan assay takes advantage of the 5' nuclease activity of Taq DNA polymerase to digest a DNA probe annealed specifically to the accumulating amplification product. TaqMan probes are labeled with a donor-acceptor dye pair that interacts via fluorescence energy transfer. Cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time (see Livak et al., 1995). In an alternative homogeneous hybridization based procedure, molecular beacons are used for allele discriminations. Molecular beacons are hairpin-shaped oligonucleotide probes that report the presence of specific nucleic acids in homogeneous solutions. When they bind to their targets they undergo a conformational reorganization that restores the fluorescence of an internally quenched fluorophore (Tyagi et al., 1998).

The polynucleotides provided herein can be used in hybridization assays for the detection of biallelic marker alleles in biological samples. These probes are characterized in that they preferably comprise between 8 and 50 nucleotides, and in that they are sufficiently complementary to a sequence comprising a biallelic marker of the present invention to hybridize thereto and preferably sufficiently specific to be able to discriminate the targeted sequence for only one nucleotide variation. Preferably, the biallelic marker is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof. The GC content in the probes of the invention usually ranges between 10 and 75%, preferably between 35 and 60%, and more preferably between 40 and 55%. The length of these probes can range from 10, 15, 20, or 30 to at least 100 nucleotides, preferably from 10 to 50, more preferably from 18 to 35 nucleotides. A particularly preferred probe is 25 nucleotides in length. Preferably the biallelic marker is within 4 nucleotides of the center of the polynucleotide probe. In particularly preferred probes the biallelic marker is at the center of said polynucleotide. Shorter probes may lack specificity for a target nucleic acid sequence and generally require cooler temperatures to form sufficiently stable hybrid complexes with the template. Longer probes are expensive to produce and can sometimes self-hybridize to form hairpin structures. Methods for the synthesis of oligonucleotide probes have been described above and can be applied to the probes of the present invention.

Preferably the probes of the present invention are labeled or immobilized on a solid support. Labels and solid supports are further described in "Polynucleotides and polypeptides of the present invention". Detection probes are generally nucleic acid sequences or uncharged nucleic acid analogs such as, for example peptide nucleic acids which are disclosed in International Patent Application WO 92/20702, the disclosure of which is incorporated by reference herein in its entirety, morpholino analogs which are described in U.S. Pat. Nos. 5,185,444; 5,034,506 and 5,142,047, the disclosures of which are incorporated by reference herein in their entirety. The probe may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxy group. Alternatively, the 3' hydroxyl group simply can be cleaved, replaced or modified, U.S. patent application Ser. No. 07/049,061 filed Apr. 19, 1993 describes modifications, which can be used to render a probe non-extendable.

The probes of the present invention are useful for a number of purposes. They can be used in Southern hybridization to genomic DNA or Northern hybridization to mRNA. The probes can also be used to detect PCR amplification products. By assaying the hybridization to an allele specific probe, one can detect the presence or absence of a biallelic marker allele in a given sample.

High-throughput parallel hybridizations in array format are specifically encompassed within "hybridization assays" and are described below.

5) Hybridization to Addressable Arrays of Oligonucleotides

Hybridization assays based on oligonucleotide arrays rely on the differences in hybridization stability of short oligonucleotides to perfectly matched and mismatched target sequence variants. Efficient access to polymorphism information is obtained through a basic structure comprising high-density arrays of oligonucleotide probes attached to a solid support (the chip) at selected positions. Each DNA chip can contain thousands to millions of individual synthetic DNA probes arranged in a grid-like pattern and miniaturized to the size of a dime.

The chip technology has already been applied with success in numerous cases. For example, the screening of mutations has been undertaken in the BRCA1 gene, in *S. cerevisiae* mutant strains, and in the protease gene of HIV-1 virus (Hacia et al., 1996; Shoemaker et al., 1996; Kozal et al., 1996). Chips of various formats for use in detecting biallelic polymorphisms can be produced on a customized basis by Affymetrix (GeneChip™), Hyseq (HyChip and HyGnostics), and Protogene Laboratories.

In general, these methods employ arrays of oligonucleotide probes that are complementary to target nucleic acid sequence segments from an individual which target sequences include a polymorphic marker. EP 785280, the disclosure of which is incorporated by reference herein in its entirety, describes a tiling strategy for the detection of single nucleotide polymorphisms. Briefly, arrays may generally be "tiled" for a large number of specific polymorphisms. By "tiling" is generally meant the synthesis of a defined set of oligonucleotide probes which is made up of a sequence complementary to the target sequence of interest, as well as preselected variations of that sequence, e.g., substitution of one or more given positions with one or more members of the basis set of monomers, i.e. nucleotides. Tiling strategies are further described in PCT application No. WO 95/11995, the disclosure of which is incorporated by reference herein in its entirety. In a particular aspect, arrays are tiled for a number of specific, identified biallelic marker sequences. In particular, the array is tiled to include a number of detection blocks, each detection block being specific for a specific biallelic marker or a set of biallelic markers. For example, a detection block may be tiled to include a number of probes, which span the sequence segment that includes a specific polymorphism. To ensure probes that are complementary to each allele, the probes are synthesized in pairs differing at the biallelic marker. In addition to the probes differing at the polymorphic base, monosubstituted probes are also generally tiled within the detection block. These monosubstituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the biallelic marker. The monosubstituted probes provide internal controls for the tiled array, to distinguish actual hybridization from artifactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the biallelic marker are present in the sample. Hybridization and scanning may be carried out as described in PCT application No. WO 92/10092 and WO 95/11995 and U.S. Pat. No. 5,424,186, the disclosures of which are incorporated by reference herein in their entirety.

Thus, in some embodiments, the chips may comprise an array of nucleic acid sequences of fragments of about 15 nucleotides in length. In a preferred embodiment, the chip may comprise a probe as defined in "Polynucleotide of the invention". In further embodiments, the chip may comprise an array including at least one of the sequences selected from the group consisting of SEQ ID Nos 2–12 and SEQ ID No 1 and the sequences complementary thereto, or a fragment thereof at least about 8 consecutive nucleotides, preferably 10, 15, 20, more preferably 25, 30, 40, 47, or 50 consecutive nucleotides. In some embodiments, the chip may comprise an array of at least 2, 3, 4, 5, 6, 7, 8 or more of these polynucleotides of the invention. Solid supports and polynucleotides of the present invention attached to solid supports are further described in "Polynucleotides and polypeptides of the present invention".

6) Integrated Systems

Another technique, which may be used to analyze polymorphisms, includes multicomponent integrated systems, which miniaturize and compartmentalize processes such as PCR and capillary electrophoresis reactions in a single functional device. An example of such technique is disclosed in U.S. Pat. No. 5,589.136, the disclosure of which is incorporated by reference herein in its entirety, which describes the integration of PCR amplification and capillary. electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts. Varying the voltage controls the liquid flow at intersections between the micro-machined channels and changes the liquid flow rate for pumping across different sections of the microchip.

For genotyping biallelic markers, the microfluidic system may integrate nucleic acid amplification, microsequencing, capillary electrophoresis and a detection method such as laser-induced fluorescence detection.

IV. Methods of Genetic Analysis Using the Biallelic Markers of the Present Invention Different methods are available for the genetic analysis of complex traits (see Lander and Schork, 1994). The search for disease-susceptibility genes is conducted using trio main methods: the linkage approach in which evidence is sought for cosegregation between a locus and a putative trait locus using family studies, and the association approach in which evidence is sought for a statistically significant association between an allele and a trait or a trait causing allele (Khoury et al., 1993). In general, the biallelic markers of the present invention find use in any method known in the art to demonstrate a statistically significant correlation between a genotype and a phenotype. The biallelic markers may be used in parametric and non-parametric linkage analysis methods. Preferably, the biallelic markers of the present invention are used to identify genes associated with detectable traits using association studies, an approach which does not require the use of affected families and which permits the identification of genes associated with complex and sporadic traits.

The genetic analysis using the biallelic markers of the present invention may be conducted on any scale. The whole set of biallelic markers of the present invention or any subset of biallelic markers of the present invention may be used. Further, any set of genetic markers including a biallelic marker of the present invention may be used. A set of biallelic polymorphisms that could be used as genetic markers in combination with the biallelic markers of the present invention has been described in WO 98/201 65, the disclosure of which is incorporated by reference herein in its entirety. As mentioned above, it should be noted that the biallelic markers of the present invention may be included in any complete or partial genetic map of the human genome. These different uses are specifically contemplated in the present invention and claims.

The invention also comprises methods of detecting an association between a genotype and a phenotype, comprising the steps of a) genotyping at least one LSR-related biallelic marker in a trait positive population according to a genotyping method of the invention; b) genotyping said LSR-related biallelic marker in a control population according to a genotyping method of the invention; and c) determining whether a statistically significant association exists between said genotype and said phenotype. In addition, the methods of detecting an association between a genotype and a phenotype of the invention encompass methods with any further limitation described in this disclosure, or those following, specified alone or in any combination. Preferably, the LSR-related biallelic marker is present in one or more of SEQ ID Nos: 1 to 13, 15, and 17, and more preferably is selected from the group consisting of A1 to A32 and the complements thereof. More preferably, the biallelic marker is selected from the group consisting of A2, A16, A7, A24, A26, and A31, and the complements thereof. Attentively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof. Optionally, said control population may be a trait negative population, or a random population. Optionally, each of said genotyping steps a) and b) may be performed on a single pooled biological sample derived from each of said populations. Optionally, each of said genotyping of steps a) and b) is performed separately on biological samples derived from each individual in said population or a subsample thereof. Optionally, said phenotype is a disease involving the partitioning of dietary lipids between the liver and peripheral tissues, more particularly obesity and disorders related to obesity, or a response to an agent acting on the partitioning of dietary lipids between the liver and peripheral tissues, or side effects to an agent acting on the partitioning of dietary lipids between the liver and peripheral tissues. Optionally, said disorder related to obesity is selected from the group consisting of atherosclerosis, insulin resistance. hypertension, hyperlipidemia, hypertriglyceridemia myocardial infarction/cardiovascular disease (primarily for women), microangiopathic in obese individuals with Type II diabetes, ocular lesions associated with microangiopathy in obese individuals with Type II diabetes, renal lesions associated with microangiopathy in obese individuals with Type II diabetes, and Syndrome X.

The invention also encompasses methods of estimating the frequency of a haplotype for a set of biallelic markers in a population, comprising the steps of: a) genotyping at least two LSR-related biallelic marker for each individual in said population or a subsample thereof, according to a genotyping method of the invention; and b) applying a haplotype determination method to the identities of the nucleotides determined in steps a) to obtain an estimate of said frequency. In addition, the methods of estimating the frequency of a haplotype of the invention encompass methods with any further limitation described in this disclosure, or those following, specified alone or in any combination. Preferably, the LSR-related biallelic marker is present in one or more of SEQ ID Nos: 1 to 13,15, and 17, and more preferably is selected from the group consisting of A1 to A32 and the complements thereof. More preferably), the biallelic marker is selected from the group consisting of A2, A16, A17, A24, A26, and A31, and the complements thereof Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof. Optionally, said haplotype determination method is selected from the group consisting of asymmetric PCR amplification, double PCR amplification of specific alleles, the Clark algorithm, or an expectation-maximization algorithm. Optionally, said second biallelic marker is an LSR-related biallelic marker that is distinct from said first biallelic marker. Preferably said second marker is present in one or more of SEQ ID Nos: 1 to 13, 15, and 17, and more preferably said second biallelic marker is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof.

An additional embodiment of the present invention encompasses methods of detecting an association between a haplotype and a phenotype, comprising the steps of: a) estimating the frequency of at least one haplotype in a trait positive population, according to a method of the invention for estimating the frequency of a haplotype; b) estimating the frequency of said haplotype in a control population, according to a method of the invention for estimating the frequency of a haplotype; and c) determining whether a statistically significant association exists between said haplotype and said phenotype. In addition, the methods of detecting an association between a haplotype and a phenotype of the invention encompass methods with any further limitation described in this disclosure, or those following. Preferably, the LSR-related biallelic marker is present in one or more of SEQ ID Nos: 1 to 13, 15, and 17, and more preferably is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'and the complements thereof. Optionally, said control population is a trait negative population, or a random population. Optionally, said phenotype is a disease involving the partitioning of dietary lipids between the liver and peripheral tissues, more particularly obesity and disorders related to obesity, or a response to an agent acting on the partitioning of dietary lipids between the liver and peripheral tissues, or side effects to an agent acting on the partitioning of dietary lipids between the liver and peripheral tissues. Optionally, said disorder related to obesity is selected from the group consisting of atherosclerosis, insulin resistance, hypertension, hyperlipidemia, hypertriglyceridemia, myocardial infarction/cardiovascular disease (primarily for women), microangiopathic in obese individuals with Type II diabetes, ocular lesions associated with microangiopathy in obese individuals with Type II diabetes, renal lesions associated with microangiopathy in obese individuals with Type II diabetes, and Syndrome X. Optionally, said method comprises the additional steps of determining the phenotype in said trait positive and said control populations prior to step c).

The invention also encompasses association methods employed to examine the association between any LSR-related biallelic marker, alone or as part of a haplotype, with a phenotype that involves a disorder resulting in disruption of normal carbohydrate or lipid metabolism, transport or storage, including disorders relating to insulin, triglycerides, and leptin, in particular cardiovascular disease (including atherosclerosis), hypertension, obesity, hyperinsulinemia, insulin-resistance and related syndromes and diseases including any of those described in this application.

Linkage Analysis

Linkage analysis is based upon establishing a correlation between the transmission of genetic markers and that of a specific trait throughout generations within a family. Thus, the aim of linkage analysis is to detect marker loci that show cosegregation with a trait of interest in pedigrees.

Parametric Methods

When data are available from successive generations there is the opportunity to study the degree of linkage between pairs of loci. Estimates of the recombination fraction enable loci to be ordered and placed onto a genetic map. With loci that are genetic markers, a genetic map can be established, and then the strength of linkage between markers and traits can be calculated and used to indicate the relative positions of markers and genes affecting those traits (Weir, 1996) The classical method for linkage analysis is the logarithm of odds (lod) score method (see Morton, 1955; Orr 1991). Calculation of lod scores requires specification of the mode of inheritance for the disease (parametric method). Generally, the length of the candidate region identified using linkage analysis is between 2 and 20 Mb. Once a candidate region is identified as described above, analysis of recombinant individuals using additional markers allows further delineation of the candidate region. Linkage analysis studies have generally relied on the use of a maximum of 5,000 microsatellite markers, thus limiting the maximum theoretical attainable resolution of linkage analysis to about 600 kb on average.

Linkage analysis has been successfully applied to map simple genetic traits that show clear Mendelian inheritance patterns and which have a high penetrance (i.e., the ratio between the number of trait positive carriers of allele a and the total number of a carriers in the population However, parametric linkage analysis suffers from a variety of drawbacks. First, it is limited by its reliance on the choice of a genetic model suitable for each studied trait. Furthermore, as already mentioned, the resolution attainable using linkage analysis is limited, and complementary studies are required to refine the analysis of the typical 2 Mb to 20 Mb regions initially identified through linkage analysis. In addition, parametric linkage analysis approaches have proven difficult when applied to complex genetic traits, such as those due to the combined action of multiple genes and/or environmental factors. It is very difficult to model these factors adequately in a lod score analysis. In such cases, too large an effort and cost are needed to recruit the adequate number of affected families required for applying linkage analysis to these situations as recently discussed by Risch, N. and Merikangas, K. (1996).

Non-parametric Methods

The advantage of the so-called non-parametric methods for linkage analysis is that they do not require specification of the mode of inheritance for the disease, they tend to be more useful for the analysis of complex traits. In non-parametric methods, one tries to prove that the inheritance pattern of a chromosomal region is not consistent with random Mendelian segregation by showing that affected relatives inherit identical copies of the region more often than expected by chance. Affected relatives should show excess "allele sharing" even in the presence of incomplete penetrance and polygenic inheritance. In non-parametric linkage analysis the degree of agreement at a marker locus in two individuals can be measured either by the number of alleles identical by state (IBS) or by the number of alleles identical by descent (IBD). Affected sib pair analysis is a well-known special case and is the simplest form of these methods.

The biallelic markers of the present invention may be used in both parametric and non-parametric linkage analysis. Preferably biallelic markers may be used in non-parametric methods which allow the mapping of genes involved in complex traits. The biallelic markers of the present invention may be used in both IBD- and IBS-methods to map genes affecting a complex trait. In such studies, taking advantage of the high density of biallelic markers, several adjacent biallelic marker loci may be pooled to achieve the efficiency attained by multi-allelic markers (Zhao et al., 1998).

Population Association Studies

The preserved invention comprises methods for identifying if the LSR gene is associated with a detectable trait using the biallelic markers of the present invention. In one embodiment the present invention comprises methods to detect an association between a biallelic marker allele or a biallelic marker haplotype and a trait. Further, the invention comprises methods to identify a trait causing allele in linkage disequilibrium with any biallelic marker allele of the present invention.

As described above, alternative approaches can be employed to perform association studies: genome-wide association studies, candidate region association studies and candidate gene association studies. In a preferred embodiment, the biallelic markers of the present invention are used to perform candidate gene association studies. The candidate gene analysis clearly provides a short-cut approach to the identification of genes and gene polymorphisms related to a particular trait when some information concerning the biology of the trait is available. Further, the biallelic markers of the present invention may be incorporated in any map of genetic markers of the human genome in order to perform genome-wide association studies. Methods to generate a high-density map of biallelic markers has been described in U.S. patent application Ser. No. 60/082, 614. The biallelic markers of the present invention may further be incorporated in any map of a specific candidate region of the genome (a specific chromosome or a specific chromosomal segment for example):

As mentioned above, association studies may be conducted within the general population and are not limited to studies performed on related individuals in affected families. Association studies are extremely valuable as they permit the analysis of sporadic or multifactor traits. Moreover, association studies represent a powerful method for fine-scale mapping enabling much finer mapping of trait causing alleles than linkage studies. Studies based on pedigrees often only narrow the location of the trait causing allele. Association studies using the biallelic markers of the present invention can therefore be used to refine the location of a trait causing allele in a candidate region identified by Linkage Analysis methods. Moreover, once a chromosome segment of interest has been identified, the presence of a candidate gene such as a candidate gene of the present invention, in the region of interest can provide a shortcut to the identification of the trait causing allele. Biallelic markers of the present invention can be used to demonstrate that a candidate gene is associated with a trait. Such uses are specifically contemplated in the present invention and claims.

Determining the Frequency of a Biallelic Marker Allele or of a Biallelic Marker Haplotype in a Population Association studies explore the relationships among frequencies for sets of alleles between loci.

Determining the Frequency of an Allele in a Population

Allelic frequencies of the biallelic markers in a populations can be determined using one of the methods described above under the heading "Methods for genotyping an individual for biallelic markers", or any genotyping procedure suitable for this intended purpose. Genotyping pooled samples or individual samples can determine the frequency of a biallelic marker allele in a population. One way to reduce the number of genotypings required is to use pooled samples. A major obstacle in using pooled samples is in terms of accuracy and reproducibility for determining accurate DNA concentrations in setting up the pools. Genotyping individual samples, which provides higher sensitivity, reproducibility and accuracy, is the preferred method used in the present invention. Preferably, each individual is genotyped separately and simple gene counting is applied to determine the frequency of an allele of a biallelic marker or of a genotype in a given population.

Determining the Frequency of a Haplotype in a Population

The gametic phase of haplotypes is unknown when diploid individuals are heterozygous at sore than one locus. Using genealogical information in families gametic phase can sometimes be inferred (Perlin et al., 1994). When no genealogical information is available different strategies may be used. One possibility is that the multiple-site heterozygous diploids can be eliminated from the analysis, keeping only the homozygotes and the single-site heterozygote individuals, but this approach might lead to a possible bias in the sample composition and the underestimation of low-frequency haplotypes. Another possibility is that single chromosomes can be studied independently, for example, by asymmetric PCR amplification (see Newton et al, 1989; Wu et al., 1989) or by isolation of single chromosome by limit dilution followed by PCR amplification (see Ruano et al., 1990). Further, a sample may be haplotyped for sufficiently close biallelic markers by double PCR amplification of specific alleles (Sarkar G. and Sommer S. S., 1991). These approaches are not entirely satisfying either because of their technical complexity, the additional cost they entail, their lack of generalization at a large scale or the possible biases they introduce. To overcome these difficulties, an algorithm to infer the phase of PCR-amplified DNA genotypes introduced by Clark A. G. (1990) may be used. Briefly, the principle is to start filing a preliminary list of haplotypes present in the sample by examining unambiguous individuals, that is, the complete homozygotes and the single-site heterozygotes. Then other individuals in the same sample are screened for the possible occurrence of previously recognized haplotypes. For each positive identification, the complementary haplotype is added to the list of recognized haplotypes, until the phase information for all individuals is either resolved or identified as unresolved. This method assigns a single haplotype to each multiheterozygous individual, whereas several haplotypes are possible when there are more than one heterozygous site. Alternatively, one can use methods estimating haplotype frequencies in a population without assigning haplotypes to each individual. Preferably, a method based on an expectation-maximization (EM) algorithm (Dempster et al., 1977) leading to maximum-likelihood estimates of haplotype frequencies under the assumption of Hardy-Weinberg proportions (random mating) is used (see Excoffier L. and Slatkin M., 1995). The EM algorithm is a generalized iterative maximum-likelihood approach to estimation that is useful when data are ambiguous and/or incomplete. The EM algorithm is used to resolve heterozygotes into haplotypes. Haplotype estimations are further described below under the heading "Statistical methods". Any other method known in the art to determine or to estimate the frequency of a haplotype in a population may be used.

Linkage Disequilibrium Analysis

Linkage disequilibrium is the non-random association of alleles at two or more loci and represents a powerful tool for mapping genes involved in disease traits (see Ajioka R. S. et al., 1997). Biallelic markers, because they are densely spaced in the human genome and can be genotyped in more numerous numbers than other types of genetic markers (such as RFLP or VNTR markers), are particularly useful in genetic analysis based on linkage disequilibrium.

When a disease mutation is first introduced into a population (by a new mutation or the immigration of a mutation carrier), it necessarily resides on a single chromosome and thus on a single "background" or "ancestral" haplotype of linked markers. Consequently, there is complete disequilibrium between these markers and the disease mutation one finds the disease mutation only in the presence of a specific set of marker alleles. Through subsequent generations recombinations occur between the disease mutation and these marker polymorphisms, and the disequilibrium gradually dissipates. The pace of this dissipation is a function of the recombination frequency, so the markers closest to the disease gene will manifest higher levels of disequilibrium than those that are further away. When not broken up by recombination "ancestral" haplotypes and linkage disequilibrium between marker alleles at different loci can be tracked not only through pedigrees but also through populations. Linkage disequilibrium is usually seen as an association between one specific allele at one locus and another specific allele at a second locus.

The pattern or curve of disequilibrium between disease and marker loci is expected to exhibit a maximum that occurs at the disease locus. Consequently, the amount of linkage disequilibrium between a disease allele and closely linked genetic markers may yield valuable information regarding the location of the disease gene. For fine-scale mapping of a disease locus, it is useful to have some knowledge of the patterns of linkage disequilibrium that exist between markers in the studied region. As mentioned above the mapping resolution achieved through the analysis of linkage disequilibrium is much higher than that of linkage studies. The high density of biallelic markers combined with linkage disequilibrium analysis provides powerful tools for fine-scale mapping. Different methods to calculate linkage disequilibrium are described below under the heading "Statistical Methods".

Population-based Case-control Studies of Trait-marker Associations

As mentioned above, the occurrence of pairs of specific alleles at different loci on the same chromosome is not random and the deviation from random is called linkage disequilibrium. Association studies focus on population frequencies and rely on the phenomenon of linkage disequilibrium. If a specific allele in a given gene is directly involved in causing a particular trait, its frequency will be statistically increased in an affected (trait positive) population, when compared to the frequency in a trait negative population or in a random control population. As a consequence of the existence of linkage disequilibrium, the frequency of all other alleles present in the haplotype carrying the trait-causing allele will also be increased in trait positive individuals compared to trait negative individuals or random controls. Therefore, association between the trait and any allele (specifically a biallelic marker allele) in linkage disequilibrium with the trait-causing allele will suffice to suggest the presence of a trait-related gene in that particular region. Case-control populations can be genotyped for biallelic markers to identify associations that narrowly locate a trait causing allele. As any marker in linkage disequilibrium with one given marker associated with a trait will be associated with the trait. Linkage disequilibrium allows the relative frequencies in case-control populations of a limited number of genetic polymorphisms (specifically biallelic markers) to be analyzed as an alternative to screening all possible functional polymorphisms in order to find trait-causing alleles. Association studies compare the frequency of marker alleles in unrelated case-control populations, and represent powerful tools for the dissection of complex traits.

Case-control Populations (Inclusion Criteria)

Population-based association studies do not concern familial inheritance but compare the prevalence of a particular genetic marker, or a set of markers, in case-control populations. They are case-control studies based on comparison of unrelated case (affected or trait positive) individuals and unrelated control (unaffected or trait negative or random) individuals. Preferably the control group is composed of unaffected or trait negative individuals. Further, the control group is ethnically matched to the case population. Moreover, the control group is preferably matched to the case-population for the main known confusion factor for the trait under study (for example age-matched for an age-dependent trait). Ideally, individuals in the two samples are paired in such a way that they are expected to differ only in their disease status. In the following "trait positive population", "case population" and "affected population" are used interchangeably.

An important step in the dissection of complex traits using association studies is the choice of case-control populations (see Lander and Schork, 1994). A major step in the choice of case-control populations is the clinical definition of a given trait or phenotype. Any genetic trait may be analyzed by the association method proposed here by carefully selecting the individuals to be included in the trait positive and trait negative phenotypic groups. Four criteria are often useful: clinical phenotype, age at onset, family history and severity. The selection procedure for continuous or quantitative traits (such as blood pressure for example) involves selecting individuals at opposite ends of the phenotype distribution of the trait under study, so as to include in these trait positive and trait negative populations individuals with non-overlapping phenotypes. Preferably, case-control populations consist of phenotypically homogeneous populations. Trait positive and trait negative populations consist of phenotypically uniform populations of individuals representing each between 1 and 98%, preferably between 1 and 80%, more preferably between 1 and 50%, and more preferably between 1 and 30%, most preferably between 1 and 20% of the total population under study, and selected among individuals exhibiting non-overlapping phenotypes. The clearer the difference between the two trait phenotypes, the greater the probability of detecting an association with biallelic markers. The selection of those drastically different but relatively uniform phenotypes enables efficient comparisons in association studies and the possible detection of marked differences at the genetic level, provided that the sample sizes of the populations under study are significant enough.

In preferred embodiments, a first group of between 50 and 300 trait positive individuals, preferably about 100 individuals, are recruited according to their phenotypes. A similar number of trait negative individuals are included in such studies.

In the present invention, typical examples of inclusion criteria include obesity and disorders related to obesity. More particularly, the inclusion criteria may be based on a "BMI" (weight/height$^2$ (kg/m$^2$)). Preferably, the trait positive individuals present a BMI that is in the highes 3%.

Association Analysis

The general strategy to perform association studies using biallelic markers derived from a region carrying a candidate gene is to scan two groups of individuals (case-control populations) in order to measure and statistically compare the allele frequencies of the biallelic markers of the present invention in both groups.

If a statistically significant association with a trait is identified for at least one or more of the analyzed biallelic markers, one can assume that: either the associated allele is directly responsible for causing the trait (the associated allele is the trait causing allele), or more likely the associated allele is in linkage disequilibrium with the trait causing allele. The specific characteristics of the associated allele with respect to the candidate gene function usually gives further insight into the relationship between the associated allele and the trait (causal or in linkage disequilibrium). If the evidence indicates that the associated allele within the candidate gene is most probably not the trait causing allele but is in linkage disequilibrium with the real trait causing allele, then the trait causing allele can be found by sequencing the vicinity of the associated marker.

Association studies are usually run in two successive steps. In a first phase, the frequencies of a reduced number of biallelic markers from the candidate gene are determined in the trait positive and trait negative populations. In a second phase of the analysis, the position of the genetic loci responsible for the given trait is further refined using a higher density of markers from the relevant region. However, if the candidate gene under study is relatively small in length, as it is the case for many of the candidate genes analyzed included in the present invention, a single phase may be sufficient to establish significant associations.

Haplotype Analysis

As described above, when a chromosome carrying a disease allele first appears in a population as a result of either mutation or migration, the mutant allele necessarily resides on a chromosome having a set of linked markers: the ancestral haplotype. This haplotype can be tracked through populations and its statistical association with a given trait can be analyzed. Complementing single point (allelic) association studies with multi-point association studies also called haplotype studies increases the statistical power of association studies. Thus, a haplotype association study allows one to define the frequency and the type of the ancestral carrier haplotype. A haplotype analysis is important in that it increases the statistical power of an analysis involving individual markers.

In a first stage of a haplotype frequency analysis, the frequency of the possible haplotypes based on various combinations of the identified biallelic markers of the invention is determined. The haplotype frequency is then compared for distinct populations of trait positive and control individuals. The number of trait positive individuals, which should be, subjected to this analysis to obtain statistically significant results usually ranges between 30 and 300, with a preferred number of individuals ranging between 50 and 150. The same considerations apply to the number of unaffected individuals (or random control) used in the study. The results of this first analysis provide haplotype frequencies in case-control populations, for each evaluated haplotype frequency a p-value and an odd ratio are calculated. If a statistically significant association is found the relative risk for an individual carrying the given haplotype of being affected with the trait under study can be approximated.

Interaction Analysis

The biallelic markers of the present invention may also be used to identify patterns of biallelic markers associated with detectable traits resulting from polygenic interactions. The analysis of genetic interaction between alleles at unlinked loci requires individual genotyping using the techniques described herein. The analysis of allelic interaction among a selected set of biallelic markers with appropriate level of statistical significance can be considered as a haplotype analysis. Interaction analysis consists in stratifying the case-control populations with respect to a given haplotype for the first loci and performing a haplotype analysis with the second loci with each subpopulation.

Statistical methods used in association studies are further described below.

Testing for Linkage in the Presence of Association

The biallelic markers of the present invention may further be used in TDT (transmission/disequilibrium test). TDT tests for both linkage and association and is not affected by population stratification. TDT requires data for affected individuals and their parents or data from unaffected sibs instead of from parents (see Spielmann S. et al., 1993; Schaid D. J. et al., 1996, Spielmann S. and Ewens W. J., 1998). Such combined tests generally reduce the false—positive errors produced by separate analyses.

Statistical Methods

In general, any method known in the art to test whether a trait and a genotype show a statistically significant correlation may be used.

1) Methods in Linkage Analysis

Statistical methods and computer programs useful for linkage analysis are well-known to those skilled in the art (see Terwilliger J. D. and Ott J. 1994; Ott J., 1991).

2) Methods to Estimate Haplotype Frequencies in a Population

As described above, when genotypes are scored, it is often not possible to distinguish heterozygotes so that haplotype frequencies cannot be easily inferred. When the gametic phase is not known, haplotype frequencies can be estimated from the multilocus genotypic data. Any method known to person skilled in the art can be used to estimate haplotype frequencies (see Lange K., 1997; Weir, B. S, 1996) Preferably, maximum-likelihood haplotype frequencies are computed using an Expectation-Maximization (EM) algorithm (see Dempster et al. 1977; Excoffier L. and Slatkin M., 1995). This procedure is an iterative process aiming at obtaining maximum-likelihood estimates of haplotype frequencies from multi-locus genotype data when the gametic phase is unknown Haplotype estimations are usually performed by applying the EM algorithm using for example the EM-HAPLO program (Hawley M. E. et al., 1994) or the Arlequin program (Schneider et al., 1997). The EM algorithm is a generalized iterative maximum likelihood approach to estimation and is briefly described below.

In the following part of this text, phenotypes will refer to multi-locus genotypes with unknown phase. Genotypes will refer to known-phase multi-locus genotypes.

Suppose a sample of N unrelated individuals roped for K markers. The data observed are the unknown-phase K-locus phenotypes that can categorized in F different phenotypes. Suppose that we have H underlying possible haplotypes (in care of K biallelic markers, $H=2^K$).

For phenotype j, suppose that $c_j$ genotypes are possible. We thus have the following equation $$P_j = \sum_{i=1}^{c_j} pr(genotype_i) = \sum_{i=1}^{c_j} pr(h_k, h_l) \qquad \text{Equation 1}$$

where Pj is the probability of the phenotype j. $h_k$ and $h_l$ are the two haplotypes constituent the genotype i. Under the Hardy-Weinberg equilibrium, $pr(h_k, h_l)$ becomes:

$$pr(h_k,h_l)=pr(h_k)^2 \text{ if } h_k=h_l, \; pr(h_k,h_l)=2pr(h_k).pr(h_l) \text{ if } h_k \neq h_l. \qquad \text{Equation 2}$$

The successive steps of the E-M algorithm can be described as follows:

Starting with initial values of the of haplotypes frequencies, noted $p_1^{(0)}, p_2^{(0)}, \ldots p_H^{(0)}$, these initial values serve to estimate the genotype frequencies (Expectation step) and then estimate another set of haplotype frequencies (Maximization step), noted $p_1^{(1)}, p_2^{(1)}, \ldots p_H^{(1)}$, these two steps are iterated until changes in the sets of haplotypes frequency are very small.

A stop criterion can be that the maximum difference between haplotype frequencies between two iterations is less than $10^{-7}$. These values can be adjusted according to the desired precision of estimations.

In details, at a given iteration, the Expectation step consists in calculating the genotypes frequencies by the following equation:

$$pr(genotype_i)^{(s)} = pr(phenotype_j) \cdot \qquad \text{Equation 3}$$
$$pr(genotype_i|phenotype_j)^{(s)}$$
$$= \frac{n_j}{N} \cdot \frac{pr(h_k, h_l)^{(s)}}{P_j^{(s)}}$$

where genotype i occurs in phenotypes, and where $h_k$ and $h_l$ constitute genotype i. Each probability is derived according to eq.1, and eq.2 described above.

Then the Maximization step simply estimates another set of haplotype frequencies given the genotypes frequencies. This approach is also known as gene-counting method (Smith, 1957).

$$p_t^{(s+1)} = \frac{1}{2} \sum_{j=1}^{F} \sum_{i=1}^{c_j} \delta_{it} \cdot pr(genotype_i)^{(s)} \qquad \text{Equation 4}$$

where $\delta_{it}$ is an indicator variable which count the number of time haplotype t in genotype i. It takes the values of 0, 1 or 2.

To ensure that the estimation finally obtained is the maximum-likelihood estimation several values of departures are required. The estimations obtained are compared and if they are different the estimations leading to the best likelihood are kept.

3) Methods to Calculate Linkage Disequilibrium Between Markers

A number of methods can be used to calculate linkage disequilibrium between any two genetic positions, in practice linkage disequilibrium is measured by applying a statistical association test to haplotype data taken from a population.

Linkage disequilibrium between any pair of biallelic markers comprising at least one of the biallelic markers of the present invention ($M_i, M_j$) having alleles ($a_i/b_i$) at marker $M_i$ and alleles ($a_j/b_j$) at marker $M_j$ can be calculated for every allele combination ($a_i,a_j; a_i,b_j; b_i,a_j$ and $b_i,b_j$). according to the Piazza formula:

$$\Delta_{aiaj}=\sqrt{\theta 4}-\sqrt{(\theta 4+\theta 3)(\theta 4+\theta 2)},$$

where:

θ4=−−−=frequency of genotypes not having allele $a_i$ at $M_i$ and not having allele $a_j$ at $M_j$ θ3=−+=frequency of genotypes not having allele $a_i$ at $M_i$ and having allele $a_j$ at $M_j$ θ2=+−=frequency of genotypes having allele $a_i$ at $M_i$ and not having allele $a_j$ at $M_j$ Linkage disequilibrium (LD) between pairs of biallelic markers ($M_i$, $M_j$) can also be calculated for every allele combination (ai,aj; ai,bj; $b_i$,$a_j$ and $b_i$,$b_j$), according to the maximum-likelihood estimate (MLE) for delta (the composite genotypic disequilibrium coefficient), as described by Weir (Weir B. S., 1996). The MLE for the composite linkage disequilibrium is:

$$D_{aiaj} = (2n_1 + n_2 + n_3 + n_4/2)/N - 2(pr(a_i) \cdot pr(a_j))$$

where $n_1 = \Sigma$ phenotype ($a_i/a_i$, $a_j/a_j$), $n_2 = \Sigma$ phenotype ($a_i/a_i$, $a_j/b_j$), $n_3 = \Sigma$ phenotype ($a_i/b_i$, $a_j/a_j$), $n_4 = \Sigma$ phenotype ($a_i/b_i$, $a_j/b_j$) and N is the number of individuals in the sample.

This formula allows linkage disequilibrium between alleles to be estimated when only genotype, and not haplotype, data are available.

Another means of calculating the linkage disequilibrium between markers is as follows. For a couple of biallelic markers, $M_i$ ($a_i/b_i$) and $M_j$ ($a_j/b_j$), fitting the Hardy-Weinberg equilibrium, one can estimate the four possible haplotype frequencies in a given population according to the approach described above.

The estimation of gametic disequilibrium between ai and aj is simply:

$$D_{aiaj} = pr(\text{haplotype}(a_i,a_j)) - pr(a_i) \cdot pr(a_j).$$

Where $pr(a_i)$ is the probability of allele $a_i$ and $pr(a_j)$ is the probability of allele $a_j$ and where $pr(\text{haplotype}(a_i,a_j))$ is estimated as in Equation 3 above.

For a couple of biallelic marker only one measure of disequilibrium is necessary to describe the association between $M_i$ and $M_j$.

Then a normalized value of the above is calculated as follows:

$$D'_{aiaj} = D_{aiaj}/\max(-pr(a_i) \cdot pr(a_j), -pr(b_i) \cdot pr(b_j)) \text{ with } D_{aiaj} < 0$$

$$D'_{aiaj} = D_{aiaj}/\max(-pr(b_i) \cdot pr(a_j), pr(a_i) \cdot pr(b_j)) \text{ with } D_{aiaj} > 0$$

The skilled person will readily appreciate that other LD calculation methods can be used without undue experimentation.

Linkage disequilibrium among a set of biallelic markers having an adequate heterozygosity rate can be determined by genotyping between 50 and 1000 unrelated individuals, preferably between 75 and 200, more preferably around 100.

4) Testing for Association

Methods for determining the statistical significance of a correlation between a phenotype and a genotype, in this case an allele at a biallelic marker or a haplotype made up of such alleles, may be determined by any statistical test known in the art and is with any accepted threshold of statistical significance being required. The application of particular methods and thresholds of significance are well with in the skill of the ordinary practitioner of the art.

Testing for association is performed by determining the frequency of a biallelic marker allele in case and control populations and comparing these frequencies with a statistical test to determine if their is a statistically significant difference in frequency which would indicate a correlation between the trait and the biallelic marker allele under study. Similarly, a haplotype analysis is performed by estimating the frequencies of all possible haplotypes for a given set of biallelic markers in case and control populations, and comparing these frequencies with a statistical test to determine if their is a statistically significant correlation between the haplotype and the phenotype (trait) under study Any statistical tool useful to test for a statistically significant association between a genotype and a phenotype may be used. Preferably the statistical test employed is a chi-square test with one degree of freedom. A P-value is calculated (the P-value is the probability that a statistic as large or larger than the observed one would occur by chance).

Statistical Significance

In preferred embodiments, significance for diagnosis purposes, either as a positive basis for further diagnostic tests or as a preliminary starting point for early preventive therapy, the p value related to a biallelic marker association is preferably about $1 \times 10^{-2}$ or less, more preferably about $1 \times 10^{-4}$ or less, for a single biallelic marker analysis and about $1 \times 10^{-3}$ or less, still more preferably $1 \times 10^{-6}$ or less and most preferably of about $1 \times 10^{-8}$ or less, for a haplotype analysis involving several markers. These values are believed to be applicable to any association studies involving single or multiple marker combinations.

The skilled person can use the range of values set forth above as a starting point in order to carry out association studies With biallelic markers of the present invention. In doing so, significant associations between the biallelic markers of the present invention and obesity or disorders related to obesity can be revealed and used for diagnosis and drug screening purposes.

Phenotypic Permutation

In order to confirm the statistical significance of the first stage haplotype analysis described above, it might be suitable to perform further analyses in which genotyping data from case-control individuals are pooled and randomized with respect to the trait phenotype. Each individual genotyping data is randomly allocated to two groups, which contain the same number of individuals as the case-control populations used to compile the data obtained in the first stage. A second stage haplotype analysis is preferably run on these artificial groups, preferably for the markers included in the haplotype of the first stage analysis showing the highest relative risk coefficient. This experiment is reiterated preferably at least between 100 and 10000 times. The repeated iterations allow the determination of the percentage of obtained haplotypes with a significant p-value level below about $1 \times 10^{-3}$.

Assessment of Statistical Association

To address the problem of false positives similar analysis may be performed with the same case-control populations in random genomic regions. Results in random regions and the candidate region are compared as described in U.S. Provisional Patent Application entitled "Methods, software and apparat for identifying genomic region harboring a gene associated as with a detectable trait".

5) Evaluation of Risk Factors

The association between a risk factor (in genetic epistemology the risk factor is the presence or the absence of a certain allele or haplotype at marker loci) and a disease is measured by the odds ratio (OR) and by the relative risk (RR). If $P(R^+)$ is the probability of developing the disease for individuals with R and $P(R^-)$ is the probability for individuals without the risk factor, then the relative risk is simply the ratio of the two probabilities that is:

$$RR = P(R^+)/P(R^-)$$

In case-control studies, direct measures of the relative risk cannot be obtained because of the sampling design. However, the odds ratio allows a good approximation of the relative risk for low-incidence diseases and can he calculated:

$$OR = \left[\frac{F^-}{1-F^+}\right] / \left[\frac{F^-}{(1-F^-)}\right]$$

$$OR = (F^+/(1-F^-))/(F^-/(1-F^-))$$

$F^+$ is the frequency of the exposure to the risk factor in cases and $F^-$ is the frequency of the exposure to the risk factor in controls. $F^+$ and $F^-$ are calculated using the allelic or haplotype frequencies of the study and further depend on the underlying genetic model (dominant, recessive, additive . . . ).

One can further estimate the attributable risk (AR) which describes the proportion of individuals in a population exhibiting a trait due to a given risk factor. This measure is important in quantifying the role of a specific factor in disease etiology and in terms of the public health impact of a risk factor. The public health relevance of this measure lies in estimating the proportion of cases of disease in the population that could be prevented if the exposure of interest were absent. AR is determined as follows:

$$AR = P_E(RR-1)/(P_E(RR-1)+1)$$

AR is the risk attributable to a biallelic marker allele or a biallelic marker haplotype. $P_E$ is the frequency of exposure to an allele or a haplotype within the population at large; and RR is the relative risk which, is approximated with the odds ratio when the trait under study has a relatively low incidence in the general population.

Identification of Biallelic Markers in Linkage Disequilibrium with the Biallelic Markers of the Invention Once a first biallelic marker has been identified in a genomic region of interest the practitioner of ordinary skill in the art, using the teachings of the present invention, can easily identify additional biallelic markers in linkage disequilibrium with this first marker. As mentioned before any marker in linkage disequilibrium with a first marker associated with a trait will be associated with the trait. Therefore, once an association has been demonstrated between a given biallelic marker and a trait, the discovery of additional biallelic markers associated with this trait is of great interest in order to increase the density of biallelic markers in this particular region. The causal gene or mutation will be found in the vicinity of the marker or set of markers showing the highest correlation with the trait.

Identification of additional markers in linkage disequilibrium with a given marker involves: (a) amplifying a genomic fragment comprising a first biallelic marker from a plurality of individuals; (b) identifying of second biallelic markers in the genomic region harboring said first biallelic marker; (c) conducting a linkage disequilibrium analysis between said first biallelic marker and second biallelic markers; and (d) selecting said second biallelic markers as being in linkage disequilibrium with said first marker. Subcombinations comprising steps (b) and (c) are also contemplated.

Methods to identify biallelic markers and to conduct linkage disequilibrium analysis are described herein and can be carried out by the skilled person without undue experimentation. The present invention then also concerns biallelic markers which are in linkage disequilibrium with the specific biallelic markers A1 to A32 and which are expected to present similar characteristics in terms of their respective association with a given trait.

Mapping Studies: Identification of Functional Mutations

Once a positive association is confirmed with a biallelic marker of the present invention, the associated candidate gene can be scanned for mutations by comparing the sequences of a selected number of trait positive and trait negative individuals. In a preferred embodiment, functional regions such as exons and splice sites, promoters and other regulatory regions of the candidate gene are scanned for mutations. Preferably, trait positive individuals carry the haplotype shown to be associated with the trait and trait negative individuals do not carry the haplotype or allele associated with the trait. The mutation detection procedure is essentially similar to that used for biallelic site identification.

The method used to detect such mutations generally comprises the following steps: (a) amplification of a region of the candidate gene comprising a biallelic marker or a group of biallelic markers associated with the trait from DNA samples of trait positive patients and trait negative controls; (b) sequencing of the amplified region; (c) comparison of DNA sequences from trait-positive patients and trait-negative controls; and (d) determination of mutations specific to trait-positive patients. Subcombinations which comprise steps (b) and (c) are specifically contemplated. Preferably, the biallelic marker is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment the biallelic marker is selected from the group consisting of A15, A17, and A21 or any combination thereof, and the complements thereof. Optionally, the biallelic marker is selected from the group consisting of A'1 to A'20 and the complements thereof.

It is preferred that candidate polymorphisms be then verified by screening a larger population of cases and controls by means of any genotyping procedure such as those described herein, preferably using a microsequencing technique in an individual test format. Polymorphisms are considered as candidate mutations when present in cases and controls at frequencies compatible with the expected association results.

Biallelic Markers of the Invention in Methods of Genetic Diagnostics

The biallelic markers of the present invention can also be used to develop diagnostic tests capable of identifying individuals who express a detectable trait as the result of a specific genotype or individuals whose genotype places them at risk of developing a detectable trait at a subsequent time.

It will of course be understood by practitioners skilled in the treatment or diagnosis of obesity and disorders related to obesity that the present invention does not intend to provide an absolute identification of individuals who could be at risk of developing a particular disease involving obesity and disorders related to obesity but rather to indicate a certain degree or likelihood of developing a disease. However, this information is extremely valuable as it can, in certain circumstances, be used to initiate preventive treatments or to allow an individual carrying a significant haplotype to foresee warning signs such as minor symptoms. In diseases in which attacks may be extremely violent and sometimes fatal if not treated on time, the knowledge of a potential predisposition, even if this predisposition is not absolute, might contribute in a very significant manner to treatment efficacy.

The diagnostic techniques of the present invention may employ a variety of methodologies to determine whether a test subject has a biallelic marker pattern associated with an increased risk of developing a detectable trait or whether the individual suffers from a detectable trait as a result of a particular mutation, including methods which enable the analysis of individual chromosomes for haplotyping, such as family studies, single sperm DNA analysis or somatic hybrids. The trait analyzed using the present diagnostics may be any detectable trait, including obesity and disorders related to obesity.

Another aspect of the present invention relates to a method of determining whether an individual is at risk of developing a trait or whether an individual expresses a trait as a consequence of possessing a particular trait-causing allele. The present invention relates to a method of determining whether an individual is at risk of developing a plurality of traits or whether an individual expresses a plurality of traits as a result of possessing a particular trait-causing allele. These methods involve obtaining a nucleic acid sample from the individual and determining whether the nucleic acid sample contains one or more alleles of one or more biallelic markers indicative of a risk of developing the trait or indicative that the individual expresses the trait as a result of possessing a particular trait-causing allele.

These methods involve obtaining a nucleic acid sample from the individual and, determining, whether the nucleic acid sample contains at least one allele or at least one biallelic marker haplotype, indicative of a risk of developing the trait or indicative that the individual expresses the trait as a result of possessing a particular LSR polymorphism or mutation (trait-causing allele).

Preferably, in such diagnostic methods, a nucleic acid sample is obtained from the individual and this sample is genotyped using methods described above in "Methods Of Genotyping DNA Samples For Biallelic markers. The diagnostics may be based on a single biallelic marker or a on group of biallelic markers. In each of these methods, a nucleic acid sample is obtained from the test subject and the biallelic marker pattern of one or more of the biallelic markers A1 to A32 is determined.

In one embodiment, a PCR amplification is conducted on the nucleic acid sample to amplify regions in which polymorphisms associated with a detectable phenotype have been identified. The amplification products are sequenced to determine whether the individual possesses one or more LSR polymorphisms associated with a detectable phenotype. The primers used to generate amplification products may comprise the primers listed in Table 1.

Alternatively, the nucleic acid sample is subjected to microsequencing reactions as described above to determine whether the individual possesses one or more LSR polymorphisms associated with a detectable phenotype resulting from a mutation or a polymorphism in the LSR gene. The primers used in the microsequencing reactions may include the primers listed in Table 4. In another embodiment, the nucleic acid sample is contacted with one or more allele specific oligonucleotide probes which, specifically hybridize to one or more LSR alleles associated with a detectable phenotype. The probes used in the hybridization assay may include the probes listed in Table 3. In another embodiment, the nucleic acid sample is contacted with a second LSR oligonucleotide capable of producing an amplification product when used with the allele specific oligonucleotide in an amplification reaction. The presence of an amplification product in the amplification reaction indicates that the individual possesses one or more LSR alleles associated with a detectable phenotype.

As described herein, the diagnostics may be based on a single biallelic marker or a group of biallelic markers. Preferably, the biallelic marker is selected from the group consisting of A1 to A32 and the complements thereof. More preferably, the biallelic marker is selected from the group consisting of A2, A16, A17, A24, A26, and A31, and the complements thereof.

Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof.

Diagnostic kits comprise any of the polynucleotides of the present invention.

These diagnostic methods are extremely valuable as they can, in certain circumstances, be used to initiate preventive treatments or to allow an individual carrying a significant haplotype to foresee warning signs stanch as minor symptoms.

Diagnostics, which analyze and predict response to a drug or side effects to a drug, may be used to determine whether an individual should be treated with a particular drug. For example, if the diagnostic indicates a likelihood that an individual will respond positively to treatment with a particular drug, the drug may be administered to the individual. Conversely, if the diagnostic indicates that an individual is likely to respond negatively to treatment with a particular drug, an alternative course of treatment may be prescribed. A negative response may be defined as either the absence of an efficacious response or the presence of toxic side effects.

Clinical drug trials represent another application for the markers of the present invention. One or more markers indicative of response to an agent acting against an obesity-related disease or to side effects to an agent acting against an obesity-related disease may be identified using the methods described above. Thereafter, potential participants in clinical trials of such an agent may be screened to identify those individuals most likely to respond favorably to the drug and exclude those likely to experience side effects. In that way, the effectiveness of drug treatment may be measured in individuals who respond positively to the drug, without lowering the measurement as a result of the inclusion of individuals who are unlikely to respond positively in the study and without risking undesirable safety problems.

Recombinant Vectors

The term "vector" is used herein to designate either a circular or a linear DNA or RNA molecule, which is either double-stranded or single-stranded, and which comprise at least one polynucleotide of interest that is sought to be transferred in a cell host or in a unicellular or multicellular host organism.

The present invention relates to recombinants vectors comprising any one of the polynucleotide described herein.

The present invention encompasses a family of recombinant vectors that comprise a regulatory polynucleotide derived from the LSR genomic sequence, or a coding polynucleotide either derived from the LSR genomic sequence or from a cDNA sequence, said polynucleotide comprising at least one of the biallelic markers of the present invention. Preferably, the biallelic marker is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof.

More particularly, the invention encompasses recombinants vectors that comprise a polynucleotide described in "Polynucleotides and polypeptides of the present invention" "Polynucleotides," or "Polypeptides."

In a first preferred embodiment, a recombinant vector of the invention is used to amplify the inserted polynucleotide in a suitable cell host, this polynucleotide being amplified at every time that the recombinant vector replicates.

A second preferred embodiment of the recombinant vectors according to the invention consists of expression vectors comprising either a regulatory or a coding polynucleotide of the invention, or both, said polynucleotide containing at least one biallelic of the present invention. Within certain embodiments, expression vectors are employed to express a LSR polypeptide, preferably a modified LSR described in the present invention, which can be then purified and, for example be used in ligand screening assays or as an immunogen in order to raise specific antibodies directed against a modified LSR protein. In other embodiments, the expression vectors are used for constructing transgenic animals and also for gene therapy. Expression requires that appropriate signals are provided in the vectors, said signals including various regulator elements, such as enhancers/promoters from both viral and mammalian sources that drive expression of the genes of interest in host cells. Dominant drug selection markers for establishing permanent stable cell clones expressing the products are generally included in the expression vectors of the invention, as they are elements that link expression of the drug selection markers to expression of the polypeptide.

More particularly, the present invention relates to expression vectors which include nucleic acids encoding a LSR protein, preferably a modified LSR protein bearing at least one substitution or deletion set forth in SEQ ID Nos 14, 16 and 18 or variants or fragments thereof, under the control of a regulatory sequence selected among the LSR regulatory polynucleotides, or alternatively under the control of an exogenous regulatory sequence.

Consequently, preferred expression vectors of the invention are selected from the group consisting of: (a) a LSR regulatory sequence comprising a biallelic marker of the invention and driving the expression of a coding polynucleotide operably linked thereto; (b) the LSR coding sequence comprising a biallelic marker of the invention and being operably linked to regulation sequences allowing its expression in a suitable cell host and/or host organism. Preferably, the biallelic marker is selected from the group consisting of A1 to A32 and the complements thereof. More preferably, the biallelic marker is selected from the group consisting of A2, A16, A17, A24, A26, and A31, and the complements thereof Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. Optionally, the biallelic marker is selected from the group consisting of A'1 to A'20 and the complements thereof.

The invention also encompasses a recombinant expression vector comprising a polynucleotide selected from the following group of polynucleotides:

a) a polynucleotide of a nucleotide sequence selected from the group consisting of SEQ ID Nos 1–12, 13, 15 and 17 or a variant or a fragment thereof comprising at least one biallelic marker of the invention;

b) a nucleic acid encoding for a LSR protein or a fragment thereof, preferably a modified LSR protein bearing at least one substitution or deletion set forth in SEQ ID Nos 14, 16 and 18 or variants or fragments thereof.

In a preferred embodiment, the biallelic marker is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. In a further embodiment, the biallelic marker is selected from the group consisting of A'1 to A'20 and the complements thereof.

Some of the elements which can be found in the vectors of the present invention are described in further detail in the following sections.

1) General Features of the Expression Vectors of the Invention

A recombinant vector according to the invention comprises, but is not limited to, a YAC (Yeast Artificial Chromosome), a BAC (Bacterial Artificial Chromosome), a phage, a phagemid, a cosmid, a plasmid or even a linear DNA molecule which may consist of a chromosomal, non-chromosomal, semi-synthetic and synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription.

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation site, splice donor and acceptor sites, transcriptional termination sequences, and 5'-flanking non-transcribed sequences. DNA sequences derived from the SV40 viral genome, for example SV40 origin, early promoter, enhancer, splice and polyadenylation sites may be used to provide the required non-transcribed genetic elements.

2) Regulatory Elements

Promoters

The suitable promoter regions used in the expression vectors according to the present invention are chosen taking into account the cell host in which the heterologous gene has to be expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors.

Preferred bacterial promoters are the LacI, LacZ, the T3 or T7 bacteriophage RNA polymerase promoters, the gpt, larnbda PR, PL and trp promoters (EP 0036776), the disclosure of which is incorporated by reference herein in its entirety, the polyhedrin promoter, or the p10 protein promoter from baculovirus (Kit Novagen) (Smith et al. 1983; O'Reilly et al., 1992), the lambda PR promoter or also the trc promoter.

Eukaryotic promoters include CMV immediate early, HSV thymidine kinase, early and late SV40, LTRs from retrovirus, and mouse metallothionein-L. Selection of a convenient vector and promoter is well within the level of ordinary skill in the art.

The choice of a promoter is well within the ability of a person skilled in the field of genetic engineering. For example, one may refer to the book of Sambrook et al. (1989) or also to the procedures described by Fuller et al. (1996).

Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

The vector containing the appropriate DNA sequence as described above, more preferably LSR gene regulatory polynucleotide, a polynucleotide encoding the LSR polypeptide 1, or both of them, and comprising a biallelic marker of the present invention can be utilized to transform an appropriate host to allow the expression of the desired polypeptide or polynucleotide.

3) Selectable Markers

Such markers would confer an identifiable change to the cell permitting easy identification of cells containing the expression construct. The selectable marker genes for selection of transformed host cells are preferably dihydrofolate reductase or neomycin resistance for eukaryotic cell culture, TRP1 for S. cerevisiae or tetracycline, rifampicin or ampicillin resistance in E. coli, or levan saccharase for mycobacteria, this later marker being a negative selection marker.

4) Preferred Vectors.

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKKZ223-3 (Pharmacia, Uppsala, Sweden), and GEM 1 (Promega Biotec, Madison, Wis., USA).

Large numbers of other suitable vectors are known to those of skill in the art, and commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSV3, pBPV, pMSG, pSVL (Pharmacia); pQE-30 (QIAexpress).

Bacteriophage Vectors

The P1 bacteriophage vector may contain large inserts ranging from about 80 to about 100 kb.

The construction of P1 bacteriophage vectors such as p158 or p158/neo8 are notably described by Sternberg (1992, 1994). Recombinant P1 clones comprising LSR nucleotide sequences may be designed for inserting large polynucleotides of more than 40 kb (Linton et al., 1993). To generate P1 DNA for transgenic experiments, a preferred protocol is the protocol described by McCormick et al. (1994). Briefly, E. coli (preferably strain NS3529) harboring the P1 plasmid are grown overnight in a suitable broth medium containing 25 µg/ml of kanamycin. The P1 DNA is prepared from the E. coli by alkaline lysis using the Qiagen Plasmid Maxi kit (Qiagen, Chatsworth, Calif., USA), according to the manufacturer's instructions. The P1 DNA is purified from the bacterial lysate on two Qiagen-tip 500 columns, using the washing and elution buffers contained in the kit. A phenol/chloroform extraction is then performed before precipitating the DNA with 70% ethanol. After subilizing the DNA in TE (10 mM Tris-HCl, pH 7.4, 1 mM EDTA), the concentration of the DNA is assessed by spectrophotometry.

When the -goal is to express a P1 clone comprising LSR nucleotide sequences in a transgenic animal, typically in transgenic mice, it is desirable to remove vector sequences from the P1 DNA fragment, for example by cleaving the P1 DNA at rare-cutting sites within the P1 polylinker (SfiI, NotI or SalI). The P1 insert is then purified from vector sequences on a pulsed-field agarose gel, using methods similar using methods similar to those originally reported for the isolation of DNA from YACs (Schedl et al., 1993a; Peterson et al., 1993). At the stage, the resulting purified insert DNA can be concentrated, if necessary, on a Millipore Ultrafree-MC Filter Unit (Millipore. Bedford, Mass., USA—3000 molecular weight limit) and then dialyzed against microinjection buffer (10 mM Tris-HCl, pH 7.4; 250 µM EDTA) containing, 100 mM NaCl, 30 µM spermidine, 70 µM spermidine on a microdyalisis membrane (type VS, 0.025 µM from Millipore). The intactness of the purified P1 DNA insert is assessed by electrophoresis on 1% agarose (Sea Kem GTG; FMC Bio-products) pulse-field gel and staining with ethidium bromide.

Baculovirus Vectors

A suitable vector for the expression of a modified LSR polypeptide, preferably a LSR polypeptide bearing at least one substitution or deletion set forth in SEQ ID Nos 14, 16 and 18, or fragments or variants thereof is a baculovirus vector that can be propagated in insect cells and in insect cell lines. A specific suitable host vector system is the pVL1392/1393 baculovirus transfer vector (Pharmingen) that is used to transfect the SF9 cell line (ATCC No CRL 1711) which is derived from *Spodoptera frugiperda*.

Other suitable vectors for the expression of a LSR polypeptide in a baculovirus expression system include those described by Chai et al (1993), Vlasak et al. (1983) and Lenhard et al. (1996).

Viral Vectors

In one specific embodiment, the vector is derived from an adenovirus. Preferred adenovirus vectors according to the invention are those described by Feldman and Steg (1996) or Ohno et al. (1994). Another preferred recombinant adenovirus according to this specific embodiment of the present invention is the human adenovirus type 2 or 5 (Ad 2 or Ad 5) or an adenovirus of animal origin (French patent application No FR-93.05954).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host.

Particularly preferred retroviruses for the preparation or construction of retroviral in vitro or in vitro gene delivery vehicles of the present invention include retroviruses selected from the group consisting of Mink-Cell Focus Inducing Virus, Iurine Sarcoma Virus, Reticuloendotheliosis virus and Rous Sarcoma virus. Particularly preferred Murine Leukemia Viruses include the 4070A and the 1504A viruses. Abelson (ATCC No VR-999), Friend (ATCC No VR-245). Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR-659 and VR-728). Other preferred retroviral vectors are those described in Roth et al. (1996), PCT Application No WO 93/25234, PCT Application No WO 94/06920, the disclosures of which are incorporated by reference herein in their entirety, Roux et al., 1989. Julan et al., 1992 and Neda et al., 1991.

Yet another viral vector system that is contemplated by the invention consists in the adeno-associated virus (AAV). The adeno-associated virus is a naturally occurring defective virus that requires another virus, such as an adenovirus or a herpes virus, as a helper virus for efficient replication and a productive life cycle (Muzyczka et al., 1992). It is also one of the few viruses that may integrate its DNA into non-dividing cells, and exhibits a high frequency of stable integration (Flotte et al., 1992; Samulski et al., 1989; McLaughlin et al., 1989). One advantageous feature of AAV derives from its reduced efficacy for transducing pr4mary cells relative to transformed cells.

BAC Vectors

The bacterial artificial chromosome (BAC) cloning system (Shizuya et al., 1992) has been developed to stably maintain large fragments of genomic DNA (100–300 kb) in *E. coli*. A preferred BAC vector consists of pBeloBAC11 vector that has been described by Kim et al. (1996). BAC libraries are prepared with this vector using size-selected genomic DNA that has been partially digested using enzymes that permit ligation into either the Bam HI or HindIII sites in the vector. Flanking these cloning sites are T7 and SP6 RNA polymerase transcription initiation sites that can be used to generate end probes by either RNA transcription or PCR methods. After the construction of a BAC library in *E. coli*, BAC DNA is purified from the host cell as a supercoiled circle. Converting these circular molecules into a linear form precedes both size determination and introduction of the BACs into recipient cells. The cloning site is flanked by two Not I sites, permitting cloned segments to be excised from the vector by Not I digestion. Alternatively, the DNA insert contained in the pBeloBAC11 vector .nay be linearized by treatment of the BAC vector with the commercially available enzyme lambda terminase that leads to the cleavage at the unique cosN site, but this cleavage method results in a full length BAC clone containing both the insert DNA and the BAC sequences.

5) Delivery of the Recombinant Vectors

In order to effect expression of the polynucleotides of the invention, these constructs must be delivered into a cell. This delivery may be accomplished in vitro, as in laboratory procedures for transforming cell lines, or in vivo or ex vivo, as in the treatment of certain diseases states.

One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al., 1973; Chen et al., 1987;), DEAE-dextran (Gopal, 1985), electroporation (Tur-Kaspa et al., 1986; Potter et al., 1984), direct microinjection (Harland et al., 1985), DNA-loaded liposomes (Nicolau et al., 1982; Fraley et al., 1979), and receptor-mediate transfection (Wu and Wu, 1987; 1988). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non specific location (gene augmentation). In yet further embodiments, the nucleic acid may be stably maintained in the cell as a separate, episomal segment of DNA Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application No WO 90/11092 (Vical Inc.) and also in PCT application No WO 95/11307 (Institut Pasteur, INSERM, Université d'Ottawa), the disclosures of which are incorporated by reference herein in their enitirety, as well as in the articles of Tacson et al. (1996) and of Huygen et al. (1996).

In still another embodiment of the invention, the transfer of a naked polynucleotide of the invention, including a polynucleotide construct of the invention, into cells may be proceeded with a particle bombardment (biolistic), said particles being DNA-coated microprojectiles accelerated to a high velocity allowing them to pierce cell membranes and enter cells without killing them, such as described by Klein et al. (1987).

In a further embodiment, the polynucleotide of the invention may be entrapped in a liposome (Ghosh and Bacchawat, 1991; Wong et al., 1980; Nicolau et al., 1987).

In a specific embodiment, the invention provides a composition for the in vivo production of a LSR protein or polypeptide described herein. It comprises a naked polynucleotide operatively coding for this polypeptide, in solution in a physiologically acceptable carrier, and suitable for introduction into a tissue to cause cells of the tissue to express the said protein or polypeptide.

The amount of vector to be injected to the desired host organism varies according to the site of injection. As an indicative dose, it will be injected between 0.1 and 100 µg of the vector in an animal body, preferably a mammal body, for example a mouse body.

In another embodiment of the vector according to the invention, it may be introduced in vitro in a host cell, preferably in a host cell previously harvested from the animal to be treaty and more preferably a somatic cell such as a muscle cell. In a subsequent step, the cell that has been transformed with the vector coding for the desired LSR polypeptide or the desired fragment thereof is reintroduced into the animal body in order to deliver the recombinant protein within the body either locally or systemically.

Cell Hosts

Another object of the invention consists of a host cell that have been transformed or transfected with one of the polynucleotides described therein, and more precisely a polynucleotide comprising:

a regulatory or a coding polynucleotide of the LSR gene; and at least one biallelic marker of the present invention.

Are included host cells that are transformed (prokaryotic cells) or that are transfected (eukaryotic cells) with a recombinant vector such as one of those described above.

Generally, a recombinant host cell of the invention comprises any one of the polynucleotides or the recombinant vectors of the invention at which are described herein.

The invention also encompasses a recombinant express ion vector comprising a polynucleotide selected from the following group of polynucleotides:

a) a polynucleotide of a nucleotide sequence selected from the group consisting of SEQ ID Nos 1–12, 13, 15 and 17 or a variant or a fragment thereof comprising at least one biallelic marker of the invention;

b) a nucleic acid encoding for a LSR protein or a fragment thereof, preferably a modified LSR protein bearing at least one substitution or deletion set forth in SEQ ID Nos 14, 16 and 18 or variants or fragments thereof.

In a preferred embodiment, the biallelic marker is selected from the group consisting of A1 to A32 and the complements thereof. More preferably, the biallelic marker is selected from the group consisting of A2, A16, A17, A24, A26 and A31, and the complements thereof. Alternatively, the biallelic marker is selected from the group consisting of A21, A23 and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. In a further embodiment, the biallelic marker is selected from the group consisting of A'1 to A'20 and the complements thereof.

Another preferred recombinant cell host according to the present invention is characterized in that its genome or genetic background (including chromosome, plasmids) is modified by the nucleic acid coding for a LSR polypeptide, preferably a modified LSR protein bearing at least one substitution or deletion set forth in SEQ ID Nos 14, 16, and 18 or variants or fragments thereof.

Preferred host cells used as recipients for the expression vectors of the invention are the following:

a) Prokaryotic host cells: *Escherichia coli* strains (I.E. DH5-α strain), *Bacillus subtilis, Salmonella typhimurium,* and strains from species like Pseudomonas, Streptomyces and Staphylococcus.

b) Eukaryotic host cells: HeLa cells (ATCC No CCL2; No CCL2.1; No CCL2.2), Cv 1 cells (ATCC No CCL70), COS cells (ATCC No CRL1650; No CRL1651), Sf-9 cells (ATCC No CRL1711), C127 cells (ATCC No CRL-18041) 3T3 (ATCC No CRL-6361), CHO (ATCC No CCL-61), human kidney 293 (ATCC No 45504; No CRL-1573) and BHK (ECACC No 84100501; No 84111301).

c) Other mammalian host cells: The LSR gene expression in mammalian, and typically human, cells may be rendered defective, or alternatively it may be proceeded at with the insertion of a LSR genomic or cDNA sequence with the replacement of the LSR gene counterpart in the genome of an animal cell by a LSR polynucleotide according to the invention. These genetic alterations may be generated by homologous recombination events.

One kind of cell hosts that may be used are mammal zygotes, such as murine zygotes. For example, murine zygotes may undergo microinjection with a purified DNA molecule of interest, for example a purified DNA molecule that has previously been adjusted to a concentration range from 1 ng/ml—for BAC inserts—3 ng/µl—for P1 bacteriophage inserts—in 10 mM Tris-HCl, pH 7.4, 250 µM EDTA containing 100 mM NaCl, 30 µM spermidine, and70 µM spermidine. When the DNA to be microinjected has a large size, polyamines and high salt concentrations can be used in order to avoid mechanical breakage of this DNA, as described by Schedl et al (1993b).

Anyone of the polynucleotides of the invention may be introduced in an embryonic stem (ES) cell line, preferably a mouse ES cell line. ES cell lines are derived from pluripotent, uncommitted cells of the inner cell mass of pre-implantation blastocysts. Preferred ES cell lines are the following: ES-E14TG2a (ATCC No CRL-1821), ES-D3 (ATCC No CRL1934 and No CRL-11632), YS001 (ATCC No CRL-1776), 36.5 (ATCC No CRL-11116). To maintain ES cells in an Recommitted state, they are cultured in the presence of growth inhibited feeder cells which provide the appropriate signals to preserve this embryonic phenotype and serve as a matrix for ES cell adherence. Preferred feeder cells consist of primary embryonicfibroblasts that are established from tissue of day 13-day 14 embryos of virtually any mouse strain, that are maintained in culture, such as described by Abbondanzo et al. (1993) and are inhibited in growth by irradiation, such as described by Robertson (1987), or by the presence of an inhibitory concentration of LIF, such as described by Pease and Williams (1990).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skill artisan.

Transgenic Animals

The terms "transgenic animals" or "host animals" are used herein designate animals that have their genome genetically and artificially manipulated so as to include one of the nucleic acids according to the invention. Preferred animals are non-human mammals and include those belonging to a genus selected from Mus (e.g. mice), Rattus (e.g. rats) and Oryctogalus (e.g. rabbits) which have their genome artificially and genetically altered by the insertion of a nucleic acid according to the invention.

The transgenic animals of the invention all include within a plurality of their cells a cloned recombinant or synthetic DNA sequence, more specifically one of that purified or isolated nucleic acids comprising:

a LSR coding sequence, a LSR regulatory polynucleotide or a DNA sequence encoding an antisense polynucleotide such as described in the present specification; and at least one biallelic marker of the present invention.

Preferred transgenic animals according to the invention contains in their somatic cells and/or in their germ line cells a polynucleotide selected from the following soup of polynucleotides:

a) a polynucleotide of a nucleotide sequence selected from the group consisting of SEQ ID Nos 1–12, 13, 15 and 17 or a variant or a fragment thereof comprising at least one biallelic marker of the invention;

b) a nucleic acid encoding for a LSR protein or a fragment thereof, preferably a modified LSR protein bearing at least one substitution or deletion set forth in SEQ ID Nos 14, 16 and 18 or variants or fragments thereof.

In a preferred embodiment, the biallelic marker is selected from the group consisting of A1 to A32 and the complements thereof. More preferably, the biallelic marker is selected from the group consisting of A2, A16, A17, A24, A26, and A31, and the complements thereof. Alternatively, the biallelic marker is selected from the group consisting of A21, A23, and A24 and the complements thereof. In an especially preferred embodiment, the biallelic marker is A26. In another especially preferred embodiment, the biallelic marker is selected from the group consisting of A15, A17, and A21 or any combination thereof, and the complements thereof. In a further embodiment, the biallelic marker is selected from the group consisting of A'1 to A'20 and the complements thereof.

The transgenic animals of the invention thus contain specific sequences of exogenous genetic material such as the nucleotide sequences described above in detail.

In a first preferred embodiment, these transgenic animals may be good experimental models in order to study the diverse pathologies related to cell differentiation, in particular concerning the transgenic animals within the genome of which has been inserted one or several copies of a polynucleotide encoding a native LSR protein and comprising at least one biallelic marker of the present invention, or alternatively a modified LSR protein comprising at least one substitution or deletion described in the present disclosure.

In a second preferred embodiment, these transgenic animals may express a desired polypeptide of interest under the control of a regulatory polynucleotide of the LSR gene which comprises at least one biallelic marker of the present invention, leading to good yields in the synthesis of this protein of interest, and eventually a tissue specific expression of this protein of interest.

The design of the transgenic animals of the invention may be made according to the conventional techniques well known from the one skilled in the art For more details regarding the production of transgenic animals, and specifically transgenic mice, it may be referred to U.S. Pat. Nos. 4,873,191, issued Oct. 10, 1989, 5,464,764 issued Nov. 7, 1995 and 5,789,215, issued Aug. 4, 1998, these documents being herein incorporated by reference to disclose methods producing transgenic mice.

Transgenic animals of the present invention are produced by the application of procedures that result in an animal with a genome that has incorporated exogenous genetic material. The procedure involves obtaining the genetic material, or a portion thereof, which encodes either a LSR coding polynucleotide, a LSR regulatory polynucleotide or a DNA sequence encoding a LSR antisense polynucleotide such as described in the present specification, said polynucleotide comprising at least one biallelic marker of the present invention.

A recombinant polynucleotide of the invention is inserted into an embryonic or ES stem cell line. The insertion is preferably made using electroporation, such as described by Thomas et al. (1987). The cells subjected to electroporation are screened (e.g. by selection via selectable markers by PCR or by Southern blot analysis) to find positive cells which have integrated the exogenous recombinant polynucleotide into their genome, preferably via an homologous recombination event An illustrative positive-negative selection procedure that may be used according to the invention is described by Mansour et al. (1988).

Then, the positive cells are isolated, cloned and injected into 3.5 days old blastocysts from mice, such as described by Bradley (1987). The blastocysts are then inserted into a female host animal and allowed to grow to term.

Alternatively, the positive ES cells are brought into contact with embryos at the 2.5 days old 8–16 cell stage (morulae) such as described by Wood et al. (1993) or by Nagy et al. (1993), the ES cells being internalized to colonize extensively the blastocyst including the cells which will give rise to the germ line.

The offspring of the female host are tested to determine which animals are transgenic e.g. include the inserted exogenous DNA sequence and which are wild-type.

Thus, the present invention also concerns a transoenic animal containing a nucleic acid, a recombinant expression vector or a recombinant host cell according to the invention.

Recombinant Cell Lines Derived from the Transgenic Animals of the Invention.

A further object of the invention consists of recombinant host cells obtained from a transgenic animal described herein.

Recombinant cell lines may be established in vitro from cells obtained from any tissue of a transgenic animal according to the invention, for example by transfection of primary cell cultures with vectors expressing onc-genes such as SV40 large T antigen, as described by Chou (1989) and Shay et al. (1991).

Method for Producing a Modified LSR Polypeptide

It is now easy to produce proteins in high amounts by genetic engineering techniques through expression vectors such as plasmids, phages or phagemids. The polynucleotide that codes for a modified LSR protein or a fragment or a variant thereof which comprises at least one substitution or deletion set forth in SEQ ID Nos 14, 16, and 18 is inserted in an appropriate expression vector in order to produce the polypeptide of interest in vitro.

Thus, the present invention also concerns a method for producing a modified LSR protein or a fragment or a variant thereof which comprises at least one substitution or deletion set forth in SEQ ID Nos 14, 16, and 18, wherein said method comprises the steps of:

a) culturing, in an appropriate culture medium, a cell host previously transformed or transfected with the recombinant vector comprising a nucleic acid encoding the modified LSR protein;

b) harvesting the culture medium thus conditioned or lyse the cell host, for example by sonication or by an osmotic shock;

c) separating or purifying, from the said culture medium, or from the pellet of the resultant host cell lysate the thus produced polypeptide of interest.

d) Optionally characterizing the produced polypeptide of interest.

In a specific embodiment of the above method, step a) is preceded by a step wherein the nucleic acid coding for the modified LSR protein is inserted in an appropriate vector, optionally after an appropriate cleavage of this amplified nucleic acid with one or several restriction endonucleases. In a preferred embodiment, the nucleic acid encoding for the modified LSR protein is selected from a group consisting of SEQ ID Nos 1, 13, 15 and 17 or a fragment thereof and comprises at least one of the biallelic markers A1 to A32. The nucleic acid coding for a modified LSR protein may be the resulting product of an amplification reaction using a pair of primers according to the invention (by SDA, TAS, 3SR NASBA, TMA etc.).

The polypeptides according to the invention may be characterized by binding onto an immunoaffinity chromatography column on which polyclonal or monoclonal antibodies directed to a LSR polypeptide comprising a substitution or a deletion set forth in SEQ ID Nos 14, 16, and 18 which have previously been immobilized.

The polypeptides or peptides thus obtained may be purified, for example by high performance liquid chromatography, such as reverse phase and/or cationic exchange HPLC, as described by Rougeot et al. (1994). The reason to prefer this kind of peptide or protein purification is the lack of byproducts found in the elution samples which renders the resultant purified protein or peptide more suitable for a therapeutic use.

Purification of the recombinant proteins or peptides according to the present invention may also be carried out by passage onto a Nickel or Cupper affinity chromatography column. The Nickel chromatography column may contain the Ni-NTA resin (Porath et al. 1975).

In a first specific embodiment, polypeptides derived from a modified LSR protein and comprising at least one substitution or deletion described in the present disclosure are used to prepare polyclonal or monoclonal antibodies against the modified LSR protein. In a preferred embodiment, the polypeptides are preferably covalently or non-covalently bound to a carrier molecule, such as human or bovine serum albumin (HSA or BSA).

In a second specific embodiment, a polypeptide of the invention may consist of a fusion molecule between, on one hand, a modified LSR protein or a fragment or variant thereof, and on the other hand, a MBP (Maltose Binding Protein) and GST (Glutathion S Transferase) or with a tag such as Strep tag, Bio tag and flag peptide epitope tag.

The modified LSR protein or a fragment or variant thereof can be overexpressed and purified in a bacterial system such as E. coli as described in Kiefer et al. (1996) and Tucker et al. (1996), incorporated herein by reference The modified LSR protein, or fragment or variant thereof, coding sequence can be fused to its N-terminus with GST (Glutathion S Transferase) or MBP (Maltose Binding Protein) and to its C-terminus with poly-histidine tag, Bio tag or Strep tag for facilitating the purification of the expressed protein. The Bio tag is 13 amino acid residues long, is biotinylated in vivo in E. coli, and will therefore bind to both avidin and streptavidin. The Strep tag is 9 amino acid residues long and binds specifically tp streptavidin, but not to avidin. Therewith, a purification step by affinity can be carried out based on the interaction of a poly-histidine tail with immobilized metal ions, of the biotinylated Bio tag with monomeric avidin, of the Strep tag with streptavidin, of the GSJ segment with the glutathione, or of the MBP segment with maltose. Thioredoxin can be eventually inserted between the receptor C-terminus and the tag and could increase the expression level. It is purified by affinity chromatography. The MBP, GST or tag segment can be then removed.

Antibodies That Bind LSR Polypeptides of the Invention

Any LSR polypeptide or whole protein may be used to generate antibodies capable of specifically binding to expressed LSR protein or fragments thereof as described. The antibody compositions of the invention are capable of specifically binding or specifically bind to the 363-Ser, 363-Asp, 420-Pro, 420-Arg, 519-Arg, or 519-Del variants of SEQ ID NO: 14; the 344-Ser, 344-Asp, 401-Pro, 401-Arg, 500-Arg, or 500-Del variants of SEQ ID NO: 16; or the 295-Ser, 295-Asp, 352-Pro, 352-Arg, 451-Arg, or 451-Del variants of SEQ ID NO: 18 for the LSR protein. In order for an antibody composition to specifically bind to a particular variant of LSR it must demonstrate at least a 5% or 10%, preferably at least a 15%, or 20%, more preferably at least a 25%, 50%, or 100% greater binding activity for the full length protein of that particular variant of LSR than for the full length LSR protein with the alternative amino acid, insertion or deletion at the amino acid position named in the variant. Such binding affinity can be measured by any method known in the art, including ELISAs, RIAs, or other antibody-based binding assays.

In a preferred embodiment of the invention antibody compositions are capable of selectively binding, or selectively bind to, an epitope-containing fragment of a polypeptide comprising a contiguous span of at least 6 amino acids, preferably at least 8 to 10 amino acids, more preferably at least 12, 15, 20, 25, 30, 40, 50, or 100 amino acids of any one of SEQ ID Nos: 14, 16, and 18, wherein said epitope comprises one of the following: a serine residue at position 363 of SEQ ID NO: 14; an asparagine residue at position 363 of SEQ ID NO: 14; a proline residue at position 420 of SEQ ID NO: 14; an arginine residue at position 420 of SEQ ID NO: 14; an arginine residue at position 519 of SEQ ID NO: 14; a one amino acid deletion at position 519 of SEQ ID NO: 14; a serine residue at position 344 of SEQ ID NO: 16; an asparagine residue at position 344 of SEQ ID NO: 16; a proline residue at position 401 of SEQ ID NO: 16; an arginine residue at position 401 of SEQ ID NO: 16; an arginine residue at position 500 of SEQ ID NO: 16; a one amino acid deletion at position 500 of SEQ ID NO: 16; a serine residue at position 295 of SEQ ID NO: 18; an asparagine residue at position 295 of SEQ ID NO: 18; a proline residue at position 352 of SEQ ID NO: 18; an arginine residue at position 352 of SEQ ID NO: 18; an arginine residue at position 451 of SEQ ID NO: 18; and a one amino acid deletion at position 451 of SEQ ID NO: 18; optionally, wherein said antibody composition is either polyclonal or monoclonal.

The present invention also contemplates the use of polypeptides comprising a contiguous span of at least 6 amino acids, preferably at least 8 to 10 amino acids, more preferably at least 12, 15, 20, 25, 50, or 100 amino acids of a LSR polypeptide in the manufacture of antibodies, wherein said contiguous span comprises one of the following: a serine residue at position 363 of SEQ ID NO: 14; an asparagine residue at position 363 of SEQ ID NO: 14; a proline residue at position 420 of SEQ ID NO: 14; an arginine residue at position 420 of SEQ ID NO: 14; an arginine residue at position 519 of SEQ ID NO: 14; a one amino acid deletion at position 519 of SEQ ID NO: 14; a serine residue at position 344 of SEQ ID NO: 16; an asparagine residue at position 344 of SEQ ID NO: 16; a proline residue at position 401 of SEQ ID NO: 16; an arginine residue at position 401 of SEQ ID NO: 16; an arginine residue at position 500 of SEQ ID NO: 16; a one amino acid deletion at position 500 of SEQ ID NO: 16; a serine residue at position 295 of SEQ ID NO: 18; an asparagine residue at position 295 of SEQ ID NO: 18; a proline residue at position 352 of SEQ ID NO: 18; an arginine residue at position 352 of SEQ ID NO: 18; an arginine residue at position 451 of SEQ ID NO: 18; and a one amino acid deletion at position 451 of SEQ ID NO: 18. In a preferred embodiment such polypeptides are useful in the manufacture of antibodies to detect the presence and absence of the various LSR variant polypeptides of the invention.

Non-human animals or mammals, whether wild-type or transgenic, which express a different species of LSR than the one to which antibody binding is desired, and animals which do not express LSR (i.e. an LSR knock out animal as described in herein) are particularly useful for preparing antibodies. LSR knock out animals will recognize all or most of the exposed regions of LSR as foreign antigens, and therefore produce antibodies with a wider array of LSR epitopes Moreover, smaller polypeptides with only 10 to 30 amino acids may be useful in obtaining specific binding to the LSR variants of the invention. In addition, the humoral immune sem of animals which produce a species of LSR that resembles the antigenic sequence will preferentially recognize the differences between the animal's native LSR species and the antigen sequence, and produce antibodies to these unique sites in the antigen sequence. Such a technique will be particularly useful in obtaining antibodies that specifically bind to the LSR variants of the invention.

The antibodies may be prepared from hybridomas according to the technique described by Kohler and Milstein in 1975. The polyclonal antibodies may be prepared by immunization of a mammal, especially a mouse or a rabbit, with a polypeptide according to the invention that is combined with an adjuvant of immunity, and then by purifying of the specific antibodies contained in the serum of the immunized animal on a affinity chromatography column on which has previously been immobilized the polypeptide that has been used as the antigen.

The present invention also deals with antibodies directed against a modified LSR protein or a fragment or variant thereof, bearing at least one substitution or deletion according to the invention. In a particular embodiment, said antibodies are able to discriminate between a native and a modified LSR proteins. Optionally the antibodies are produced by the trioma technique and by the human B-cell hybridoma technique (Kozbor et al., 1983).

The present invention also includes, chimeric single chain Fv antibody fragments (U.S. Pat. No. 4,946,778; Martineau et al., 1998), the disclosure of which is incorporated by reference herein in its entirety, antibody fragments obtained through phage display libraries (Ridder et al., 1995) and humanized antibodies (Reinmann et al., 1997; Lezer et al., 1997). Also, transgenic mice, or other organisms such as other mammals, may be used to express antibodies, including for example, humanized antibodies directed against a modified LSR protein or a fragment or a variant thereof, bearing at least one substitution or deletion according to the invention.

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

The antibodies of the invention may be labeled, either by a radioactive, a fluorescent, or an enzymatic label.

Consequently, the invention is also directed to a method for detecting specifically the presence of a modified LSR polypeptide according to the invention in a biological sample, said method comprising the following steps:
 a) bringing into contact the biological sample with a polyclonal or monoclonal antibody directed against a modified LSR protein or a fragment or variant thereof bearing at least one substitution or deletion according to the invention;
 b) detecting the antigen-antibody complex formed.

The invention also concerns a diagnostic kit for detecting in vitro the presence of a modified LSR polypeptide according to the present invention in a biological sample wherein said kit comprises:
 a) a polyclonal or monoclonal antibody directed against a modified LSR protein or a fragment or variant thereof, bearing at least one substitution or deletion according to the invention, optionally labeled;
 b) a reagent allowing the detection of the antigen-antibody complexes formed, said reagent carrying optionally a label, or being able to be recognized itself by a labeled reagent, more particularly in the case when the above-mentioned monoclonal or polyclonal antibody is not labeled by itself.

Polynucleotide of the Invention for use in an Antisense Strategy

A therapeutic composition according to the present invention comprises advantageously an oligonucleotide fragment of the nucleic sequence of the LSR comprising an allele of at least one of the biallelic markers A2, A15, A16, A17, A21, A23, A24, A26, and A31 as an antisense tool that inhibits the expression of the LSR gene having the corresponding allele. Preferred methods using antisense polynucleotide according to the present invention are the procedures described by Sczakiel et al. (1995).

Preferred antisense polynucleotides according to the present invention are complementary to a sequence of the mRNAs of LSR that contains either the translation initiation codon ATG or a splicing donor or acceptor site.

The antisense nucleic acids should have a length and melting temperature sufficient to permit formation of an intracellular duplex having sufficient stability to inhibit the expression of the LSR mRNA in the duplex. Strategies for designing antisense nucleic acids suitable for use in gene therapy are disclosed in Green et al., (1986) and Izant and Weintraub, (1984), the disclosures of which are incorporated herein by reference.

In some strategies, antisense molecules are obtained by reversing the orientation of the LSR coding region with respect to a promoter so as to transcribe the opposite strand from that which is normally transcribed in the cell. The antisense molecules may be transcribed using in vitro transcription systems such as those that employ T7 or SP6 polymerase to generate the transcript. Another approach involves transcription of LSR antisense nucleic acids in vivo by operably linking DNA containing the antisense sequence to a promoter in a suitable expression vector.

Alternatively, suitable antisense strategies are those described by Rossi et al. (1991), in the International Applications Nos. WO 94/23026, WO 95/04141, WO 92/18522 and in the European Patent Application No. EP 0572 287 A2, the disclosures of which are incorporated by reference herein in their entirety.

An alternative to the antisense technology used according to the present invention consists in using ribozymes that will bind to a target sequence via their complementary polynucleotide tail and that will cleave the corresponding RNA by hydrolying its target site (namely "hammerhead ribozymes"). Briefly the simplified cycle of a hammerhead ribozyme consists of (1) sequence specific binding to the target RNA via complementary antisense sequences; (2) site-specific hydrolysis of the cleavable motif of the target strand; and (3) release of cleavage products, which gives rise to another catalytic cycle. Indeed the use of long-chain antisense polynucleotide (at least 30 bases long) or ribozymes with long antisense arms are advantageous. A preferred delivery system for antisense ribozyme is achieved by covalently linking these antisense ribozymes to lipophilic groups or to use liposome; as a convenient vector. Preferred antisense ribozymes according to the present invention are prepared as described by Sczakiel et al. (1995), the specific preparation procedures being referred to in said article being herein incorporated by reference.

Throughout this application, various publications, patents, and published patent applications are cited. The disclosures of the publications, patents, and published patent specifications referenced in this application are hereby incorporated by reference into the present disclosure to more fully describe the state of the art to which this invention pertains.

EXAMPLES

Example 1

Identification of Biallelic Markers: DNA Extraction

Donors were unrelated and healthy. They presented a sufficient diversity for being representative of a French heterogeneous population. The DNA from 100 individuals was extracted and tested for the detection of the biallelic markers.

30 mL of peripheral venous blood were taken from each donor in the presence of EDTA. Cells (pellet) were collected after centrifugation for 10 minutes at 2000 rpm. Red cells were lysed by a lysis solution (50 mL final volume: 10 mM Tris pH7.6; 5 mM $MgCl_2$; 10 mM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:

3 ml TE 10-2 (Tris-HCl 10 mM, EDTA2 mM)/NaCl 0.4 M

200 µL SDS 10%

500 µL K-proteinase (2 mg K-proteinase in TE 10-2/NaCl 0.4 M).

For the extraction of proteins, 1 mL saturated NaCl (6M) 1/3.5 v/v) was added. After vigorous agitation, the solution was centrifuged for 20 minutes at 10000 rpm.

For the precipitation of DNA, 2 to 3 volumes of 100% ethanol were added to the previous supernatant, and the solution was centrifuged for 30 minutes 2000 rpm. The DNA solution was rinsed three times with 70% ethanol to eliminate salts, and centrifuged for 20 minutes at 2000 rpm. The pellet was dried at 37° C., and resuspended in 1 ml TE 10-1 or 1 mL water. The DNA concentration was evaluated by measuring the OD at 260 nm 1 unit OD=50 µg/mL DNA).

To determine the presence of proteins in the DNA solution the OD 260/OD 280 ratio was determined. Only DNA preparations having a OD 260/OD 280 ratio between 1.8 and 2 were used in the subsequent examples described below.

The pool was constituted by mixing equivalent quantities of DNA from each individual.

Example 2

Identification of Biallelic Markers: Amplification of Genomic DNA by PCR

The amplification of specific genomic sequences of the DNA samples of example 1 was carried out on the pool of DNA obtained previously. In addition, 50 individual samples were similarly amplified.

PCR assays were performed using the following protocol.

| | |
|---|---|
| Final volume | 25 µL |
| DNA | 2 ng/µL |
| $MgCl_2$ | 2 mM |
| dNTP (each) | 200 µM |
| primer (each) | 2.9 ng/µL |
| Ampli Taq Gold DNA polymerase | 0.05 unit/µL |
| PCR buffer (10x = 0.1 M TrisHCl pH 8.3 0.5 M KCl | 1x |

Each pair of first primers was designed using the sequence information of the LSR gene disclosed herein and the OSP software (Hillier & Green 1991). This first pair of primers was about 20 nucleotides in length and had the sequences disclosed in Table 1 in the columns labeled PU and RP.

TABLE 1

| Amplicon | Amplicon Sequence | PU | Position Of PU Primer | RP | Position Of RP Primer |
|---|---|---|---|---|---|
| 99-14410 | SEQ ID No 2 | B1 | 1–21 of SEQ ID No 2 | C1 | 445–465 of SEQ ID No 2 |
| 99-14424 | SEQ ID No 3 | B2 | 1–20 of SEQ ID No 3 | C2 | 388408 of SEQ ID No 3 |
| 99-14418 | SEQ ID No 4 | B3 | 1–20 of SEQ ID No 4 | C3 | 434–452 of SEQ ID No 4 |
| 99-14417 | SEQ ID No 5 | B4 | 1–21 of SEQ ID No 5 | C4 | 447–465 of SEQ ID No 5 |
| 99-14415 | SEQ ID No 6 | B5 | 1–20 of SEQ ID No 6 | C5 | 443–462 of SEQ ID No 6 |
| 99-11413 | SEQ ID No 7 | B6 | 1–20 of SEQ ID No 7 | C6 | 457–477 of SEQ ID No 7 |
| 99-4575 | SEQ ID No 8 | B7 | 1–19 of SEQ ID No 8 | C7 | 458–476 of SEQ ID No 8 |
| 99-4576 | 946–1402 of SEQ ID No 1 | B8 | 946–963 of SEQ ID No 1 | C8 | 1385–1402 of SEQ ID No 1 |
| 9-19 | 1096–1635 of SEQ ID No 1 | B9 | 1096–1115 of SEQ ID No 1 | C9 | 1616–1635 of SEQ ID No 1 |
| 9-20 | 1602–2093 of SEQ ID No 1 | B10 | 1602–1621 of SEQ ID No 1 | C10 | 2074–2093 of SEQ ID No 1 |
| 99-4557 | 2036–2580 of SEQ ID No 1 | B11 | 2036–2053 of SEQ ID No 1 | C11 | 2563–2580 of SEQ ID No 1 |
| 9-1 | 2084–2500 of SEQ ID No 1 | B12 | 2084–2102 of SEQ ID No 1 | C12 | 2483–2500 of SEQ ID No 1 |
| 9-21 | 2062–2489 of SEQ ID No 1 | B13 | 2062–2081 of SEQ ID No 1 | C13 | 2470–2489 of SEQ ID No 1 |
| 9-3 | 3455–3901 of SEQ ID No 1 | B14 | 3455–3474 of SEQ ID No 1 | C14 | 3882–3901 of SEQ ID No 1 |
| 99-4558 | 3775–4356 of SEQ ID No 1 | B15 | 3775–3792 of SEQ ID No 1 | C15 | 4336–4356 of SEQ ID No 1 |
| 99-14419 | 4444–4920 of SEQ ID No 1 | B16 | 4444–4463 of SEQ ID No 1 | C16 | 4902–4920 of SEQ ID No 1 |
| 99-4577 | 6638–7089 of SEQ ID No 1 | B17 | 6638–6655 of SEQ ID No 1 | C17 | 7072–7089 of SEQ ID No 1 |
| 99-4559 | 7995–8593 of SEQ ID No 1 | B18 | 7995–8012 of SEQ ID No 1 | C18 | 8576–8593 of SEQ ID No 1 |
| 99-3148 | 9622–10040 of SEQ ID No 1 | B19 | 9622–9639 of SEQ ID No 1 | C19 | 10023–10040 of SEQ ID No 1 |
| 99-4560 | 9964–10563 of SEQ ID No 1 | B20 | 9964–9981 of SEQ ID No 1 | C20 | 10546–10563 of SEQ ID No 1 |
| 99-14411 | 10492–10996 of SEQ ID No | B21 | 10492–10512 of SEQ ID No 1 | C21 | 10996–11015 of SEQ ID No 1 |
| 99-4561 | 11972–12501 of SEQ ID No 1 | B22 | 11972–11990 of SEQ ID No 1 | C22 | 12481–12501 of SEQ ID No 1 |
| 9-4 | 12005–12436 of SEQ ID No 1 | B23 | 12005–12023 of SEQ ID No 1 | C23 | 12417–12436 of SEQ ID No 1 |
| 99-4562 | 14102–14563 of SEQ ID No 1 | B24 | 14102–14119 of SEQ ID No 1 | C24 | 14543–14563 of SEQ ID No 1 |
| 99-3149 | 14431–14865 of SEQ ID No 1 | B25 | 14431–14448 of SEQ ID No 1 | C25 | 14848–14865 of SEQ ID No 1 |
| 9-22 | 14748–15218 of SEQ ID No 1 | B26 | 14748–14767 of SEQ ID No 1 | C26 | 15198–15218 of SEQ ID No 1 |
| 9-24 | 14748–15351 of SEQ ID No I | B26 | 14748–14767 of SEQ ID No 1 | C27 | 15333–15351 of SEQ ID No 1 |
| 9-5 | 15002–15351 of SEQ ID No 1 | B27 | 15002–15019 of SEQ ID No 1 | C27 | 15333–15351 of SEQ ID No 1 |
| 9-6 | 15640–16089 of SEQ ID No 1 | B28 | 15641–15657 of SEQ ID No 1 | C28 | 16072–16089 of SEQ ID No 1 |
| 99-4563 | 15800–16199 of SEQ ID No 1 | B29 | 15800–15817 of SEQ ID No 1 | C29 | 16179–16199 of SEQ ID No 1 |
| 99-3150 | 119295–19746 of SEQ ID No 1 | B30 | 19295–19312of SEQ ID No 1 | C30 | 19729–19746 of SEQ ID No 1 |
| 9-7 | 19420–19841 of SEQ ID No 1 | B31 | 19420–19438 of SEQ ID No 1 | C31 | 19824–19841 of SEQ ID No 1 |
| 9-8 | 19798–20155 of 1SEQ ID No 1 | B32 | 19798–19815 of SEQ ID No 1 | C32 | 20137–20155 of SEQ ID No 1 |
| 9-9 | 19913–20346 of SEQ ID No 1 | B33 | 19913–I9931 of SEQ ID No 1 | C33 | 20329–20346 of SEQ ID No 1 |
| 99-4564 | 20139–20599 of SEQ ID No 1 | B34 | 20139–20157 of SEQ ID No 1 | C34 | 20582–20599 of SEQ ID No 1 |
| LSRX9 (17-1) | 20354-20832 of SEQ ID No 1 | B35 | 20354–20372 of SEQ ID No 1 | C35 | 20811–20832 of SEQ ID No 1 |
| LSRX9-110 | 20570–21214 of SEQ ID No 1 | B36 | 20570–20591 of SEQ ID No 1 | C36 | 21195–21214 of SEQ ID No 1 |
| LSRI9-110 | 1013–21214 of SEQ ID No 1 | B37 | 21013–21032 of SEQ ID No 1 | C36 | 21195–21214 of SEQ ID No 1 |

TABLE 1-continued

| Amplicon | Amplicon Sequence | PU | Position Of PU Primer | RP | Position Of RP Primer |
|---|---|---|---|---|---|
| 9-10 | 20238–20662 of SEQ ID No 1 | B38 | 20238–20256 of SEQ ID No 1 | C37 | 20645–20662 of SEQ ID No 1 |
| 9-26 | 20410–20706 of SEQ ID No 1 | B39 | 20410–20424 of SEQ ID No 1 | C38 | 20690–20706 of SEQ ID No 1 |
| 9-23 | 20569–21262 of SEQ ID No 1 | B40 | 20569–20588 of SEQ ID No 1 | C39 | 21243–21262 of SEQ ID No 1 |
| 9-11 | 20583–21034 of SEQ ID No 1 | B41 | 20583–20604 of SEQ ID No 1 | C40 | 21015–21034 of SEQ ID No 1 |
| 99-15285 | 20139–20601 of SEQ ID No 1 | B42 | 20139–20158 of SEQ ID No 1 | C41 | 20584–20601 of SEQ ID No 1 |
| 99-15287 | 20207–20659 of SEQ ID No 1 | B43 | 20207–20227 of SEQ ID No 1 | C42 | 20642–20659 of SEQ ID No 1 |
| 99-15286 | 20238–20709 of SEQ ID No 1 | B44 | 20238–20257 of SEQ ID No 1 | C43 | 20691–20709 of SEQ ID No 1 |
| 9-2 | 20943–21312 of SEQ ID No 1 | B45 | 20943–20960 of SEQ ID No 1 | C44 | 21295–21312 of SEQ ID No 1 |
| 99-152284 | 20582–21031 of SEQ ID No 1 | B46 | 20582–20602 of SEQ ID No 1 | C45 | 21013–21031 of SEQ ID No 1 |
| 99-14407 | 20571–21038 of SEQ ID No 1 | B47 | 20571–20589 of SEQ ID No 1 | C46 | 21019–21038 of SEQ ID No 1 |
| 99-15283 | 20638–21097 of SEQ ID No 1 | B48 | 20638–20655 of SEQ ID No 1 | C47 | 21079–21097 of SEQ ID No 1 |
| 99-4580 | SEQ ID No 9 | B49 | 1–20 of SEQ ID No 9 | C48 | 470–489 of SEQ ID No 9 |
| 99-4567 | SEQ ID No 10 | B50 | 1–18 of SEQ ID No 10 | C49 | 503–523 of SEQ ID No 10 |
| 99-14420 | SEQ ID No 11 | B51 | 1–19 of SEQ ID No 11 | C50 | 522–542 of SEQ ID No 11 |
| 99-4582 | SEQ ID No 12 | B52 | 1–19 of SEQ ID No 12 | C51 | 582–599 of SEQ ID No 12 |
| 17-2 | SEQ ID No 1 | B53 | 523–544 of SEQ ID No 1 | C52 | 1047–1068 of SEQ ID No 1 |

Preferably, the primers contained a common oligonucleotide tail upstream of the specific bases targeted for amplification which was useful for sequencing.

Primers PU contain the following additional PU 5' sequence: TGTAAAACGACGGCCAGT; primers RP contain the following RP 5' sequence: CAGGAAACAGCTAT-GACC. The primer containing the additional PU 5' sequence is listed in SEQ ID No 19. The primer containing the additional RP 5' sequence is listed in SEQ ID No 20.

The synthesis of these primers was performed following the phosphoramidite method, on a GENSET UFPS 24.1 synthesizer.

DNA amplification was performed on a Genius II thermocycler. After heating at 95° C. for 10 min, 40 cycles were performed. Each cycle comprised: 30 sec at 95° C., 54° C. for 1 min, and 30 sec at 72° C. For final elongation, 10 min at 72° C. ended the amplification. The quantities of the amplification products obtained were determined on 96-well microtiter plates, using a fluorometer and Picogreen as intercalant agent (Molecular Probes).

Example 3

Identification of Biallelic Markers: Sequencing of Amplified Genomic DNA and Identification of Polymorphisms The sequencing of the amplified DNA obtained in example 2 was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were determined using gel image analysis (ABI Prism DNA Sequencing Analysis software (2.1.2 version) and the above mentioned proprietary "Trace" basecaller).

The sequence data were further evaluated using the above mentioned polymorphism analysis software designed to detect the presence of biallelic markers among the pooled amplifier fragments. The polymorphism search was based on the presence of superimposed peaks in the electrophoresis pattern resulting from different bases occurring at the same position as described previously.

The 53 fragments of amplification were analyzed. In these 53 fragments, 31 biallelic markers were detected. The location of these biallelic markers is shown in Table 2.

TABLE 2

| Amplicon | Biallelic Marker | Marker Name | Origin of DNA | Localization in LSR Gene | Polymorphism | Marker Position |
|---|---|---|---|---|---|---|
| 99-14410 | 99-14410/373 | A1 | Pool | 5' regulatory region | Allele 1: C<br>Allele 2: T | 373 of SEQ ID No 2 |
| 99-14424 | 99-14424/353 | A2 | Pool | 5' regulatory region | Allele 1: A<br>Allele 2: G | 353 of SEQ ID No 3 |
| 99-14418 | 99-14418/322 | A3 | Pool | 5' regulatory region | Allele 1: A<br>Allele 2: G | 322 of SEQ ID No 4 |
| 99-14417 | 99-14417/126 | A4 | Pool | 5' regulatory region | Allele 1: C<br>Allele 2: T | 126 of SEQ ID No 5 |
| 99-14417 | 99-14417/334 | A5 | Pool | 5' regulatory region | Allele 1: C<br>Allele 2: T | 334 of SEQ ID No 5 |
| 99-14415 | 99-14415/106 | A6 | Pool | 5' regulatory region | Allele 1: C<br>Allele 2: T | 106 of SEQ ID No 6 |
| 99-14413 | 99-14413/250 | A7 | Pool | 5' regulatory region | Allele 1: A<br>Allele 2: C | 250 of SEQ ID No 7 |
| 99-14413 | 99-14413/353 | A8 | Pool | 5' regulatory region | Allele 1: G<br>Allele 2: T | 383 of SEQ ID No 7 |
| 99-4575 | 99-4575/226 | A9 | Pool | 5' regulatory region | Allele 1: T<br>Allele 2: C | 226 of SEQ ID No 8 |
| 9-19 | 9-19/148 | A10 | Ind | 5' regulatory region | Allele 1: C<br>Allele 2: T | 1243 of SEQ ID No 1 |
| 9-19 | 9-19/307 | A11 | Ind | 5' regulatory region | Allele 1: A<br>Allele 2: T | 1401 of SEQ ID No 1 |
| 9-19 | 9-19/442 | A12 | Pool | 5' regulatory region | Allele 1: C<br>Allele 2: Del C | 1535 of SEQ ID No 1 |
| 9-20 | 9-20/187 | A13 | Ind | 5' regulatory region | Allele 1: A<br>Allele 2: C | 1788 of SEQ ID No 1 |
| 9-1 | 9-1/308 | A14 | Ind | Intron 1 | Allele 1: C<br>Allele 2: G | 2391 of SEQ ID No 1 |
| 9-3 | 9-3/324 | A15 | Ind | Exon2 | Allele 1: C<br>Allele 2: T | 3778 of SEQ ID No 1<br>595 of SEQ ID Nos 13, 15, and 17 |
| 99-14419 | 99-14419/424 | A16 | Pool | Intron2 | Allele 1: T<br>Allele 2: G | 4498 of SEQ ID No 1 |
| 9-24 | 9-24/260 | A17 | Pool | Intron 3 | Allele 1: A<br>Allele 2: G | 15007 of SEQ ID No 1 |
| 9-24 | 9-24/486 | A18 | Ind | Intron 4 | Allele 1: G<br>Allele 2: A | 15233 of SEQ ID No 1 |
| 9-6 | 9-6/187 | A19 | Ind | Exon 5 | Allele 1: C<br>Allele 2: T | 15826 of SEQ ID No 1;<br>940 of SEQ ID No 13<br>883 of SEQ ID No 15 |
| 9-7 | 9-7/148 | A20 | Pool | Intron 5 | Allele 1: G<br>Allele 2: A | 19567 of SEQ ID No 1 |
| 9-7 | 9-7/325 | A21 | Ind | Exon 6 | Allele 1: G<br>Allele 2: A | 19744 of SEQ ID No 1<br>1191 of SEQ ID No 13<br>1134 of SEQ ID No 15<br>987 of SEQ ID No 17 |
| 9-7 | 9-7/367 | A22 | Ind | Intron 6 | Allele 1: A<br>Allele 2: C | 19786 of SEQ ID No 1 |
| 9-9 | 9-9/246 | A23 | Ind | Exon 8 | Allele 1: C<br>Allele 2: G | 20158 of SEQ ID No 1<br>1362 of SEQ ID No 13<br>1305 of SEQ ID No 15<br>1158 of SEQ ID No 17 |
| LSRX9 (17-1) | L5RX9-BM (17-11240) | A24 | Pool | Exon 9 | Allele 1: AGG<br>Allele 2: Del AGG | 20595 of SEQ ID No 1<br>1658 of SEQ ID No 13<br>1601 of SEQ ID No 15<br>1454 of SEQ ID No 17 |
| LSRX9-110 | LSRX10-BM | A25 | Pool | Exon 10 | Allele 1: T<br>Allele 2: G | 21108 of SEQ ID No 1;<br>2079 of SEQ ID No 13;<br>2022 of SEQ ID No 15; |

TABLE 2-continued

| Amplicon | Biallelic Marker | Marker Name | Origin of DNA | Localization in LSR Gene | Polymorphism | Marker Position |
|---|---|---|---|---|---|---|
| 99-4580 | 99-4580/296 | A26 | Pool | 3' regulatory region | Allele 1: A<br>Allele 2: G | 1875 of SEQ ID No 17<br>296 of SEQ ID No 9 |
| 99-4567 | 99-4567/424 | A27 | Pool | 3' regulatory region | Allele 1: C<br>Allele 2: T | 424 of SEQ ID No 10 |
| 99-14420 | 99-14420/477 | A28 | Pool | 3' regulatory region | Allele 1: G<br>Allele 2: T | 542 of SEQ ID No 11 |
| 99-4582 | 99-4582/62 | A29 | Pool | 3' regulatory region | Allele 1: A<br>Allele 2: G | 62 of SEQ ID No 12 |
| 99-4582 | 99-4582/359 | A30 | Pool | 3' regulatory region | Allele 1: G<br>Allele 2: T | 359 of SEQ ID No 12 |
| 17-2 | 17-2/297 | A31 | Ind | 5' regulatory region | Allele 1: C<br>Allele 2: G | 818 of SEQ ID No 1 |
| 9-19 | 9-19-256 | A32 | Ind | 5' regulatory region | Allele 1: A<br>Allele 2: G | 1374 of SEQ ID No 1 |

Example 4

Validation of the Polymorphisms Through Microsequencing

The biallelic markers identified in example 3 were further confirmed and their respective frequencies were determined through microsequencing. Microsequencing was carried out for each individual DNA sample described in Example 1.

Amplification from genomic DNA of individuals was performed by PCR as described above for the detection of the biallelic markers with the same set of PCR primers (Table 1).

The preferred primers used in microsequencing were about 19 nucleotides in length and hybridized just upstream of the considered polymorphic base. According to the invention, the primers used in microsequencing are detailed in Table 3.

TABLE 3

| Marker Name | Marker | Mis. 1 | Position Of Mis 1 | Mis. 2 | Position Of Mis 2 |
|---|---|---|---|---|---|
| 99-14410/373 | A1 | D1 | 350–372 of SEQ ID No 2 | E1 | 374–392 of SEQ ID No 2 |
| 99-14424/353 | A2 | D2 | 334–352 of SEQ ID No 3 | E2 | 354–376 of SEQ ID No 3 |
| 99-14418/322 | A3 | D3 | 299–321 of SEQ ID No 4 | E3 | 323–345 of SEQ ID No 4 |
| 99-14417/126 | A4 | D4 | 103–125 of SEQ ID No 5 | E4 | 127–149 of SEQ ID No 5 |
| 99-14417/334 | A5 | D5 | 311–333 of SEQ ID No 5 | E5 | 335–357 of SEQ ID No 5 |
| 99-14415/106 | A6 | D6 | 83–105 of SEQ ID No 6 | E6 | 107–125 of SEQ ID No 6 |
| 99-14413/250 | A7 | D7 | 227–249 of SEQ ID No 7 | E7 | 251–273 of SEQ ID No 7 |
| 99-14413/383 | A8 | D8 | 360–382 of SEQ ID No 7 | E8 | 384–402 of SEQ ID No 7 |
| 99-4575/226 | A9 | D9 | 207–225 of SEQ ID No 8 | E9 | 227–249 of SEQ ID No 8 |
| 9-19/148 | A10 | D10 | 1224–1242 of SEQ ID No 1 | E10 | 1244–1262 of SEQ ID No 1 |
| 9-19/307 | A11 | D11 | 1382–1400 of SEQ ID No 1 | E11 | 1402–1420 of SEQ ID No 1 |
| 9-19/442 | A12 | D12 | 1516–1534 of SEQ ID No 1 | | |
| 9-20/187 | A13 | D13 | 1769–1787 of SEQ ID No 1 | E12 | 1789–1807 of SEQ ID No 1 |
| 9-1/308 | A14 | D14 | 2372–2390 of SEQ ID No 1 | E13 | 2392–2410 of SEQ ID No 1 |
| 9-3/324 | A15 | D15 | 3759–3777 of SEQ ID No 1 | E14 | 3779–3797 of SEQ ID No 1 |
| 99-14419/424 | A16 | D16 | 4979–4997 of SEQ ID No 1 | E15 | 4999–5017 of SEQ ID No 1 |
| 9-24/260 | A17 | D17 | 14988–15006 of SEQ ID No 1 | E16 | 15008–15026 of SEQ ID No 1 |
| 9-24/486 | A18 | D18 | 15214–15232 of SEQ ID No 1 | E17 | 15234–15252 of SEQ ID No 1 |
| 9-6/187 | A19 | D19 | 15807–15825 of SEQ ID No 1 | E18 | 15827–15845 of SEQ ID No 1 |
| 9-7/148 | A20 | D20 | 19548–19566 of SEQ ID No 1 | E19 | 19568–19586 of SEQ ID No 1 |
| 9-7/325 | A21 | D21 | 19725–19743 of SEQ ID No 1 | E20 | 19745–19763 of SEQ ID No 1 |
| 9-7/367 | A22 | D22 | 19767–19785 of SEQ ID No 1 | E21 | 19787–19805 of SEQ ID No 1 |
| 9-9/246 | A23 | D23 | 20139–20157 of SEQ ID No 1 | E22 | 20159–20177 of SEQ ID No 1 |
| LSRX9-BM | A24 | D24 | 20576–20594 of SEQ ID No 1 | E23 | 20596–20614 of SEQ ID No 1 |

TABLE 3-continued

| Marker Name | Marker | Mis. 1 | Position Of Mis 1 | Mis. 2 | Position Of Mis 2 |
|---|---|---|---|---|---|
| (17-1/240) | | | SEQ ID No 1 | | SEQ ID No 1 |
| LSRX10-BM | A25 | D25 | 21089–21107 of SEQ ID No 1 | E24 | 21109–21127 of SEQ ID No 1 |
| 99-4580/296 | A26 | D26 | 273–295 of SEQ ID No 9 | E25 | 297–315 of SEQ ID No 9 |
| 99-4567/424 | A27 | D27 | 401–423 of SEQ ID No 10 | E26 | 425–443 of SEQ ID No 10 |
| 99-14420/477 | A28 | D28 | 454–476 of SEQ ID No 11 | E27 | 478–500 of SEQ ID No 11 |
| 99-4582/62 | A29 | D29 | 43–61 of SEQ ID No 12 | E28 | 63–85 of SEQ ID No 12 |
| 99-4582/359 | A30 | D30 | 336–358 of SEQ ID No 12 | E29 | 360–378 of SEQ ID No 12 |
| 17-2/297 | A31 | D31 | 799–817 of SEQ ID No 1 | E30 | 819–837 of SEQ ID No 1 |
| 9-19/256 | A32 | D32 | 1330–1373 of SEQ ID No 1 | E31 | 1375–1393 of SEQ ID No 1 |

Mis 1 and Mis 2 respectively refer to microsequencing primers that hybridized with the non-coding strand of the LSR gene or with the coding strand of the LSR gene.

A particular microsequencing primer, namely E24, has been developed for the biallelic marker A24. Indeed, as this polymorphism corresponds to a deletion of three nucleotides AGG, the microsequencing assay needed to be adapted. The deletion variant is detected as follows.

Expected genotypes are diagrammed as shown below with the proximal sequence of the A24 biallelic marker.

In one allele of the A24 biallelic marker, the trinucleotide AGG is present and is in bold. The underlined nucleotides correspond to the possible nucleotide positions detected by the microsequencing assay.

5-TCTCCCACGAGTAATGGTGGGAGGAGAAGCC
GGGCCTACATGCCC-3 (Cr1)

3-AGAGGGTGCTCATTACCACCC
TCCTCTTCGGCCCGGATGTACGGG-5 (W1)

Tcctcttcggcccggatgta (MIS1)

In the other allele of the A24 biallelic marker, the trinucleotide AGG is deleted.

5-TCTCCCACGAGTAATGGTGGG-
AGAAGCCGGGCCTACATGCCC-3 (Cr2)

3-AGAGGGTGCTCATTACCA
CCC-TCTTCGCCCGGATGTACGGG-5 (W2)

Ccctcttcggcccggatgta (MIS2)

The polynucleotide "Cr" is comprised in SEQ ID No 1. It begins at the position 20573 and ends at the position 20618. The polynucleotides Cr1 and Cr2 comprise respectively the allele 1 and the allele 2 of the A24 biallelic marker (see Table 2). The polynucleotides W1 and W2 have respectively the complementary sequence of the polynucleotide Cr1 and Cr2. The polynucleotides MIS1 and MIS2 correspond to the microsequencing primer E23 with either a nucleotide T (MIS1) or a nucleotide C at its 5' end (MIS2).

This microsequencing assay directly detects a "C" or a "T". The incorporation of "T" in the reverse direction correlates to an "A" in the forwards direction that represents the allele comprising the trinucleotide AGG while the incorporation of a "C" translates to a "G" in the forward strand and tests positive for the allele having the deletion of the trinucleotide AGG.

The microsequencing reaction was performed as follows:

The microsequencing reactions were performed as follows: 5 µl of PCR products were added to 5 µl purification mix (2U SAP (Shrimp alkaline phosphate) (Amersham E70092X)); 2U Exonuclease 1 (Amersham E70073Z); and 1 µl SAP buffer (200 mM Tris-HCl pH8, 100 mM MgCl₂) in a microtiter plate. The reaction mixture was incubated 30 minutes at 37° C., and denatured 10 minutes at 94° C. afterwards. To each well was then added 20 µl of microsequencing reaction mixture containing: 10 pmol microsequencing oligonucleotide (19 mers, GENSET, crude synthesis, 5 OD), 1 U Thermosequenase (Amersham E79000G), 1.25 µl Thermosequenase buffer (260 mM Tris HCl pH 9.5, 65 mM MgCl₂), and the two appropriate fluorescent ddNTPs complementary to the nucleotides at the polymorphic site corresponding to both polymorphic bases (11.25 nM TAMRA-ddTTP; 16.25 nM ROX-ddCTP; 1.675 nM REG-ddATP; 1.25 nM RHO-ddGTP; Perkin Elmer, Dye Terminator Set 401095). After 4 minutes at 94° C., 20 PCR cycles of 15 sec at 55° C., 5 sec at 72° C., and 10 sec at 94° C. were carried out in a Tetrad thermocycler (MJ Research). The unincorporated dye terminators were then removed by ethanol precipitation. Samples were finally resuspended in formamide-EDTA loading buffer and heated for 2 min at 95° C. before being loaded on a polyacrylamide sequencing gel. The data were collected by an ABI PRISM 377 DNA sequencer and processed using the GENESCAN software (Perkin Elmer).

Following gel analysis, data were automatically processed with software that allows the determination of the alleles of biallelic markers present in each amplified fragment.

The software evaluates such factors as whether the intensities of the signals resulting from the above microsequencing procedures are weak, normal, or saturated, or whether the signals are ambiguous. In addition, the software identifies significant peaks (according to shape and height criteria). Among the significant peaks, peaks corresponding to the targeted site are identified based on their position. When two significant peaks are detected for the same position, each sample is categorized classification as homozygous or heterozygous type based on the height ratio.

Example 5

Preparation of Antibody Compositions to LSR Variants

Substantially pure protein or polypeptide is isolated from transfected or transformed cells containing an expression vector encoding the LSR protein or a portion thereof. The concentration of protein in the final preparation is adjusted, for example, by concentration on an Amicon filter device, to the level of a few micrograms/mL. Monoclonal or polyclonal antibody to the protein can then be prepared as follows:

A. Monoclonal Antibody Production by Hybridoma Fusion

Monoclonal antibody to epitopes in the LSR protein or a portion thereof can be prepared from murine hybridomas according to the classical method of Kohler. G. and Milstein, C., Nature 256:495 (1975) or derivative methods thereof. Also see Harlow, E., and D., Lane, 1988. Antibodies A Laboratory Manual, Cold Spring Harbor Laboratory, pp. 53–242.

Briefly, a mouse is repetitively inoculated with a few micrograms of the LSR protein or a portion thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., Meth. Enzymol. 70:419 (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, N.Y. Section 21-2.

B. Polyclonal Antibody Production by Immunization

Polyclonal antiserum containing antibodies to heterogeneous epitopes in the LSR protein or a portion thereof can be prepared by immunizing suitable non-human animal with the LSR protein or a portion thereof, which can be unmodified or modified to enhance immunogenicity. A suitable non-human animal is preferably a non-human mammal is selected, usually a mouse, rat, rabbit, goat or horse. Alternatively, a crude preparation which has been enriched for LSR concentration can be used to generate antibodies. Such proteins, fragments or preparations are introduced into the non-human mammal in the presence of an appropriate adjuvant (e.g. aluminum hydroxide, RIBI, etc.) which is known in the art. In addition the protein, fragment or preparation can be pretreated with an agent which will increase antigenicity, such agents are known in the art and include, for example, methylated bovine serum albumin (mBSA). bovine serum albumin (BSA), Hepatitis B surface antigen, and keyhole limpet hemocyanin (KLH). Serum from the immunized animal is collected, treated and tested according to known procedures. If the serum contains polyclonal antibodies to undesired epitopes, the polyclonal antibodies can be purified by immunoaffinity chromatography.

Effective polyclonal antibody production is affected by many factors related both to the antigen and the host species. Also, host animals vary in response to site of inoculations and dose, with both inadequate or excessive doses of antigen resulting in low titer antisera. Small doses (ng level) of antigen administered at multiple intradermal sites appears to be most reliable. Techniques for producing and processing polyclonal antisera are known in the art, see for example, Mayer and Walker (1987). An effective immunization protocol for rabbits can be found in Vaitukaitis, J. et al. J. Clin. Endocrinol. Metab. 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al, Chap. 19 in: Handbook of Experimental Immunology D. Wier (ed) Blackwell (1973). Plateau concentration of antibody is usually in the range of 0.1 to 0.2 mg/ml of serum (about 12 $\mu$M). Affinity of the antisera for the antigen is determined by preparing competitive binding curves, as described, for example, be Fisher, D., Chap. 42 in: Manual of Clinical Immunology, 2d Ed. (Rose and Friedman, Eds.) Amer. Soc. For Microbiol., Washington, D.C. (1980).

Antibody preparations prepared according to either the monoclonal or the polyclonal protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

Example 6

Association of a Frequent LSR Polymorphism with Elevated Plasma TG in Obese Adolescents The association of selected SNPs with clinical values related to metabolic disorders was determined. This example and the following are exemplary only and do not indicate that there are not other significant associations between markers, clinical values, and metabolic disease. However, they do provide examples of methods useful for identifying significant associations useful in diagnostics, predictive medicine, and pharmacogenomics.

1. Marker Selection

Figure 2:
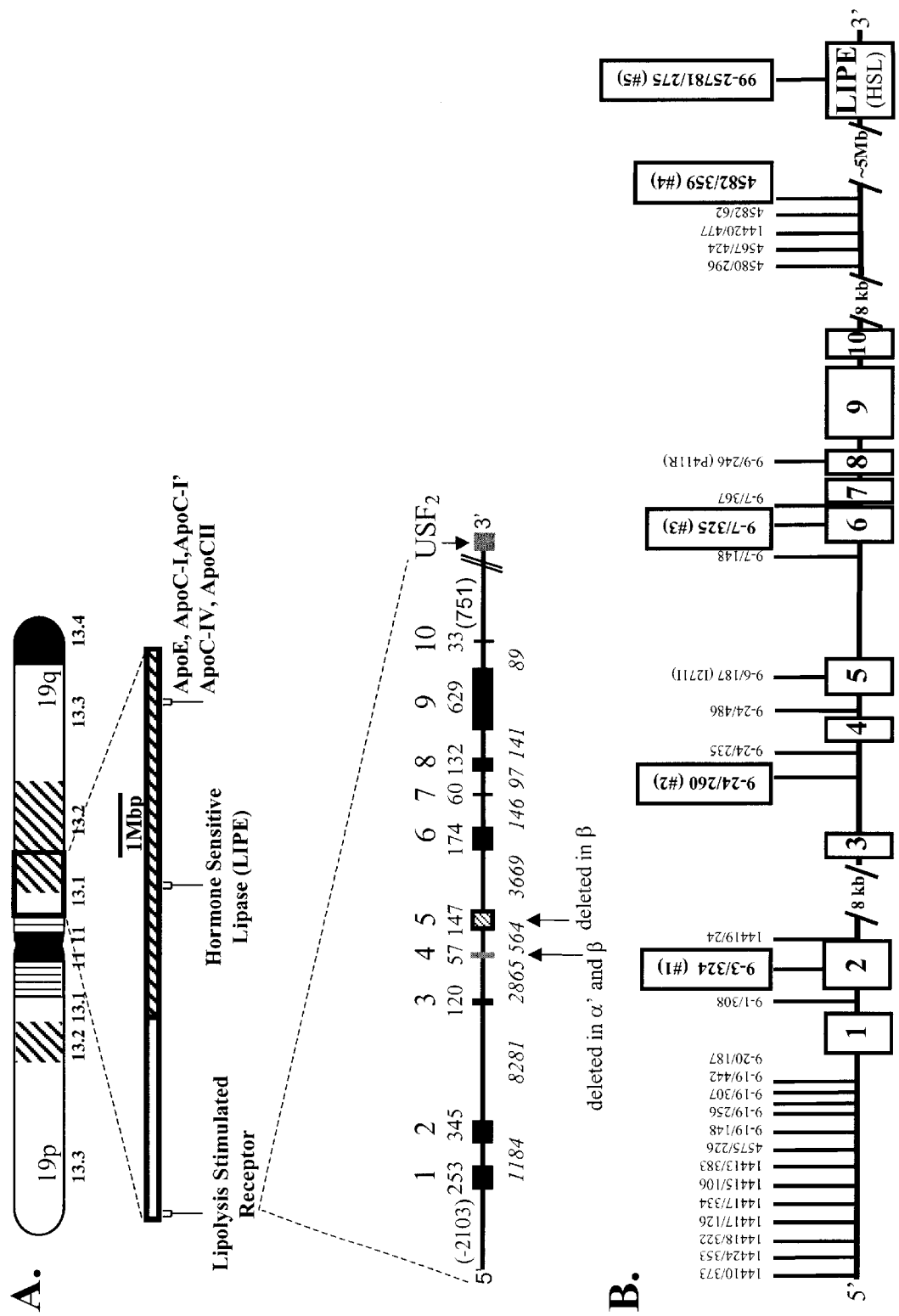
FIGS. 2A and 2B show the chromosomal localization and genomic organization of the LSR gene.

Five markers were selected based on the following three criteria: 1) equidistant coverage of the LSR gene; 2) within the USF2 and LIPE genes; and 3) allele freuency>10%. That the SNPs result in an amino acid change in the LSR protein was not a criteria; many intronic markers can also modulate gene function by affecting the stability of mRNA, the rate of splicing or the production of splice variants. The positions of the five marker, are indicated by open boxes in FIG. 2B. Markers 1, 2, and 3 are A15, A17, and A21, respectiely. Three of the markers are located within the LSR gene (markers 1–3). Markers #1 and #3 are within coding regions. Polymorphism at the site of marker #1 does not translate into variation at the protein level (Val→Val). Marker #3 causes a Ser→Asn substitution in the extracellular domain of the receptor that contains the putative lipoprotein binding site. Marker #2 is located in intron 3, 137 bp upstream of the splice site that generates the different LSR informs. Markers #4 and #5 are found in introns of the USF2 gene and LIPE gene, respectively. The relative locations of USF2 and LIPE to LSR are shown in FIG. 2A.

As a control, 18 random markers distributed in various genomic regions were selected. Chromosomal localization, allele frequency, and Hardy-Weinberg equilibrium testing of those markers is provided in Table 4. All markers used in these studies were in Hardy-Weinberg equilibrium (Table 4). Quality control using known polymoltic sites inserted within each genotyping plate was performed systematically; results indicated an accuracy>98%. Automatic genotype calling on the 23 different SNP's used four this study led to unambiguous genotyping in 96.7% of cases. Ambiguous genotypes were not considered for the analysis. The percentage of ambiguous genotyping occurring for each marker is given in Table 4, which begins on the next page.

| SNPs* | Chromosomal Localization | Allelic variation | Allele Frequency (%) | Hardy-Weinberg Equilibrium $\chi^2$ | Ambiguous Genotype (%) |
|---|---|---|---|---|---|
| SNP ≠ | | | | | |
| 1 | 19q13.1 | C → T | 73 | 0.365 | 1.3 |
| 2 | 19q13.1 | A → G | 62 | 1.660 | 3.1 |
| 3 | 19q13.1 | G → A | 89 | 0.735 | 0.6 |
| 4 | 19q13.1 | G → T | 70 | 0.681 | 0.0 |
| 5 | 19q13.2 | T → C | 65 | 0.091 | 8.2 |
| Random SNP | | | | | |
| A | 7p12–p14 | T → C | 65 | 0252 | 3.1 |
| B | 12p13 | G → A | 52 | 0.049 | 1.3 |
| C | 12p13 | C → A | 63 | 2.172 | 2.5 |
| D | 13q22 | T → C | 74 | 1.194 | 0.6 |
| E | 14q24.1 | A → G | 54 | 0.027 | 1.3 |
| F | 14q31 | T → C | 62 | 0.322 | 1.3 |
| G | 14q31 | G → C | 64 | 0.092 | 6.3 |
| H | 14q22–q23 | T → A | 79 | 0.594 | 6.3 |
| I | 16q22–q24 | G → A | 54 | 1.166 | 5.7 |
| J | 16q24 | A → G | 62 | 0.656 | 3.8 |
| K | 17p13.3 | T → C | 72 | 1.790 | 3.8 |
| L | 17p13.3 | A → G | 78 | 0.562 | 4.4 |
| M | 18p11–p31 | A → G | 51 | 0.319 | 2.5 |
| N | 21q22.8 | A → G | 56 | 0.054 | 7.5 |
| O | 21q22 | C → T | 59 | 1.475 | 3.1 |
| P | 21q22.3 | A → G | 70 | 2.070 | 3.1 |
| Q | 21q22.3 | T → C | 60 | 1.709 | 4.4 |
| R | 21q22.1 | A → G | 56 | 1.060 | 0.0 |

*SNPs were identified using a pool of 100 DNA clones, as described herein. The allele frequency and Hardy-Weinberg equilibrium were measured for each marker. The % of each ambiguous genotype that was not considered in the analysis is provided in the last column.

2. Subject Selection

The subjects participating in the study were 161 unrelated Caucasian girls that lived in the region of Paris. Obese girls attended weight reduction program at the Margency clinic or Saint Vincent de Paul hospital. All subjects developed severe obesity in early childhood as defined by a BMI exceeding the 98$^{th}$ percentile of the population.

At the time of admission weights and heights were recorded, blood samples were collected, the buffy coat was isolated for DNA preparation and the plasma was separated for biochemical analysis. Plasma TG, total cholesterol and FFA, were determined using commercially available enzymatic kits and following manufacturer instructions. Blood sampling and testing of these subjects were performed prior to any weight reduction treatment.

3. DNA Extraction

Blood samples were centrifuged 20 min at 2000 rpm (Beckman Allegra 6 centrifuge, GH-3.8A rotor). The middle leukocyte layer was removed and washed 2 times in large volumes of mM Tris HCl, pH 7.6 containing 5 mM $MgCl_2$ and 10 mM NaCl (repelleting was performed by centrifuging 15 min at 2400 rpm). To the cell pellet was added 3 mL of 10 mM Tris HCl, pH 7.6 containing 1 mM EDTA and 0.4 mM NaCl, 200 μL 10% (w/v) SDS, and 500 μL proteinase K (1 mg/mL). After mixing vigorously by vortexing, tubes were placed in a shaking water bath at 42° C. for 5 h. Tubes were then chilled on ice for 10 min. To precipitate proteins, 1 mL of 5 M NaCl was added followed by vortexing for 20 sec. The precipitates there pelleted by centrifugation for 20 min at 3750 rpm with no brake, and the supernatant removed. To precipitate the DNA, isopropanol (5 mL) was added to the supernatant, followed by recentrifugation at 3750 rpm for 20 min. The supernatant was discarded and 5 mL of 70% ethanol was added to the DNA pellet. After leaving 6 h or overnight at 4° C., the samples were spun at 3500 rpm for 5 min. The supernatant was poured off and discarded, and the pellet left to air dry. Once dry, 1.5 mL 10 mM Tris HCl containing 10 mM EDTA was added and samples were incubated at room temperature on a rocker platform to rehydrate the DNA. DNA concentration was evaluated and the DNA was stored at −20° C.

4. Clinical Characteristics

The subjects clinical characteristics are described in Table 5. These values are for plasma samples collected after an overnight fast without standardization of the meal taken the night prior to admission in the clinical laboratory. It has been shown that under these conditions, plasma TG concentrations can vary considerably from day to day in the same individual (21).

TABLE 5

| Characteristics of Obese Children | |
|---|---|
| Parameter | Value* |
| n | 161 |
| Age (yrs) | 12 ± 0.2 |
| Body mass index (kg/m²) | 30.4 ± 0.5 |
| Plasma triglycerides (mg/dl) | 104 ± 4.0 |
| Plasma total cholesterol (mg/dl) | 172 ± 3.0 |
| Plasma FFA (mM) | 0.612 ± 0.022 |

*Mean ± SEM

5. SNP Identification

The amplicon of interest included the exons and introns of the LSR, USF, and LIPE genes. Random markers were generated from amplicons derived from BAC sequences of the indicated genomic regions (Table 1). PCR primers were used to amplify the corresponding genomic sequence in a pool of DNA from 100 unrelated individuals (blood donors of French origin).

The PCR reaction (25 mL) contained 2 ηg/μL pealed DNA, 2 mM $MgCl_2$, 200 μM of each dNTP, 2.9 ηg/μL each primer, 0.05 unit/μL Ampli Taq Gold DNA polymerase, Perkin Elmer, Foster City, Calif.) and 1×PCR buffer (10 mM Tris HCl pH 8.3, 50 mM KCl). Amplification reactions there performed in a PTC200 MJ Research Thermocycler, with initial denaturation at 95° C. for 30 sec, annealing at 54° C. for 1 min, and extension at 72° C. for 30 sec. After cycling, a final elongation step was performed at 72° C. for 10 min.

Amplification products from pooled DNA samples were sequenced on both strands by fluorescent automated sequencing on ABI 377 sequences (Perkin Elmer), using a dye-primer cycle analysis and DNA sequence extraction with ABI Prism DNA sequencing Analysis software. Sequence data analysis were automatically processed with AnaPolys (Genset, Paris, France), a software program designed to detect the presence of SNPs among pooled amplified fragments. The polymorphism search is based on the presence of superimposed peaks in the electrophoresis pattern from both strands, resulting from two bases occurring at the same position. The detection limit for the frequency of SNPs detected by microsequencing pools of 100 individuals is about 10% for the minor allele, as verified by sequencing pool of known allelic frequencies. However, more than 90% of the SNPs detected by the pooling method have a frequency for minor allele higher than 20%.

6. Genotyping

Genotyping of individual DNA samples was performed using a microsequencing procedure. Amplification products containing the SNPs were obtained by performing PCR reactions similar to those described for SNP identification (and supra). After purification of the amplification products, the microsequencing reaction mixture was prepared by adding in a 20 μL final volume: 10 pmol microsequencing primer (which hybridizes just upstream of the polymorphic base). 1 U of Thermosequense (Amersham Pharmacia Biotech, Piscataway, N.J.) or TaqFS (Perkin Elmer) and the 2 appropriate fluorescent ddNTPs (Perkin Elmer, Dye Terminator Set) complementary to the nucleotides at the polymorphic site of each SNP tested. After 4 minutes at 94° C.; 20 microsequencing cycles of 15 sec at 55° C., 5 sec at 72° C., aid 10 sec at 94° C. were carried out in a GeneAmp PCR System 9700 (PE Applied Biosystem). After the reaction, the 3'-extended primers were precipitated to remove the unincorporated fluorescent ddNTPs and analysed by electrophoresis on ABI 377 sequencers. Following gel analysis with GENESCAN software (Perkin Elmer), data were automatically processed with AnaMIS (Genset), a software program that allows the determination of the alleles of SNPs present in each amplified fragment based on a fluorescent intensity ratio. Genotype data were compiled and checked for scoring accuracy with 32 duplicate samples.

7. Statistical Analysis

Allelic frequencies and $\chi^2$ test of Hardy Weinberg proportions were performed as data were collected (Hill, W. G. (1974) in *Heredity*, (Edinburgh), pp. 229–239; Terwilliger, J. O. (1994) *Handbook for Human Genetic Linkage* (John Hopkins University Press, Baltimore); Schneider et al. (1997) *Arlequin: A software for population genetic data analysis*, 1.1 edition (Genetics and Biometry Laboratory, Department of Anthropology, University of Geneva, Geneva)). Differences in genotype frequencies within obese subjects separated according to the secondary phenotype were analyzed using $3 \times 2\chi^2$ analysis. Two locus linkage disequilibrium (D) values were calculated from unphased genotypic data for pairs of SNPs located within the 19q13 locus (Hill, W. G. (1974) in *Heredity*, (Edinburgh), pp. 229–239; Terwilliger, J. O. (1994) *Handbook for Human Genetic Linkage* (John Hopkins University Press, Baltimore)) and were tested for significance from estimates of the four haplotypes frequencies which were obtained from the output of EH computer program (Schneider et al. (1997) *Arlequin: A software for population genetic data analysis*, 1.1 edition (Genetics and Biometry Laboratory, Department of Anthropology, University of Geneva, Geneva)). D' was calculated as $D/D_{max}$ using $D_{max}$ positive and negative obtained from allele frequency products. The SAS programming language was used to construct, analyze and format databases for input into other genetic linkage computer programs.

8. Comparison of Genotypic Frequencies

Figure 3:
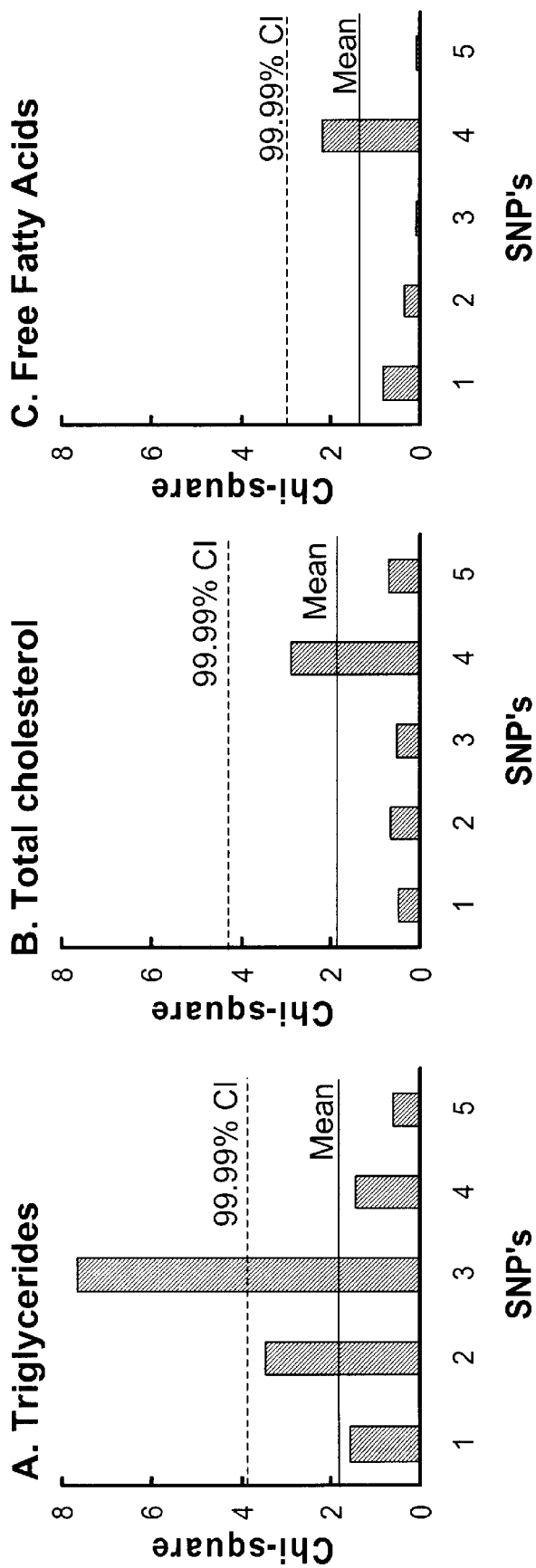
FIGS. 3A, 3B, and 3C are graphical representations of an association study of plasma lipid values with LSR SNPs. Differences in genotype frequency in two groups of adolescent girls that were separated according to their plasma TG (FIG. 3A), total cholesterol (FIG. 3B) and free fatty acid (FIG. 3C) values being greater or lower than the mean of the entire population (Table 5) were analyzed by $3 \times 2 \chi^2$ (chi square) analysis, $\chi^2$ values for each test marker are represented as bars. The mean $\chi^2$ value obtained with the 18 random markers is shown as a solid line; the calculated 99.99% confidence interval of this mean is shown as a dotted line for each parameter.

The genotype frequencies (for test and control markers) of subjects that had plasma TG, total cholesterol, and FFA values above the mean value of the population were compared with the genotype frequencies of subjects with values below the mean. The $\chi^2$ value obtained for each of the 5 candidate markers is shown in FIG. 3. Only the genotype frequency of LSR SNP #3 shows a significant difference between the two groups of obese subjects, and only for those subjects with plasma TG above or below the mean of the population (FIG. 3A). This $\chi^2$ value exceeded the 99.99% confidence interval of the mean $\chi^2$ obtained with the random markers and that of any $\chi^2$ obtained with the 18 random markers. The random marker mean and 99.99% confidence interval are shown as a solid and dotted line, respectively. No significant changes in genotype frequency of LSR markers were observed when the obese population was separated according to the total cholesterol or FFA levels. These data suggest that the mutation G→A at base 19739, causing a Ser→Asn substitution (amino acid residue 363), selectively influences plasma TG levels in obese adolescent girls.

In adolescent girls, normal plasma TG values range between 37 and 131 mg/dl (20); hypertriglycerdemia is >130 mg/dl TG. A comparison of the genotype frequency of hypertriglyceridemic individuals relative to those with normal TG showed that 33% of the hypertriglyceridemic individuals (n=35) had at least one A allele, while only 16% of the normotriglyceridemic individuals (n=125) had the A allele ($\chi^2$=4.5, p<0.04). Calculation of the odds ratio of being hypertriglyceridemic for obese girls as a direct consequence of LSR mutation returned a value of 2.5.

The LSR SNP #3 polymorphism that causes an asparagine to serine mutation in the external domain of the LSR protein, is in close proximity with the LSR putative lipoprotein binding domain. Thus, this polymorphism of the LSR gene appears to cause a mutation in the LSR protein that decreases the activity, of LSR as lipoprotein receptor. Since LSR serves primarily for the removal of TG rich lipoprotein, impairment of this function due to genetic polymorphism is therefore likely to cause hyperlipidemia in obese adolescent girls. Although this result was found in studies with adolescent girls, there is no apriori reason to suspect that a similar result will not be found with adolescent boys, or that a similar effect is not also present in adults of both sexes.

Example 7

Association of a Frequent LSR Polymorphism with Postprandial Lipemia in Obese Adolescents In this study, both fasting and postprandial plasma TG were determined for 34 obese adolescent girls admitted to clinical research centers. The plasma TG values were measured in a research laboratory. Except as otherwise indicated, the materials and methods were the same as those described for Example 6, above.

1. Subject Selection and Testing

A subset of the subjects described in Example 6 (n=34) ere admitted to the clinic on the evening prior to the test. They consumed a normal standard test meal, and were not allowed anything except water for 12 h. At 8:00 AM, plasma was collected and the individuals consumed a standardized high fat test meal within 15 min. The high fat test meal provided 1000 kcal, contained 62% fat (29% saturated, 27% monounsaturated and 44% polyunsaturated fat), 29% carbohydrate and 9% protein, and consisted of bread and butter, eggs with mayonnaise, cheese, salad with sunflower oil, and applesauce. Blood samples were collected before, and 2 and 4 hour after this meal.

All parents of obese children provided informed consent for biological testing and the use of DNA for genetic analysis. All analyses were conducted anonymously according to the rule of the *French Comission Nationale Informatique et Libertés*. The study protocol was approved by the *Conité Consultatif de Protection des Personnes Participants `a la Recherche Clinique*.

2. Comparison of Genotypic Frequencies

Figure 4:
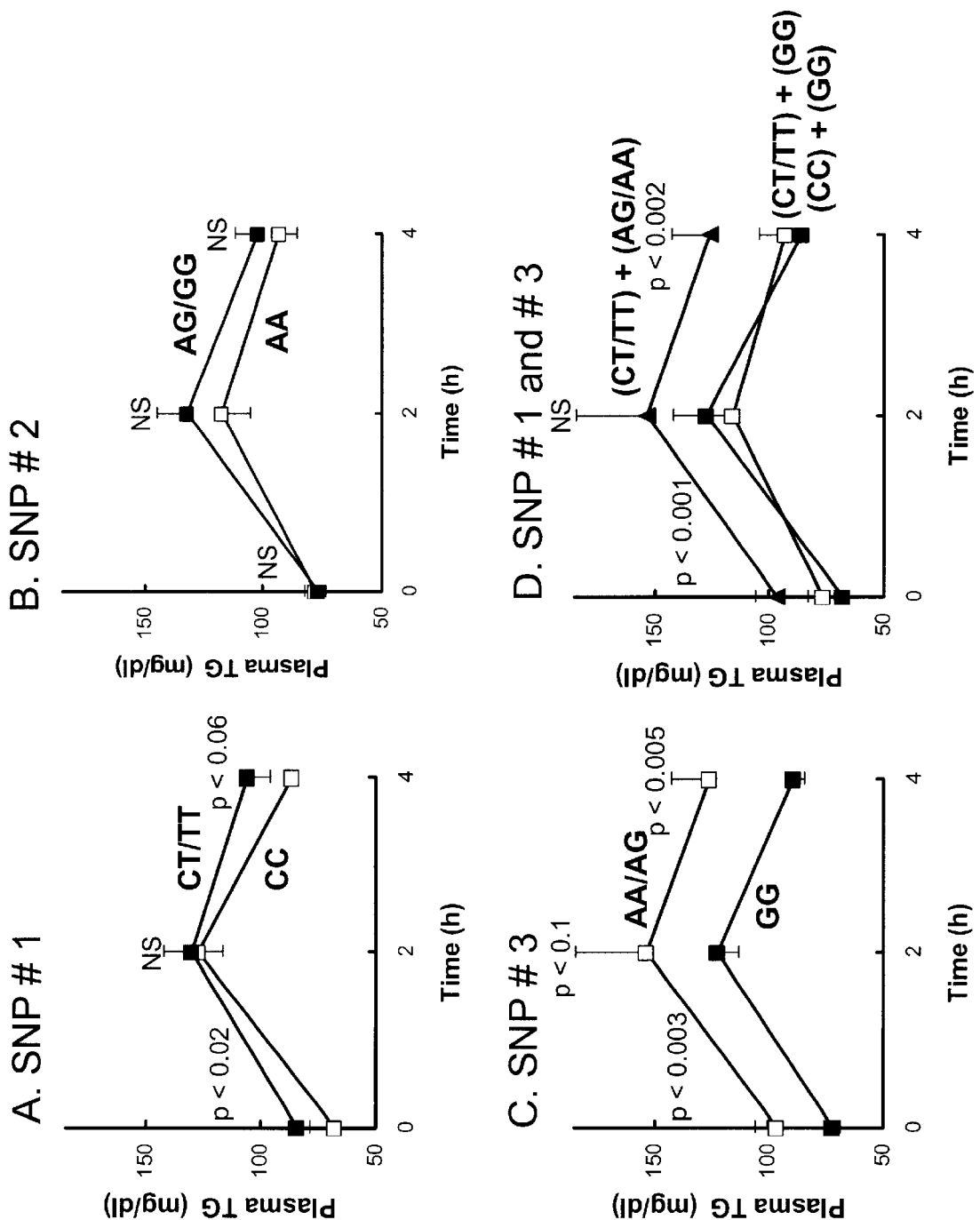
FIGS. 4A, 4B, 4C, and 4D shots a graphical representation of the effect of the LSR exon 6 coding mutation on postprandial lipemia in obese adolescent girls. Thirty-four overnight-fasted obese adolescent girls consumed a high-fat test meal. Plasma TG were determined before, 2, and 4 hr after this meal. The genotypes of LSR markers #1, 2, and 3 were determined as described herein. The postprandial response (mean±SEM) as a function of genotype difference at each polymorphic site is shown in FIG. 4A, 4B, and 4C.

The effect of LSK genotype (Markers #1, 2 and 3) on the postprandial triglyceride response to the test meal is shown in FIG. 4A–C. Subjects that were homozygous GG (Ser) for marker #3 had a significantly lower plasma TG level both before and 4 h after the meal (FIG. 4C). Genotype differences at LSR marker #2 had no detectable effect on fasting and postprandial lipemia (FIG. 4B). Interestingly, LSR marker #1 appeared to exert significant influence on fasting plasma TG levels (FIG. 4A).

To determine whether the apparent fasting effect of genotype at marker #1 was independent of LSR marker #3, we plotted the plasma TG response, taking into account the genotype of both marker #1 and #3 (FIG. 4D). LSR marker #1 polymorphisms had no influence on the postprandial response of individuals that had the normal GG genotype at marker #3. However, no individual was found to combine the frequent allele at marker #1 and the rare allele at marker #3. Thus, it is not possible to determine whether such associations would aggravate or reduce the abnormal lipid response seen in subjects with the Asn mutation.

The simplest explanation for the influence of SNP marker #1 on fasting plasma lipid values is that this marker is in linkage disequilibrium with marker #3 and simply translates, although to a lower degree, the abnormality of function caused by amino acid substitution. To test for this possibility, the degree of linkage disequilibrium among all 5 test markers was determined. The data show that all 3 markers within the LSR gene are in linkage disequilibrium (data not shown). It is therefore not surprising that although silent at the protein level, marker #1 influences significantly plasma TG by virtue of linkage with marker #3. This also explains why none of the 161 subjects had both CC and AG or AA genotype for marker #1 and #3, respectively.

3. Sequence Analysis

Genomic DNA of subjects homozygous for either the Ser (n=12) or Asn (n=3) substitution was amplified by PCR and all LSR exons were sequenced in both directions. No other coding mutation besides the Ser→Asn substitution were detected. Thus, the influence of marker #3 on plasma TG appears to result directs from the mutation it causes in the LSR protein. SNP#3 appears to directly influence both fasting and postprandial plasma TG per se, not simply signaling the presence of another unidentified mutation.

4. Significance and Hypotheses

Although not intending to be limited in any may, the inventors hypothesize that the mutation of LSR exon 6 that removes an alcohol function group and introduces a basic amino acid reduces the efficiency of the receptor and decreases the rate of removal of dietary TG. The fact that this mutation is associated with lower levels of fasting and 4 h postprandial plasma TG, but does not significantly affect plasma TG measured 2 h after the meal, is in keeping with this interpretation. The inventors further hypothesize that at the time of the postprandial peak (2 h), plasma TG levels are mostly determined by the rate of release of chylomicrons by the intestine and the rate of TG hydrolysis by lipoprotein lipase and possibly also hepatic lipase. After 4 h, however, alternate mechanisms relying on cellular uptake of chylomicron remnants appear to play a significant role (Karpe, et al. (1997) *J. Lipid Res.* 38, 2335–2343).

The current study establishes that at leas, in obese adolescent girls, polymorphisms of the LSR gene significantly influence the metabolism of TG-rich lipoproteins. Thus, current genetic evidence supports the notion that the LDL-receptor and the LSR contribute to the removal of lipoproteins. Defects of the LDL-receptor cause primarily hypercholesterolemia, while defects of the LSR influence in obese adolescent girls hypertriolyceridemia without hypercholesterolemia. Although functional mutation of the LDL-receptor causes massive hypercholesterolemia in most affected individuals, mutation of the LSR gene only increased by 2.5 fold the odds of being hypertriglyceridemic for obese adolescent girls. In addition, a number of individuals with the mutation have low levels of TG and conversely about two-thirds of obese subjects with hypertriglyceridemia show no abnormalities at the level of the LSR gene. Clearly, environmental factors and other genes also influence plasma TG levels. With the availability of large-scale genotyping, it will be possible to simultaneously analyze the influence of those genes and thereby to determine their relative importance with respect to each other.

In women, hypertriglyceridemia, which is the most common lipid abnormality observed in survivor, of myocardial infarction (Goldstein et al. (1973) *J. Clin. Invest.* 52, 1533–1543), is considered an independent risk factor of cardiovascular disease (Austin, et al. (1998) *Am. J. Cardiol.* 81, 7B–12B). Thus, genotyping LSR marker #3 may provide a diagnostic tool to predict the risk of cardiovascular complication in obese subjects (and potentially even in non-obese subjects).

The inventors also postulate that it is possible that LSR polymorphisms contribute to hypertriglyceridemia only in subjects with excess body weight. Indeed, decreased LSR expression may reveal the functional effect of small mutations in the LSR protein that would otherwise remain silent. In this perspective, it is interesting to note that defective clearance of chylomicrons that occurs in type III hyperlipidemia is often rapidly corrected by weight reduction (Mahley, R. W., and Rail, Jr., S. C. (1995) in *The Molecular Basis of Inherited Disease*, eds. Scriver, et al. (McGraw Hill Inc., New York), pp. 1953–1980). Since LSR does not bind β-VLDL isolated from a subject with type III hyperlipidemia and with the apoE2/2 phenotype (Yen, et al. (1994) *Biochemistry* 33, 1172–1180.), this suggests that reduced LSR expression due to excess body weight causes, in conjunction with abnormal apoE isoforms, the appearance of type III hyperlipidemia.

To our knowledge, this study is the first report taking advantage of the SNP technology to validate the function of newly identified genes. Currently, the most definitive evidence to assign a function to a gene are obtained through transgenics or knock-out technologies. Although this approach has provided definitive and invaluable information, it has also significant limitations (Breslow. J. L. (1994) *Annu. Rev. Physiol.* 56. 797–810). Indeed, inactivation of vital genes often cause embryonic or neonatal mortality (Herz, et al. (1992) *Cell* 71, 411–421). Also, it remains difficult to extrapolate mice data to human physiology. For example, mice deficient for the LDL-receptor are far less hypercholesterolemic than human subjects homozygous for familial hypercholesterolemia (Brown & Goldstein (1986) *Science* 232, 34–47; Ishibashi, et al. (1993) *J. Clin. Invest.* 92, 883–893). Finally, with the progress of the genome project, identification of genes will proceed at a pace that exceeds the possibility of transgenic or knock-out production, even when envisioned at the industrial level. Clearly, there is a need for an experimental method allowing rapid evaluation of the function of a gene in a context directly relevant to human pathology. The study reported here takes LSR as an example to show that systematic SNP analysis that includes a large number of random control markers, allows testing of the function of a newly identified gene in the context of a pathology directly relevant to humans.

Example 8

Figure 5:
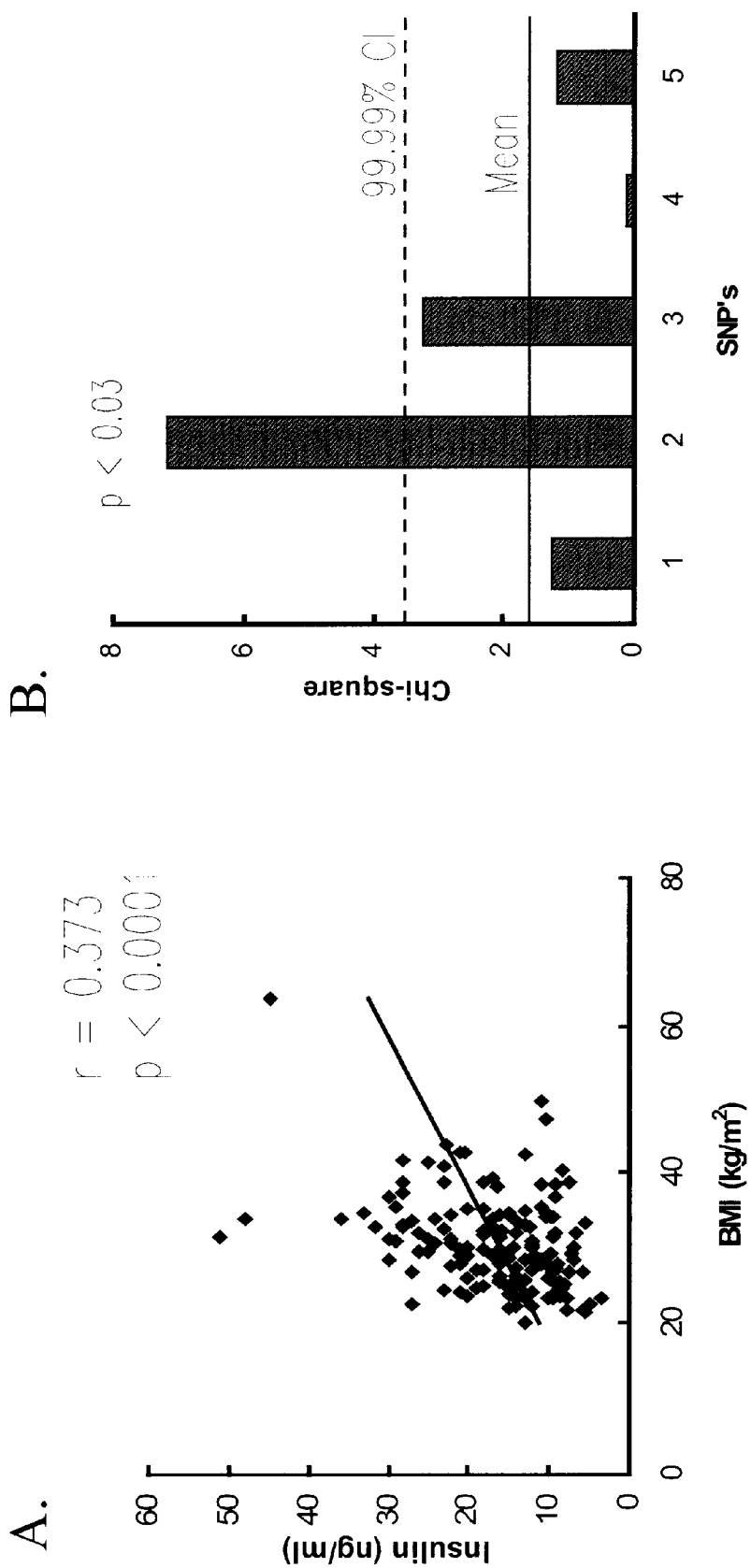
FIGS. 5A and 5B show the effect of LSR polymorphisms on the insulin to BMI relationship in obese adolescent girls. Fasting plasma insulin levels were determined in a population of obese adolescent girls and ere plotted against their BMI and a regression line was generated (FIG. 5A). Genotype frequencies of the 5 LSR markers were compared based on whether individuals were above or below the regression line and presented as a $\chi^2$ analysis (FIG. 5B). The results show that LSR marker 2 significantly influences the relationship between insulin and BMI in obese adolescent girls. The mean and 99.99% confidence interval of random markers are shown as solid and dotted lines, respectively.

Association of a Frequent LSR Polymorphism with Insulin and Glucose Levels in Obese Adolescents Insulin:

In obese children, insulin is strongly and positively correlated with BMI, in agreement with previous studies (FIG. 5A). The association of LSR polymorphism with these variables was determined using an analysis similar to that described above (Example 6).

The obese population was divided into separate populations based on whether the individual fell above or below the insulin-BMI regression line; genotype frequencies in each group were compared (FIG. 5B). The results show that LSR polymorphism shows an association with insulin levels relative to BMI. Genotype frequencies of marker #2 were significantly different in subjects with high insulin to BMI ratios (p<0.03). The $\chi^2$ value largely exceeded that defined by the distribution of random markers. Subjects homozygous for the A allele, had significantly higher Insulin to BMI ratios than subjects that were either heterozygous or homozygous for the G allele: 0.571+/−0.058 and 0.505+/−0.058 (p<0.05) respectively.

Thus, the data indicate that in individuals homozygous for the A allele, the level of circulating insulin normalized to BMI is higher than in those with the G allele. This suggests that LSR plays a previously unsuspected role in determining plasma insulin levels, and may also influence the level of insulin resistance in obese adolescent girls. Again, there is no reason to suspect that similar results would not be found for adolescent boost or adults of both sexes.

Glucose Response:

To further validate the association of LSR marker #2 with insulin sensitivity, a subset of 120 overnight fasted obese children received 50 g of glucose per os. Both plasma glucose and insulin concentrations were measured on samples collected prior and 2 hours after this test.

Subjects with AA genotype for marker #2 showed a significantly higher increase in plasma glucose relative to insulin than those that were GG (FIG. 6B). Subjects heterozygous for marker #2 had an intermediate response. In the group that were AA at marker #2, 7 individuals out of 54 had plasma glucose levels at 2 h greater than 120 mg/dl. In the AG/GG group only 2 out of 66 had values greater than 120 mg/dl (p<0.05). Genotype differences at the site of markers #1, 3, or 4 did not significantly influence the glucose to insulin changes after glucose load (FIG. 6A, 6C, and 6D).

Figure 6:
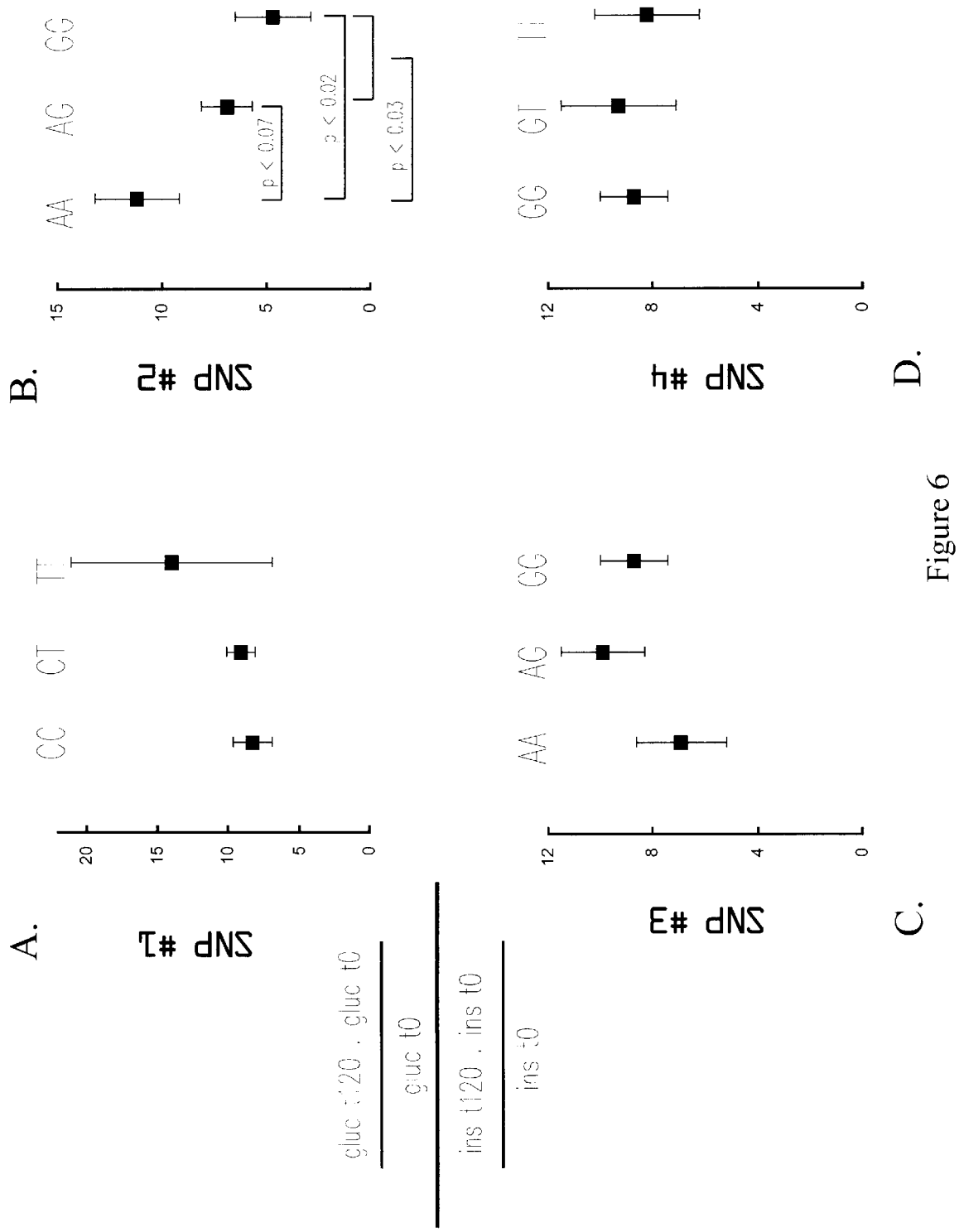
FIGS. 6A, 6B, 6C, and 6D show the effect of the LSR polymorphism on glucose tolerance in obese adolescent girls. Glucose and insulin concentrations were determined on plasma samples taken before (t0) and 2h after (t120) a glucose tolerance test and the relative increase of plasma glucose compared with the increase in plasma insulin was calculated and plotted as a function of SNP genotype. SNP #1 is shown in FIG. 6A. SNP #2 in FIG. 6B, SNP #3 in FIG. 6C, and SNP #4 in FIG. 6D. The data show that only the polymorphism at LSR marker 2 significantly influences the ratio of the relative increase of plasma glucose to that of the relative increase in plasma insulin.
Figure 7:
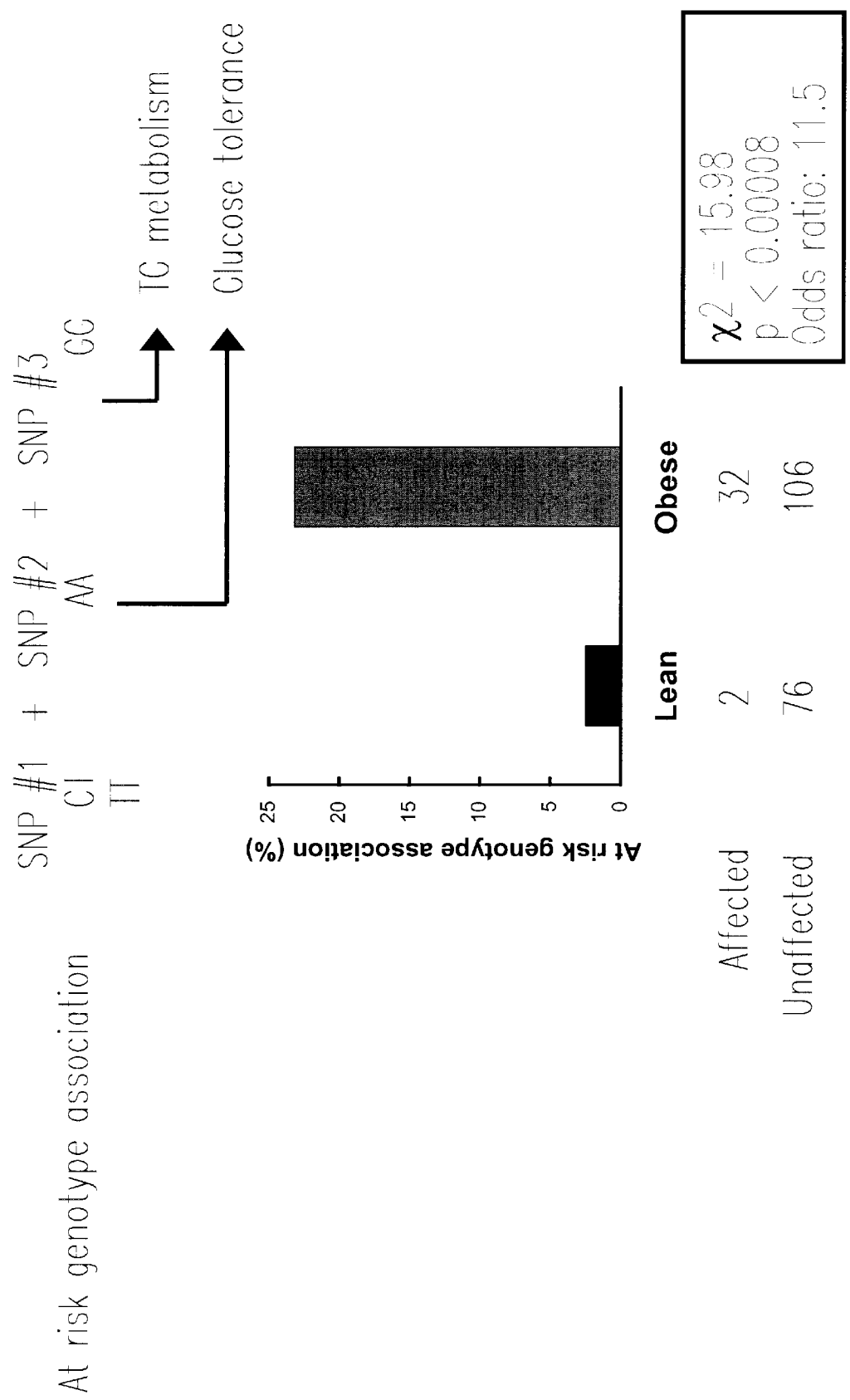
FIG. 7 shows the association of LSR polymorphisms with obesity in human subjects. The genotype of 3 LSR SNPs was determined in a population of lean adult Caucasians (Lean), as well as in a population of obese Caucasian girls (Obese). Genotype comparisons showed an association between obese subjects and the CT/TT, AA, GG genotype for marker #1, #2 and #3, respectively. The calculated $\chi^2$ (chi square) and odds ratio are also provided.

Consistent with the association of marker #2 with sinsulin to BMI ratios (FIG. 5), subjects homozygous for the A allele at the level of LSR marker 2 had a significantly higher increase in glucose relative to insulin than those heterozygous or homozygous for the G allele (FIG. 6). This indicates that individuals with relatively higher insulin to body weight ratio (FIG. 5), are also those with a relatively higher degree of glucose intolerance. Thus, genotyping LSR marker 2 allows prediction not only of the insulin to BMI ratio, but also of the level of glucose tolerance. This indicates that this marker is a significant predictor of the risk in developing type II diabetes at a later age and thus useful for predictive medicine and diagnostics.

The putative molecular mechanisms through which the products of the LSR gene influence insulin sensitivity are two-fold (although the inventors do not wish to be limited by the following hypotheses). First LSR is a receptor that undergos conformational changes upon binding of FFA. The LSR primary sequence is compatible with a function of receptor signaling through phosphorylation. FFA concentration in the portal system have been shown to significantly influence the risk of development of type II diabetes. We therefore speculate that FFA binding to LSR causes signaling to the cell that decreases the efficiency of insulin signaling to the insulin receptor. Second, the LSR α' subunit binds with leptin with high affinity and causes mobilization of LSR from intracellular vesicles to the cell surface. Leptin has been previously shown to modulate insulin sensitivity. Thus, it is possible that the polymorphism at the level of LSR marker #2, indicates a disfunction of the receptor in either its ability to bind leptin, to bind FFA or to signal to the cell.

Example 9

Association of Frequent LSR Polymorphisms Keith Obesity in Adolescents

All subjects (case and control) were female Caucasians. Subjects in the case group developed severe excess body weight during childhood (BMI>than 98th percentile (n=138)), while control subjects remained lean throughout adulthood (BMI 18-23 (n=78)). All subjects participating to this study lived in the regions of Paris or Brussels. Some clinical characteristics of case and controls are summarized in Table 5 (above).

The genotype of markers 1, 2, and 3 of LSR were determined for the populations of lean and obese subjects. Analysis of the genotype association showed that obese subjects had a much greater frequency of CT/TT, AA, GG genotypes at markers #1, #2 and #3, respectively. This genotype association was found with a frequency of 23% in the obese group, and with a frequency of 2.5% in the lean group.

Estimation of the probability that this difference in frequency occurred randomly was determined by Chi square analysis. The calculated Chi square was 15.98 (p<0.00008). Thus it unlikely that the genotype association defined above occurred with a greater frequency in the obese population by chance. It is more probable that this polymorphism indicates the presence of a disfunction of the receptor that directly increases the chance that an individual will become obese.

Estimation of the probability that the SNPs correlate with obesity and indicate a receptor disfunction was determined by calculation of the odds ratio. This calculation returned an estimate of 11.5. Thus, individuals who are CT/TT+AA+GG for LSR markers 1, 2 and 3 are 11.5 times more likely to become obese than those individuals with a different genotype for those markers. Thus, genotyping LSR Markers #1, #2 and #3 allows a prediction of the probability that an individual will become obese. The molecular mechanisms through which LSR could cause obesity have been described previously, and include 1) binding of plasma FFA, 2) processing of dietary lipids, 2) processing of leptin, 3) leptin signaling, 4) modulation of insulin sensitivity, and 5) leptin transport across the blood brain barrier.

In General:

Our data show for the first time that SNP polymorphism analysis provides a readily accessible tool to test the predicted function of a newly identified gene directly in the context of relevant human pathology. Further, SNP analysis performed in the context of a dense network of secondary phenotypic data may lead to the discovery of previously unsuspected functions and to the formulation of new physiologically relevant hypotheses.

The data presented herein provide genetic arguments validating the hypothesis that LSR contributes in a quantitatively significant way to the clearance from plasma of TGRL. In girls, defect of function does directly cause massive obesity in early childhood. However, it remains possible that defective clearance of dietary lipids will also lead to late onset obesity. Indeed mice with a defect of lipid oxidation in the liver develop obesity and hyperlipidemia at the age of 6 months. The influence of the LSR gene on the occurrence of obesity in early childhood is linked to a previously unsuspected role of the LSR gene product in the regulation of insulin signaling. It is striking that a single gene, primarily expressed in the liver, directly influences 3 of the 4 symptoms that characterize Syndrome X. This highly prevalent syndrome associates obesity, insulin resistance, hypertriglyceridemia and hypertension. The predictive value of LSR markers for hypertension and in determining the occurrence of syndrome X in obese adults can also be investigated using similar association studies.

While preferred embodiments of the invention have been illustrated and described, it will be appreciated that various changes can be made therein by one skilled in the art without departing from the spirit and scope of the invention.

The following references are incorporated herein by reference in their entirety.

REFERENCES

Abbondanzo S J et al., 1993, Methods in Enzymology, Academic Press, New York, pp. 803–823.

Ajioka R. S. et al., *Am. J. Hum. Genet.*, 60:1439–1447, 1997.

Austin M. A., Hokanson, J. E., Edwards, K. L. (1998) *Am. J. Cardiol.* 81, 7B–12B.

Ausubel et al., 1989, Current Protocols in Molecular Biology, Green Publishing Associates and Wiley Interscience, N.Y.

Beaucage et al., *Tetrahedron Lett* 1981, 22: 1859–1862.

Bradley A., 1987, Production and analysis of chimaeric mice, In: E. J. Robertson (Ed.), Teratocarcinomas and embryonic stem cells: A practical approach, IRL Press, Oxford, pp. 113.

Breslow, J. L. (1994) *Annu. Rev. Physiol.* 56, 797–810.

Brown E L, Belagaje R, Ryan M J, Khorana H G, *Methods Enzymol* 1979; 68:109–151.

Brown & Goldstein (1986) *Science* 232, 34–47.

Chai H. et al., 1993, *Biotechnol. Appl. Biochem.*, 18:259–273.

Chee et al., 1996, *Science*, 274:610–614.

Chen et al., 1987, Mol. Cell. Biol., 7: 2745–2752.

Chen and Kwok *Nucleic Acids Research* 25:347–353, 1997.

Chen et al. *Proc. Natl. Acad. Sci. USA* 94/20 10756–10761, 1997.

Chou J. Y., 1989, Mol. Endocrinol., 3: 11511–1514.

Clark A. G. *Mol. Biol. Evol.*, 7: 111–122, 1990.

Compton J. *Nature.* 1991 Mar. 7: 350(6313): 91–92.

Dempster et al., *J. R. Stat. Soc.* 39B: 1–38, 1977.

Excoffier L. and Slatkin M., *Mol. Biol. Evol.*, 12(5): 921–927, 1995.

Feldman and Steg, 1996, Medecine/Sciences, synthese, 12:47–55.

Flotte et al., 1992, *Am. J. Respir. Cell Mol. Biol.*, 7: 349–356.

Fodor et al., Science, 251:767–777, 1991.

Fraley et al., 1979, Proc. Natl. Acad. Sci. USA, 76: 3348–3352.

Fuller S. A. et al., 1996, *Immunology in Current Protocols in Molecular Biology*, Ausubel et al. Eds, John Wiley & Sons, Inc., USA.

Goldstein et al. (1973) *J. Clin. Invest.* 52, 1533–1543.

Ghosh and Bacchawat, 1991, Targeting of liposomes to hepatocytes, IN: *Liver Diseases, Targeted diagnosis and therapy using specific receptors and ligands*, Wu et al. Eds., Marcel Dekeker, New York, pp. 87–104.

Gopal, 1985, Mol. Cell. Biol., 5: 1188–1190.

Graham et al., 1973, Virology, 52: 456–457.

Green et al., *Ann. Rev. Biochem.* 55:569–597 (1986).

Grompe, M. et al., *Proc. Natl. Acad. Sci. U.S.A.* 1989; 86:5855–5892.

Grompe, M. *Nature Genetics* 1993; 5:111–117.

Guatelli J C et al., *Proc. Natl. Acad. Sci. USA*, 35: 273–286.

Gura, Science 275: 751 (1997).

Hacia J G, et al., *Nat Genet* 1996; 14(4):441–447.

Haff L. A. and Smirnov I. P., *Genome Research*, 7:378–388, 1997.

Hames B D and Higgins S J, 1985, "Nucleic acid hybridization: a practical approach", Hames and Higgins Ed., IRL Press, Oxford.

Harju L, et al., 1993, *Clin Chem.*, 39(11 Pt 1): 2282–2287.

Harland et al., 1985, J. Cell. Biol., 101: 1094–1095.

Hawley M. E. et al., *Am. J. Phys. Anthropol.*, 18:104, 1994.

Herz, J., Clouthier, D. E., & Hammer R. E. (1992) *Cell* 71, 411–421.

Hill, W. G. (1974) in *Heredity*, (Edinburgh), pp. 229–239.

Hillier L. and Green P. *Methods Appl.*, 1991, 1: 124–8.

Huygen et al., 1996, *Nature Medicine*, 2(8):893–898.

Ishibashi, et al. (1993) *J. Clin. Invest.* 92, 883–893.

Izant J G, Weintraub H, *Cell* 1984 Apr.; 36(4): 1007–15.

Julan et al., 1992, *J. Gen. Virol.*, 73: 3251–3255.

Karpe, et al. (1997) *J. Lipid Res.* 38, 2335–2343.

Khoury J. et al., *Fundamentals of Genetic Epistemology*, Oxford University Press, NY, 1993.

Kiefer H et al., 1996, Biochiemistry, 35(50):16077–16084.

Kim U.-J., et al., 1996, Genomics, 34: 213–218.

Klein et al., 1987, Nature, 327, 70–73.

Kohler G. and Milstein C., 1975, Nature, 256: 495.

Kozal M J, et al., *Nat Med* 1996; 2(7):753–759.

Kozbor et al., 1983, Hybridoma, 2(1):7–16.

Landegren U. et al., *Genome Research*, 8:769–776, 1998.

Lander and Schork, *Science*, 265, 2037–2048, 1994.

Lange K., *Mathematical and Statistical Methods for Genetic Analysis*, Springer, New York, 1997.

Leger O J, et al., 1997, Hum Antibodies, 8(1): 3–16.

Lenhard T. et al., 1996, *Gene*, 169:187–190.

Linton M. F. et al., 1993, J. Clin. Invest., 92: 3029–3037.

Livak K J and Hainer J W, 1994, *Hun. Mutat.*, 3(4): 379–385.

Mahley, R. W., and Rall, Jr., S. C. (1995) in *The Molecular Basis of Inherited Disease*, eds. Scriver, C. R., Beaudet, A. L., Sly, W. S. & Valle, D. (McGraw Hill Inc., New York), pp. 1953–1980.

Mansour S L et al. 1988, *Nature*, 336: 348–352.

Marshall R. L. et al. *PCR Methods and Applications* 4:80–84, 1994.

Martineau P, Jones P, Winter G, 1998, J Mol Biol. 280(1): 117–127.

McCormick et al., 1994, Genet. Anal. Tech. Appl., 11: 158–164.

McLaughlin B A et al. 1996, *Am. J. Hum. Genet.*, 59: 561–569.

Montague et al., *Nature* 387:903 (1997).

Morton N. E., *Am. J. Hum. Genet.*, 7:277–318, 1955.

Muzyczka et al., 1992, *Curr. Topics in Micro. and Immunol.*, 158: 97–129.

Nagy A. et al., 1993, Proc. Natl. Acad. Sci. USA, 90: 8424–8428.

Narang S A, Hsiung H M, Brousseau R, *Methods Enzymol* 1979; 68:90–98.

Neda et al., 1991, *J. Biol. Chem.*, 266: 14143–14146.

Newton et al., *Nucleic Acids Res.*, 17:2503–2516, 1989.

Nickerson D. A. et al. *Proc. Natl. Acad. Sci. U.S.A.* 87:8923–8927, 1990.

Nicolau et al., 1982, Biochim. Biophys. Acta, 1:185–190.

Nyren P. et al., 1993. Anal. Biochem., 208(1): 171–175.

O'Reilly et al., 1992. Baculovirus expression vetcrs: a Laboratory Manual, W.H. Freeman and Co., New York.

Ohno et al., 1994, *Science*, 265:781–784.

Orita et al., *Proc. Natl. Acad Sci. U.S.A.* 1989:86: 2776–2770.

Ott J., *Analysis of Hunman Genetic Linkage*, John Hopkins University Press, Baltimore, 1991.

Pastinen et al. *Genome research* 7:606–614, 1997.

Pease S. and William R. S., 1990, Exp. Cell. Res., 190: 209–211.

Perlin et al., *Am. J. Hum. Genet.*, 55:777–787, 1994.

Peterson et al., 1993, Proc. Nati. Acad. Sci. USA, 90: 7593–7597.

Porath J et al., 1975, Nature, 258(5536): 598–599.

Potter et al., 1984, Proc Natl Acad Sci U.S.A.; 81(22) :7161–5.

Reimann K A, et al., 1997, AIDS Res Hum Retroviruses, 13(11): 933–943.

Ridder R, Schmitz R, Legay F, Gram H, 1995. Biotechnology (NY), 13(3):255–260.

Risch, N. and NLerikangas, K. *Science*, 273: 1516–1517, 1996.

Robertson E., 1987, Embryo-derived stem cell lines. In: E. J. Robertson Ed. *Teratocarcinomas and embryonic stem cells: a practical approach*, IRL Press, Oxford, pp. 71.

Rossi et al., Pharmacol. Ther. 50:245–254, (1991).

Roth J. A. et al., 1996, *Nature Medicine*, 2(9):985–991.

Rougeot, C. et al., *Eur. J. Biochem.* 219 (3): 765–773, 1994.

Roux et al., 1989, *Proc. Natl Acad. Sci. USA,* 86: 9079–9083.

Ruano et al., Proc. Natl. Acad. Sci. USA, 87:6296–6300, 1990.

Sambrook. J. Fritsch, E. F., and T. Maniatis, 1989, Molecular cloning: a laboratory manual, 2ed. Cold Sprinmg Harbor Laboratory, Cold spring Harbor, N.Y.

Samulski et al., 1989, *J. Virol.*, 63:3822–3828.

Sarkar, G. and Sommer S. S., *Biotechniques*, 1991.

Schaid D. J. et al., *Genet. Epidemiol.*, 13:423–450, 1996.

Schedl A. et al., 1993a, Nature, 362: 258–261.

Schedl et al., 1993b, Nucleic Acids Res., 21: 4783–4787.

Schneider et al., (1997) *Arlequin: A software for population genetic data analysis*, 1.1 edition (Genetics and Biometry laboratory, Department of Anthropology, University of Geneva, Geneva).

Sczakiel G et al., 1995, *Trends Microbiol.*, 1995, 3(6) :213–217.

Shay J. W. et al., 1991, Biochem. Biophys. Acta, 1072: 1–7.

Sheffield. V. C. et al., *Proc. Natl. Acad. Sci.*

Shizuya et al., 1992, Porc. Natl Acad. Sci. USA 89: 8794–8797.

Shoemaker D D, et al., *Nat Genet* 1996; 14:450–456.

Smith, *Ann. Hum. Genet.*, 21:254–276, 1957.

Spielmann S. and Ewens W. J., *Am. J. Hum. Genet.*, 62:450–458, 1998.

Spielmann S. et al., *Am. J. Hum. Genet.*, 52:506–516, 1993.

Stemberg N. L., 1992, Trends Genet., 8: 1–16.

Sternberg N. L., 1994, Mamm. Genome, 5: 397–404.

Syvanen A C. et al., 1994, *Clin Chim Acta.*, 226(2): 225–236.

Tacson et al., 1996, *Nature Medicine*, 2(8):888–892.

Terwilliger J. D. and Ott J., *Handbook of Human Genetic Linkage*, John Hopkins University Press, London, 1994.

Thomas K. R. et al., 1986, Cell, 44: 419–428.

Thomas K. R. et al., 1987, Cell, 51: 503–512.

Tucker J, Grisshammer R, *Biochem J* 1996; 317(Pt 3):891–899.

Tur-Kaspa et al, 1986, Mol. Cell. Biol., 6: 716–718.

Tyagi et al., *Nature Biotechnology*, 16:49–53, 1998.

Vlasak R. et al., 1983, *Eur. J. Biochem.* 135:123–126.

Walker et al. *Clin. Chem.* 42:9–13, 1996.

Weir, B. S., *Genetic data Analysis II: Methods for Discrete population genetic Data*, Sinauer Assoc., Inc., Sunderland, Mass., USA, 1996.

White, B. A. Molecular Cloning to Genetic Engineering, Ed. in *Methods in Molecular Biology* 67: Humana Press, Totowa (1997).

White, M. B. et al., *Genoimics* 12:301–306 (1992).

Wolcott M. J., Clin. Mcrobiol. Rev. 5:370–386, 1992.

Wong et al., 1980, Gene, 10: 87–94.

Wood S. A. et al., 1993, Proc. Natl. Acad. Sci. USA, 90: 4582–4585.

Wu et al., *Proc. Natl. Acad. Sci. USA*, 86:2757, 1989.

Wu and Wu, 1987, J. Biol. Chem, 262: 4429–4432.

Wu and Wu, 1988, Biochemistry, 27: 887–892.

Yen et al., 1994, Biochemistry, 33: 1172–1180.

Zhao et al., *Am. J. Hum. Genet.*, 63:225–240, 1998.

What is claimed is:

1. A method of genotyping, comprising the step of determining the identity of a nucleotide at a biallelic marker of SEQ ID No:1, or the complement thereof, in a biological sample.

2. The method according to claim 1, further comprising amplifying a portion of said sequence comprising the biallelic marker prior to said determining.

3. The method according to claim 1, wherein said determining is performed by a hybridization assay.

4. The method according to claim 1, wherein said determining is performed by a sequencing assay.

5. The method according to claim 1, wherein said determining is performed by a microsequencing assay.

6. The method according to claim 1, wherein said determining is performed by an allele-specific amplification assay.

7. A method of estimating the frequency of an allele in a population, comprising the step of determining the proportional representation of a nucleotide at a biallelic marker in SEQ ID No:1, or the complement thereof, in a pooled biological sample derived from said population.

8. A method of determining the existence of an association between a genotype and a phenotype, comprising the steps of:
   a) genotyping at least one biallelic marker in a trait positive population according to the method of claim 1;
   b) genotyping said biallelic marker in a control population according to the method of claim 1; and
   c) determining whether a statistically significant association exists between said genotype and said phenotype.

9. The method of claim 8, wherein said phenotype is a disease involving obesity or disorders related to obesity.

10. The method of claim 9, wherein said disorder related to obesity is selected from the group consisting of atherosclerosis, insulin resistance, hypertension, hyperlipidemia, hypertriglyceridemia, cardiovascular disease, microangiopathic in obese individuals with Type II diabetes, ocular lesions associated with microangiopathy in obese individuals with Type II diabetes, renal lesions associated with microangiopathy in obese individuals with Type II diabetes, and Syndrome X.

11. The method of claim 8, wherein said biallelic marker is selected from the group consisting of A'1 to A'20.

12. The method of claim 8, wherein said biallelic marker is selected from the group consisting of A1 to A32.

13. The method of claim 12, wherein said biallelic marker is A15.

14. The method of claim 12, wherein said biallelic marker is A17.

15. The method of claim 12, wherein said biallelic marker is A21.

16. A method of estimating the frequency of a haplotype for a set of biallelic markers in a population, comprising the steps of:
   a) genotyping at least one biallelic marker according to claim 1 for each individual in said population;
   b) genotyping a second biallelic marker by determining the identity of the nucleotides at said second biallelic marker for both copies of said second biallelic marker present in the genome of each individual in said population; and
   c) applying a haplotype determination method to the identities of the nucleotides determined in steps a) and b) to obtain an estimate of said frequency.

17. The method of claim 16, wherein said haplotype determination method is asymmetric PCR amplification.

18. The method of claim 16, wherein said haplotype determination method is double PCR amplification of specific alleles.

19. The method of claim 16, wherein said haplotype determination method is the Clark algorithm.

20. The method of claim 16, wherein said haplotype determination method is an expectation-maximization algorithm.

21. A method of determining the existence of an association between a haplotype and a phenotype, comprising:
   a) estimating the frequency of at least one haplotype in a trait positive population according to the method of claim 16;
   b) estimating the frequency of said haplotype in a control population according to the method of claim 16; and
   c) determining whether a statistically significant association exists between said haplotype and said phenotype.

* * * * *

UNITED STATES PATENT AND TRADEMARK OFFICE
CERTIFICATE OF CORRECTION

PATENT NO. : 6,479,238 B1
DATED : November 12, 2002
INVENTOR(S) : Marta Blumenfeld, Lydie Bougueleret and Bernard Bihain It is certified that error appears in the above-identified patent and that said Letters Patent is hereby corrected as shown below:

Column 6,
Line 49, "of 2' SEQ" should read -- of SEQ --.

Column 7,
Lines 41-42, "response, treatment" should read -- response to treatment --.

Column 8,
Line 10, "shots" should read -- show --.
Line 30, "ere" should read -- were --.

Column 11,
Line 20, "Generation" should read -- generation --.

Column 14,
Line 16, "pure 30, polypeptide" should read -- pure polypeptide --.

Column 15,
Line 63, dietary, lipids" should read -- dietary lipids --.

Column 16,
Line 39, "lives" should read -- gives --.

Columns 23-24,
Table A, at Marker Name A2, "99-144241353" should read -- 99-14424/353 --.

Column 26,
Line 58, "361" should read -- 363 --.

Column 36,
Line 12, "poolin" should read -- pooling --.
Line 32, "allots" should read -- allow --.

Column 41,
Line 35, "4,693,202" should read -- 4,683,202 --.
Line 36, "be" should read -- by --.
Line 49, "diethylphosphoramridite" should read -- diethylphosphoramidite --.

Column 42,
Line 5, "primer the" should read -- primer, the --.

UNITED STATES PATENT AND TRADEMARK OFFICE
CERTIFICATE OF CORRECTION

PATENT NO. : 6,479,238 B1
DATED : November 12, 2002
INVENTOR(S) : Marta Blumenfeld, Lydie Bougueleret and Bernard Bihain It is certified that error appears in the above-identified patent and that said Letters Patent is hereby corrected as shown below:

<u>Column 43,</u>
Line 15, "sortable" should read -- suitable --.
Line 31, "5'-" should read -- a 5'- --.
Line 32, "triphosphuates" should read -- triphosphates --.
Line 39, "fluoreszence" should read -- fluorescence --.

<u>Column 44,</u>
Linhe 16, "phosplutase" should read -- phosphatase --.

<u>Column 46,</u>
Line 2, "ashen" should read -- when --.

<u>Column 48,</u>
Line 18, "hydroxy" should read -- hydroxyl --.

<u>Column 50,</u>
Line 12, "trio" should read -- two --.
Line 37, "WO 98/201 65" should read -- WO 98/20165 --.
Line 61, "A7" should read -- A17 --.
Line 62, "Attentively" should read -- Alternatively --.

<u>Column 51,</u>
Line 21, "hypertriglyceridemia myocardial" should read -- hypertriglyceridemia, myocardial --.

<u>Column 53,</u>
Line 33, "A' and" should read -- A' 20 and --.

<u>Column 53,</u>
Line 14, "Orr" should read -- Ott --.

<u>Column 54,</u>
Line 10, "preserved" should read -- present --.

<u>Column 55,</u>
Line 16, "sore" should read -- more --.

<u>Column 56,</u>
Line 12, "mutation one" should read -- mutation: one --.

UNITED STATES PATENT AND TRADEMARK OFFICE
CERTIFICATE OF CORRECTION

PATENT NO. : 6,479,238 B1
DATED : November 12, 2002
INVENTOR(S) : Marta Blumenfeld, Lydie Bougueleret and Bernard Bihain It is certified that error appears in the above-identified patent and that said Letters Patent is hereby corrected as shown below:

Column 59,
Line 53, "roped" should read -- typed --.

Column 60,
Line 27, "phenotypes" should read -- phenotype $j$ --.
Line 64, "$\theta4$=—=frequency" should read -- $\theta4$ = -- = frequency --.
Line 66, "$\theta3$= + = frequency" should read -- $\theta3$= - + = frequency --.

Column 61,
Line 1, "$\theta2$= += frequency" should read -- $\theta2$= + - = frequency --.
Line 30, ($a_i a_j$)" should read -- ($a_i$, $a_j$)) --.
Line 39, "/max(–pr(" should read -- /max(pr( --.
Line 53, "and is with" should read -- and with --.

Column 62,
Line 22, "With" should read -- with --.
Line 50, "apparat" should read -- apparati --.
Line 50, "region" should read -- regions --.
Lines 53-54, "epistemology" should read -- epidemiology --.
Line 60, "probabilities that is:" should read -- probabilities, that is: --.
Line 66, "he" should read -- be --.

Column 63,
First formula, "OR = [$\frac{E-}{}$ " should read -- OR = [$\frac{F+}{}$ --.
Second formula, "OR=(F$^+$/(1-F$^-$))" should read -- OR= (F$^+$/(1-F$^+$)) --.

Column 66,
Line 22, "stanch" should read -- such --.

Column 67,
Line 13, "invention" should read -- invention, --.

Column 69,
Line 41, "larnbda" should read -- lambda --.

Column 70,
Line 4, "polypeptide 1, or" should read -- polypeptide or --.
Line 25, "pKKZ 223-3" should read -- pKK223-3 --.
Line 35, "pSV3" should read -- pSVK3 --.
Line 41, "Stemberg" should read -- Sternberg --.

UNITED STATES PATENT AND TRADEMARK OFFICE
CERTIFICATE OF CORRECTION

PATENT NO. : 6,479,238 B1
DATED : November 12, 2002
INVENTOR(S) : Marta Blumenfeld, Lydie Bougueleret and Bernard Bihain It is certified that error appears in the above-identified patent and that said Letters Patent is hereby corrected as shown below:

Column 70 (cont'd),
Lines 56-57, "subilizing" should read -- solubilizing --.

Column 71,
Line 2, "At the stage" should read -- At this stage --.
Line 4, "3000" should read -- 30,000 --.
Line 7, "30 $\mu$m spermidine" should read -- 30 $\mu$m spermine --.
Line 47, "Iurine" should read -- Murine --.

Column 72,
Line 4, "pr4mary" should read -- primary --.
Line 26, ".nay" should read -- may --.

Column 73,
Line 37, "treaty" should read -- treated --.
Line 56, "invention at which" should read -- invention which --.

Column 74,
Line 32, "CRL-18041" should read -- CRL-1804 --.
Lines 38-39, "proceeded at with" should read -- proceeded with --.
Line 52, "30 $\mu$m spermidine" should read -- 30 $\mu$m spermine --.
Line 64, "CRL-1776" should read -- CRL-11776 --.
Line 65, "an Recommitted state" should read -- an uncommitted state --.

Column 75,
Line 44, "soup" should read -- group --.

Column 76,
Line 43, "markers by" should read -- markers, by --.
Line 53, "hot" should read -- host --.
Line 63, "transoenic" should read -- transgenic --.

Column 78,
Line 52, "activity" should read -- affinity --.

Column 79,
Line 58, "sem" should read -- system --.

Column 80,
Line 21, "Lezer" should read -- Leger --.

UNITED STATES PATENT AND TRADEMARK OFFICE
CERTIFICATE OF CORRECTION

PATENT NO.    : 6,479,238 B1
DATED         : November 12, 2002
INVENTOR(S)   : Marta Blumenfeld, Lydie Bougueleret and Bernard Bihain It is certified that error appears in the above-identified patent and that said Letters Patent is hereby corrected as shown below:

Column 81,
Line 49, "liposome:" should read -- liposomes --.

Column 82,
Line 24, "1/3.5 v/v)" should read -- (1/3.5 v/v) --.
Line 33, "260 nm 1 unit" should read -- 260 nm (1 unit --.

Column 86,
Line 59, "amplifier" should read -- amplified --.

Column 87,
Table 2, penultimate amplicon, Column 2, "(17-11240)" should read -- (17-1/240) --.

Column 90,
Table 3, Marker A4, "103-125 of SEQ ID No S" should read -- 103-125 of SEQ ID No 5 --.

Column 91,
Lines 30-31,
"5-TCTCCCACGAGTAATGGTGGGAGGAGAAGCCGGGCCTACATGCCC-3"
should read
-- 5 TCTCCCACGAGTAATGGTGGGAGGAGAAGCCGGGCCTACATGCCC-3 --.
Lines 32-33,
"3-AGAGGGTGCTCATTACCA<u>C</u>CC<u>T</u>CCTCTTCGGCCCGGATGTACGGG-5"
should read
-- AGAGGGTGCTCATTACCA<u>C</u>CC<u>T</u>CCTCTTCGGCCCGGATGTACGGG-5 --.
Line 34, "Tcctcttcggcccggatgta" should read -- Tcctcttcggcccggatgta --.
Lines 40-41,
"3-AGAGGGTGCTCATTACCA<u>C</u>CC-TCTTCGCCCGGATGTACGGG-5"
should read
-- 3-AGAGGGTGCTCATTACCA<u>C</u>CC-TCTTCGGCCCGGATGTACGGG-5 --.
Line 42, "Ccctcttcggcccggatgta" should read -- Ccctcttcggcccggatgta --.

Column 92,
Line 27, "Tetrad thermocycler" should read -- Tetrad PTC-225 thermocycler --.

Column 94,
Line 40, "marker," should read -- markers --.
Line 41, "respectiely" should read -- respectively --.
Line 49, "informs" should read -- isoforms --.

UNITED STATES PATENT AND TRADEMARK OFFICE
CERTIFICATE OF CORRECTION

PATENT NO. : 6,479,238 B1
DATED : November 12, 2002
INVENTOR(S) : Marta Blumenfeld, Lydie Bougueleret and Bernard Bihain It is certified that error appears in the above-identified patent and that said Letters Patent is hereby corrected as shown below:

Column 94 (cont'd),
Line 60, "polymoltic" should read -- polymorphic --.
Line 63, "four" should read -- for --.

Column 96,
Line 31, "USF," should read -- $USF_2$ --.
Line 37, "pealed" should read -- pooled --.

Column 98,
Line 56, "*Conité*" should read -- *Comité* --.
Line 59, "LSK" should read -- LSR --.

Column 99,
Line 31, "directs" should read -- directly --.
Line 36, "may" should read -- way --.
Line 52, "leas," should read -- least --.
Line 59, "hypertriolyceridemia" should read -- hypertriglyceridemia --.

Column 100,
Line 7, "survivor," should read -- survivors --.
Line 22, "Rail" should read -- Rall --.

Column 101,
Line 20, "boost" should read -- boys --.

Column 102,
Line 3, "Keith" should read -- with --.

Column 103,
Line 42, "3:11511-1514" should read -- 3:1511-1514 --.

UNITED STATES PATENT AND TRADEMARK OFFICE
CERTIFICATE OF CORRECTION

PATENT NO.    : 6,479,238 B1
DATED         : November 12, 2002
INVENTOR(S)   : Marta Blumenfeld, Lydie Bougueleret and Bernard Bihain It is certified that error appears in the above-identified patent and that said Letters Patent is hereby corrected as shown below:

<u>Column 104,</u>
Line 30, "Epistemology" should read -- Epidemiology --.

Signed and Sealed this

Eleventh Day of May, 2004

JON W. DUDAS
*Acting Director of the United States Patent and Trademark Office*

SEQUENCE LISTING

<160> NUMBER OF SEQ ID NOS: 20

<210> SEQ ID NO 1
<211> LENGTH: 23187
<212> TYPE: DNA
<213> ORGANISM: Homo sapiens
<220> FEATURE:
<221> NAME/KEY: exon
<222> LOCATION: 2001..2356
<223> OTHER INFORMATION: exon1
<220> FEATURE:
<221> NAME/KEY: exon
<222> LOCATION: 3540..3884
<223> OTHER INFORMATION: exon2
<220> FEATURE:
<221> NAME/KEY: exon
<222> LOCATION: 12163..12282
<223> OTHER INFORMATION: exon3
<220> FEATURE:
<221> NAME/KEY: exon
<222> LOCATION: 15144..15200
<223> OTHER INFORMATION: exon4
<220> FEATURE:
<221> NAME/KEY: exon
<222> LOCATION: 15765..15911
<223> OTHER INFORMATION: exon5
<220> FEATURE:
<221> NAME/KEY: exon
<222> LOCATION: 19579..19752
<223> OTHER INFORMATION: exon6
<220> FEATURE:
<221> NAME/KEY: exon
<222> LOCATION: 19899..19958
<223> OTHER INFORMATION: exon7
<220> FEATURE:
<221> NAME/KEY: exon
<222> LOCATION: 20056..20187
<223> OTHER INFORMATION: exon8
<220> FEATURE:
<221> NAME/KEY: exon
<222> LOCATION: 20329..20957
<223> OTHER INFORMATION: exon9
<220> FEATURE:
<221> NAME/KEY: exon
<222> LOCATION: 21047..21187
<223> OTHER INFORMATION: exon10
<220> FEATURE:
<221> NAME/KEY: polyA_signal
<222> LOCATION: 21168..21173
<223> OTHER INFORMATION: AATAAA
<220> FEATURE:
<221> NAME/KEY: misc_feature
<222> LOCATION: 1..2000
<223> OTHER INFORMATION: potential 5'regulatory region
<220> FEATURE:
<221> NAME/KEY: misc_feature
<222> LOCATION: 22324..23187
<223> OTHER INFORMATION: homology with USF2 gene in ref:
      embl Y07661
<220> FEATURE:
<221> NAME/KEY: primer_bind
<222> LOCATION: 523..544
<223> OTHER INFORMATION: upstream amplification primer 17-2
<220> FEATURE:
<221> NAME/KEY: primer_bind
<222> LOCATION: 1047..1068
<223> OTHER INFORMATION: downstream amplification primer 17-2 ,
      complement
<220> FEATURE:
<221> NAME/KEY: primer_bind
<222> LOCATION: 946..963
<223> OTHER INFORMATION: upstream amplification primer 99-4576
<220> FEATURE:
<221> NAME/KEY: primer_bind
<222> LOCATION: 1385..1402
<223> OTHER INFORMATION: downstream amplification primer 99-4576 ,

```
                                 -continued complement
<220> FEATURE:
<221> NAME/KEY: primer_bind
<222> LOCATION: 1096..1115
<223> OTHER INFORMATION: upstream amplification primer 9-19
<220> FEATURE:
<221> NAME/KEY: primer_bind
<222> LOCATION: 1616..1635
<223> OTHER INFORMATION: downstream amplification primer 9-19 ,
      complement
<220> FEATURE:
<221> NAME/KEY: primer_bind
<222> LOCATION: 1602..1621
<223> OTHER INFORMATION: upstream amplification primer 9-20
<220> FEATURE:
<221> NAME/KEY: primer_bind
<222> LOCATION: 2074..2093
<223> OTHER INFORMATION: downstream amplification primer 9-20 ,
      complement
<220> FEATURE:
<221> NAME/KEY: primer_bind
<222> LOCATION: 2036..2053
<223> OTHER INFORMATION: upstream amplification primer 99-4557
<220> FEATURE:
<221> NAME/KEY: primer_bind
<222> LOCATION: 2563..2580
<223> OTHER INFORMATION: downstream amplification primer 99-4557 ,
      complement
<220> FEATURE:
<221> NAME/KEY: primer_bind
<222> LOCATION: 2084..2102
<223> OTHER INFORMATION: upstream amplification primer 9-1
<220> FEATURE:
<221> NAME/KEY: primer_bind
<222> LOCATION: 2483..2500
<223> OTHER INFORMATION: downstream amplification primer 9-1 ,
      complement
<220> FEATURE:
<221> NAME/KEY: primer_bind
<222> LOCATION: 2470..2489
<223> OTHER INFORMATION: upstream amplification primer 9-21 ,
      complement
<220> FEATURE:
<221> NAME/KEY: primer_bind
<222> LOCATION: 2062..2081
<223> OTHER INFORMATION: downstream amplification primer 9-21
<220> FEATURE:
<221> NAME/KEY: primer_bind
<222> LOCATION: 3455..3474
<223> OTHER INFORMATION: upstream amplification primer 9-3
<220> FEATURE:
<221> NAME/KEY: primer_bind
<222> LOCATION: 3882..3901
<223> OTHER INFORMATION: downstream amplification primer 9-3 ,
      complement
<220> FEATURE:
<221> NAME/KEY: primer_bind
<222> LOCATION: 3775..3792
<223> OTHER INFORMATION: upstream amplification primer 99-4558
<220> FEATURE:
<221> NAME/KEY: primer_bind
<222> LOCATION: 4336..4356
<223> OTHER INFORMATION: downstream amplification primer 99-4558 ,
      complement
<220> FEATURE:
<221> NAME/KEY: primer_bind
<222> LOCATION: 4902..4920
<223> OTHER INFORMATION: upstream amplification primer 99-14419 ,
      complement
<220> FEATURE:
<221> NAME/KEY: primer_bind
<222> LOCATION: 4444..4463
<223> OTHER INFORMATION: downstream amplification primer 99-14419
<220> FEATURE:
<221> NAME/KEY: primer_bind
<222> LOCATION: 6638..6655
<223> OTHER INFORMATION: upstream amplification primer 99-4577
<220> FEATURE:
<221> NAME/KEY: primer_bind
```

-continued

```
<222> LOCATION: 7072..7089
<223> OTHER INFORMATION: downstream amplification primer 99-4577 ,
      complement
<220> FEATURE:
<221> NAME/KEY: primer_bind
<222> LOCATION: 7995..8012
<223> OTHER INFORMATION: upstream amplification primer 99-4559
<220> FEATURE:
<221> NAME/KEY: primer_bind
<222> LOCATION: 8576..8593
<223> OTHER INFORMATION: downstream amplification primer 99-4559 ,
      complement
<220> FEATURE:
<221> NAME/KEY: primer_bind
<222> LOCATION: 9622..9639
<223> OTHER INFORMATION: upstream amplification primer 99-3148
<220> FEATURE:
<221> NAME/KEY: primer_bind
<222> LOCATION: 10023..10040
<223> OTHER INFORMATION: downstream amplification primer 99-3148 ,
      complement
<220> FEATURE:
<221> NAME/KEY: primer_bind
<222> LOCATION: 9964..9981
<223> OTHER INFORMATION: upstream amplification primer 99-4560
<220> FEATURE:
<221> NAME/KEY: primer_bind
<222> LOCATION: 10546..10563
<223> OTHER INFORMATION: downstream amplification primer 99-4560 ,
      complement
<220> FEATURE:
<221> NAME/KEY: primer_bind
<222> LOCATION: 10996..11015
<223> OTHER INFORMATION: upstream amplification primer 99-14411 ,
      complement
<220> FEATURE:
<221> NAME/KEY: primer_bind
<222> LOCATION: 10492..10512
<223> OTHER INFORMATION: downstream amplification primer 99-14411
<220> FEATURE:
<221> NAME/KEY: primer_bind
<222> LOCATION: 11972..11990
<223> OTHER INFORMATION: upstream amplification primer 99-4561
<220> FEATURE:
<221> NAME/KEY: primer_bind
<222> LOCATION: 12481..12501
<223> OTHER INFORMATION: downstream amplification primer 99-4561 ,
      complement
<220> FEATURE:
<221> NAME/KEY: primer_bind
<222> LOCATION: 12005..12023
<223> OTHER INFORMATION: upstream amplification primer 9-4
<220> FEATURE:
<221> NAME/KEY: primer_bind
<222> LOCATION: 12417..12436
<223> OTHER INFORMATION: downstream amplification primer 9-4 ,
      complement
<220> FEATURE:
<221> NAME/KEY: primer_bind
<222> LOCATION: 14102..14119
<223> OTHER INFORMATION: upstream amplification primer 99-4562
<220> FEATURE:
<221> NAME/KEY: primer_bind
<222> LOCATION: 14543..14563
<223> OTHER INFORMATION: downstream amplification primer 99-4562 ,
      complement
<220> FEATURE:
<221> NAME/KEY: primer_bind
<222> LOCATION: 14431..14448
<223> OTHER INFORMATION: upstream amplification primer 99-3149
<220> FEATURE:
<221> NAME/KEY: primer_bind
<222> LOCATION: 14848..14865
<223> OTHER INFORMATION: downstream amplification primer 99-3149 ,
      complement
<220> FEATURE:
<221> NAME/KEY: primer_bind
<222> LOCATION: 14748..14767
<223> OTHER INFORMATION: upstream amplification primer 9-22
```

-continued

```
<220> FEATURE:
<221> NAME/KEY: primer_bind
<222> LOCATION: 15198..15218
<223> OTHER INFORMATION: downstream amplification primer 9-22 ,
      complement
<220> FEATURE:
<221> NAME/KEY: primer_bind
<222> LOCATION: 14748..14767
<223> OTHER INFORMATION: upstream amplification primer 9-24
<220> FEATURE:
<221> NAME/KEY: primer_bind
<222> LOCATION: 15333..15351
<223> OTHER INFORMATION: downstream amplification primer 9-24 ,
      complement
<220> FEATURE:
<221> NAME/KEY: primer_bind
<222> LOCATION: 15002..15019
<223> OTHER INFORMATION: upstream amplification primer 9-5
<220> FEATURE:
<221> NAME/KEY: primer_bind
<222> LOCATION: 15333..15351
<223> OTHER INFORMATION: downstream amplification primer 9-5 ,
      complement
<220> FEATURE:
<221> NAME/KEY: primer_bind
<222> LOCATION: 15640..15657
<223> OTHER INFORMATION: upstream amplification primer 9-6
<220> FEATURE:
<221> NAME/KEY: primer_bind
<222> LOCATION: 16072..16089
<223> OTHER INFORMATION: downstream amplification primer 9-6 ,
      complement
<220> FEATURE:
<221> NAME/KEY: primer_bind
<222> LOCATION: 15800..15817
<223> OTHER INFORMATION: upstream amplification primer 99-4563
<220> FEATURE:
<221> NAME/KEY: primer_bind
<222> LOCATION: 16179..16199
<223> OTHER INFORMATION: downstream amplification primer 99-4563 ,
      complement
<220> FEATURE:
<221> NAME/KEY: primer_bind
<222> LOCATION: 19295..19312
<223> OTHER INFORMATION: upstream amplification primer 99-3150
<220> FEATURE:
<221> NAME/KEY: primer_bind
<222> LOCATION: 19729..19746
<223> OTHER INFORMATION: downstream amplification primer 99-3150 ,
      complement
<220> FEATURE:
<221> NAME/KEY: primer_bind
<222> LOCATION: 19420..19438
<223> OTHER INFORMATION: upstream amplification primer 9-7
<220> FEATURE:
<221> NAME/KEY: primer_bind
<222> LOCATION: 19824..19841
<223> OTHER INFORMATION: downstream amplification primer 9-7 ,
      complement
<220> FEATURE:
<221> NAME/KEY: primer_bind
<222> LOCATION: 19798..19815
<223> OTHER INFORMATION: upstream amplification primer 9-8
<220> FEATURE:
<221> NAME/KEY: primer_bind
<222> LOCATION: 20137..20155
<223> OTHER INFORMATION: downstream amplification primer 9-8 ,
      complement
<220> FEATURE:
<221> NAME/KEY: primer_bind
<222> LOCATION: 19913..19931
<223> OTHER INFORMATION: upstream amplification primer 9-9
<220> FEATURE:
<221> NAME/KEY: primer_bind
<222> LOCATION: 20329..20346
<223> OTHER INFORMATION: downstream amplification primer 9-9 ,
      complement
<220> FEATURE:
<221> NAME/KEY: primer_bind
```

```
<222> LOCATION: 20139..20157
<223> OTHER INFORMATION: upstream amplification primer 99-4564
<220> FEATURE:
<221> NAME/KEY: primer_bind
<222> LOCATION: 20582..20599
<223> OTHER INFORMATION: downstream amplification primer 99-4564 ,
      complement
<220> FEATURE:
<221> NAME/KEY: primer_bind
<222> LOCATION: 20238..20256
<223> OTHER INFORMATION: upstream amplification primer 9-10
<220> FEATURE:
<221> NAME/KEY: primer_bind
<222> LOCATION: 20645..20662
<223> OTHER INFORMATION: downstream amplification primer 9-10 ,
      complement
<220> FEATURE:
<221> NAME/KEY: primer_bind
<222> LOCATION: 20410..20424
<223> OTHER INFORMATION: upstream amplification primer 9-26
<220> FEATURE:
<221> NAME/KEY: primer_bind
<222> LOCATION: 20690..20706
<223> OTHER INFORMATION: downstream amplification primer 9-26 ,
      complement
<220> FEATURE:
<221> NAME/KEY: primer_bind
<222> LOCATION: 20569..20588
<223> OTHER INFORMATION: upstream amplification primer 9-23
<220> FEATURE:
<221> NAME/KEY: primer_bind
<222> LOCATION: 21243..21262
<223> OTHER INFORMATION: downstream amplification primer 9-23 ,
      complement
<220> FEATURE:
<221> NAME/KEY: primer_bind
<222> LOCATION: 20583..20604
<223> OTHER INFORMATION: upstream amplification primer 9-11
<220> FEATURE:
<221> NAME/KEY: primer_bind
<222> LOCATION: 21015..21034
<223> OTHER INFORMATION: downstream amplification primer 9-11 ,
      complement
<220> FEATURE:
<221> NAME/KEY: primer_bind
<222> LOCATION: 20584..20601
<223> OTHER INFORMATION: upstream amplification primer 99-15285 ,
      complement
<220> FEATURE:
<221> NAME/KEY: primer_bind
<222> LOCATION: 20139..20158
<223> OTHER INFORMATION: downstream amplification primer 99-15285
<220> FEATURE:
<221> NAME/KEY: primer_bind
<222> LOCATION: 20642..20659
<223> OTHER INFORMATION: upstream amplification primer 99-15287 ,
      complement
<220> FEATURE:
<221> NAME/KEY: primer_bind
<222> LOCATION: 20207..20227
<223> OTHER INFORMATION: downstream amplification primer 99-15287
<220> FEATURE:
<221> NAME/KEY: primer_bind
<222> LOCATION: 20691..20709
<223> OTHER INFORMATION: upstream amplification primer 99-15286 ,
      complement
<220> FEATURE:
<221> NAME/KEY: primer_bind
<222> LOCATION: 20238..20257
<223> OTHER INFORMATION: downstream amplification primer 99-15286
<220> FEATURE:
<221> NAME/KEY: primer_bind
<222> LOCATION: 20943..20960
<223> OTHER INFORMATION: upstream amplification primer 9-2
<220> FEATURE:
<221> NAME/KEY: primer_bind
<222> LOCATION: 21295..21312
<223> OTHER INFORMATION: downstream amplification primer 9-2 ,
      complement
```

-continued

```
<220> FEATURE:
<221> NAME/KEY: primer_bind
<222> LOCATION: 21013..21031
<223> OTHER INFORMATION: upstream amplification primer 99-15284 ,
      complement
<220> FEATURE:
<221> NAME/KEY: primer_bind
<222> LOCATION: 20582..20602
<223> OTHER INFORMATION: downstream amplification primer 99-15284
<220> FEATURE:
<221> NAME/KEY: primer_bind
<222> LOCATION: 21019..21038
<223> OTHER INFORMATION: upstream amplification primer 99-14407 ,
      complement
<220> FEATURE:
<221> NAME/KEY: primer_bind
<222> LOCATION: 20571..20589
<223> OTHER INFORMATION: downstream amplification primer 99-14407
<220> FEATURE:
<221> NAME/KEY: primer_bind
<222> LOCATION: 21079..21097
<223> OTHER INFORMATION: upstream amplification primer 99-15283 ,
      complement
<220> FEATURE:
<221> NAME/KEY: primer_bind
<222> LOCATION: 20638..20655
<223> OTHER INFORMATION: downstream amplification primer 99-15283
<220> FEATURE:
<221> NAME/KEY: primer_bind
<222> LOCATION: 21013..21032
<223> OTHER INFORMATION: upstream amplification primer LSRi9f15s
<220> FEATURE:
<221> NAME/KEY: primer_bind
<222> LOCATION: 21195..21214
<223> OTHER INFORMATION: downstream amplification primer LSRi10r14s ,
      complement
<220> FEATURE:
<221> NAME/KEY: primer_bind
<222> LOCATION: 20354..20372
<223> OTHER INFORMATION: upstream amplification primer LSRx9f13s (17-1)
<220> FEATURE:
<221> NAME/KEY: primer_bind
<222> LOCATION: 20570..20591
<223> OTHER INFORMATION: upstream amplification primer LSRx9f14s
<220> FEATURE:
<221> NAME/KEY: primer_bind
<222> LOCATION: 20811..20832
<223> OTHER INFORMATION: downstream amplification primer LSRx9r13s
      (17-1), complement
<220> FEATURE:
<221> NAME/KEY: allele
<222> LOCATION: 818
<223> OTHER INFORMATION: 17-2-297  :  polymorphic  base  G  or  C
<220> FEATURE:
<221> NAME/KEY: allele
<222> LOCATION: 1243
<223> OTHER INFORMATION: 9-19-148  :  polymorphic  base  C  or  T
<220> FEATURE:
<221> NAME/KEY: allele
<222> LOCATION: 1374
<223> OTHER INFORMATION: 9-19-256  :  polymorphic  base  A  or  G
<220> FEATURE:
<221> NAME/KEY: allele
<222> LOCATION: 1401
<223> OTHER INFORMATION: 9-19-307  :  polymorphic  base  A  or  T
<220> FEATURE:
<221> NAME/KEY: allele
<222> LOCATION: 1535
<223> OTHER INFORMATION: 9-19-442  :  polymorphic base deletion of C
<220> FEATURE:
<221> NAME/KEY: allele
<222> LOCATION: 1788
<223> OTHER INFORMATION: 9-20-187  :  polymorphic  base  A  or  C
<220> FEATURE:
<221> NAME/KEY: allele
<222> LOCATION: 2391
<223> OTHER INFORMATION: 9-1-308  :  polymorphic  base  G  or  C
<220> FEATURE:
<221> NAME/KEY: allele
```

```
<222> LOCATION: 3778
<223> OTHER INFORMATION: 9-3-324 : polymorphic base C or T
<220> FEATURE:
<221> NAME/KEY: allele
<222> LOCATION: 4498
<223> OTHER INFORMATION: 99-14419-424 : polymorphic base T or G
<220> FEATURE:
<221> NAME/KEY: allele
<222> LOCATION: 15007
<223> OTHER INFORMATION: 9-24-260 : polymorphic base A or G
<220> FEATURE:
<221> NAME/KEY: allele
<222> LOCATION: 15233
<223> OTHER INFORMATION: 9-24-486 : polymorphic base A or G
<220> FEATURE:
<221> NAME/KEY: allele
<222> LOCATION: 15826
<223> OTHER INFORMATION: 9-6-187 : polymorphic base C or T
<220> FEATURE:
<221> NAME/KEY: allele
<222> LOCATION: 19567
<223> OTHER INFORMATION: 9-7-148 : polymorphic base A or G
<220> FEATURE:
<221> NAME/KEY: allele
<222> LOCATION: 19744
<223> OTHER INFORMATION: 9-7-325 : polymorphic base A or G
<220> FEATURE:
<221> NAME/KEY: allele
<222> LOCATION: 19786
<223> OTHER INFORMATION: 9-7-367 : polymorphic base A or C
<220> FEATURE:
<221> NAME/KEY: allele
<222> LOCATION: 20158
<223> OTHER INFORMATION: 9-9-246 : polymorphic base G or C
<220> FEATURE:
<221> NAME/KEY: allele
<222> LOCATION: 20595
<223> OTHER INFORMATION: LSRX9-BM (17-1-240) : polymorphic base
      deletion of AGG
<220> FEATURE:
<221> NAME/KEY: allele
<222> LOCATION: 21108
<223> OTHER INFORMATION: LSRX10-BM : polymorphic base T or G
<220> FEATURE:
<221> NAME/KEY: allele
<222> LOCATION: 606
<223> OTHER INFORMATION: potential polymorphic base C or T
<220> FEATURE:
<221> NAME/KEY: allele
<222> LOCATION: 5141
<223> OTHER INFORMATION: potential polymorphic base insertion of G
<220> FEATURE:
<221> NAME/KEY: allele
<222> LOCATION: 7428
<223> OTHER INFORMATION: potential polymorphic base insertion of C
<220> FEATURE:
<221> NAME/KEY: allele
<222> LOCATION: 8394
<223> OTHER INFORMATION: potential polymorphic base C or G
<220> FEATURE:
<221> NAME/KEY: allele
<222> LOCATION: 8704
<223> OTHER INFORMATION: potential polymorphic base T or C
<220> FEATURE:
<221> NAME/KEY: allele
<222> LOCATION: 9028
<223> OTHER INFORMATION: potential polymorphic base G or A
<220> FEATURE:
<221> NAME/KEY: allele
<222> LOCATION: 9950
<223> OTHER INFORMATION: potential polymorphic base deletion of
      GAATGAAA
<220> FEATURE:
<221> NAME/KEY: allele
<222> LOCATION: 9977
<223> OTHER INFORMATION: potential polymorphic base T or C
<220> FEATURE:
<221> NAME/KEY: allele
<222> LOCATION: 10021
```

```
<223> OTHER INFORMATION: potential  polymorphic  base  A  or  G
<220> FEATURE:
<221> NAME/KEY: allele
<222> LOCATION: 11878
<223> OTHER INFORMATION: potential  polymorphic  base  C  or  T
<220> FEATURE:
<221> NAME/KEY: allele
<222> LOCATION: 19040
<223> OTHER INFORMATION: potential  polymorphic  base  deletion  of  G
<220> FEATURE:
<221> NAME/KEY: allele
<222> LOCATION: 21363
<223> OTHER INFORMATION: potential  polymorphic  base  A  or  G
<220> FEATURE:
<221> NAME/KEY: allele
<222> LOCATION: 21449
<223> OTHER INFORMATION: potential  polymorphic  base  C  or  T
<220> FEATURE:
<221> NAME/KEY: allele
<222> LOCATION: 21451
<223> OTHER INFORMATION: potential  polymorphic  base  G  or  C
<220> FEATURE:
<221> NAME/KEY: allele
<222> LOCATION: 21454
<223> OTHER INFORMATION: potential  polymorphic  base  A  or  G
<220> FEATURE:
<221> NAME/KEY: allele
<222> LOCATION: 21455
<223> OTHER INFORMATION: potential  polymorphic  base  G  or  A
<220> FEATURE:
<221> NAME/KEY: allele
<222> LOCATION: 21569
<223> OTHER INFORMATION: potential  polymorphic  base  T  or  A
<220> FEATURE:
<221> NAME/KEY: allele
<222> LOCATION: 21683
<223> OTHER INFORMATION: potential  polymorphic  base  deletion  of  C
<220> FEATURE:
<221> NAME/KEY: allele
<222> LOCATION: 21694
<223> OTHER INFORMATION: potential  polymorphic  base  insertion  of  T
<220> FEATURE:
<221> NAME/KEY: allele
<222> LOCATION: 21728
<223> OTHER INFORMATION: potential  polymorphic  base  deletion  of  G
<220> FEATURE:
<221> NAME/KEY: misc_binding
<222> LOCATION: 799..817
<223> OTHER INFORMATION: 17-2-297.mis1
<220> FEATURE:
<221> NAME/KEY: misc_binding
<222> LOCATION: 819..837
<223> OTHER INFORMATION: complement 17-2-297.mis2
<220> FEATURE:
<221> NAME/KEY: misc_binding
<222> LOCATION: 1224..1242
<223> OTHER INFORMATION: 9-19-148.mis1
<220> FEATURE:
<221> NAME/KEY: misc_binding
<222> LOCATION: 1244..1262
<223> OTHER INFORMATION: complement 9-19-148.mis2  potential
<220> FEATURE:
<221> NAME/KEY: misc_binding
<222> LOCATION: 1330..1373
<223> OTHER INFORMATION: 9-19-256.mis1
<220> FEATURE:
<221> NAME/KEY: misc_binding
<222> LOCATION: 1375..1393
<223> OTHER INFORMATION: complement 9-19-256.mis2
<220> FEATURE:
<221> NAME/KEY: misc_binding
<222> LOCATION: 1382..1400
<223> OTHER INFORMATION: 9-19-307.mis1
<220> FEATURE:
<221> NAME/KEY: misc_binding
<222> LOCATION: 1402..1420
<223> OTHER INFORMATION: complement 9-19-307.mis2  potential
<220> FEATURE:
<221> NAME/KEY: misc_binding
```

```
<222> LOCATION: 1516..1534
<223> OTHER INFORMATION: 9-19-442.mis1
<220> FEATURE:
<221> NAME/KEY: misc_binding
<222> LOCATION: 1769..1787
<223> OTHER INFORMATION: 9-20-187.mis1
<220> FEATURE:
<221> NAME/KEY: misc_binding
<222> LOCATION: 1789..1807
<223> OTHER INFORMATION: complement 9-20-187.mis2
<220> FEATURE:
<221> NAME/KEY: misc_binding
<222> LOCATION: 2372..2390
<223> OTHER INFORMATION: 9-1-308.mis1  potential
<220> FEATURE:
<221> NAME/KEY: misc_binding
<222> LOCATION: 2392..2410
<223> OTHER INFORMATION: complement 9-1-308.mis2
<220> FEATURE:
<221> NAME/KEY: misc_binding
<222> LOCATION: 3759..3777
<223> OTHER INFORMATION: 9-3-324.mis1
<220> FEATURE:
<221> NAME/KEY: misc_binding
<222> LOCATION: 3779..3797
<223> OTHER INFORMATION: complement 9-3-324.mis2  potential
<220> FEATURE:
<221> NAME/KEY: misc_binding
<222> LOCATION: 4979..4997
<223> OTHER INFORMATION: 99-14419-424.mis2
<220> FEATURE:
<221> NAME/KEY: misc_binding
<222> LOCATION: 4999..5017
<223> OTHER INFORMATION: complement 99-14419-424.mis1
<220> FEATURE:
<221> NAME/KEY: misc_binding
<222> LOCATION: 14988..15006
<223> OTHER INFORMATION: 9-24-260.mis1
<220> FEATURE:
<221> NAME/KEY: misc_binding
<222> LOCATION: 15008..15026
<223> OTHER INFORMATION: complement 9-24-260.mis2  potential
<220> FEATURE:
<221> NAME/KEY: misc_binding
<222> LOCATION: 15214..15232
<223> OTHER INFORMATION: 9-24-486.mis1
<220> FEATURE:
<221> NAME/KEY: misc_binding
<222> LOCATION: 15234..15252
<223> OTHER INFORMATION: complement 9-24-486.mis2
<220> FEATURE:
<221> NAME/KEY: misc_binding
<222> LOCATION: 15807..15825
<223> OTHER INFORMATION: 9-6-187.mis1
<220> FEATURE:
<221> NAME/KEY: misc_binding
<222> LOCATION: 15827..15845
<223> OTHER INFORMATION: complement 9-6-187.mis2  potential
<220> FEATURE:
<221> NAME/KEY: misc_binding
<222> LOCATION: 19548..19566
<223> OTHER INFORMATION: 9-7-148.mis1  potential
<220> FEATURE:
<221> NAME/KEY: misc_binding
<222> LOCATION: 19568..19586
<223> OTHER INFORMATION: complement 9-7-148.mis2
<220> FEATURE:
<221> NAME/KEY: misc_binding
<222> LOCATION: 19725..19743
<223> OTHER INFORMATION: 9-7-325.mis1  potential
<220> FEATURE:
<221> NAME/KEY: misc_binding
<222> LOCATION: 19745..19763
<223> OTHER INFORMATION: complement 9-7-325.mis2
<220> FEATURE:
<221> NAME/KEY: misc_binding
<222> LOCATION: 19767..19785
<223> OTHER INFORMATION: 9-7-367.mis1
<220> FEATURE:
```

```
<221> NAME/KEY: misc_binding
<222> LOCATION: 19787..19805
<223> OTHER INFORMATION: complement 9-7-367.mis2
<220> FEATURE:
<221> NAME/KEY: misc_binding
<222> LOCATION: 20139..20157
<223> OTHER INFORMATION: 9-9-246.mis1
<220> FEATURE:
<221> NAME/KEY: misc_binding
<222> LOCATION: 20159..20177
<223> OTHER INFORMATION: complement 9-9-246.mis2   potential
<220> FEATURE:
<221> NAME/KEY: misc_binding
<222> LOCATION: 20576..20594
<223> OTHER INFORMATION: LSRX9-BM.mis1(17-1-240)   potential
<220> FEATURE:
<221> NAME/KEY: misc_binding
<222> LOCATION: 20596..20614
<223> OTHER INFORMATION: complement LSRX9-BM.mis2(17-1-240)
<220> FEATURE:
<221> NAME/KEY: misc_binding
<222> LOCATION: 21089..21107
<223> OTHER INFORMATION: LSRX10-BM.mis1   potential
<220> FEATURE:
<221> NAME/KEY: misc_binding
<222> LOCATION: 21109..21127
<223> OTHER INFORMATION: complement LSRX10-BM.mis2   potential
<220> FEATURE:
<221> NAME/KEY: misc_binding
<222> LOCATION: 587..605
<223> OTHER INFORMATION: potentialsite606.mis1   potential
<220> FEATURE:
<221> NAME/KEY: misc_binding
<222> LOCATION: 607..625
<223> OTHER INFORMATION: complement potentialsite606.mis2   potential
<220> FEATURE:
<221> NAME/KEY: misc_binding
<222> LOCATION: 5122..5140
<223> OTHER INFORMATION: potentialsite5141.mis1   potential
<220> FEATURE:
<221> NAME/KEY: misc_binding
<222> LOCATION: 5142..5160
<223> OTHER INFORMATION: complement potentialsite5141.mis2   potential
<220> FEATURE:
<221> NAME/KEY: misc_binding
<222> LOCATION: 7409..7427
<223> OTHER INFORMATION: potentialsite7428.mis1   potential
<220> FEATURE:
<221> NAME/KEY: misc_binding
<222> LOCATION: 7429..7447
<223> OTHER INFORMATION: complement potentialsite7428.mis2   potential
<220> FEATURE:
<221> NAME/KEY: misc_binding
<222> LOCATION: 8375..8393
<223> OTHER INFORMATION: potentialsite8394.mis1   potential
<220> FEATURE:
<221> NAME/KEY: misc_binding
<222> LOCATION: 8395..8413
<223> OTHER INFORMATION: complement potentialsite8394.mis2   potential
<220> FEATURE:
<221> NAME/KEY: misc_binding
<222> LOCATION: 8685..8703
<223> OTHER INFORMATION: potentialsite8704.mis1   potential
<220> FEATURE:
<221> NAME/KEY: misc_binding
<222> LOCATION: 8705..8723
<223> OTHER INFORMATION: complement potentialsite8704.mis2   potential
<220> FEATURE:
<221> NAME/KEY: misc_binding
<222> LOCATION: 9009..9027
<223> OTHER INFORMATION: potentialsite9028.mis1   potential
<220> FEATURE:
<221> NAME/KEY: misc_binding
<222> LOCATION: 9029..9047
<223> OTHER INFORMATION: complement potentialsite9028.mis2   potential
<220> FEATURE:
<221> NAME/KEY: misc_binding
<222> LOCATION: 9931..9949
<223> OTHER INFORMATION: potentialsite9950.mis1   potential
```

```
<220> FEATURE:
<221> NAME/KEY: misc_binding
<222> LOCATION: 9951..996
<223> OTHER INFORMATION: complement potentialsite9950.mis2  potential
<220> FEATURE:
<221> NAME/KEY: misc_binding
<222> LOCATION: 9958..9976
<223> OTHER INFORMATION: potentialsite9977.mis1  potential
<220> FEATURE:
<221> NAME/KEY: misc_binding
<222> LOCATION: 9978..9996
<223> OTHER INFORMATION: complement potentialsite9977.mis2  potential
<220> FEATURE:
<221> NAME/KEY: misc_binding
<222> LOCATION: 10002..10020
<223> OTHER INFORMATION: potentialsite10021.mis1  potential
<220> FEATURE:
<221> NAME/KEY: misc_binding
<222> LOCATION: 10022..10040
<223> OTHER INFORMATION: complement potentialsite10021.mis2  potential
<220> FEATURE:
<221> NAME/KEY: misc_binding
<222> LOCATION: 11859..11877
<223> OTHER INFORMATION: potentialsite11878.mis1  potential
<220> FEATURE:
<221> NAME/KEY: misc_binding
<222> LOCATION: 11879..11897
<223> OTHER INFORMATION: complement potentialsite11878.mis2  potential
<220> FEATURE:
<221> NAME/KEY: misc_binding
<222> LOCATION: 19021..19039
<223> OTHER INFORMATION: potentialsite19040.mis1  potential
<220> FEATURE:
<221> NAME/KEY: misc_binding
<222> LOCATION: 19041..19059
<223> OTHER INFORMATION: complement potentialsite19040.mis2  potential
<220> FEATURE:
<221> NAME/KEY: misc_binding
<222> LOCATION: 21344..21362
<223> OTHER INFORMATION: potentialsite21363.mis1  potential
<220> FEATURE:
<221> NAME/KEY: misc_binding
<222> LOCATION: 21364..21382
<223> OTHER INFORMATION: complement potentialsite21363.mis2  potential
<220> FEATURE:
<221> NAME/KEY: misc_binding
<222> LOCATION: 21430..21448
<223> OTHER INFORMATION: potentialsite21449.mis1  potential
<220> FEATURE:
<221> NAME/KEY: misc_binding
<222> LOCATION: 21450..21468
<223> OTHER INFORMATION: complement potentialsite21449.mis2  potential
<220> FEATURE:
<221> NAME/KEY: misc_binding
<222> LOCATION: 21432..21450
<223> OTHER INFORMATION: potentialsite21451.mis1  potential
<220> FEATURE:
<221> NAME/KEY: misc_binding
<222> LOCATION: 21452..21470
<223> OTHER INFORMATION: complement potentialsite21451.mis2  potential
<220> FEATURE:
<221> NAME/KEY: misc_binding
<222> LOCATION: 21435..21453
<223> OTHER INFORMATION: potentialsite21454.mis1  potential
<220> FEATURE:
<221> NAME/KEY: misc_binding
<222> LOCATION: 21455..21473
<223> OTHER INFORMATION: complement potentialsite21454.mis2  potential
<220> FEATURE:
<221> NAME/KEY: misc_binding
<222> LOCATION: 21436..21454
<223> OTHER INFORMATION: potentialsite21455.mis1  potential
<220> FEATURE:
<221> NAME/KEY: misc_binding
<222> LOCATION: 21456..21474
<223> OTHER INFORMATION: complement potentialsite21455.mis2  potential
<220> FEATURE:
<221> NAME/KEY: misc_binding
<222> LOCATION: 21550..21568
```

```
<223> OTHER INFORMATION: potentialsite21569.mis1  potential
<220> FEATURE:
<221> NAME/KEY: misc_binding
<222> LOCATION: 21570..21588
<223> OTHER INFORMATION: complement potentialsite21569.mis2  potential
<220> FEATURE:
<221> NAME/KEY: misc_binding
<222> LOCATION: 21664..21682
<223> OTHER INFORMATION: potentialsite21683.mis1  potential
<220> FEATURE:
<221> NAME/KEY: misc_binding
<222> LOCATION: 21684..21702
<223> OTHER INFORMATION: complement potentialsite21683.mis2  potential
<220> FEATURE:
<221> NAME/KEY: misc_binding
<222> LOCATION: 21675..21693
<223> OTHER INFORMATION: potentialsite21694.mis1  potential
<220> FEATURE:
<221> NAME/KEY: misc_binding
<222> LOCATION: 21695..21713
<223> OTHER INFORMATION: complement potentialsite21694.mis2  potential
<220> FEATURE:
<221> NAME/KEY: misc_binding
<222> LOCATION: 21709..21727
<223> OTHER INFORMATION: potentialsite21728.mis1  potential
<220> FEATURE:
<221> NAME/KEY: misc_binding
<222> LOCATION: 21729..21747
<223> OTHER INFORMATION: complement potentialsite21728.mis2  potential

<400> SEQUENCE: 1
ccataatcaa gaaatggat aataagtttt ggtggggatg tggagaaatt ggaatcctcc      60
gtgcattgct ggtgggaatg tacaatagtg cagtcattgg ggaaaacagt ttggcagttc    120
ctcaaaaggt taaaaataga actaccaagt cacccagcaa ttccattctt aggcatatat    180
tcaaaagaaa tgaaagcaga tatttgtaca ccagtgttca cagctgcact atttacaata    240
gtcaaaaggt agaaacaacc taggtccatc cacaaatgaa tggataaata aaacgtagca    300
tatacataca atggtacact agtccgctgt aaaaagaaat tttgatctta ctgcatgcta    360
catggcttcg acatactaca acatggatgg accttgaaaa cattattctt tgtgaaataa    420
actagacaca ggacaaatgt tagacgattc cacttatatg aggcacctag aatgggcaat    480
ttggtaagca aagtagaata gaaattacta ggggcacagg tagcagggaa tggggagtta    540
ctgtttaatg gtcacagagt ttatgttggg gatgatgaaa cagtttcggg gataaagagt    600
ggtgactggt acacgacatt gtgaatatac ttaatgccac tgaattttac acttgaagtg    660
gttaaagcga taaatattat agtttgcata ttttatcata aaaatatttt tttaaacgat    720
gaagggacgt gaacgggttg aaattttata aaaagtggcc agggaaggtg tcactgcaat    780
ggtgtcctac aggaggagga agatcatgtg gacatctccg ggaagggtgt tctggcagag    840
ggagtagcac gggcgatggc tctgaggact gtgagaagta tagttggaaa cagcgaggag    900
gccagggtgt ccgaagctga gtaagccaga gagagtggga ggaggtgaga taagaggggg    960
aaggtcagtt tctgctgaga gtgaggagga gccacaggag ggctgtgagc aggtggacgt   1020
gatctggctt gagttttaac agggccagta gaacaaagca cgcctgggta ccgaaaccag   1080
ccactggcca gttggcaacc tgggggagtc taacgcgagg aagcgcccag ggttcccca    1140
ggatgcgctt tccctcgccg ccacctggag acagcagagt cacgcccagc gctgcgcagg   1200
ctgatcgccg cgccgcgccc ccgccctcgg tcgcaggtgg ctcgttccgg gaattcctaa   1260
gcggaaaccg gtcccaagcc ccgcgccttc gctcggcccc tttaagagcc agaatttccg   1320
gagggctgac ccggggctag ggatgcccag gggccgaacc acaagtttggg aacgggtggg   1380
ggaggtggcg aaaacttccg aagtggaatt ccaactttc ctggccctga ttccccttgg   1440
```

```
gcatccctga ggggcagag cttcccttcc ggggacttta gagggttcct caggtcatct    1500
aactgggaga cacaggaggc ccgaagcgcc cccctccac ccgtccgga ggaaccccag    1560 tggaagtgga gaagtcaggc gccaccaaca agcctctccc agccaggact ttgcttagac    1620
tcgctcctcc cggcagggcg cacctaggcg gtccatcgc cagccgggga gaggggtttg    1680
ggcagggagg gaacaggtgc gcggcgggac ccgccctatc tcaacaggtg aatcgctcca    1740
agtgggtctc ggttgcatgg atctcggtgc gcttggtttg gccggagcag atggggccg    1800 gaagggacct gtggtccgca ggcgcccctcc cagcgggcca gtcacttggt tcgggccctg    1860
ggggacggag cgcacctggg tcagcccact ccggggagg gaggcagagg aaccctccc     1920 cgccgctcac ccctaagccc agccctcggc tcccacccctt gtgtacctgg gccgaaccat    1980
tcaccggagc gcgcagcggg tggagtgtgg ctcggaggac cgcggcgggt caagcacctt    2040
tctcccccat atctgaaagc atgcccttg tccacgtcgt ttacgctcat taaaacttcc    2100
agaatgcaac aggacggact tggagtaggg acaaggaacg gaagtgggaa ggggaggagc    2160
gtgcacccct cctggccttg gtgcgcgccg cgcccctaa ggtactttgg aagggacgcg    2220
cgggccagac gcgcccagac ggccgcgatg gcgctgttgg ccggcgggct ctccagaggg    2280
ctgggctccc accggccgc cgcaggccgg gacgcggtcg tcttcgtgtg gcttctgctt    2340
agcacctggt gcacaggtac ggggcacggg gcctctgacg ctgcgaacg ccggagggaa    2400 ctgtagaggg ggatggatgg agttggaggc ggcgggaagc gggaagcggg ggtctcagag    2460
gctgggacct tccgatcccc tgggtcttgg gcgatctgtt gcgcgcggga gtgagaggaa    2520 ttcccccattt gtgccggga gcgctccccg cgcccttatc tggaagatag caggaagtga    2580
aactccctgg acgtgagac ccggagcggc agggagaatg gaactctttg tggggaggga    2640
gtggaagacc gcccgatctc tgggaaaaga aagccgggga tgggacttgg gcgcacccgg    2700
ggatttctaa gttttggagt aacggggaga gggcacggga gggctggatc agacgcttcc    2760
tagagggaca gagacgaagg aacaatgcct aggcctcggg tgggtgtggg actggggact    2820
ccccatcccc cgcaccccac ccacctcccg cgggctccgg attatacgtg cgtaagagtc    2880
tggtgggatg gatttacgga cttgaaaccg acttctgctg gcaggctttc acctggatgg    2940
gatatttggg tggtgatgag gtctttcccg agacactttt ggttcagtca tttgaaatga    3000
ctttagagta gggtgaggtg gtgggaggct gatggagata ttgtgggggc tttagtccct    3060
ccatggcaaa gcagttcagg caaacaactc catggttttc cctccaaatt caaaaggccc    3120
cgggtaacct ggaatccttc gtagtcggtt ttgaagtggg gccttgggcg ctggggcat    3180 caacatggcc atctgggctt gcctgcccag gccacacaga ggccccttgt tgtgggtgaa    3240 tgcaaaggg aagaggggac tggtgtggtt cagaggccac aggctgggaa gagggatggc    3300
gggcgagtcc aaggaaactg gccgtgtcac cgtgcacctg ccacttcagc cccacgggtc    3360
tataaaatgg gcatgattat cgtggctacc tcactggtcc tggcaattaa ggaacaatgt    3420
gtgccaggca ctctgtaaac cacatacttg cgagtgtcaa gctggtgaca ggtggcgttc    3480
ctgttgaagc acctccctga gctcacagca acccttgctg tctctcctct tgccctcagc    3540
tcctgccagg gccatccagg tgaccgtgtc caaccctac cacgtggtga tcctcttcca    3600
gcctgtgacc ctgccctgta cctaccagat gacctcgacc cccacgcaac ccatcgtcat    3660
ctggaagtac aagtctttct gccgggaccg catcgccgat gccttctccc cggccagcgt    3720
cgacaaccag ctcaatgccc agctggcagc cgggaaccca ggctacaacc cctacgtcga    3780
```

-continued

```
gtgccaggac agcgtgcgca ccgtcaggt cgtggccacc aagcagggca acgctgtgac      3840
cctgggagat tactaccagg gccggaggat taccatcacc ggaagtatgt tgggcagggc      3900 aggggatga ggctgggctt gcccgggtgg tgggactggc gtccttgtgc gggacctgga      3960
gtccccatct gaaagctctt gagtgccagt gtctgaaagg accattgaag ggagcaattc      4020
tttttttttt ttttttgaa gatggagtct tgctctggac tccaggctgg agtgcagtgg      4080
tgcgatctca gctcactgca acctccacct cccaggttca agcaattctc ttgcctcagc      4140
ctcccgagta gctgggactc caggtgcgtg ccaccacgcc cagttaattt ttgtattttt      4200
agtagagatg gggtttcacc atgttggcca ggctggtctc aaactcctga cctcaaatga      4260
tctgcccgcc ttggcctcgc aaagtgctga gagacaccat acccagccta agggagcga      4320 ttctattcta ctattcttcc ttctgctaat ccttccattc tttaatttaa taacgaagat      4380
tttttgagta cctgtcatat accaggtgct gttctgggcc ctgggaatac agctgttaac      4440
aaaatcatca aaccacttcc ctcgtggagc ccacattgca gtgagagaga caaacacgac      4500
acacactctc aagtccttga agataaagaa aactgggtaa cggagagaag aggccagggt      4560
ttgttctata atcattaata acacgagcag taagaagtaa aatttatcta agtaacaact      4620
tataaagggt ctactgtgtg ctaagctctc atccaggttc ccaaggatta actcagacca      4680
cacagtaatt gaatagattc tatcattgtc atcttacaga ggcccagaga gagaaagtga      4740
cttgcctagt gtcatagctg gtaacggggc tgggattcta actcagccac tttgggtcta      4800
gtggccaagc tcctaatccc tttgcttgcc tagggtggtc cgcagaggac tcacagagga      4860
gatggcagga gtgaactgca ggggcaagag agcttaatgg agaaagcctg tgacatgcca      4920
ggaactgcac acatattctc ccattgagtc ctctcctcta ccctcctgac agctgaggca      4980
cagagaggtt accttgttca aatgggtgca taggaagtca agtctggag ctggggtttg      5040 aacccaggca gccctgagaa ccttgttctt ttttttgag acggagtctc gctctgtcgc      5100
ccaggctgga gtgcagtggc gggatctcgg ctcactgcaa gctccgcctc ccgggttcac      5160
gccattctcc tgcctcagcc tcccaagtag ctgggactac aggcgcccgc cactacgcct      5220
ggctaatttt ttgtattttt agtagagacg gggtttcacc gttttagccg gatggtctc      5280 gatctcctga cctcgtgatc cgcccgcctc ggcctcccaa agtgctggga ttacaggcgt      5340
gagccaccgc gcccggcccc ttgttcttaa ctgtaatgct gcctcctgat aggatgtgcc      5400
tgttgggact aagtaagggg cagtcattca ttcattcatt tggtatttat caagcatcga      5460
ctatgtgtcg ttggtgctgg ggatagaggt gattgggatg gctgaagttt ctgtcgtcaa      5520
ggagatgaca ttctggtgga gtgagactgg cagtaaataa gcagataaag aaagagtatg      5580
agaatttcaa agtctgggca cggtggctca cgtctgtaat ctcagcactt tgggaggcca      5640
aggtgggtgg atcacctgag gtcaggagtt ccagaccagc ctggccaaca tggtgaaacc      5700
ccgtctctac taaaaataca aagattagcc aggcatggtg gcacatgcct gtaatcccag      5760
ctactcagga ggctgaggca tgagaatcgc ttgaacccag gaggcagagg ttgcagtgag      5820
ctgagatcgc accactgtac tgcagtctgg gcgacagagt gagactctgt ctcaaaaaaa      5880
aaaaaaaaaa aaaagactcc gtcaaggtat aagaatgtca gagagtacta agtgttgcaa      5940
agaaaataac accaggctgg gtgcattggc tcatgcctgt aaatttcagc actttgggag      6000
gccaaggcag gaggatcact tgagcctagg agtttgagac cagcctggac aacaaaatga      6060
gaccccatgt ctacaaaaat tttaaaaatt taaaaattag ctgggcatgg tggcatgtgc      6120
ctgtggtccc ggctgctcag gaggctgagg tgggaggatt gcttgggctt gagaggtcaa      6180
```

```
ggcttcagtg agtcatgatc gtgccactgc attccagcct gggtgacaga gtgagaccct    6240
gtcttgaaat gaaaagaaaa taggctgggc gcagtggctc acacctgtaa tcccagcact    6300
ttgggaggcc gaggtgggtg gatcacctga ggtcaggaga tcgagaccag cctggccaac    6360
atggtgaaat cccatctcta ctaaaaatac aaaatttagc cgggcgtggt ggtgggcgcc    6420
tgtaatccca gctactcggg aggctgaggc aggagaatcg cttgaacctg ggaggcgaag    6480
gttgcggtgc gccaagattg cgccactgca ctctagcctg ggaaacagtg agactccgtc    6540
ttaaaaaaaa aagaaaaaag aaaatagcac tgggtgatgt gctacatgga atgacttggg    6600
ctgtgaatat gatttgagga gggcctgggc ctgggcctta cagaacctag aaggcagaga    6660 ggaagggag gggcagggtg ccagggatga aggctcacgt acctcatgtc ttagtgtgtg    6720
ttcactgtct taaacaagaa tttaaagttg ggcatggggc agagcgggga agggagcatc    6780
cctttgcaga ccccaagaag ccaggaactg gagcacattc tgctagagga tcgatgggaa    6840
gcagggttcc aggggctgag cctatgtcag tcctgtttca gaggaggcac caggcttgct    6900
tgccctgaat ttctgtgggc agctcagcca tgagcatcct actgttattg aggtcacagg    6960
gctgcttagg cccctcctc tctaacccag ggattgtgcc tgcctggacc aggcgtgact    7020
gctaagcttc tgccaggaca agccaaatac tgagggtgct tcctctgctg gacgcaaaag    7080
tccaggatga ccccccaggc tctgtctcgg ggaagggcc ctgcatgctc caggggcctc    7140
acaggcctgg tctttcaaa ccaccccac ctgggcctgt gtttgatcaa ggccctgagt    7200
gtaaacatcc attgtgtgtg tcctttcagg aaatcccata gccataggag cttcctctgt    7260
ttcagctttg aggatgggga aaagtggact ccccgtggtg ttcctagggt cacccactgt    7320
gctggggttt ttctgttgtt gttgtttttt ttctgttgcc caggctggag tgcagtggtg    7380
caatctcagc tcactgcaac ctctgcctcg caagttcaag tgattctccc gcctcagcct    7440
cctgagtagc tgggattaca ggtgcacacc accacacctg gctaattttt gtatcttttt    7500
ggtagagatg gggatttcgcc atgttggcca ggctggtctc aaactcctga cctcaggtga    7560
tctgcctgcc ttggcctccc aaagttctgg gattacagat gtgagccacc atgcccggcc    7620
tatcctggtt tcaaaagtga aaatagtcct ggataaggta gaaggctgtc cactccaggc    7680
atccctccgg tccggtggct cattccctgc tttgtccttc catgctttgg gtgatggacc    7740
agcacctgga caggaggccc tgttccacct cctcgggctc cttggggtcc aagtgccccc    7800
acctccagct gcactgcagc agagagccca tgggacctct gaaatcatga aggtcacctt    7860
tgcggtgtat aaagaaggaa ccagaggttg gagatgtgga ggaggcctgg ctgctgttcc    7920
cactggagac ctggcatctt ctccccgacc taaaacaatg aaagcagtgc tcagcccgga    7980
tgagatcacg gccagcccaa gaccaggaac agggtacgcc ctgcaggaag aaggtgtgcc    8040
cagaccttag gatggatcaa aagaagccgg aaaactatat ttttgtgag ttttgaaaat    8100 gtcagacagg tcaaacaaaa cacagtgagg tccagcctcg gcctacaaga tgccagattt    8160
caaccccctg cctatatgat ctgtttgcca tggcaggcgg ttcctgtcca cctcttttgt    8220
ttatagcagg gaccagctct tgagctccag tgttgaagag gcacggtcag ggtctgatct    8280
gaagacactg gtggctcatg cctgtaatcc cagcacttca ggaggccgag gcaggaggat    8340
tgcttgagga caggagctgg gagaccagcc tgggcaacac agtgagaccc agacactaca    8400
aaaaaataaa tttagcgggg catgatggca caccctgcta ctctgagat gggaagattg    8460 cttgagccta ggagttcgaa gctgcagtga cccatgatcg caccactgca ctccagcctg    8520
```

```
ggcgaccaag ctaggccctc tcaaaaaaga tacaggtgga aaaatgatgg acgaagaggg    8580
cattgtggca aacctgggga tttaggagaa cctagtttgg aattctatga ggattcaatg    8640
aaagaatgtg tgtagagggg cccagcacat agtaagagct caataaacgg tgggggctag    8700
gggtggtggc tcatgcctgt aatcccagca cttttgggagg ctgaggcagg tggatcactt    8760
gagccctgga gttcaagatc aacctggaca acaaagcaag atcccatctc aaaattaaaa    8820
aacaacacca acaacaaaaa aacagtggct tagatgcctg atcattaggg taagtcgtgt    8880 cctcaaccccc ttcacatctg ctctgaaggt caccatatcc ggaagccttc cctggcctcc    8940
ttgtttaaaa tggcacagcc cccactccac gcctggcact ctctgctgtc cctgattcgt    9000
tttctccata cagcttatct ttgtctggta tgtgacatag ttaacatttt atatttgtct    9060
ttctttccta gttagaatct gaactctaga agggcaaggg caaggattta aactcaaag    9120 attccgggct taggcctctt ttatattctt gattttgagg ttaattaaga gctcaggcct    9180
agcgaggtgg ctcatgcctg aatcccagc actttgggag gcccaggcgg gcagatcact    9240
tgaggtcagg agttccagac ctgcctggcc aacacagtga aaacctgtc tctactaaaa    9300 atacaaaaat tagccagtta tgttggcagg cgcctataat cccagctact caagaggctg    9360
aggcaggaga atcgcttgaa cccaggaggc agaggctgca gtgagccaag atcgtgccac    9420
tgcactccag cctgggcaac agagcgagac tccatctcaa aaaaaaaaaa aaattaaga    9480 gctcaaagag tttgttttca taggcagcag aatgagaaaa gtttacaaaa tagtttaaat    9540
gacaataaag tcattataga ttaacataaa taaaatacct tttatgaaaa aaataatcat    9600
tttctgaaat cagacaaaac attgtgaatg agaaggtggc atggttttat ttttttgcaa    9660
gtctccgaag cctggctgga tagaagagcc tggcttctca gagctgcttc agtctgttgt    9720
gatatctatt gtatgtcacg tagcctctgg aaaactccac agttagtatt gttgggaaaa    9780
taactttgac ctcaggatct cctgaaaacg tcttggggaa ccccagggtc tagaggctgc    9840
agtttgagaa ctgttgctgt ggtatcccag gtgtctcaaa tactgcctag aacataggtg    9900
gtactcagta attattgttg aaggatgaat gaatgaatga atgaatgaat gaagaaaga    9960 aatgtgtctt tgaatctagc catgtgccca gaatgatgag acagatgaca aaagctaagg    10020
gactttagca tgaggagagg gggttcgttt cctttttttt ctttttttt tgagatggag    10080 tctcactcta ctgcccaggc tagagtgcag tggtgcaatc tcagctcact gcaatctctg    10140
cctcctgagt tcaagcaatt ctcctgcctc agcctccagg gtagctggga ctacaggtgc    10200
gtgccaccat gcctagctaa ttttttacat ttttggtaga gatgggttt taccatgttg    10260 gccgggctgg tctggaactc ctgacctcaa gtgatccacc tgcctcagcc tcccaaagtg    10320
ttaggattac aggtgtgagc caccatgtcc ggccaagagg gtgttcattt ctgctccttg    10380
ccaggtattg tgtcaggcac tggggaccca gcagtggctg agacagacag gctctgcct    10440 cacggagccc acatttttcac caggcaaagg atggtcggcc cctaagctgg gagataagac    10500
ttcagcagtt gggtggggga gccgtgggag aagcccagcc cacaggggga cagtgcaaat    10560
ctagaaccaa ggcgatggca ggggtgaggc tggcacggta gctagagacc acgtcgtgcc    10620
aagggccttg ggaccatgg gactatggga cctagggaa ggcgtctgga atgctgtagc    10680
cagacactgt tgcaaggagg attttttctgt agacatgagg ccttccttat gaagaaagca    10740
agggttcttt cattcctggg ggtgccaggt gctgtggact gcagcacgcg tggttgctgc    10800
cgtcacagag ctgtcatgca ggagggcagc gcgtccttgg gaaggtggca ggcaggtcag    10860
gctaggagga aagaggccgg gaagctgagg gcatttcctg cccgagatgc ccaatgtagc    10920
```

```
ctacttctgt ccccagtggc ttaaggcaga gttgcctggt aggtgccctg gtcccaccct   10980
ggtgaaaggc tgaaggtatt taattagtgc ctgagaagca gagaggaaac aggatgtgcc   11040
aaaacacttt gatggatggt agagttaaca ggctccttgc ctgcagctgc ttcagacaag   11100
agcgtcccca agccctgggc ctgacctgga atgtggggat ggaagggag ggggaggaac    11160 caaggcactg ggagggtaag tctctctctc ccacatagac acacccactc cttatgggtg   11220
cctgggcatc tcctggtacc tagaatctgg cctgtttatc tccacaccca tccctggggt   11280
ctacactagg ccctgtgggt ggcagttcac atcagggag ttctgacttt ggctctgaga    11340
ggtggttcag agatggctgt aagttgagaa gcacagactg ctgggtgtgg tggttcacgc   11400
ctgtaatccc agcactttgg gaggctgagg tgggggtgga tcacctgagg tctggagttc   11460
aaaaccaact tggtcaacat ggcgaaactc catctctact aaaaatgcaa aaattagcca   11520
ggtgtggtgg caggtgccta taatcccagc tacatgggag gctgaggcag gagaatcgct   11580
tgaatctggg aggcgaagat tgtagtgagc cgagattagt tcgcaccatt gcatgccagc   11640
ctgggcaaca agagtgaaac tccgattcaa acaaacaaaa aaaaaagct gggcatggtg    11700 gagtgcctgt agtcctaact actcaggtgg gaggattgct tgagtccagg aggttgaagt   11760
tgcagtgggc tataattaca ccactgcact ccagccaggg ccacagagtg agaccctgtc   11820
tctaaagaaa gaaaaaaaaa aacaacctca ggctccgagg gcaccattac tgctctacac   11880
tgaagagctg tgcagctttt ccagacccga aatgtcatcc acaaaacaga agtgataatg   11940
gtcctgcctc acagacttct tgcagtagtc caggtgttta aacgggtg taaaaggccg     12000 tgtgcccttg gtaggaatct ttgcatatgc atttgatcat ctgcagcctg cccagcccac   12060
tgcttgcccc ctcctggggtg tgctgggaag gggtctttgg ccctccaggg gttaggtgcc   12120
ccagcctcca aggtgccctc acgccttttc atcccgactc agatgctgac ctgacctttg   12180
accagacggc gtgggggac agtggtgtgt attactgctc cgtggtctca gcccaggacc    12240
tccaggggaa caatgaggcc tacgcagagc tcatcgtcct tggtgagtgg gcctgggaag   12300
ggggaggcat ggcccttcct tttgtccgct tctgttctgt ctgccctccc ctgtgtccgc   12360
cctctgccct ccagcttacc ctctgggctc tgtcgcctgc tctgctctcc ccaggctct    12420 gccagtcact taggctcccc tgtgccctgc accccaggca gggaccactg gccacagtg    12480 cctccaatca cccaagccaa actaagagaa gagtggagac aattggagac tctgccttt    12540 caaagtctca tttttaaaaa aaatccagac ttggggtccg ggtgcggtag ttcatgcctg   12600
taatcccagc actttgggag gccgaggcgg gtggatcact tgaggccagg agttcgagac   12660
tagcctggcc aacgtggcaa aatcccgtct ctataaaaaa tataaaagcc aggcgtggtg   12720
gtgcacatgc ctgtaatccc agttactcag aaggctgagg catgaggatt gcttgaacct   12780
gggaggcaga ggatgcagta agccaagatc aagccactgc actccagcct gggcgacaga   12840
gtgagactct gtccaaaaaa aaaaaaaatc cagacgtggt cagagtccat gggcagtgaa   12900
tgaggacagt tgatggtgtg caaatcgac ccacctcttg ctacatcccc aaggcctcat    12960
ctcacccgag tccctcgcca agcacagcg gttttgccgt gtgccctgct gggatggcgc    13020
tgcatggcac acacactgtg taagtttgag tgcagctgaa acgaagccga ttccagacac   13080
ccaggggcag gcgggggtgt ccgtgtggct gggaggcctc cttgtgttag ggggatgttg   13140
ccatcggcca ggtgccctgc tgtaagccaa cacatggagt cttgtatgac atgtgctctg   13200
catgagtgat gccgctgggc tgtacactgc catcttcaca tgtgtgaatg agcacgtgac   13260
```

-continued

```
tgggggtac ttgggctgca agacagagtt catgtgtggg ggatggaaca cgtgcaccag    13320
tgacccagga acctctgcct gttcttcggt aaaatgcacc atttgcatca gcagttccca    13380
aaattagtct ccaggtctat ttacactcta aaacattatc gagggtctcc aagagctttt    13440
gtttgtttct gtgggtttta tgtctatctg ttgcttaaca tattaggaat taaaatgggg    13500
agattttcct tttttttttt tttttttga gatggagtct cgttctgtcg cccaggctgg    13560
agtgcagtgg ctcgatctcg gctcactgca agcttcacct cctgggttca cgccattctc    13620
ctgcctcagc ctcccaagta gctgggacta caggcacccg ccaccacacc cggctaattt    13680
tttttgtatt tttagtagag actgggtttc accatgttag ccaggatggt ctcgatctcc    13740
tgacctcgtg atccacccac ctgggcctcc caaagtgctg ggattacagg catgagccac    13800
tgcccggcct aaaatgggg agattttca agcccaagat acacaaggaa gactgggcaa    13860
catggcaaga ccctgactct acaaaaaatt ttaaaattaa ccaggcatgg tggcatgcac    13920
ctgtgagccc agcttcttgg gaggctgagg caggagtatc gcttgcaccc aggaggtcaa    13980
ggctgcagtg agccatgact atgctactgc actctagcat gagtgacaga gaccctggct    14040
caagaaacac aaacacacac acacacacac acacgcatat agtccattag gcatcagggc    14100
gatgatggca tcagggagcc tgggaaactc tactggacat tcatgggaga acaagtgaaa    14160
aaggcaaata acatcttagt gttattctaa aatttcttct tttggccttg tggacaggac    14220
cacgctttga gagctgtgac tgacatgcct ctgtcctgtt gcgagggcct atagtgccaa    14280
gtgcatgagc tctggggagg gcttcgtggg tgcagagctg ggcctgtgga ggcccctcag    14340
acacaacact ggtggggctc agagctccag gggcactcga gggaagacaa gaaccggctc    14400
tgagatgcgt gaatgtgaca gtgcatgagt agagatggag accttgtggg tcccagaacc    14460
aggactgcat atgactttca tatgtgggta ttttgcctt catgggtccc ttcctgtttt    14520 aaaaaaatg tgtgattatg ttgtcacaaa gagtttattc ctgtatattg tgttaatttg    14580
tgttcagatt tgtaaagtaa aattaaacca tttcagccag gtgtggtgac acatgcctgt    14640
agccctagct acttacccca gaggctgagg tgggaggatc gcctgagccc acgaggttga    14700
agctgcagtg agccatgatc acaccctgc actccagact gggcgacaga gctgagatcc    14760
tatttcgtgg gccctaggtc cctgtgcctg ctggaacagg acatccctat caccgtggtt    14820
ggagcccttt ggggtgctaa gacctatgaa tgagggaaac ttagggtgcc caagctgagg    14880
tagagccctc agaaccccct gggatttgta ttggagccct cgtggcataa acaggtgga    14940 ttatgcaatg ggagtttctt acctataagc acccacatgt gggcgggtgg agggtaggag    15000
ccatgcgcta gggcttcagc ccccagcccc ttcccgcttc agggcacacc ttgcacttgg    15060
ccagcctgga gctgggcttt cggggtggc acagcctggg ctggctctgg ccagcataat    15120
ctgtttctct tttgtccctc cagggaggac ctcaggggtg gctgagctct tacctggttt    15180
tcaggcgggg cccatagaag gtacgggggg tggatcctga gttgggcttc tcgggagctc    15240
ccatacatca cctactgctt ctgactctag ttagtatccc cttccccact aaaccctgct    15300
cactgtggac ccctcactaa cctggcctga ctgtggctct gaggcatcta gtggtctggc    15360
gctgggccta ggctaggctg ggctgaggag agcctgggt gcaggccagg gctctgtgac    15420
tggcacctgc ggtgctcttg agggtgtggc gtctgggcag ctggctctct ctttggtctg    15480
ggggctgcag tctgtctccc tctgtgcagg ctgcctcgtt ttctgccttg tgttttttgc    15540
acctggggga gggccgtaac tggggaatgg ccggatggt agaatgggga gtgtgctgtg    15600
cccagcctct ggcacaaaaa atccagccag ggctgcaggt tccttggtga gctttgcaaa    15660
```

-continued

```
tcgtccccga cctcagtgct ggctccgcac catgtacccc tgctgtgccg ttagccctgt    15720
tccctcccag gcctccgggc tcagggcctg ttgtctttct gcagactggc tcttcgtggt    15780
tgtggtatgc ctggctgcct tcctcatctt cctcctcctg ggcatctgct ggtgccagtg    15840
ctgcccgcac acttgctgct gctacgtcag gtgcccctgc tgcccagaca agtgctgctg    15900
ccccgaggcc cgtaagtgtc ccgctcatgg ccaccctggt ttgggcaaca tcctgcatcc    15960
aagggaagga ggtggccatc cacctgcccc aggacagtg gcgttggtct ggagggtgtg    16020
aatttagcca gtggggagaa agtaggctga ggagggtctg ctgtttagat tgtcgtttac    16080
ttcctccaac ttttagttta tttttattta tgttgttctt ttcttttgta agtataatcc    16140
atacacatgg taaaaatgtc caacagtaca agatactagt cacatggaag taaagccctc    16200
taaaaaaacc aaatcttggc taggcgcagt gattacgcct gtaatcccag cactttggga    16260
ggccaagacg agtggatcac ttgaggtcag gagttccaga tcagcctggc caacatggta    16320
aaacccagtt ctctactaaa aatacaaaaa ttagctgggc atggtggtga tcgcctgtaa    16380
tcccagctac tcaggagact gaggcatgag aatcgcttaa acccaagaag tggaggttgc    16440
agtgagctga gatcacgcca ctgcactcca gcctgggcga cagagtgaga ctctgtctca    16500
aaaaaaaaag aaaaaaaaat gttaagtgaa aaagttaaga aaccaaacaa ggtttacaac    16560
actacatgat ttaagcaaaa aaaattttttt ttgttttaga gaaagggtct cattctgtca    16620
tccaggcagt gcagtgcgat catagctctc tgcagcctca aactcccggg ttcaagcagt    16680
cctcccgcct cagcctctgg agcagctggg actgtaggca cacaccacca tgcccagcta    16740
attttttgat ttttgttttt tgtagagacg gggtctcagt atgttgccca gcctgatctc    16800
aaactcctgg cctcaggtga tcctccgaag tcagcctccc caaagtgctg ggattacagg    16860
catgtgccac catgctggcc aatttttaaa aattttctgt agagacaggg tcttgctatg    16920
ttgcccaggc tggtcttgaa ctcttgacct caagtgatcc tgcctcaggc tcccaaagtg    16980
atgggattac aggcatgaac taccacacct ggccttaaac ttaagcaaat ttttttttt    17040 ttttggagac agtttcactc tgtcgcccag gctggagtaa agtggcgtga tctctgctca    17100
ctgcaacctc cgcccccccgg gtttaagcta ttctcctgcc tcagcctccc gagtagctgg    17160
gatataggcg cctgccacca cgcctgacta attttttgtat ttttagtaga gacggggttt    17220
tgccatgttg gccaggctgg tctcgaactc ctgacctcag gcaatccgct cccccgcacc    17280
cctaccttgg cctcccaaag tgttaggact acaggtgtga gccaccatgc ctggccaaat    17340
ttaagcaaat gtttgaaaac acatacccac aggaatgctg cacattttac ccagctacta    17400
tgtctagggt cgtatctagc acaccagcat ggctactgtg gagagctggg actggatgtg    17460
agatgagagc taaagggggaa gtaagcaaac caagcagggg aaggtaagag aagacagaag    17520
acagagagag agggacctaa ctctatgaga ggagtcagac atgtgcaatt gaaaaagact    17580
tgctcctgtc tctcttctgt gaatgtttgt gaatatccca acgggacact ttcacagagg    17640
agctgattga cgtggtcaca gccatcagcc ttgggacacc agaccacagt gtgtacacta    17700
agtggcactg atggacactt cagcatccct ctagctgctg tcccgtttcc cctcctcggg    17760
gaccacagct gttgccagtc cttggtttcc ttcaggaggg tgtctgggta gaccagcctg    17820
tgtgcacaca gtccaagata catgaacagt gaagtgccag gcaatccttg caagcatggg    17880
caggtggaga gctgaggcct gcttgacacc ttcctgctca gaagcccagt gagcagtttc    17940
cctccctagg gctcagtgtc atcccctata aaatggggct tatggcagag ctcaccacac    18000
```

```
tgggtgcatc tggggatttg gcgagctcat gtgcacacca ttgagcatgg ggcccaacct   18060
atataaaata ttctacgtct gtcagctgct gggcactgcc actatcagcc tcagtagtga   18120
ctgagggaca gggcaccagt cagagccctg gtgcacacag agtgacccca gagaagcagc   18180
cttccctctc tgagtcctgt ttccttctgt taggtcctga cttcatgggt tgttgttagc   18240
attaaggaag tcgctggcta attttatagt cattgaagtc agtggtgtgc aacctggttc   18300
ctcaaaggat cacttccctg aaaaaattcc actgctccct ggaggcttat gcaggccatc   18360
ccatcccctc cctcttgttg tgttcagctg acagcttttt gctcagtgag taagtgttag   18420
gtccatttca cagatgggct gcaaccaagt ttgcagtgaa cccactaaga ccagagctag   18480
ggccaggact aaatgctggt cccaatgcca cattccctg tccccacacc acatttcctc   18540
catccggaga ccctgttacc caacccagg gccccattaa ctccctggca gaggccctgt   18600
tacatctgct gctgccacag cctccgccca cccttcagga ggcagcaggt cccactgctg   18660
atgataaagt tgcaggctgc ctgagctaat gaagggctt cctctaggct gtgcacttag   18720
tcttctgctt ccaaaccaaa tcagaggtga ggcaccctct ctgggcccat ctctctcctc   18780
cattttcctg ttggggtccc agggaggaag ccacttgcct agggcccagg aattttgcaa   18840
gcctcttgcc ctaggaggaa aggaaggag gaggatctta ccttgaactg tcaagcctag   18900
agcctggtgg ggcaggcaga aatgggtgca gtccatgagt tagaaacact agaggagaca   18960
ctttgctgct tggccgggc aggcaagtta attcccgagg ctcctgccac tgcatctcaa   19020
tctggaaggt gaccaggtgg ggcaggaccc acgtctccca gatgactcat ttttctaga   19080 acagggcttt ggctgccaaa gaggatactt gatttcggct tgtggggaca gtggtggacc   19140
cagcatctgg gctttatata aagggcagct ttgttgccct gtaaacacac agaccatggg   19200
tggccacttc ttccagtaag ttagctgggg agttggaagt ttaggtaaaa ccttttgatt   19260
gacaaatgtt ggcgaattac catgctgtta aatgaaacat tgttctgcca ccctgggggct   19320 gtgggtgcct gcgtgcaccc tctgaaaaat cacacaggaa gtggggtggg gtctctgtga   19380
agctggtgtc cccagcctc agggatgctg cagaaatgga atgaggacca acagggactc   19440
agatgtccaa ggaagctcta cagcggagag gacggcttgg gaaggaggtc caggcccagg   19500
tccctccgga acccaatggg tatggggcag cctggctcct gcctcatccc ccttctcctg   19560
ttgattatgt cctcacagtg tatgccgccg gcaaagcagc cacctcaggt gttcccagca   19620
tttatgcccc cagcacctat gcccacctgt ctcccgccaa gaccccaccc ccaccagcta   19680
tgattcccat gggccctgcc tacaacgggt accctggagg atacctggga gacgttgaca   19740
ggagtagctc agtgaggcc gggggaagca ggaacagctg gtgggagtgt gctgggcatc   19800
tggacactga ggggcagggg ctggaaggaa gagtgtcttg ggagccgagg aggggctctg   19860
ctcctggtgc gcggccactg acagccactc tcccccagct ggtggccaag gctcctatgt   19920
acccctgctt cgggacacgg acagcagtgt ggcctctggt gagaatccat cgtcccgaag   19980
ttggatgtgc ctgtaaggga gagggtgggg ccaggatcca tcctcccaaa ccgaccacca   20040
cccccctgtc cctagaagtc cgcagtggct acaggattca ggccagccag caggacgact   20100
ccatgcgggt cctgtactac atggagaagg agctggccaa cttcgaccct tctcgacctg   20160 gccccccccag tggccgtgtg gagcggggta agcaggagcc ttgggtctg agggcttttta   20220 aggtgggggg gtgaaacatg tctccctgat acctgccgca gggactcttg gtgcaaaccc   20280 tggacccgg gctcctccag cagtcagtga caccccctt ccctgcagcc atgagtgaag   20340
tcacctccct ccacgaggac gactggcgat ctcggccttc ccggggccct gccctcaccc   20400
```

-continued

```
cgatccggga tgaggagtgg ggtggccact cccccggag tcccagggga tgggaccagg    20460
agcccgccag ggagcaggca ggcggggct ggcgggccag gcggcccgg gcccgctccg    20520 tggacgccct ggacgacctc accccgccga gcaccgccga gtcagggagc aggtctccca    20580
cgagtaatgg tgggaggaga agccgggcct acatgccccc gcggagccgc agccgggacg    20640
acctctatga ccaagacgac tcgagggact tcccacgctc ccgggacccc cactacgacg    20700
acttcaggtc tcgggagcgc cctcctgccg accccaggtc ccaccaccac cgtacccggg    20760
accctcggga caacggctcc aggtccggga acctccccta tgatgggcgg ctactggagg    20820
aggctgtgag gaagaagggg tcggaggaga ggaggagacc ccacaaggag gaggaggaag    20880
aggcctacta cccgcccgcg ccgcccccgt actcggagac cgactcgcag gcgtcccgag    20940
agcgcaggct caagaaggtg agggccgccc tccctggcgt ccagaccgtc cctgggcccc    21000
cagccggtcc ccgcggctca tacccttctt tctttctccc ttgcagaact tggccctgag    21060
tcgggaaagt ttagtcgtct gatctgacgt tttctacgta gcttttgtat tttttttttt    21120
aatttgaagg aacactgatg aagccctgcc atacccctcc cgagtctaat aaaacgtata    21180
atcacaagct ctggagagaa ccatttgttc ggccgcgcgg ggcggggac cggggctgct    21240 cccgtatgcg tctgtaaagc gccgcgtccc ggggcaccg gagtccgggg ccggaggaa    21300 gagacccagc ctggcccggc ccgcgcccgc gccgccggcc ggagaacgtg ccccgcgcag    21360
ccaccgcccg cctgcgtgcg cgccccggcc ccgcccaggc gtgcgcatgc gccccggccc    21420
tccgccttcg cgcaccgcag gctggccgcc gggagcgcgc gcgcgctcct ctcccttcc    21480 agcccatccc ccccagcccc ccaccgacct actttactgt ctccaaactc gggcagccca    21540
cctggccccc gacgacccca gcccctgctc cgggtacccc gacgttccat ccagacccgc    21600
gtttcaccag ggcggcgcgc ggcgacctcg cgccccgcgg agcccgggc tcgcgcgcgc    21660 ccgcccgccc ccggagacag acagcgcgcg cgctcccggg ccgcctcccc ccagcgcgcg    21720
tccgccccgg gctcgcgccg ccgccgccgc gccgccgcg cgcgcgcagc tcaagtaaag    21780
gaggaaaaaa aaagggga aaatagaaa gcggcggcgg ctgcagcagc gatccgccgc    21840
cggactgggc caagccgggc ggcggccgcg cgagccggcg atccagggca ctggcggcgg    21900
ccagccaggg cgggccgtgt tcaaaaaaaa aagtcgcggc ggcggcggct gctcaggaa    21960 ggaggcctga gggccgcgtg cagcgggcg gcagctgggt gggctggggg cggccgcgcg    22020
gcgtcccgga gcctcgggcc gcccggagcc ggcgggcggg cggaggcgga ggcggcggcg    22080
gctgcagcgg ctgcaggagc ggcggcggct gcngcggcgg cngcggcatc tcctcctcac    22140 atgacccccac tgtttgtccc cgtgatcagc gcgagcggct cccgtatctc ctccgtcccc    22200
tcctgccgcg cggcgtgagc gccgggnctc gggccccccc cggccgcccg ccccctcccc    22260
tccntccntc ccctccctc ccctccccc cgggcccccg gcccccccg ccccgcccc    22320 ccccatggac atgctggacc cgggtctgga tcccgctgcc tcggccaccg ctgctgccgc    22380
cgccaggtaa gatccccggc ccggccgtgc cccgcgccc cggcccggc ccggcccccg    22440 cggcctgcag gccggggccg ccatgatccc gagcggccgc gggccccgct caaaatggag    22500
gccgccggcg cggggggac ctggcgcctc ccgcccccgg ccccggcct cggcggcgcc    22560 cccggcctca ggcgcggccg ggtgggactg gggccctgca gctgggcgcg ggggcggggg    22620
cgcgggcgcg ggccgcgctg accctgctcc ctcctgtgcc cctggcagcc acgacaaggg    22680
acccgaggcg gaggagggcg tcgagctgca ggaaggtgag tgcttgccgg gccggccgcg    22740
```

```
cccggggagg gctgggggcg ctcggcgcgg ccctgaccgt gccccgaccc tcctcggccc    22800
caggcgggga cggcccagga gcggaggagc agacagcggt ggccatcacc agcgtccagc    22860
aggcggcgtt cggcgaccac aacatccagt accagttccg cacagagaca aatggaggac    22920
aggtgagcgg cgggccgcga gagcgaacgg gcgggcgggc gggcgcgccg ggaaggctcg    22980
gacctggccc cagcgccggc ctcgccgctc tgccgccccc tgcaggtgac ataccgcgta    23040
gtccaggtga ctgatggtca gctggacggc cagggcgaca cagctggcgc cgtcagcgtc    23100
gtgtccaccg ctgccttcgc ggggggggcag caggctgtga cccaggtggg tgtggacggg    23160
gcagcccagc gcccgggccc cgccgct                                       23187
```

<210> SEQ ID NO 2
<211> LENGTH: 465
<212> TYPE: DNA
<213> ORGANISM: Homo sapiens
<220> FEATURE:
<221> NAME/KEY: allele
<222> LOCATION: 373
<223> OTHER INFORMATION: 99-14410-373 : polymorphic base C or T
<220> FEATURE:
<221> NAME/KEY: misc_binding
<222> LOCATION: 350..372
<223> OTHER INFORMATION: 99-14410-373.mis1 potential
<220> FEATURE:
<221> NAME/KEY: misc_binding
<222> LOCATION: 374..392
<223> OTHER INFORMATION: 99-14410-373.mis2 real, complement
<220> FEATURE:
<221> NAME/KEY: misc_binding
<222> LOCATION: 1..21
<223> OTHER INFORMATION: upstream amplification primer
<220> FEATURE:
<221> NAME/KEY: misc_binding
<222> LOCATION: 445..465
<223> OTHER INFORMATION: downstream amplification primer, complement
<400> SEQUENCE: 2

```
gttggaaggt aatctctaag cccttggaat gttctgcctg ataagagtgt ctctatttac     60
atagggacct agggccacac cagatcattt ctaacagtgt gatttccatt gaggaatgtg    120
ggccacacag tatcagctcc acccctggag gggctggaaa ctaatgtcgg ccacacgtgt    180
ggtcaattac gtctatgtga ctgagcccca gtaaaaactc tggacgccaa ggctcgagtg    240
ggtttccctg attggcaaca ctctgcgtgt actgtcccac atgggtgccc gcagaagaca    300
gcgctgggag gagacagctg gaagctttgc acttgggaca ttcctggatg cttccgcatg    360
tgtctctgtc cttggctggc tttcatctgt ttccttcac tataataaac cctaacntgt     420
gagtctgaga gcattcggtg agttccgtga ntccttgtag tgaat                    465
```

<210> SEQ ID NO 3
<211> LENGTH: 408
<212> TYPE: DNA
<213> ORGANISM: Homo sapiens
<220> FEATURE:
<221> NAME/KEY: allele
<222> LOCATION: 353
<223> OTHER INFORMATION: 99-14424-353 : polymorphic base A or G
<220> FEATURE:
<221> NAME/KEY: misc_binding
<222> LOCATION: 334..352
<223> OTHER INFORMATION: 99-14424-353.mis1 real
<220> FEATURE:
<221> NAME/KEY: misc_binding
<222> LOCATION: 354..376
<223> OTHER INFORMATION: 99-14424-353.mis2 potential, complement
<220> FEATURE:
<221> NAME/KEY: misc_binding

```
<222> LOCATION: 1..20
<223> OTHER INFORMATION: upstream  amplification  primer
<220> FEATURE:
<221> NAME/KEY: misc_binding
<222> LOCATION: 388..408
<223> OTHER INFORMATION: downstream  amplification  primer,  complement

<400> SEQUENCE: 3
aggctagtga ctggacactg gaatggtaca gccaaaaaaa ctcaacactt tcaccatcct      60
atgagctcac agcaaacagc aaatggcaca gaaagatggt ctcttttggt cttccaangt    120
cttctgtgag ggcctctaat tcgcagagct gaatnccaca cccaaaancc acatctttga    180
gcgcatctgg gaaacatagt attggcgttt tcatcccgac cccatggaag atagaatgag    240
tggcgagaga acaccgaggg ccaacccac tcatccccc ttgagttagt accgcctcta      300
ttctgcgcaa ggaagctgtc aggtattctc ctgaactgac gtggtagcac acgacatggc    360
tttaggcccc aaacaaggta aaatcatgtt gagtcacatg gtcagaaa                 408

<210> SEQ ID NO 4
<211> LENGTH: 452
<212> TYPE: DNA
<213> ORGANISM: Homo sapiens
<220> FEATURE:
<221> NAME/KEY: allele
<222> LOCATION: 322
<223> OTHER INFORMATION: 99-14418-322  :  polymorphic  base  A  or  G
<220> FEATURE:
<221> NAME/KEY: misc_binding
<222> LOCATION: 299..321
<223> OTHER INFORMATION: 99-14418-322.mis1  potential
<220> FEATURE:
<221> NAME/KEY: misc_binding
<222> LOCATION: 323..345
<223> OTHER INFORMATION: 99-14418-322.mis2  potential
<220> FEATURE:
<221> NAME/KEY: misc_binding
<222> LOCATION: 1..20
<223> OTHER INFORMATION: upstream  amplification  primer
<220> FEATURE:
<221> NAME/KEY: misc_binding
<222> LOCATION: 434..452
<223> OTHER INFORMATION: downstream  amplification  primer,  complement

<400> SEQUENCE: 4
caactctata agtcagcatc ccccagcccc tacaagggtt gtcaaacctt tatgagcaca      60
ctgctagtca gcagtgacca agacctggtc cctgccctgg cacaggctgt cctaaaagga    120
cgggggcaca ctttactcaa ccacaaaaac acatataaac acgtgcctta tgtgtgctat    180
gttctataca cctgctatga aggagaagta taggaattca tgagagaaga taacagaagg    240
aattcgaaca aggcttctcc aaggacacga agtttgagca gagacttaaa ggatgagggg    300
atttaactag acaaagaatg cggggaacag tatttcaatg agaaggaata gtgtgtacaa    360
aagaccagtg ctgagagagg atggtgagtc tgcacagcat agctggagtg gagaggatgt    420
agcagcagag tgagagatgr agataccagg ct                                  452

<210> SEQ ID NO 5
<211> LENGTH: 465
<212> TYPE: DNA
<213> ORGANISM: Homo sapiens
<220> FEATURE:
<221> NAME/KEY: allele
<222> LOCATION: 126
<223> OTHER INFORMATION: 99-14417-126  :  polymorphic  base  C  or  T
<220> FEATURE:
<221> NAME/KEY: misc_binding
<222> LOCATION: 103..125
```

```
<223> OTHER INFORMATION: 99-14417-126.mis1 potential
<220> FEATURE:
<221> NAME/KEY: misc_binding
<222> LOCATION: 127..149
<223> OTHER INFORMATION: 99-14417-126.mis2 potential, complement
<220> FEATURE:
<221> NAME/KEY: allele
<222> LOCATION: 334
<223> OTHER INFORMATION: 99-14417-334 : polymorphic base C or T
<220> FEATURE:
<221> NAME/KEY: misc_binding
<222> LOCATION: 311..333
<223> OTHER INFORMATION: 99-14417-334.mis1 potential
<220> FEATURE:
<221> NAME/KEY: misc_binding
<222> LOCATION: 335..357
<223> OTHER INFORMATION: 99-14417-334.mis2 potential
<220> FEATURE:
<221> NAME/KEY: misc_binding
<222> LOCATION: 1..21
<223> OTHER INFORMATION: upstream amplification primer
<220> FEATURE:
<221> NAME/KEY: misc_binding
<222> LOCATION: 447..465
<223> OTHER INFORMATION: downstream amplification primer, complement

<400> SEQUENCE: 5
gagttaaacc agacaaagca gttctctact gttgcctaag aaatcatcta aaatggctta      60
aaacaacatt gatggattta tctgtccatt ctgcaggttg gtaatgtagg ttgggctcac     120
tcatgtatct gtggccagca ctgtgtagct aggtggctct gcctcagggg gctggatggg     180
cagttcgctg gggagcctcc agcctctcat cctccagcag gctagcccgg tcatgttcac     240
aaggtcatgg caaggtcaa ctaagagagt acatggaagc ggcaaggttt cttgaagtct     300
aggcttgaaa ctaacacagc attactttca ccatgtttga ttggccaaaa gaaattacaa     360
ggtcagccca gattcaaggg gtggagacac agactccatc ccttgatggg aagagtggca     420 aagtcaccttt gtaagaatgt acacaaggag ncatgaaaga gtgtg               465

<210> SEQ ID NO 6
<211> LENGTH: 462
<212> TYPE: DNA
<213> ORGANISM: Homo sapiens
<220> FEATURE:
<221> NAME/KEY: allele
<222> LOCATION: 106
<223> OTHER INFORMATION: 99-14415-106 : polymorphic base C or T
<220> FEATURE:
<221> NAME/KEY: misc_binding
<222> LOCATION: 83..105
<223> OTHER INFORMATION: 99-14415-106.mis1 potential
<220> FEATURE:
<221> NAME/KEY: misc_binding
<222> LOCATION: 107..125
<223> OTHER INFORMATION: 99-14415-106.mis2 real, complement
<220> FEATURE:
<221> NAME/KEY: misc_binding
<222> LOCATION: 1..20
<223> OTHER INFORMATION: upstream amplification primer
<220> FEATURE:
<221> NAME/KEY: misc_binding
<222> LOCATION: 443..462
<223> OTHER INFORMATION: downstream amplification primer, complement

<400> SEQUENCE: 6 tgccagggt ttcctaactc ataccagaag cctgctgggc cactcatgga gcaggctaga     60
agctgggcag ttgacacccc aggagcagtc cttaacctcg agggatggga acggagcac     120 ccagcttcct caccctgta aggcacactc tacacatcct cttgcaggtc cccagggta     180 acattcacag gtgctgggga ttagagtgac atctttggga ggtgttattc agcctacccc     240
```

```
aagcagttgc aggcacaggc agcgtatata agggctctgg ggctgggtgt ctacttggtg    300
gacggagctg attaggacag gaaggcaact gtggagagaa catcaaggag gtcaccaggg    360
ccgagagtgt gtgggactct gtaggccagg atagcagctg tgggctttat ttgaaatgaa    420
atgggagcca cgtgagggtt ttgagcagtg gagagacatg ac                      462
```

```
<210> SEQ ID NO 7
<211> LENGTH: 477
<212> TYPE: DNA
<213> ORGANISM: Homo sapiens
<220> FEATURE:
<221> NAME/KEY: allele
<222> LOCATION: 250
<223> OTHER INFORMATION: 99-14413-250 : polymorphic base A or C
<220> FEATURE:
<221> NAME/KEY: misc_binding
<222> LOCATION: 227..249
<223> OTHER INFORMATION: 99-14413-250.mis1 potential
<220> FEATURE:
<221> NAME/KEY: misc_binding
<222> LOCATION: 251..273
<223> OTHER INFORMATION: 99-14413-250.mis2 potential, complement
<220> FEATURE:
<221> NAME/KEY: allele
<222> LOCATION: 383
<223> OTHER INFORMATION: 99-14413-383 : polymorphic base G or T
<220> FEATURE:
<221> NAME/KEY: misc_binding
<222> LOCATION: 360..382
<223> OTHER INFORMATION: 99-14413-383.mis1 potential
<220> FEATURE:
<221> NAME/KEY: misc_binding
<222> LOCATION: 384..402
<223> OTHER INFORMATION: 99-14413-383.mis2 real, complement
<220> FEATURE:
<221> NAME/KEY: misc_binding
<222> LOCATION: 1..20
<223> OTHER INFORMATION: upstream amplification primer
<220> FEATURE:
<221> NAME/KEY: misc_binding
<222> LOCATION: 457..477
<223> OTHER INFORMATION: downstream amplification primer, complement

<400> SEQUENCE: 7
tagcctttct tgccccactc tgtgagccta gatgttaatc agctgtgcct acaaggacct    60
ttgccagcga gccctactct caggcagtga tgctgtcctg aagtgtgacc atcccatggc    120
actctggtac ttctcttcca ttcttgggga agatccttct ctgcttaatt caatgcctga    180
cataaggaaa ctgcctgggg gtagccttca attgaccaac cctcagccct cccagactgg    240
cctctatcgc tgccagggca atgatgatac cctcatggta caatacgaga tcgacttcca    300
ggttgtcacc acccttcatg ttacgcacaa gagcctggac caaaagtccc tgcagaatga    360
gaccctgatc ctggatggca agktactcat ctttacccac tgggaccccc ggcaggactg    420
taaccgctgt ggggaactgg gtgagtgcag acgcctgggg tactgctaca ttgagga      477
```

```
<210> SEQ ID NO 8
<211> LENGTH: 476
<212> TYPE: DNA
<213> ORGANISM: Homo sapiens
<220> FEATURE:
<221> NAME/KEY: allele
<222> LOCATION: 226
<223> OTHER INFORMATION: 99-4575-226 : polymorphic base C or T
<220> FEATURE:
<221> NAME/KEY: misc_binding
<222> LOCATION: 207..225
<223> OTHER INFORMATION: 99-4575-226.mis1 real
<220> FEATURE:
```

```
<221> NAME/KEY: misc_binding
<222> LOCATION: 227..249
<223> OTHER INFORMATION: 99-4575-226.mis2  potential, complement
<220> FEATURE:
<221> NAME/KEY: misc_binding
<222> LOCATION: 1..19
<223> OTHER INFORMATION: upstream amplification primer
<220> FEATURE:
<221> NAME/KEY: misc_binding
<222> LOCATION: 458..476
<223> OTHER INFORMATION: downstream amplification primer, complement

<400> SEQUENCE: 8
aaatggcata aatggcaaga tgtgttcatg gatagaaaga cttaacatta aaaatgtcaa      60
tactacccaa aacaatctac agattcaaca caatgctgat caaaattcca acgtcttttc     120
ccaaagaaat ggaagcagat cctcaaattc atatggagtt ttaagggcc cccaataacc      180 aaaacaatac tgaaagagaa gaataaagtt agaggactca cactttccat ctgtgaactt     240
actacagagc tatagtaatt aaaacatatg gtacttgcat aaggataggc gtatagatca     300
atgaaataga atacagaacc gagaaacaaa ccctcacata tatgattaat tgattttga     360 caaggaagcc aagaccactt aatgggaaaa ggacagtgtt ttcaacaaat ggtagaggga     420
aaactgaata tccatatgca aaaaaatgaa gttggacct tctaccacat actaaa         476

<210> SEQ ID NO 9
<211> LENGTH: 489
<212> TYPE: DNA
<213> ORGANISM: Homo sapiens
<220> FEATURE:
<221> NAME/KEY: allele
<222> LOCATION: 296
<223> OTHER INFORMATION: 99-4580-296 : polymorphic base A or G
<220> FEATURE:
<221> NAME/KEY: misc_binding
<222> LOCATION: 273..295
<223> OTHER INFORMATION: 99-4580-296.mis1  potential
<220> FEATURE:
<221> NAME/KEY: misc_binding
<222> LOCATION: 297..315
<223> OTHER INFORMATION: 99-4580-296.mis2  real, complement
<220> FEATURE:
<221> NAME/KEY: misc_binding
<222> LOCATION: 1..20
<223> OTHER INFORMATION: upstream amplification primer
<220> FEATURE:
<221> NAME/KEY: misc_binding
<222> LOCATION: 470..489
<223> OTHER INFORMATION: downstream amplification primer, complement

<400> SEQUENCE: 9
tgagcgttct ttcctgtccc cacggtgcct ggtgctgggn cttggcagcc agggttggga      60
cagcctggct ttagcaggtc ctgagtcagg ggtctcaggn tccgcagcac wcagtcccca     120
ggcaggtgtc aggatgggat gtggccagag aaaggcatgt gctctgtctg gggatagctg     180
ccacccagct gacacagttg gcatgagatt gtggagtttt atggagtaaa atcacaaatc     240
tgggtttttt aagtaaaacc ttctatgagt tgccatctct ggccttcaac ataggatttg     300
ggtctttcct gggtgagctg gtgctttgtg ggccaggccc tgggagctgc aagtanccag     360
ttgggatctg ccattgccct gtggaaggat tttaagcagg ggtgaaacat ggtcagactt     420
ggatttagag atgaggaaaa aaaacaaaat cacggtgcca gagtctctgg ggagactgga     480
gaatgcagt                                                            489

<210> SEQ ID NO 10
<211> LENGTH: 523
```

```
<212> TYPE: DNA
<213> ORGANISM: Homo sapiens
<220> FEATURE:
<221> NAME/KEY: allele
<222> LOCATION: 424
<223> OTHER INFORMATION: 99-4567-424 : polymorphic base C or T
<220> FEATURE:
<221> NAME/KEY: misc_binding
<222> LOCATION: 401..423
<223> OTHER INFORMATION: 99-4567-424.mis1 potential
<220> FEATURE:
<221> NAME/KEY: misc_binding
<222> LOCATION: 425..443
<223> OTHER INFORMATION: 99-4567-424.mis2 real
<220> FEATURE:
<221> NAME/KEY: misc_binding
<222> LOCATION: 1..18
<223> OTHER INFORMATION: upstream amplification primer
<220> FEATURE:
<221> NAME/KEY: misc_binding
<222> LOCATION: 503..523
<223> OTHER INFORMATION: downstream amplification primer, complement

<400> SEQUENCE: 10
gctgtgactc tgttttccgc agtggagcgg aggcgsaggg acaagatcaa caactggatc      60
gtccagcttt cgaaaatcat tccagactgt aacgcagaca acagcaagac gggagcggtg     120
agcaccccgg accctcagtg tctgcggtgg tcccggcccc cgaccttgc atgcagaaag      180 tccaacagcc atggggctcg ggagtcatcc ctggggtgga ggccggtggg cggtgcctgc     240
cctaaggctc ctggtcccct cgcccccccag agtaaaggag ggatcctgtc caaggcctgc   300
gattacatcc gggagttgcg ccagaccaac cagcgcatgc aggagacctt caaagaggcc   360
gagcggctgc agatggacaa cgagctcctg aggcagcagg tgggtgcggg gcctggagcg   420
ggtcagggcc caggagcccc agatgcaagg cgctggccct cagctccctt gacctccgtc   480
gtgtccgcca gatcgaggag ctgaagaatg agaacgccct gct                      523

<210> SEQ ID NO 11
<211> LENGTH: 542
<212> TYPE: DNA
<213> ORGANISM: Homo sapiens
<220> FEATURE:
<221> NAME/KEY: allele
<222> LOCATION: 477
<223> OTHER INFORMATION: 99-14420-477 : polymorphic base G or T
<220> FEATURE:
<221> NAME/KEY: misc_binding
<222> LOCATION: 454..476
<223> OTHER INFORMATION: 99-14420-477.mis1 potential
<220> FEATURE:
<221> NAME/KEY: misc_binding
<222> LOCATION: 478..500
<223> OTHER INFORMATION: 99-14420-477.mis2 potential
<220> FEATURE:
<221> NAME/KEY: misc_binding
<222> LOCATION: 1..19
<223> OTHER INFORMATION: upstream amplification primer
<220> FEATURE:
<221> NAME/KEY: misc_binding
<222> LOCATION: 522..542
<223> OTHER INFORMATION: downstream amplification primer, complement

<400> SEQUENCE: 11
ttgtgggaag agacgagtgc agggagtggg ggaattgggg aggaaaggca gatggagctc     60
cacaaggtga gcagagtggc aagcccagct cctgggagtt gaaggtgct gcaggctgaa    120 gcagggccca gtgaataggg gtgtgctcac ctggggagac acaggagcag ccccagccc    180 taccaggcat cgctgcatct cagctgagga caggtttcat catcagcagg ggcagggtc    240
```

-continued

```
acagcacagg cgccagagcc ttggtgcaag gcgacaggct gacgggccaa gcttggcgcc      300
ctggccatct gccctccctg ggggtgaggg gctcaaggcc aggccccact attggctggt      360
gcagagggga gggctttggc ccagcagggc agggccaggg gctggttgtg ttttcaggaa      420
ctgttgacac ggagacccct gcctctcctc caacatggga catgtccttg accccatctc      480
cccacaccct catgcacgtc taggncctca aagggnacat tcattcctta attcctccat      540
cc                                                                    542
```

<210> SEQ ID NO 12
<211> LENGTH: 599
<212> TYPE: DNA
<213> ORGANISM: Homo sapiens
<220> FEATURE:
<221> NAME/KEY: allele
<222> LOCATION: 359
<223> OTHER INFORMATION: 99-4582-359 : polymorphic base G or T
<220> FEATURE:
<221> NAME/KEY: misc_binding
<222> LOCATION: 336..358
<223> OTHER INFORMATION: 99-4582-359.mis1 potential
<220> FEATURE:
<221> NAME/KEY: misc_binding
<222> LOCATION: 360..378
<223> OTHER INFORMATION: 99-4582-359.mis2 real, complement
<220> FEATURE:
<221> NAME/KEY: allele
<222> LOCATION: 62
<223> OTHER INFORMATION: 99-4582-62 : polymorphic base A or G
<220> FEATURE:
<221> NAME/KEY: misc_binding
<222> LOCATION: 43..61
<223> OTHER INFORMATION: 99-4582-62.mis1 real
<220> FEATURE:
<221> NAME/KEY: misc_binding
<222> LOCATION: 63..85
<223> OTHER INFORMATION: 99-4582-62.mis2 potential, complement
<220> FEATURE:
<221> NAME/KEY: misc_binding
<222> LOCATION: 1..19
<223> OTHER INFORMATION: upstream amplification primer
<220> FEATURE:
<221> NAME/KEY: misc_binding
<222> LOCATION: 582..599
<223> OTHER INFORMATION: downstream amplification primer, complement

<400> SEQUENCE: 12

```
gggggaaggg aatgtgaaga tgaagatgcc atacagagaa aggcccggaa cagatcctca      60 caccctcag aaggaaccaa cactgccagc acttgatctt gttgatctyg gaattcaagc       120
tcaattctgg cagggttttt tgtttgtttg tttgbttgtt tgtttgagtc ggagtcttgc      180
tctgttgccc agcctggagt gcagtggcgc aatctccgmt cactgccagc ccgcctccc      240 gggttcacgc cattctcctg cctcagcctc ctgagtagct gggactacag gcgcctgcca      300
ccatgcccgg ctaatttttt gtattttag tagagacagg gtttcaccgt gttagccagg      360
atggtctcga tctcctgacc tcgtgatctg cccgccttgg cctcccaaag cactgggagt      420
acaggtgtga gccaccgtgc atggcctcaa ttccggtttt taagccaccc agttgtgaa       480 actttgttgt aacagccctg gaaaactgat acacctgctc tctcgtaaaa gatcagctga     540
tacggcagca ccggccactg gatctgcggg tcagttgtcc ccttagacag ggcacctgc      599
```

<210> SEQ ID NO 13
<211> LENGTH: 2158
<212> TYPE: DNA
<213> ORGANISM: Homo sapiens
<220> FEATURE:
<221> NAME/KEY: allele

```
<222> LOCATION: 595
<223> OTHER INFORMATION: 9-3-324  :  polymorphic  base  C  or  T
<220> FEATURE:
<221> NAME/KEY: allele
<222> LOCATION: 940
<223> OTHER INFORMATION: 9-6-187  :  polymorphic  base  C  or  T
<220> FEATURE:
<221> NAME/KEY: allele
<222> LOCATION: 1191
<223> OTHER INFORMATION: 9-7-325  :  polymorphic  base  A  or  G
<220> FEATURE:
<221> NAME/KEY: allele
<222> LOCATION: 1362
<223> OTHER INFORMATION: 9-9-246  :  polymorphic  base  G  or  C
<220> FEATURE:
<221> NAME/KEY: allele
<222> LOCATION: 1658
<223> OTHER INFORMATION: LSRX9f13-BM  :  polymorphic  base  deletion  of
       AGG
<220> FEATURE:
<221> NAME/KEY: allele
<222> LOCATION: 2079
<223> OTHER INFORMATION: LSRX9f14-BM  :  polymorphic  base  T  or  G

<400> SEQUENCE: 13
tggagtgtgg ctcggaggac cgcggcgggt caagcacctt tctcccccat atctgaaagc      60
atgccctttg tccacgtcgt ttacgctcat taaaacttcc aga atg caa cag gac      115
                                               Met Gln Gln Asp
                                                 1 gga ctt gga gta ggg aca agg aac gga agt ggg aag ggg agg agc gtg      163
Gly Leu Gly Val Gly Thr Arg Asn Gly Ser Gly Lys Gly Arg Ser Val
 5              10                  15                  20 cac ccc tcc tgg cct tgg tgc gcg ccg cgc cct agg tac ttt gga          211
His Pro Ser Trp Pro Trp Cys Ala Pro Arg Pro Leu Arg Tyr Phe Gly
             25                  30                  35 agg gac gcg cgg gcc aga cgc gcc cag acg gcc gcg atg gcg ctg ttg      259
Arg Asp Ala Arg Ala Arg Ala Gln Thr Ala Ala Met Ala Leu Leu
         40                  45                  50 gcc ggc ggg ctc tcc aga ggg ctg ggc tcc cac ccg gcc gcc gca ggc      307
Ala Gly Gly Leu Ser Arg Gly Leu Gly Ser His Pro Ala Ala Ala Gly
     55                  60                  65 cgg gac gcg gtc gtc ttc gtg tgg ctt ctg ctt agc acc tgg tgc aca      355
Arg Asp Ala Val Val Phe Val Trp Leu Leu Leu Ser Thr Trp Cys Thr
 70                  75                  80 gct cct gcc agg gcc atc cag gtg acc gtg tcc aac ccc tac cac gtg      403
Ala Pro Ala Arg Ala Ile Gln Val Thr Val Ser Asn Pro Tyr His Val
85                  90                  95                 100 gtg atc ctc ttc cag cct gtg acc ctg ccc tgt acc tac cag atg acc      451
Val Ile Leu Phe Gln Pro Val Thr Leu Pro Cys Thr Tyr Gln Met Thr
             105                 110                 115 tcg acc ccc acg caa ccc atc gtc atc tgg aag tac aag tct ttc tgc      499
Ser Thr Pro Thr Gln Pro Ile Val Ile Trp Lys Tyr Lys Ser Phe Cys
         120                 125                 130 cgg gac cgc atc gcc gat gcc ttc tcc ccg gcc agc gtc gac aac cag      547
Arg Asp Arg Ile Ala Asp Ala Phe Ser Pro Ala Ser Val Asp Asn Gln
     135                 140                 145 ctc aat gcc cag ctg gca gcc ggg aac cca ggc tac aac ccc tac gtt      595
Leu Asn Ala Gln Leu Ala Ala Gly Asn Pro Gly Tyr Asn Pro Tyr Val
 150                 155                 160 gag tgc cag gac agc gtg cgc acc gtc agg gtc gtg gcc acc aag cag      643
Glu Cys Gln Asp Ser Val Arg Thr Val Arg Val Val Ala Thr Lys Gln
165                 170                 175                 180 ggc aac gct gtg acc ctg gga gat tac tac cag ggc cgg agg att acc      691
Gly Asn Ala Val Thr Leu Gly Asp Tyr Tyr Gln Gly Arg Arg Ile Thr
             185                 190                 195
```

```
                                                                -continued atc acc gga aat gct gac ctg acc ttt gac cag acg gcg tgg ggg gac         739
Ile Thr Gly Asn Ala Asp Leu Thr Phe Asp Gln Thr Ala Trp Gly Asp
            200                 205                 210 agt ggt gtg tat tac tgc tcc gtg gtc tca gcc cag gac ctc cag ggg         787
Ser Gly Val Tyr Tyr Cys Ser Val Val Ser Ala Gln Asp Leu Gln Gly
        215                 220                 225 aac aat gag gcc tac gca gag ctc atc gtc ctt ggg agg acc tca ggg         835
Asn Asn Glu Ala Tyr Ala Glu Leu Ile Val Leu Gly Arg Thr Ser Gly
    230                 235                 240 gtg gct gag ctc tta cct ggt ttt cag gcg ggg ccc ata gaa gac tgg         883
Val Ala Glu Leu Leu Pro Gly Phe Gln Ala Gly Pro Ile Glu Asp Trp
245                 250                 255                 260 ctc ttc gtg gtt gtg gta tgc ctg gct gcc ttc ctc atc ttc ctc ctc         931
Leu Phe Val Val Val Cys Leu Ala Ala Phe Leu Ile Phe Leu Leu
                265                 270                 275 ctg ggc atc tgc tgg tgc cag tgc tgc ccg cac act tgc tgc tgc tac         979
Leu Gly Ile Cys Trp Cys Gln Cys Cys Pro His Thr Cys Cys Cys Tyr
            280                 285                 290 gtc agg tgc ccc tgc tgc cca gac aag tgc tgc tgc ccc gag gcc ctg        1027
Val Arg Cys Pro Cys Cys Pro Asp Lys Cys Cys Cys Pro Glu Ala Leu
        295                 300                 305 tat gcc gcc ggg aaa gca gcc acc tca ggt gtt ccc agc att tat gcc        1075
Tyr Ala Ala Gly Lys Ala Ala Thr Ser Gly Val Pro Ser Ile Tyr Ala
    310                 315                 320 ccc agc acc tat gcc cac ctg tct ccc gcc aag acc cca ccc cca cca        1123
Pro Ser Thr Tyr Ala His Leu Ser Pro Ala Lys Thr Pro Pro Pro Pro
325                 330                 335                 340 gct atg att ccc atg ggc cct gcc tac aac ggg tac cct gga gga tac        1171
Ala Met Ile Pro Met Gly Pro Ala Tyr Asn Gly Tyr Pro Gly Gly Tyr
                345                 350                 355 cct gga gac gtt gac agg agt agc tca gct ggt ggc caa ggc tcc tat        1219
Pro Gly Asp Val Asp Arg Ser Ser Ser Ala Gly Gly Gln Gly Ser Tyr
            360                 365                 370 gta ccc ctg ctt cgg gac acg gac agc agt gtg gcc tct gaa gtc cgc        1267
Val Pro Leu Leu Arg Asp Thr Asp Ser Ser Val Ala Ser Glu Val Arg
        375                 380                 385 agt ggc tac agg att cag gcc agc cag cag gac gac tcc atg cgg gtc        1315
Ser Gly Tyr Arg Ile Gln Ala Ser Gln Gln Asp Asp Ser Met Arg Val
    390                 395                 400 ctg tac tac atg gag aag gag ctg gcc aac ttc gac cct tct cga cct        1363
Leu Tyr Tyr Met Glu Lys Glu Leu Ala Asn Phe Asp Pro Ser Arg Pro
405                 410                 415                 420 ggc ccc ccc agt ggc cgt gtg gag cgg gcc atg agt gaa gtc acc tcc        1411
Gly Pro Pro Ser Gly Arg Val Glu Arg Ala Met Ser Glu Val Thr Ser
                425                 430                 435 ctc cac gag gac gac tgg cga tct cgg cct tcc cgg ggc cct gcc ctc        1459
Leu His Glu Asp Asp Trp Arg Ser Arg Pro Ser Arg Gly Pro Ala Leu
            440                 445                 450 acc ccg atc cgg gat gag gag tgg ggt ggc cac tcc ccc cgg agt ccc        1507
Thr Pro Ile Arg Asp Glu Glu Trp Gly Gly His Ser Pro Arg Ser Pro
        455                 460                 465 agg gga tgg gac cag gag ccc gcc agg gag cag gca ggc ggg ggc tgg        1555
Arg Gly Trp Asp Gln Glu Pro Ala Arg Glu Gln Ala Gly Gly Gly Trp
    470                 475                 480 cgg gcc agg cgg ccc cgg gcc cgc tcc gtg gac gcc ctg gac gac ctc        1603
Arg Ala Arg Arg Pro Arg Ala Arg Ser Val Asp Ala Leu Asp Asp Leu
485                 490                 495                 500 acc ccg ccg agc acc gcc gag tca ggg agc agg tct ccc acg agt aat        1651
Thr Pro Pro Ser Thr Ala Glu Ser Gly Ser Arg Ser Pro Thr Ser Asn
```

```
                        505                 510                 515
ggt ggg aga agc cgg gcc tac atg ccc ccg cgg agc cgc agc cgg gac     1699
Gly Gly Arg Ser Arg Ala Tyr Met Pro Pro Arg Ser Arg Ser Arg Asp
            520                 525                 530 gac ctc tat gac caa gac gac tcg agg gac ttc cca cgc tcc cgg gac     1747
Asp Leu Tyr Asp Gln Asp Asp Ser Arg Asp Phe Pro Arg Ser Arg Asp
            535                 540                 545 ccc cac tac gac gac ttc agg tct cgg gag cgc cct cct gcc gac ccc     1795
Pro His Tyr Asp Asp Phe Arg Ser Arg Glu Arg Pro Pro Ala Asp Pro
            550                 555                 560 agg tcc cac cac cac cgt acc cgg gac cct cgg gac aac ggc tcc agg     1843
Arg Ser His His His Arg Thr Arg Asp Pro Arg Asp Asn Gly Ser Arg
565                 570                 575                 580 tcc ggg gac ctc ccc tat gat ggg cgg cta ctg gag gag gct gtg agg     1891
Ser Gly Asp Leu Pro Tyr Asp Gly Arg Leu Leu Glu Glu Ala Val Arg
                585                 590                 595 aag aag ggg tcg gag gag agg agg aga ccc cac aag gag gag gag gaa     1939
Lys Lys Gly Ser Glu Glu Arg Arg Arg Pro His Lys Glu Glu Glu Glu
            600                 605                 610 gag gcc tac tac ccg ccc gcg ccg ccc ccg tac tcg gag acc gac tcg     1987
Glu Ala Tyr Tyr Pro Pro Ala Pro Pro Pro Tyr Ser Glu Thr Asp Ser
            615                 620                 625 cag gcg tcc cga gag cgc agg ctc aag aag aac ttg gcc ctg agt cgg     2035
Gln Ala Ser Arg Glu Arg Arg Leu Lys Lys Asn Leu Ala Leu Ser Arg
            630                 635                 640 gaa agt tta gtc gtc tga tctgacgttt tctacgtagc ttttgtattt            2083
Glu Ser Leu Val Val
645 tttttttaa tttgaaggaa cactgatgaa gccctgccat acccctcccg agtctaataa    2143
aacgtataat cacaa                                                    2158

<210> SEQ ID NO 14
<211> LENGTH: 649
<212> TYPE: PRT
<213> ORGANISM: Homo sapiens
<220> FEATURE:
<221> NAME/KEY: VARIANT
<222> LOCATION: 363
<223> OTHER INFORMATION: 9-7-325  :  polymorphic  amino  acid  Ser  or
      Asn
<220> FEATURE:
<221> NAME/KEY: VARIANT
<222> LOCATION: 420
<223> OTHER INFORMATION: 9-9-246  :  polymorphic  amino  acid  Pro  or
      Arg
<220> FEATURE:
<221> NAME/KEY: VARIANT
<222> LOCATION: 519
<223> OTHER INFORMATION: LSRX9f13-BM  :  polymorphic  amino  acid
      deletion  of  Arg

<400> SEQUENCE: 14

Met Gln Gln Asp Gly Leu Gly Val Gly Thr Arg Asn Gly Ser Gly Lys
1               5                   10                  15

Gly Arg Ser Val His Pro Ser Trp Pro Trp Cys Ala Pro Arg Pro Leu
            20                  25                  30

Arg Tyr Phe Gly Arg Asp Ala Arg Ala Arg Arg Ala Gln Thr Ala Ala
        35                  40                  45

Met Ala Leu Leu Ala Gly Gly Leu Ser Arg Gly Leu Gly Ser His Pro
    50                  55                  60

Ala Ala Ala Gly Arg Asp Ala Val Val Phe Val Trp Leu Leu Leu Ser
65                  70                  75                  80
```

-continued

```
Thr Trp Cys Thr Ala Pro Ala Arg Ala Ile Gln Val Thr Val Ser Asn
                 85                  90                  95
Pro Tyr His Val Val Ile Leu Phe Gln Pro Val Thr Leu Pro Cys Thr
            100                 105                 110
Tyr Gln Met Thr Ser Thr Pro Thr Gln Pro Ile Val Ile Trp Lys Tyr
        115                 120                 125
Lys Ser Phe Cys Arg Asp Arg Ile Ala Asp Ala Phe Ser Pro Ala Ser
    130                 135                 140
Val Asp Asn Gln Leu Asn Ala Gln Leu Ala Ala Gly Asn Pro Gly Tyr
145                 150                 155                 160
Asn Pro Tyr Val Glu Cys Gln Asp Ser Val Arg Thr Val Arg Val Val
            165                 170                 175
Ala Thr Lys Gln Gly Asn Ala Val Thr Leu Gly Asp Tyr Tyr Gln Gly
        180                 185                 190
Arg Arg Ile Thr Ile Thr Gly Asn Ala Asp Leu Thr Phe Asp Gln Thr
    195                 200                 205
Ala Trp Gly Asp Ser Gly Val Tyr Tyr Cys Ser Val Val Ser Ala Gln
    210                 215                 220
Asp Leu Gln Gly Asn Asn Glu Ala Tyr Ala Glu Leu Ile Val Leu Gly
225                 230                 235                 240
Arg Thr Ser Gly Val Ala Glu Leu Leu Pro Gly Phe Gln Ala Gly Pro
            245                 250                 255
Ile Glu Asp Trp Leu Phe Val Val Val Cys Leu Ala Ala Phe Leu
        260                 265                 270
Ile Phe Leu Leu Leu Gly Ile Cys Trp Cys Gln Cys Cys Pro His Thr
    275                 280                 285
Cys Cys Cys Tyr Val Arg Cys Pro Cys Cys Pro Asp Lys Cys Cys Cys
    290                 295                 300
Pro Glu Ala Leu Tyr Ala Ala Gly Lys Ala Ala Thr Ser Gly Val Pro
305                 310                 315                 320
Ser Ile Tyr Ala Pro Ser Thr Tyr Ala His Leu Ser Pro Ala Lys Thr
            325                 330                 335
Pro Pro Pro Pro Ala Met Ile Pro Met Gly Pro Ala Tyr Asn Gly Tyr
        340                 345                 350
Pro Gly Gly Tyr Pro Gly Asp Val Asp Arg Ser Ser Ser Ala Gly Gly
    355                 360                 365
Gln Gly Ser Tyr Val Pro Leu Leu Arg Asp Thr Asp Ser Ser Val Ala
    370                 375                 380
Ser Glu Val Arg Ser Gly Tyr Arg Ile Gln Ala Ser Gln Gln Asp Asp
385                 390                 395                 400
Ser Met Arg Val Leu Tyr Tyr Met Glu Lys Glu Leu Ala Asn Phe Asp
            405                 410                 415
Pro Ser Arg Pro Gly Pro Pro Ser Gly Arg Val Glu Arg Ala Met Ser
        420                 425                 430
Glu Val Thr Ser Leu His Glu Asp Asp Trp Arg Ser Arg Pro Ser Arg
    435                 440                 445
Gly Pro Ala Leu Thr Pro Ile Arg Asp Glu Glu Trp Gly Gly His Ser
    450                 455                 460
Pro Arg Ser Pro Arg Gly Trp Asp Gln Glu Pro Ala Arg Glu Gln Ala
465                 470                 475                 480
Gly Gly Gly Trp Arg Ala Arg Arg Pro Arg Ala Arg Ser Val Asp Ala
            485                 490                 495
```

```
Leu Asp Asp Leu Thr Pro Pro Ser Thr Ala Glu Ser Gly Ser Arg Ser
            500                 505                 510

Pro Thr Ser Asn Gly Gly Arg Ser Arg Ala Tyr Met Pro Pro Arg Ser
            515                 520                 525

Arg Ser Arg Asp Asp Leu Tyr Asp Gln Asp Asp Ser Arg Asp Phe Pro
        530                 535                 540

Arg Ser Arg Asp Pro His Tyr Asp Asp Phe Arg Ser Arg Glu Arg Pro
545                 550                 555                 560

Pro Ala Asp Pro Arg Ser His His His Arg Thr Arg Asp Pro Arg Asp
                565                 570                 575

Asn Gly Ser Arg Ser Gly Asp Leu Pro Tyr Asp Gly Arg Leu Leu Glu
            580                 585                 590

Glu Ala Val Arg Lys Lys Gly Ser Glu Glu Arg Arg Arg Pro His Lys
            595                 600                 605

Glu Glu Glu Glu Glu Ala Tyr Tyr Pro Pro Ala Pro Pro Pro Tyr Ser
            610                 615                 620

Glu Thr Asp Ser Gln Ala Ser Arg Glu Arg Arg Leu Lys Lys Asn Leu
625                 630                 635                 640

Ala Leu Ser Arg Glu Ser Leu Val Val
                645

<210> SEQ ID NO 15
<211> LENGTH: 2101
<212> TYPE: DNA
<213> ORGANISM: Homo sapiens
<220> FEATURE:
<221> NAME/KEY: allele
<222> LOCATION: 595
<223> OTHER INFORMATION: 9-3-324  :  polymorphic  base  C  or  T
<220> FEATURE:
<221> NAME/KEY: allele
<222> LOCATION: 883
<223> OTHER INFORMATION: 9-6-187  :  polymorphic  base  C  or  T
<220> FEATURE:
<221> NAME/KEY: allele
<222> LOCATION: 1134
<223> OTHER INFORMATION: 9-7-325  :  polymorphic  base  A  or  G
<220> FEATURE:
<221> NAME/KEY: allele
<222> LOCATION: 1305
<223> OTHER INFORMATION: 9-9-246  :  polymorphic  base  G  or  C
<220> FEATURE:
<221> NAME/KEY: allele
<222> LOCATION: 1601
<223> OTHER INFORMATION: LSRX9f13-BM  :  polymorphic  base  deletion
      of  AGG
<220> FEATURE:
<221> NAME/KEY: allele
<222> LOCATION: 2022
<223> OTHER INFORMATION: LSRX9f14-BM  :  polymorphic  base  T  or  G

<400> SEQUENCE: 15
tggagtgtgg ctcggaggac cgcggcgggt caagcacctt tctcccccat atctgaaagc      60 atgcccttttg tccacgtcgt ttacgctcat taaaacttcc aga atg caa cag gac     115
                                                Met Gln Gln Asp
                                                  1 gga ctt gga gta ggg aca agg aac gga agt ggg aag ggg agg agc gtg     163
Gly Leu Gly Val Gly Thr Arg Asn Gly Ser Gly Lys Gly Arg Ser Val
  5                  10                  15                  20 cac ccc tcc tgg cct tgg tgc gcg ccg cgc ccc cta agg tac ttt gga     211
His Pro Ser Trp Pro Trp Cys Ala Pro Arg Pro Leu Arg Tyr Phe Gly
                 25                  30                  35 agg gac gcg cgg gcc aga cgc gcc cag acg gcc gcg atg gcg ctg ttg     259
Arg Asp Ala Arg Ala Arg Arg Ala Gln Thr Ala Ala Met Ala Leu Leu
```

```
                    40                    45                    50
gcc ggc ggg ctc tcc aga ggg ctg ggc tcc cac ccg gcc gcc gca ggc     307
Ala Gly Gly Leu Ser Arg Gly Leu Gly Ser His Pro Ala Ala Ala Gly
         55                   60                   65 cgg gac gcg gtc gtc ttc gtg tgg ctt ctg ctt agc acc tgg tgc aca     355
Arg Asp Ala Val Val Phe Val Trp Leu Leu Leu Ser Thr Trp Cys Thr
 70                   75                   80 gct cct gcc agg gcc atc cag gtg acc gtg tcc aac ccc tac cac gtg     403
Ala Pro Ala Arg Ala Ile Gln Val Thr Val Ser Asn Pro Tyr His Val
 85                   90                   95                  100 gtg atc ctc ttc cag cct gtg acc ctg ccc tgt acc tac cag atg acc     451
Val Ile Leu Phe Gln Pro Val Thr Leu Pro Cys Thr Tyr Gln Met Thr
             105                  110                  115 tcg acc ccc acg caa ccc atc gtc atc tgg aag tac aag tct ttc tgc     499
Ser Thr Pro Thr Gln Pro Ile Val Ile Trp Lys Tyr Lys Ser Phe Cys
             120                  125                  130 cgg gac cgc atc gcc gat gcc ttc tcc ccg gcc agc gtc gac aac cag     547
Arg Asp Arg Ile Ala Asp Ala Phe Ser Pro Ala Ser Val Asp Asn Gln
             135                  140                  145 ctc aat gcc cag ctg gca gcc ggg aac cca ggc tac aac ccc tac gtt     595
Leu Asn Ala Gln Leu Ala Ala Gly Asn Pro Gly Tyr Asn Pro Tyr Val
         150                  155                  160 gag tgc cag gac agc gtg cgc acc gtc agg gtc gtg gcc acc aag cag     643
Glu Cys Gln Asp Ser Val Arg Thr Val Arg Val Val Ala Thr Lys Gln
165                  170                  175                  180 ggc aac gct gtg acc ctg gga gat tac tac cag ggc cgg agg att acc     691
Gly Asn Ala Val Thr Leu Gly Asp Tyr Tyr Gln Gly Arg Arg Ile Thr
                 185                  190                  195 atc acc gga aat gct gac ctg acc ttt gac cag acg gcg tgg ggg gac     739
Ile Thr Gly Asn Ala Asp Leu Thr Phe Asp Gln Thr Ala Trp Gly Asp
             200                  205                  210 agt ggt gtg tat tac tgc tcc gtg gtc tca gcc cag gac ctc cag ggg     787
Ser Gly Val Tyr Tyr Cys Ser Val Val Ser Ala Gln Asp Leu Gln Gly
             215                  220                  225 aac aat gag gcc tac gca gag ctc atc gtc ctt gac tgg ctc ttc gtg     835
Asn Asn Glu Ala Tyr Ala Glu Leu Ile Val Leu Asp Trp Leu Phe Val
         230                  235                  240 gtt gtg gta tgc ctg gct gcc ttc ctc atc ttc ctc ctc ctg ggc atc     883
Val Val Val Cys Leu Ala Ala Phe Leu Ile Phe Leu Leu Leu Gly Ile
245                  250                  255                  260 tgc tgg tgc cag tgc tgc ccg cac act tgc tgc tgc tac gtc agg tgc     931
Cys Trp Cys Gln Cys Cys Pro His Thr Cys Cys Cys Tyr Val Arg Cys
                 265                  270                  275 ccc tgc tgc cca gac aag tgc tgc tgc ccc gag gcc ctg tat gcc gcc     979
Pro Cys Cys Pro Asp Lys Cys Cys Cys Pro Glu Ala Leu Tyr Ala Ala
             280                  285                  290 ggc aaa gca gcc acc tca ggt gtt ccc agc att tat gcc ccc agc acc    1027
Gly Lys Ala Ala Thr Ser Gly Val Pro Ser Ile Tyr Ala Pro Ser Thr
         295                  300                  305 tat gcc cac ctg tct ccc gcc aag acc cca ccc cca gct atg att        1075
Tyr Ala His Leu Ser Pro Ala Lys Thr Pro Pro Pro Ala Met Ile
         310                  315                  320 ccc atg ggc cct gcc tac aac ggg tac cct gga gga tac cct gga gac    1123
Pro Met Gly Pro Ala Tyr Asn Gly Tyr Pro Gly Gly Tyr Pro Gly Asp
325                  330                  335                  340 gtt gac agg agt agc tca gct ggt ggc caa ggc tcc tat gta ccc ctg    1171
Val Asp Arg Ser Ser Ser Ala Gly Gly Gln Gly Ser Tyr Val Pro Leu
                 345                  350                  355 ctt cgg gac acg gac agc agt gtg gcc tct gaa gtc cgc agt ggc tac    1219
```

```
Leu Arg Asp Thr Asp Ser Ser Val Ala Ser Glu Val Arg Ser Gly Tyr
            360                 365                 370 agg att cag gcc agc cag cag gac gac tcc atg cgg gtc ctg tac tac      1267
Arg Ile Gln Ala Ser Gln Gln Asp Asp Ser Met Arg Val Leu Tyr Tyr
            375                 380                 385 atg gag aag gag ctg gcc aac ttc gac cct tct cga cct ggc ccc ccc      1315
Met Glu Lys Glu Leu Ala Asn Phe Asp Pro Ser Arg Pro Gly Pro Pro
        390                 395                 400 agt ggc cgt gtg gag cgg gcc atg agt gaa gtc acc tcc ctc cac gag      1363
Ser Gly Arg Val Glu Arg Ala Met Ser Glu Val Thr Ser Leu His Glu
405                 410                 415                 420 gac gac tgg cga tct cgg cct tcc cgg ggc cct gcc ctc acc ccg atc      1411
Asp Asp Trp Arg Ser Arg Pro Ser Arg Gly Pro Ala Leu Thr Pro Ile
                425                 430                 435 cgg gat gag gag tgg ggt ggc cac tcc ccc cgg agt ccc agg gga tgg      1459
Arg Asp Glu Glu Trp Gly Gly His Ser Pro Arg Ser Pro Arg Gly Trp
                    440                 445                 450 gac cag gag ccc gcc agg gag cag gca ggc ggg ggc tgg cgg gcc agg      1507
Asp Gln Glu Pro Ala Arg Glu Gln Ala Gly Gly Gly Trp Arg Ala Arg
                455                 460                 465 cgg ccc cgg gcc cgc tcc gtg gac gcc ctg gac gac ctc acc ccg ccg      1555
Arg Pro Arg Ala Arg Ser Val Asp Ala Leu Asp Asp Leu Thr Pro Pro
470                 475                 480 agc acc gcc gag tca ggg agc agg tct ccc acg agt aat ggt ggg aga      1603
Ser Thr Ala Glu Ser Gly Ser Arg Ser Pro Thr Ser Asn Gly Gly Arg
485                 490                 495                 500 agc cgg gcc tac atg ccc ccg cgg agc cgc agc cgg gac gac ctc tat      1651
Ser Arg Ala Tyr Met Pro Pro Arg Ser Arg Ser Arg Asp Asp Leu Tyr
                505                 510                 515 gac caa gac gac tcg agg gac ttc cca cgc tcc cgg gac ccc cac tac      1699
Asp Gln Asp Asp Ser Arg Asp Phe Pro Arg Ser Arg Asp Pro His Tyr
                520                 525                 530 gac gac ttc agg tct cgg gag cgc cct cct gcc gac ccc agg tcc cac      1747
Asp Asp Phe Arg Ser Arg Glu Arg Pro Pro Ala Asp Pro Arg Ser His
            535                 540                 545 cac cac cgt acc cgg gac cct cgg gac aac ggc tcc agg tcc ggg gac      1795
His His Arg Thr Arg Asp Pro Arg Asp Asn Gly Ser Arg Ser Gly Asp
        550                 555                 560 ctc ccc tat gat ggg cgg cta ctg gag gag gct gtg agg aag aag ggg      1843
Leu Pro Tyr Asp Gly Arg Leu Leu Glu Glu Ala Val Arg Lys Lys Gly
565                 570                 575                 580 tcg gag gag agg agg aga ccc cac aag gag gag gag gaa gag gcc tac      1891
Ser Glu Glu Arg Arg Arg Pro His Lys Glu Glu Glu Glu Glu Ala Tyr
                585                 590                 595 tac ccg ccc gcg ccg ccc ccg tac tcg gag acc gac tcg cag gcg tcc      1939
Tyr Pro Pro Ala Pro Pro Pro Tyr Ser Glu Thr Asp Ser Gln Ala Ser
                600                 605                 610 cga gag cgc agg ctc aag aag aac ttg gcc ctg agt cgg gaa agt tta      1987
Arg Glu Arg Arg Leu Lys Lys Asn Leu Ala Leu Ser Arg Glu Ser Leu
            615                 620                 625 gtc gtc tga tctgacgttt tctacgtagc ttttgtattt tttttttaa              2036
Val Val
        630 tttgaaggaa cactgatgaa gccctgccat accctcccg agtctaataa aacgtataat    2096 cacaa                                                                2101

<210> SEQ ID NO 16
<211> LENGTH: 630
<212> TYPE: PRT
```

```
<213> ORGANISM: Homo sapiens
<220> FEATURE:
<221> NAME/KEY: VARIANT
<222> LOCATION: 344
<223> OTHER INFORMATION: 9-7-325 : polymorphic amino acid Ser or
      Asn
<220> FEATURE:
<221> NAME/KEY: VARIANT
<222> LOCATION: 401
<223> OTHER INFORMATION: 9-9-246 : polymorphic amino acid Pro or
      Arg
<220> FEATURE:
<221> NAME/KEY: VARIANT
<222> LOCATION: 500
<223> OTHER INFORMATION: LSRX9f13-BM : polymorphic amino acid
      deletion of Arg

<400> SEQUENCE: 16
```

Met Gln Gln Asp Gly Leu Gly Val Gly Thr Arg Asn Gly Ser Gly Lys
1               5                   10                  15

Gly Arg Ser Val His Pro Ser Trp Pro Trp Cys Ala Pro Arg Pro Leu
            20                  25                  30

Arg Tyr Phe Gly Arg Asp Ala Arg Ala Arg Arg Ala Gln Thr Ala Ala
        35                  40                  45

Met Ala Leu Leu Ala Gly Gly Leu Ser Arg Gly Leu Gly Ser His Pro
    50                  55                  60

Ala Ala Ala Gly Arg Asp Ala Val Val Phe Val Trp Leu Leu Leu Ser
65                  70                  75                  80

Thr Trp Cys Thr Ala Pro Ala Arg Ala Ile Gln Val Thr Val Ser Asn
                85                  90                  95

Pro Tyr His Val Val Ile Leu Phe Gln Pro Val Thr Leu Pro Cys Thr
            100                 105                 110

Tyr Gln Met Thr Ser Thr Pro Thr Gln Pro Ile Val Ile Trp Lys Tyr
        115                 120                 125

Lys Ser Phe Cys Arg Asp Arg Ile Ala Asp Ala Phe Ser Pro Ala Ser
    130                 135                 140

Val Asp Asn Gln Leu Asn Ala Gln Leu Ala Ala Gly Asn Pro Gly Tyr
145                 150                 155                 160

Asn Pro Tyr Val Glu Cys Gln Asp Ser Val Arg Thr Val Arg Val Val
                165                 170                 175

Ala Thr Lys Gln Gly Asn Ala Val Thr Leu Gly Asp Tyr Tyr Gln Gly
            180                 185                 190

Arg Arg Ile Thr Ile Thr Gly Asn Ala Asp Leu Thr Phe Asp Gln Thr
        195                 200                 205

Ala Trp Gly Asp Ser Gly Val Tyr Tyr Cys Ser Val Val Ser Ala Gln
    210                 215                 220

Asp Leu Gln Gly Asn Asn Glu Ala Tyr Ala Glu Leu Ile Val Leu Asp
225                 230                 235                 240

Trp Leu Phe Val Val Val Cys Leu Ala Ala Phe Leu Ile Phe Leu
                245                 250                 255

Leu Leu Gly Ile Cys Trp Cys Gln Cys Cys Pro His Thr Cys Cys Cys
            260                 265                 270

Tyr Val Arg Cys Pro Cys Cys Pro Asp Lys Cys Cys Cys Pro Glu Ala
        275                 280                 285

Leu Tyr Ala Ala Gly Lys Ala Ala Thr Ser Gly Val Pro Ser Ile Tyr
    290                 295                 300

Ala Pro Ser Thr Tyr Ala His Leu Ser Pro Ala Lys Thr Pro Pro Pro
305                 310                 315                 320

```
Pro Ala Met Ile Pro Met Gly Pro Ala Tyr Asn Gly Tyr Pro Gly Gly
                325                 330                 335
Tyr Pro Gly Asp Val Asp Arg Ser Ser Ala Gly Gly Gln Gly Ser
            340                 345                 350
Tyr Val Pro Leu Leu Arg Asp Thr Asp Ser Ser Val Ala Ser Glu Val
        355                 360                 365
Arg Ser Gly Tyr Arg Ile Gln Ala Ser Gln Gln Asp Asp Ser Met Arg
    370                 375                 380
Val Leu Tyr Tyr Met Glu Lys Glu Leu Ala Asn Phe Asp Pro Ser Arg
385                 390                 395                 400
Pro Gly Pro Pro Ser Gly Arg Val Glu Arg Ala Met Ser Glu Val Thr
                405                 410                 415
Ser Leu His Glu Asp Asp Trp Arg Ser Arg Pro Ser Arg Gly Pro Ala
            420                 425                 430
Leu Thr Pro Ile Arg Asp Glu Glu Trp Gly Gly His Ser Pro Arg Ser
        435                 440                 445
Pro Arg Gly Trp Asp Gln Glu Pro Ala Arg Glu Gln Ala Gly Gly Gly
    450                 455                 460
Trp Arg Ala Arg Arg Pro Arg Ala Arg Ser Val Asp Ala Leu Asp Asp
465                 470                 475                 480
Leu Thr Pro Pro Ser Thr Ala Glu Ser Gly Ser Arg Ser Pro Thr Ser
                485                 490                 495
Asn Gly Gly Arg Ser Arg Ala Tyr Met Pro Pro Arg Ser Arg Ser Arg
            500                 505                 510
Asp Asp Leu Tyr Asp Gln Asp Asp Ser Arg Asp Phe Pro Arg Ser Arg
        515                 520                 525
Asp Pro His Tyr Asp Asp Phe Arg Ser Arg Glu Arg Pro Pro Ala Asp
    530                 535                 540
Pro Arg Ser His His His Arg Thr Arg Asp Pro Arg Asp Asn Gly Ser
545                 550                 555                 560
Arg Ser Gly Asp Leu Pro Tyr Asp Gly Arg Leu Leu Glu Glu Ala Val
                565                 570                 575
Arg Lys Lys Gly Ser Glu Glu Arg Arg Pro His Lys Glu Glu Glu
            580                 585                 590
Glu Glu Ala Tyr Tyr Pro Pro Ala Pro Pro Tyr Ser Glu Thr Asp
        595                 600                 605
Ser Gln Ala Ser Arg Glu Arg Arg Leu Lys Lys Asn Leu Ala Leu Ser
    610                 615                 620
Arg Glu Ser Leu Val Val
625                 630

<210> SEQ ID NO 17
<211> LENGTH: 1954
<212> TYPE: DNA
<213> ORGANISM: Homo sapiens
<220> FEATURE:
<221> NAME/KEY: allele
<222> LOCATION: 595
<223> OTHER INFORMATION: 9-3-324 : polymorphic base C or T
<220> FEATURE:
<221> NAME/KEY: allele
<222> LOCATION: 987
<223> OTHER INFORMATION: 9-7-325 : polymorphic base A or G
<220> FEATURE:
<221> NAME/KEY: allele
<222> LOCATION: 1158
<223> OTHER INFORMATION: 9-9-246 : polymorphic base G or C
<220> FEATURE:
<221> NAME/KEY: allele
```

```
<222> LOCATION: 1454
<223> OTHER INFORMATION: LSRX9f13-BM : polymorphic base deletion
      of AGG
<220> FEATURE:
<221> NAME/KEY: allele
<222> LOCATION: 1875
<223> OTHER INFORMATION: LSRX9f14-BM : polymorphic base T or G

<400> SEQUENCE: 17
```

| | | | |
|---|---|---|---|
| tggagtgtgg ctcggaggac cgcggcgggt caagcacctt tctcccccat atctgaaagc | | | 60 |
| atgccctttg tccacgtcgt ttacgctcat taaaacttcc aga atg caa cag gac<br>                                                                  Met Gln Gln Asp<br>                                                                  1 | | | 115 |

```
gga ctt gga gta ggg aca agg aac gga agt ggg aag ggg agg agc gtg        163
Gly Leu Gly Val Gly Thr Arg Asn Gly Ser Gly Lys Gly Arg Ser Val
5               10                  15                  20 cac ccc tcc tgg cct tgg tgc gcg ccg cgc ccc cta agg tac ttt gga        211
His Pro Ser Trp Pro Trp Cys Ala Pro Arg Pro Leu Arg Tyr Phe Gly
            25                  30                  35 agg gac gcg cgg gcc aga cgc gcc cag acg gcc gcg atg gcg ctg ttg        259
Arg Asp Ala Arg Ala Arg Arg Ala Gln Thr Ala Ala Met Ala Leu Leu
        40                  45                  50 gcc ggc ggg ctc tcc aga ggg ctg ggc tcc cac ccg gcc gcc gca ggc        307
Ala Gly Gly Leu Ser Arg Gly Leu Gly Ser His Pro Ala Ala Ala Gly
    55                  60                  65 cgg gac gcg gtc gtc ttc gtg tgg ctt ctg ctt agc acc tgg tgc aca        355
Arg Asp Ala Val Val Phe Val Trp Leu Leu Leu Ser Thr Trp Cys Thr
70                  75                  80 gct cct gcc agg gcc atc cag gtg acc gtg tcc aac ccc tac cac gtg        403
Ala Pro Ala Arg Ala Ile Gln Val Thr Val Ser Asn Pro Tyr His Val
85                  90                  95                  100 gtg atc ctc ttc cag cct gtg acc ctg ccc tgt acc tac cag atg acc        451
Val Ile Leu Phe Gln Pro Val Thr Leu Pro Cys Thr Tyr Gln Met Thr
                105                 110                 115 tcg acc ccc acg caa ccc atc gtc atc tgg aag tac aag tct ttc tgc        499
Ser Thr Pro Thr Gln Pro Ile Val Ile Trp Lys Tyr Lys Ser Phe Cys
            120                 125                 130 cgg gac cgc atc gcc gat gcc ttc tcc ccg gcc agc gtc gac aac cag        547
Arg Asp Arg Ile Ala Asp Ala Phe Ser Pro Ala Ser Val Asp Asn Gln
        135                 140                 145 ctc aat gcc cag ctg gca gcc ggg aac cca ggc tac aac ccc tac gtt        595
Leu Asn Ala Gln Leu Ala Ala Gly Asn Pro Gly Tyr Asn Pro Tyr Val
    150                 155                 160 gag tgc cag gac agc gtg cgc acc gtc agg gtc gtg gcc acc aag cag        643
Glu Cys Gln Asp Ser Val Arg Thr Val Arg Val Val Ala Thr Lys Gln
165                 170                 175                 180 ggc aac gct gtg acc ctg gga gat tac tac cag ggc cgg agg att acc        691
Gly Asn Ala Val Thr Leu Gly Asp Tyr Tyr Gln Gly Arg Arg Ile Thr
                185                 190                 195 atc acc gga aat gct gac ctg acc ttt gac cag acg gcg tgg ggg gac        739
Ile Thr Gly Asn Ala Asp Leu Thr Phe Asp Gln Thr Ala Trp Gly Asp
            200                 205                 210 agt ggt gtg tat tac tgc tcc gtg gtc tca gcc cag gac ctc cag ggg        787
Ser Gly Val Tyr Tyr Cys Ser Val Val Ser Ala Gln Asp Leu Gln Gly
        215                 220                 225 aac aat gag gcc tac gca gag ctc atc gtc ctt gtg tat gcc gcc ggc        835
Asn Asn Glu Ala Tyr Ala Glu Leu Ile Val Leu Val Tyr Ala Ala Gly
    230                 235                 240 aaa gca gcc acc tca ggt gtt ccc agc att tat gcc ccc agc acc tat        883
Lys Ala Ala Thr Ser Gly Val Pro Ser Ile Tyr Ala Pro Ser Thr Tyr
245                 250                 255                 260
```

```
gcc cac ctg tct ccc gcc aag acc cca ccc cca gct atg att ccc    931
Ala His Leu Ser Pro Ala Lys Thr Pro Pro Pro Ala Met Ile Pro
            265                 270                 275 atg ggc cct gcc tac aac ggg tac cct gga gga tac cct gga gac gtt    979
Met Gly Pro Ala Tyr Asn Gly Tyr Pro Gly Gly Tyr Pro Gly Asp Val
                280                 285                 290 gac agg agt agc tca gct ggt ggc caa ggc tcc tat gta ccc ctg ctt   1027
Asp Arg Ser Ser Ser Ala Gly Gly Gln Gly Ser Tyr Val Pro Leu Leu
        295                 300                 305 cgg gac acg gac agc agt gtg gcc tct gaa gtc cgc agt ggc tac agg   1075
Arg Asp Thr Asp Ser Ser Val Ala Ser Glu Val Arg Ser Gly Tyr Arg
    310                 315                 320 att cag gcc agc cag cag gac gac tcc atg cgg gtc ctg tac tac atg   1123
Ile Gln Ala Ser Gln Gln Asp Asp Ser Met Arg Val Leu Tyr Tyr Met
325                 330                 335                 340 gag aag gag ctg gcc aac ttc gac cct tct cga cct ggc ccc ccc agt   1171
Glu Lys Glu Leu Ala Asn Phe Asp Pro Ser Arg Pro Gly Pro Pro Ser
                345                 350                 355 ggc cgt gtg gag cgg gcc atg agt gaa gtc acc tcc ctc cac gag gac   1219
Gly Arg Val Glu Arg Ala Met Ser Glu Val Thr Ser Leu His Glu Asp
        360                 365                 370 gac tgg cga tct cgg cct tcc cgg ggc cct gcc ctc acc ccg atc cgg   1267
Asp Trp Arg Ser Arg Pro Ser Arg Gly Pro Ala Leu Thr Pro Ile Arg
    375                 380                 385 gat gag gag tgg ggt ggc cac tcc ccc cgg agt ccc agg gga tgg gac   1315
Asp Glu Glu Trp Gly Gly His Ser Pro Arg Ser Pro Arg Gly Trp Asp
390                 395                 400 cag gag ccc gcc agg gag cag gca ggc ggg ggc tgg cgg gcc agg cgg   1363
Gln Glu Pro Ala Arg Glu Gln Ala Gly Gly Gly Trp Arg Ala Arg Arg
405                 410                 415                 420 ccc cgg gcc cgc tcc gtg gac gcc ctg gac gac ctc acc ccg ccg agc   1411
Pro Arg Ala Arg Ser Val Asp Ala Leu Asp Asp Leu Thr Pro Pro Ser
                425                 430                 435 acc gcc gag tca ggg agc agg tct ccc acg agt aat ggt ggg aga agc   1459
Thr Ala Glu Ser Gly Ser Arg Ser Pro Thr Ser Asn Gly Gly Arg Ser
        440                 445                 450 cgg gcc tac atg ccc ccg cgg agc cgc agc cgg gac gac ctc tat gac   1507
Arg Ala Tyr Met Pro Pro Arg Ser Arg Ser Arg Asp Asp Leu Tyr Asp
    455                 460                 465 caa gac gac tcg agg gac ttc cca cgc tcc cgg gac ccc cac tac gac   1555
Gln Asp Asp Ser Arg Asp Phe Pro Arg Ser Arg Asp Pro His Tyr Asp
470                 475                 480 gac ttc agg tct cgg gag cgc cct cct gcc gac ccc agg tcc cac cac   1603
Asp Phe Arg Ser Arg Glu Arg Pro Pro Ala Asp Pro Arg Ser His His
485                 490                 495                 500 cac cgt acc cgg gac cct cgg gac aac ggc tcc agg tcc ggg gac ctc   1651
His Arg Thr Arg Asp Pro Arg Asp Asn Gly Ser Arg Ser Gly Asp Leu
                505                 510                 515 ccc tat gat ggg cgg cta ctg gag gag gct gtg agg aag aag ggg tcg   1699
Pro Tyr Asp Gly Arg Leu Leu Glu Glu Ala Val Arg Lys Lys Gly Ser
        520                 525                 530 gag gag agg agg aga ccc cac aag gag gag gag gaa gag gcc tac tac   1747
Glu Glu Arg Arg Arg Pro His Lys Glu Glu Glu Glu Glu Ala Tyr Tyr
    535                 540                 545 ccg ccc gcg ccg ccc ccg tac tcg gag acc gac tcg cag gcg tcc cga   1795
Pro Pro Ala Pro Pro Pro Tyr Ser Glu Thr Asp Ser Gln Ala Ser Arg
550                 555                 560 gag cgc agg ctc aag aag aac ttg gcc ctg agt cgg gaa agt tta gtc   1843
Glu Arg Arg Leu Lys Lys Asn Leu Ala Leu Ser Arg Glu Ser Leu Val
```

-continued

```
         565                 570                 575                 580
gtc tga tctgacgttt tctacgtagc ttttgtattt ttttttttaa tttgaaggaa      1899
Val cactgatgaa gccctgccat acccctcccg agtctaataa aacgtataat cacaa        1954
```

<210> SEQ ID NO 18
<211> LENGTH: 581
<212> TYPE: PRT
<213> ORGANISM: Homo sapiens
<220> FEATURE:
<221> NAME/KEY: VARIANT
<222> LOCATION: 295
<223> OTHER INFORMATION: 9-7-325 : polymorphic amino acid Ser or Asn
<220> FEATURE:
<221> NAME/KEY: VARIANT
<222> LOCATION: 352
<223> OTHER INFORMATION: 9-9-246 : polymorphic amino acid Pro or Arg
<220> FEATURE:
<221> NAME/KEY: VARIANT
<222> LOCATION: 451
<223> OTHER INFORMATION: LSRX9f13-BM : polymorphic amino acid deletion of Arg

<400> SEQUENCE: 18

```
Met Gln Gln Asp Gly Leu Gly Val Gly Thr Arg Asn Gly Ser Gly Lys
1               5                   10                  15

Gly Arg Ser Val His Pro Ser Trp Pro Trp Cys Ala Pro Arg Pro Leu
            20                  25                  30

Arg Tyr Phe Gly Arg Asp Ala Arg Ala Arg Ala Gln Thr Ala Ala
        35                  40                  45

Met Ala Leu Leu Ala Gly Gly Leu Ser Arg Gly Leu Gly Ser His Pro
    50                  55                  60

Ala Ala Ala Gly Arg Asp Ala Val Val Phe Val Trp Leu Leu Leu Ser
65                  70                  75                  80

Thr Trp Cys Thr Ala Pro Ala Arg Ala Ile Gln Val Thr Val Ser Asn
                85                  90                  95

Pro Tyr His Val Val Ile Leu Phe Gln Pro Val Thr Leu Pro Cys Thr
            100                 105                 110

Tyr Gln Met Thr Ser Thr Pro Thr Gln Pro Ile Val Ile Trp Lys Tyr
        115                 120                 125

Lys Ser Phe Cys Arg Asp Arg Ile Ala Asp Ala Phe Ser Pro Ala Ser
    130                 135                 140

Val Asp Asn Gln Leu Asn Ala Gln Leu Ala Ala Gly Asn Pro Gly Tyr
145                 150                 155                 160

Asn Pro Tyr Val Glu Cys Gln Asp Ser Val Arg Thr Val Arg Val Val
                165                 170                 175

Ala Thr Lys Gln Gly Asn Ala Val Thr Leu Gly Asp Tyr Tyr Gln Gly
            180                 185                 190

Arg Arg Ile Thr Ile Thr Gly Asn Ala Asp Leu Thr Phe Asp Gln Thr
        195                 200                 205

Ala Trp Gly Asp Ser Gly Val Tyr Tyr Cys Ser Val Val Ser Ala Gln
    210                 215                 220

Asp Leu Gln Gly Asn Asn Glu Ala Tyr Ala Glu Leu Ile Val Leu Val
225                 230                 235                 240

Tyr Ala Ala Gly Lys Ala Ala Thr Ser Gly Val Pro Ser Ile Tyr Ala
                245                 250                 255

Pro Ser Thr Tyr Ala His Leu Ser Pro Ala Lys Thr Pro Pro Pro Pro
```

-continued

```
                    260                 265                 270
        Ala Met Ile Pro Met Gly Pro Ala Tyr Asn Gly Tyr Pro Gly Gly Tyr
                        275                 280                 285

Pro Gly Asp Val Asp Arg Ser Ser Ala Gly Gln Gly Ser Tyr
                290                 295                 300

Val Pro Leu Leu Arg Asp Thr Asp Ser Ser Val Ala Ser Glu Val Arg
        305                 310                 315                 320

Ser Gly Tyr Arg Ile Gln Ala Ser Gln Gln Asp Asp Ser Met Arg Val
                        325                 330                 335

Leu Tyr Tyr Met Glu Lys Glu Leu Ala Asn Phe Asp Pro Ser Arg Pro
                        340                 345                 350

Gly Pro Pro Ser Gly Arg Val Glu Arg Ala Met Ser Glu Val Thr Ser
                        355                 360                 365

Leu His Glu Asp Asp Trp Arg Ser Arg Pro Ser Arg Gly Pro Ala Leu
                    370                 375                 380

Thr Pro Ile Arg Asp Glu Glu Trp Gly Gly His Ser Pro Arg Ser Pro
        385                 390                 395                 400

Arg Gly Trp Asp Gln Glu Pro Ala Arg Glu Gln Ala Gly Gly Gly Trp
                        405                 410                 415

Arg Ala Arg Arg Pro Arg Ala Arg Ser Val Asp Ala Leu Asp Asp Leu
                        420                 425                 430

Thr Pro Pro Ser Thr Ala Glu Ser Gly Ser Arg Ser Pro Thr Ser Asn
                    435                 440                 445

Gly Gly Arg Ser Arg Ala Tyr Met Pro Pro Arg Ser Arg Ser Arg Asp
                450                 455                 460

Asp Leu Tyr Asp Gln Asp Asp Ser Arg Asp Phe Pro Arg Ser Arg Asp
        465                 470                 475                 480

Pro His Tyr Asp Asp Phe Arg Ser Arg Glu Arg Pro Ala Asp Pro
                        485                 490                 495

Arg Ser His His His Arg Thr Arg Asp Pro Arg Asp Asn Gly Ser Arg
                        500                 505                 510

Ser Gly Asp Leu Pro Tyr Asp Gly Arg Leu Leu Glu Glu Ala Val Arg
                    515                 520                 525

Lys Lys Gly Ser Glu Glu Arg Arg Arg Pro His Lys Glu Glu Glu Glu
                530                 535                 540

Glu Ala Tyr Tyr Pro Pro Ala Pro Pro Pro Tyr Ser Glu Thr Asp Ser
        545                 550                 555                 560

Gln Ala Ser Arg Glu Arg Arg Leu Lys Lys Asn Leu Ala Leu Ser Arg
                        565                 570                 575

Glu Ser Leu Val Val
                    580

<210> SEQ ID NO 19
<211> LENGTH: 18
<212> TYPE: DNA
<213> ORGANISM: Artificial Sequence
<220> FEATURE:
<223> OTHER INFORMATION: sequencing oligonucleotide PrimerPU

<400> SEQUENCE: 19
tgtaaaacga cggccagt                                                  18

<210> SEQ ID NO 20
<211> LENGTH: 18
<212> TYPE: DNA
<213> ORGANISM: Artificial Sequence
```

```
-continued

<220> FEATURE:
<223> OTHER INFORMATION: sequencing oligonucleotide PrimerRP

<400> SEQUENCE: 20
caggaaacag ctatgacc                                                    18
```